(12) United States Patent
Tracewell et al.

(10) Patent No.: US 11,739,355 B2
(45) Date of Patent: Aug. 29, 2023

(54) ENGINEERED BIOSYNTHETIC PATHWAYS FOR PRODUCTION OF HISTAMINE BY FERMENTATION

(71) Applicant: Zymergen Inc., Emeryville, CA (US)

(72) Inventors: Cara Ann Tracewell, Walnut Creek, CA (US); Alexander Glennon Shearer, San Francisco, CA (US); Michael Shareef Siddiqui, Oakland, CA (US); Steven M. Edgar, Albany, CA (US); Nicolaus Herman, El Cerrito, CA (US); Murtaza Shabbir Hussain, Emeryville, CA (US)

(73) Assignee: Zymergen Inc., Emeryville, CA (US)

( * ) Notice: Subject to any disclaimer, the term of this patent is extended or adjusted under 35 U.S.C. 154(b) by 352 days.

(21) Appl. No.: 17/048,553

(22) PCT Filed: Apr. 19, 2019

(86) PCT No.: PCT/US2019/028401
§ 371 (c)(1),
(2) Date: Oct. 16, 2020

(87) PCT Pub. No.: WO2019/204787
PCT Pub. Date: Oct. 24, 2019

(65) Prior Publication Data
US 2021/0180096 A1 Jun. 17, 2021

Related U.S. Application Data

(60) Provisional application No. 62/660,875, filed on Apr. 20, 2018.

(51) Int. Cl.
| | |
|---|---|
| *C12N 15/80* | (2006.01) |
| *C12P 17/10* | (2006.01) |
| *C12N 1/18* | (2006.01) |
| *C12N 1/20* | (2006.01) |
| *C12N 9/04* | (2006.01) |
| *C12N 9/10* | (2006.01) |
| *C12N 9/88* | (2006.01) |
| *C12N 15/77* | (2006.01) |
| *C12N 15/81* | (2006.01) |

(52) U.S. Cl.
CPC ............ *C12P 17/10* (2013.01); *C12N 1/18* (2013.01); *C12N 1/20* (2013.01); *C12N 9/0006* (2013.01); *C12N 9/1077* (2013.01); *C12N 9/88* (2013.01); *C12N 15/77* (2013.01); *C12N 15/81* (2013.01); *C12Y 101/01023* (2013.01); *C12Y 101/01049* (2013.01); *C12Y 204/02017* (2013.01); *C12Y 206/01009* (2013.01); *C12Y 207/06001* (2013.01); *C12Y 301/03015* (2013.01); *C12Y 305/04019* (2013.01); *C12Y 306/01031* (2013.01); *C12Y 401/01022* (2013.01); *C12Y 402/01019* (2013.01); *C12Y 403/02* (2013.01); *C12Y 503/01016* (2013.01)

(58) Field of Classification Search
CPC ................................ C12N 15/80; C12N 15/81
See application file for complete search history.

(56) References Cited

U.S. PATENT DOCUMENTS

| | | | | |
|---|---|---|---|---|
| 6,258,554 | B1 * | 7/2001 | Ikeda ................... | C12P 25/00 435/840 |
| 2005/0005315 | A1 | 1/2005 | Ohtsu | |
| 2009/0317876 | A1 | 12/2009 | Rybak et al. | |
| 2010/0209977 | A1 * | 8/2010 | Takumi ............... | C07K 14/245 435/106 |
| 2015/0284760 | A1 * | 10/2015 | Schendzielorz ........ | C12P 19/34 435/114 |
| 2021/0180096 | A1 * | 6/2021 | Tracewell ....... | C12Y 301/03015 |

FOREIGN PATENT DOCUMENTS

| | | |
|---|---|---|
| EP | 3597754 A1 | 1/2020 |
| WO | WO-2018168801 A1 | 9/2018 |

OTHER PUBLICATIONS

Morii et al., "Cloning and sequencing of the histidine decarboxylase gene from Photobacterium phosphoreum and its functional expression in *Escherichia coli*", Journal of Food Protection, vol. 69, No. 8, pp. 1768-1776, 2006 (Year: 2006).*
Brilli et al., "Molecular evolution of hisB genes", Journal of Molecular Evolution, vol. 58, pp. 225-237, 2004 (Year: 2004).*
GenBank Accession No. ACJ42158.1, published Jun. 27, 2017 (Year: 2017).*
Byun, B.Y. et al., "Occurrence of biogenic amines in Miso, Japanese traditional fermented soybean paste", Journal of Food Science, Dec. 2012, vol. 77, No. 12, pp. T216-T223.
EP Search report dated Feb. 9, 2022, in Application No. EP19789563.4.
Ferstl, R. et al., "Histamine Receptor 2 is a Key Influence in Immune Responses to Intestinal Histamine-secreting Microbes", The Journal of Allergy and Clinical Immunology, Sep. 2014, vol. 134, No. 3, pp. 744-746.

(Continued)

*Primary Examiner* — Tekchand Saidha
(74) *Attorney, Agent, or Firm* — Emily M. Haliday; Weaver Austin Villeneuve & Sampson LLP

(57) ABSTRACT

The present disclosure describes the engineering of microbial cells for fermentative production of histamine and provides novel engineered microbial cells and cultures, as well as related histamine production methods.

15 Claims, 10 Drawing Sheets

Specification includes a Sequence Listing.

(56) References Cited

OTHER PUBLICATIONS

Gezginc, Y. et al., "Biogenic Amines Formation in *Streptococcus thermophilus* Isolated From Home-made Natural Yogurt", Food Chemistry, 2013, vol. 138, pp. 655-662.
International Preliminary Report on Patentability dated Oct. 29, 2020, in PCT Application No. PCT/US2019/028401.
International Search Report and Written Opinion dated Aug. 6, 2019, in PCT Application No. PCT/US2019/028401.
Landete, J.M. et al., "Molecular Methods for the Detection of Biogenic Amine-producing Bacteria on Foods", International Journal of Food Microbiology, Jul. 15, 2007, vol. 117, No. 3, pp. 258-269.
Lee, M.E. et al., "A Highly Characterized Yeast Toolkit for Modular, Multipart Assembly", ACS Synthetic Biology, Sep. 18, 2015, vol. 4, No. 9, pp. 975-986.
Roland, B.P. et al., "Triosephosphate Isomerase I170V Alters Catalytic Site, Enhances Stability and Induces Pathology in a *Drosophila* Model of TPI Deficiency", Biochimica et Biophysica Acta, Sep. 2015, vol. 1852, pp. 61-69.
Tabanelli, G. et al., "Effect of Chemico-physical Parameters on the Histidine Decarboxylase (HdcA) Enzymatic Activity in *Streptococcus thermophilus* PRI60", Journal of Food Science, Apr. 2012, vol. 77, pp. 4, pp. M231-M237.
Wauters, G. et al., "Histidine Decarboxylase in Enterobacteriaceae Revisited", Journal of Clinical Microbiology, Dec. 2004, vol. 42, No. 12, pp. 5923-5924.
Yokoi, K. et al., "Characterization of The Histidine Decarboxylase Gene of TYH1 Coded on the Staphylococcal Cassette Chromosome", Gene, Jan. 5, 2011, Elsevier Amsterdam, NL, vol. 477, No. 1, pp. 32-41.

\* cited by examiner

SEQUENCE LISTING

```
<160> NUMBER OF SEQ ID NOS: 143

<210> SEQ ID NO 1
<211> LENGTH: 383
<212> TYPE: PRT
<213> ORGANISM: Acinetobacter baumannii (strain AB0057)

<400> SEQUENCE: 1

Met Ile Leu Ser Pro Ala Asp Gln Glu Arg Ile Glu Thr Phe Trp Asn
1               5                   10                  15

Tyr Cys Leu Lys His Gln Tyr Phe Asn Ile Gly Tyr Pro Glu Ser Ala
            20                  25                  30

Asp Phe Asp Tyr Ser Ala Leu Phe Arg Phe Phe Lys Phe Ser Ile Asn
        35                  40                  45

Asn Cys Gly Asp Trp Lys Asp Tyr Ser Asn Tyr Ala Leu Asn Ser Phe
    50                  55                  60

Asp Phe Glu Lys Asp Val Met Ala Tyr Phe Ala Glu Ile Phe Gln Ile
65                  70                  75                  80

Pro Phe Glu Glu Ser Trp Gly Tyr Val Thr Asn Gly Gly Thr Glu Gly
                85                  90                  95

Asn Met Phe Gly Cys Tyr Leu Ala Arg Glu Leu Phe Ser Asp Ser Thr
                100                 105                 110
```

Leu Tyr Tyr Ser Lys Asp Thr His Tyr Ser Val Gly Lys Ile Ala Lys
            115                 120                 125

Leu Leu Gln Met Lys Ser Cys Val Ile Glu Ser Leu Asp Asn Gly Glu
        130                 135                 140

Ile Asp Tyr Asp Leu Ile His Lys Ile Lys Thr Asn Lys Glu Ser
145                 150                 155                 160

His Pro Ile Ile Phe Ala Asn Ile Gly Thr Thr Met Thr Gly Ala Ile
                165                 170                 175

Asp Asp Ile Glu Met Ile Gln Glu Arg Leu Ala Gln Ile Gly Ile Met
            180                 185                 190

Arg Arg Asp Tyr Tyr Ile His Ala Asp Ala Ala Leu Ser Gly Met Ile
        195                 200                 205

Leu Pro Phe Val Asp His Pro Gln Ala Phe Ser Phe Ala His Gly Ile
    210                 215                 220

Asp Ser Ile Cys Val Ser Gly His Lys Met Ile Gly Ser Pro Ile Pro
225                 230                 235                 240

Cys Gly Ile Val Val Ala Lys Arg Gln Asn Val Glu Arg Ile Ser Val
                245                 250                 255

Asp Val Asp Tyr Ile Ser Thr Arg Asp Gln Thr Ile Ser Gly Ser Arg
            260                 265                 270

Asn Gly His Thr Val Leu Leu Met Trp Ala Ala Ile Arg Ser Gln Thr
        275                 280                 285

Asn Leu Gln Arg Arg Gln Arg Ile Gln His Cys Leu Lys Met Ala Gln
    290                 295                 300

Tyr Ala Val Asp Arg Phe Gln Ala Val Gly Ile Pro Ala Trp Arg Asn
305                 310                 315                 320

Pro Asn Ser Ile Thr Val Val Phe Pro Cys Pro Ser Glu His Ile Trp
                325                 330                 335

Lys Lys His Tyr Leu Ala Thr Ser Gly Asn Met Ala His Leu Ile Thr
            340                 345                 350

Thr Ala His His Arg Asp Thr Arg Gln Ile Asp Ser Leu Ile Asp Asp
        355                 360                 365

Val Ile Phe Asp Leu Gln Gly Ala Ser Lys Arg Thr Val Gly Phe
    370                 375                 380

<210> SEQ ID NO 2
<211> LENGTH: 202
<212> TYPE: PRT
<213> ORGANISM: Artificial
<220> FEATURE:
<223> OTHER INFORMATION: Codon-optimized and/or mutated sequence

<400> SEQUENCE: 2

Met Thr Val Ala Pro Arg Ile Gly Thr Ala Thr Arg Thr Thr Ser Glu
1               5                   10                  15

Ser Asp Ile Thr Val Glu Ile Asn Leu Asp Gly Thr Gly Lys Val Asp
            20                  25                  30

Ile Asp Thr Gly Leu Pro Phe Phe Asp His Met Leu Thr Ala Phe Gly
        35                  40                  45

Val His Gly Ser Phe Asp Leu Lys Val His Ala Lys Gly Asp Ile Glu
    50                  55                  60

Ile Asp Ala His His Thr Val Glu Asp Thr Ala Ile Val Leu Gly Gln
65                  70                  75                  80

Ala Leu Leu Asp Ala Ile Gly Asp Lys Lys Gly Ile Arg Arg Phe Ala
                85                  90                  95

Ser Cys Gln Leu Pro Met Asp Glu Ala Leu Val Glu Ser Val Val Asp
            100                 105                 110

Ile Ser Gly Arg Pro Tyr Phe Val Ile Ser Gly Pro Asp His Met
        115                 120                 125

Ile Thr Ser Val Ile Gly Gly His Tyr Ala Thr Val Ile Asn Glu His
    130                 135                 140

Phe Phe Glu Thr Leu Ala Leu Asn Ser Arg Ile Thr Leu His Val Ile
145                 150                 155                 160

Cys His Tyr Gly Arg Asp Pro His His Ile Thr Glu Ala Glu Tyr Lys
                165                 170                 175

Ala Val Ala Arg Ala Leu Arg Gly Ala Val Glu Met Asp Pro Arg Gln
                180                 185                 190

Thr Gly Ile Pro Ser Thr Lys Gly Ala Leu
            195                 200

<210> SEQ ID NO 3
<211> LENGTH: 297
<212> TYPE: PRT
<213> ORGANISM: Saccharomyces cerevisiae

<400> SEQUENCE: 3

Met Asp Leu Val Asn His Leu Thr Asp Arg Leu Leu Phe Ala Ile Pro
1               5                   10                  15

Lys Lys Gly Arg Leu Tyr Ser Lys Ser Val Ser Ile Leu Asn Gly Ala
                20                  25                  30

Asp Ile Thr Phe His Arg Ser Gln Arg Leu Asp Ile Ala Leu Ser Thr
            35                  40                  45

Ser Leu Pro Val Ala Leu Ile Phe Leu Pro Ala Ala Asp Ile Pro Thr
        50                  55                  60

Phe Val Gly Glu Gly Lys Cys Asp Leu Gly Ile Thr Gly Val Asp Gln
65                  70                  75                  80

Val Arg Glu Ser Asp Val Asp Val Asp Leu Ala Ile Asp Leu Gln Phe
                85                  90                  95

Gly Asn Cys Lys Leu Gln Val Gln Val Pro Val Asn Gly Glu Tyr Lys
                100                 105                 110

Lys Pro Glu Gln Leu Ile Gly Lys Thr Ile Val Thr Ser Phe Val Lys
            115                 120                 125

Leu Ala Glu Lys Tyr Phe Ala Asp Leu Glu Gly Thr Thr Val Glu Lys
        130                 135                 140

Met Thr Thr Arg Ile Lys Phe Val Ser Gly Ser Val Glu Ala Ser Cys
145                 150                 155                 160

Ala Leu Gly Ile Gly Asp Ala Ile Val Asp Leu Val Glu Ser Gly Glu
                165                 170                 175

Thr Met Arg Ala Ala Gly Leu Val Asp Ile Ala Thr Val Leu Ser Thr
                180                 185                 190

Ser Ala Tyr Leu Ile Glu Ser Lys Asn Pro Lys Ser Asp Lys Ser Leu
            195                 200                 205

Ile Ala Thr Ile Lys Ser Arg Ile Glu Gly Val Met Thr Ala Gln Arg
        210                 215                 220

Phe Val Ser Cys Ile Tyr Asn Ala Pro Glu Asp Lys Leu Pro Glu Leu
225                 230                 235                 240

Leu Lys Val Thr Pro Gly Arg Arg Ala Pro Thr Ile Ser Lys Ile Asp
                245                 250                 255

Asp Glu Gly Trp Val Ala Val Ser Ser Met Ile Glu Arg Lys Thr Lys

```
                    260                 265                 270
Gly Val Val Leu Asp Glu Leu Lys Arg Leu Gly Ala Ser Asp Ile Met
                275                 280                 285

Val Phe Glu Ile Ser Asn Cys Arg Val
            290                 295

<210> SEQ ID NO 4
<211> LENGTH: 311
<212> TYPE: PRT
<213> ORGANISM: Lactobacillus sp. (strain 30a)

<400> SEQUENCE: 4

Met Ser Glu Leu Asp Ala Lys Leu Asn Lys Leu Gly Val Asp Arg Ile
1               5                   10                  15

Ala Ile Ser Pro Tyr Lys Gln Trp Thr Arg Gly Tyr Met Glu Pro Gly
                20                  25                  30

Asn Ile Gly Asn Gly Tyr Val Thr Gly Leu Lys Val Asp Ala Gly Val
            35                  40                  45

Arg Asp Lys Ser Asp Asp Val Leu Asp Gly Ile Val Ser Tyr Asp
    50                  55                  60

Arg Ala Glu Thr Lys Asn Ala Tyr Ile Gly Gln Ile Asn Met Thr Thr
65                  70                  75                  80

Ala Ser Ser Phe Thr Gly Val Gln Gly Arg Val Ile Gly Tyr Asp Ile
                85                  90                  95

Leu Arg Ser Pro Glu Val Asp Lys Ala Lys Pro Leu Phe Thr Glu Thr
            100                 105                 110

Gln Trp Asp Gly Ser Glu Leu Pro Ile Tyr Asp Ala Lys Pro Leu Gln
        115                 120                 125

Asp Ala Leu Val Glu Tyr Phe Gly Thr Glu Gln Asp Arg Arg His Tyr
130                 135                 140

Pro Ala Pro Gly Ser Phe Ile Val Cys Ala Asn Lys Gly Val Thr Ala
145                 150                 155                 160

Glu Arg Pro Lys Asn Asp Ala Asp Met Lys Pro Gly Gln Gly Tyr Gly
                165                 170                 175

Val Trp Ser Ala Ile Ala Ile Ser Phe Ala Lys Asp Pro Thr Lys Asp
            180                 185                 190

Ser Ser Met Phe Val Glu Asp Ala Gly Val Trp Glu Thr Pro Asn Glu
        195                 200                 205

Asp Glu Leu Leu Glu Tyr Leu Glu Gly Arg Arg Lys Ala Met Ala Lys
210                 215                 220

Ser Ile Ala Glu Cys Gly Gln Asp Ala His Ala Ser Phe Glu Ser Ser
225                 230                 235                 240

Trp Ile Gly Phe Ala Tyr Thr Met Met Glu Pro Gly Gln Ile Gly Asn
                245                 250                 255

Ala Ile Thr Val Ala Pro Tyr Val Ser Leu Pro Ile Asp Ser Ile Pro
            260                 265                 270

Gly Gly Ser Ile Leu Thr Pro Asp Lys Asp Met Glu Ile Met Glu Asn
        275                 280                 285

Leu Thr Met Pro Glu Trp Leu Glu Lys Met Gly Tyr Lys Ser Leu Ser
290                 295                 300

Ala Asn Asn Ala Leu Lys Tyr
305                 310

<210> SEQ ID NO 5
<211> LENGTH: 297
```

<212> TYPE: PRT
<213> ORGANISM: Artificial
<220> FEATURE:
<223> OTHER INFORMATION: Codon-optimized and/or mutated sequence

<400> SEQUENCE: 5

```
Met Leu Asp Asn Thr Arg Leu Arg Ile Ala Ile Gln Lys Ser Gly Arg
1               5                   10                  15

Leu Ser Asp Asp Ser Arg Glu Leu Leu Ala Arg Cys Gly Ile Lys Ile
            20                  25                  30

Asn Leu His Thr Gln Arg Leu Ile Ala Met Ala Glu Asn Met Pro Ile
        35                  40                  45

Asp Ile Leu Arg Val Arg Asp Asp Ile Pro Gly Leu Val Met Asp
    50                  55                  60

Gly Val Val Asp Leu Gly Ile Ile Gly Glu Asn Val Leu Glu Glu
65                  70                  75                  80

Leu Leu Asn Arg Arg Ala Gln Gly Glu Asp Pro Arg Tyr Leu Thr Leu
                85                  90                  95

Arg Arg Leu Asp Phe Gly Gly Cys Arg Leu Ser Leu Ala Thr Pro Val
            100                 105                 110

Asp Glu Ala Trp Asp Gly Pro Ala Ala Leu Asp Gly Lys Arg Ile Ala
        115                 120                 125

Thr Ser Tyr Pro His Leu Leu Lys Arg Tyr Leu Asp Gln Lys Gly Val
    130                 135                 140

Ser Phe Lys Ser Cys Leu Leu Asn Gly Ser Val Glu Val Ala Pro Arg
145                 150                 155                 160

Ala Gly Leu Ala Asp Ala Ile Cys Asp Leu Val Ser Thr Gly Ala Thr
                165                 170                 175

Leu Glu Ala Asn Gly Leu Arg Glu Val Glu Val Ile Tyr Arg Ser Lys
            180                 185                 190

Ala Cys Leu Ile Gln Arg Asp Gly Glu Met Ala Gln Ser Lys Leu Ile
        195                 200                 205

Asp Lys Leu Leu Thr Arg Ile Gln Gly Val Ile Gln Ala Arg Glu Ser
    210                 215                 220

Lys Tyr Ile Met Met His Ala Pro Ser Glu Arg Leu Glu Glu Val Ile
225                 230                 235                 240

Ala Leu Leu Pro Gly Ala Glu Arg Pro Thr Ile Leu Pro Leu Ala Gly
                245                 250                 255

Glu Gln Gln Arg Val Ala Met His Met Val Ser Ser Glu Thr Leu Phe
            260                 265                 270

Trp Glu Thr Met Glu Lys Leu Lys Ala Leu Gly Ala Ser Ser Ile Leu
        275                 280                 285

Val Leu Pro Ile Glu Lys Met Met Glu
    290                 295
```

<210> SEQ ID NO 6
<211> LENGTH: 387
<212> TYPE: PRT
<213> ORGANISM: Chromobacterium sp. LK1

<400> SEQUENCE: 6

```
Met Ser Leu Ser Pro Leu Asp Gln Asn Arg Ile Glu Ser Phe Trp Gln
1               5                   10                  15

Tyr Cys Leu Gln His Gln Tyr Phe Asn Leu Ala Tyr Pro Glu Ser Ala
            20                  25                  30

Asp Phe Asp Tyr Ala Pro Leu His Arg Phe Leu Arg Phe Ser Ile Asn
```

```
            35                  40                  45
Asn Cys Gly Asp Trp Asn Glu Ser Ser Asn Tyr Leu Leu Asn Ser Phe
         50                  55                  60
Asp Phe Glu Arg Glu Val Met His Phe Phe Ala Glu Leu Phe His Ile
 65                  70                  75                  80
Pro Phe Asp Glu Ser Trp Gly Tyr Val Thr Asn Gly Gly Thr Glu Gly
                 85                  90                  95
Asn Met Phe Gly Cys Tyr Leu Ala Arg Glu Leu Phe Pro Asp Ala Thr
                100                 105                 110
Leu Tyr Tyr Ser Lys Asp Ser His Tyr Ser Val Ala Lys Ile Ile Lys
            115                 120                 125
Leu Leu Arg Ile Lys Ser Arg Ala Val Asp Ser Leu Pro Ser Gly Glu
        130                 135                 140
Ile Asp Tyr Asp Asp Leu Val Ala Lys Ile Gln Gln Asp Gln Glu Arg
145                 150                 155                 160
His Pro Ile Val Phe Val Asn Val Gly Thr Thr Met Lys Gly Ala Val
                165                 170                 175
Asp Asp Ile Gly Val Ile Gln His Lys Leu Ala Glu Ala Gly Ile Pro
            180                 185                 190
Arg Gln Asp Tyr Tyr Leu His Ala Asp Ala Ala Leu Ser Gly Met Ile
        195                 200                 205
Leu Pro Phe Val Asp Ala Pro Gln Pro Tyr Ser Phe Ala Asp Gly Ile
    210                 215                 220
Asp Ser Ile Ser Val Ser Gly His Lys Met Ile Gly Ser Pro Met Pro
225                 230                 235                 240
Cys Gly Ile Val Leu Ala Lys Arg Ser Asn Val Ser Arg Ile Ser Val
                245                 250                 255
Glu Ile Asp Tyr Ile Ser Ala Lys Asp Gln Thr Ile Ser Gly Ser Arg
            260                 265                 270
Asn Gly His Thr Pro Met Met Leu Trp Ala Ala Ile Lys Ser Arg Pro
        275                 280                 285
Leu Ala Glu Trp Arg Arg Lys Val Arg His Cys Leu Asp Met Ala Gln
    290                 295                 300
Tyr Ala Ile Asp Arg Leu Gln Ala Ala Gly Ile Gln Ala Trp Arg Cys
305                 310                 315                 320
Lys Asn Ser Ile Thr Val Val Phe Pro Ser Pro Ser Glu Pro Val Cys
                325                 330                 335
Asp Lys His Gly Leu Ala Arg Ser Gly Gly Thr Ala His Leu Ile Thr
            340                 345                 350
Thr Pro His His His Asp Ser Gln Arg Leu Asp Arg Leu Leu Asp Asp
        355                 360                 365
Ile Val Gln Asp Leu Gly Ala Met Thr Ala Pro Ala Gly Ala Thr Met
    370                 375                 380
Ser Ala Ala
385

<210> SEQ ID NO 7
<211> LENGTH: 281
<212> TYPE: PRT
<213> ORGANISM: Artificial
<220> FEATURE:
<223> OTHER INFORMATION: Codon-optimized and/or mutated sequence

<400> SEQUENCE: 7

Met Leu Lys Ile Ala Val Pro Asn Lys Gly Ser Leu Ser Glu Arg Ala
```

-continued

```
  1               5                   10                  15
Met Glu Ile Leu Ala Glu Ala Gly Tyr Ala Gly Arg Gly Asp Ser Lys
                    20                  25                  30

Ser Leu Asn Val Phe Asp Glu Ala Asn Asn Val Glu Phe Phe Leu
                    35                  40                  45

Arg Pro Lys Asp Ile Ala Ile Tyr Val Ala Gly Gln Leu Asp Leu
                    50                  55                  60

Gly Ile Thr Gly Arg Asp Leu Ala Arg Asp Ser Gln Ala Asp Val His
65                      70                  75                  80

Glu Val Leu Ser Leu Gly Phe Gly Ser Ser Thr Phe Arg Tyr Ala Ala
                    85                  90                  95

Pro Ala Asp Glu Glu Trp Ser Ile Glu Lys Leu Asp Gly Lys Arg Ile
                    100                 105                 110

Ala Thr Ser Tyr Pro Asn Leu Val Arg Asp Leu Ala Ala Arg Gly
                    115                 120                 125

Leu Ser Ala Glu Val Leu Arg Leu Asp Gly Ala Val Glu Val Ser Ile
                    130                 135                 140

Lys Leu Gly Val Ala Asp Ala Ile Ala Asp Val Val Ser Thr Gly Arg
145                     150                 155                 160

Thr Leu Arg Gln Gln Gly Leu Ala Pro Phe Gly Glu Val Leu Cys Thr
                    165                 170                 175

Ser Glu Ala Val Ile Val Gly Arg Lys Asp Glu Lys Val Thr Pro Glu
                    180                 185                 190

Gln Gln Ile Leu Leu Arg Arg Ile Gln Gly Ile Leu His Ala Gln Asn
                    195                 200                 205

Phe Leu Met Leu Asp Tyr Lys Val Asp Arg Asp Asn Leu Asp Ala Ala
                    210                 215                 220

Thr Ala Val Thr Pro Gly Phe Ser Gly Pro Ala Val Ser Pro Leu Ala
225                     230                 235                 240

Arg Asp Asn Trp Val Ala Val Arg Ala Met Val Pro Arg Arg Ser Ala
                    245                 250                 255

Asn Ala Ile Met Asp Lys Leu Ala Gly Leu Gly Ala Glu Ala Ile Leu
                    260                 265                 270

Ala Ser Glu Ile Arg Ile Ala Arg Ile
                    275                 280
```

<210> SEQ ID NO 8
<211> LENGTH: 334
<212> TYPE: PRT
<213> ORGANISM: Methanosarcina barkeri str. Wiesmoor

<400> SEQUENCE: 8

```
Met Gln Lys Tyr Glu Tyr Asp Pro Lys Trp Val Ile Asn Asn Ala Ile
1               5                   10                  15

Ser Ser Glu Arg Glu Phe Cys Thr Gly Tyr Gln Asn Pro Gly Ala Ser
                    20                  25                  30

Gly Asn Gly Tyr Val Thr Thr Ile Lys Leu Ser Thr Gly Leu Val Asp
                    35                  40                  45

Ile Thr Pro Trp Glu Lys Val Gln Ala Met Ser Glu His Glu Val Ile
                    50                  55                  60

Lys Phe Asp Arg Gly Cys Ser Asn Ile Val Ser Tyr Asp Arg Cys Glu
65                      70                  75                  80

Cys Asn Asp Ala Tyr Ile Gly Ala Ile Asn Met Leu Thr Ala Ser Ser
                    85                  90                  95
```

```
Phe Ser Gly Leu Gln Gly Val Ile Trp Gly Tyr Asp Ile Ala Val Val
            100                 105                 110

Glu Asn Leu Arg Ser Arg Lys Leu Tyr Asp Gln Lys Trp Pro Ser Gly
            115                 120                 125

Asp Pro Asn Ser Glu Tyr Ser Thr Pro Val Tyr Ser Ile Glu Pro Leu
        130                 135                 140

Leu Asn Ala Thr Glu Arg Leu Phe Gly His Ala Glu Pro Gly Lys Arg
145                 150                 155                 160

Arg Phe Asn Pro Ile Pro Gly Ser Met Val Val Cys Ala Asn Lys Ser
                165                 170                 175

Ala Thr Ser Asp Pro Ser Ser Asp Val Lys Glu Gly Trp Ala Phe Ser
            180                 185                 190

Val Ile Ser Leu Ala Ile Leu Glu Asn Arg Asn Ser Gly Ser Asn Leu
        195                 200                 205

Phe Ile Glu Asp Cys Asp Ile Ile Asp Ile Asn Asn Pro Asp Gly Thr
    210                 215                 220

Arg Lys Thr Lys Glu Asp Val Lys Ala Met Leu Asp Thr Thr Leu Arg
225                 230                 235                 240

Lys Val Thr Glu Cys Thr Val Leu Cys Gly Leu Asp Gln His Ile Lys
                245                 250                 255

Tyr Lys Glu Ile Phe Ile Gly Tyr Lys Val Ile Lys Phe Asn Glu Lys
            260                 265                 270

Gln Val Gly Cys Ala Leu Ala Cys Ala Pro Tyr Val Thr Leu Ala Arg
        275                 280                 285

Asn Ala Val Pro Gln Gly Met Lys Pro Ser Lys Leu Thr Asp Met Asn
    290                 295                 300

Ile Ser Gln Trp Glu Asn Ala Leu Asn Leu Gln Pro Leu Glu Lys Ile
305                 310                 315                 320

Glu Lys Ser Lys Ile Gly Ile Leu Gly Met Gly Val Leu Asp
                325                 330

<210> SEQ ID NO 9
<211> LENGTH: 349
<212> TYPE: PRT
<213> ORGANISM: Methanosarcina barkeri (strain Fusaro / DSM 804)

<400> SEQUENCE: 9

Met Thr Leu His Ser Arg Tyr Ser Lys Leu Lys Gly Glu Asn Lys Met
1               5                   10                  15

Gln Lys Tyr Glu Tyr Asp Pro Lys Trp Val Ile Asn Asn Ala Ile Ser
            20                  25                  30

Ser Glu Arg Glu Phe Cys Thr Gly Tyr Gln Asn Pro Gly Ala Ser Gly
        35                  40                  45

Asn Gly Tyr Val Thr Thr Ile Lys Leu Ser Thr Gly Leu Val Asp Ile
    50                  55                  60

Thr Pro Trp Glu Lys Val Gln Ala Met Ser Glu His Glu Val Ile Lys
65                  70                  75                  80

Phe Asp Arg Gly Cys Ser Asn Ile Val Ser Tyr Asp Arg Cys Glu Cys
                85                  90                  95

Asn Asp Ala Tyr Ile Gly Ala Ile Asn Met Leu Thr Ala Ser Ser Phe
            100                 105                 110

Ser Gly Leu Gln Gly Val Ile Trp Gly Tyr Asp Ile Ala Val Val Glu
        115                 120                 125

Asn Leu Arg Ser Arg Lys Leu Tyr Asp Gln Lys Trp Pro Ser Gly Asp
    130                 135                 140
```

```
Pro Asn Ser Glu Tyr Ser Thr Pro Val Tyr Ser Ile Glu Pro Leu Leu
145                 150                 155                 160

Asn Ala Thr Glu Arg Leu Phe Gly His Ala Glu Pro Gly Lys Arg Arg
                165                 170                 175

Phe Asn Pro Ile Pro Gly Ser Met Val Val Cys Ala Asn Lys Ser Ala
            180                 185                 190

Thr Ser Asp Pro Ser Ser Asp Val Lys Glu Gly Trp Ala Phe Ser Val
        195                 200                 205

Ile Ser Leu Ala Ile Leu Glu Asn Arg Asn Ser Gly Ser Asn Leu Phe
210                 215                 220

Ile Glu Asp Cys Asp Ile Ile Asp Ile Asn Asn Pro Asp Gly Thr Arg
225                 230                 235                 240

Lys Thr Lys Glu Asp Val Lys Ala Met Leu Asp Thr Thr Leu Arg Lys
                245                 250                 255

Val Thr Glu Cys Thr Val Leu Cys Gly Leu Asp Gln His Ile Lys Tyr
            260                 265                 270

Lys Glu Ile Phe Ile Gly Tyr Lys Val Ile Lys Phe Asn Glu Lys Gln
        275                 280                 285

Val Gly Cys Ala Leu Ala Cys Ala Pro Tyr Val Thr Leu Ala Arg Asn
    290                 295                 300

Ala Val Pro Gln Gly Met Lys Pro Ser Lys Leu Thr Asp Met Asn Ile
305                 310                 315                 320

Ser Gln Trp Glu Asn Ala Leu Asn Leu Gln Pro Leu Glu Lys Ile Glu
                325                 330                 335

Lys Ser Lys Ile Gly Ile Leu Gly Met Gly Val Leu Asp
            340                 345

<210> SEQ ID NO 10
<211> LENGTH: 847
<212> TYPE: PRT
<213> ORGANISM: Drosophila melanogaster

<400> SEQUENCE: 10

Met Asp Phe Lys Glu Tyr Arg Gln Arg Gly Lys Glu Met Val Asp Tyr
1               5                   10                  15

Ile Ala Asp Tyr Leu Glu Asn Ile Arg Glu Arg Val Phe Pro Asp
                20                  25                  30

Val Ser Pro Gly Tyr Met Arg Gln Leu Leu Pro Glu Ser Ala Pro Ile
            35                  40                  45

Glu Gly Glu Pro Trp Pro Lys Ile Phe Ser Asp Val Glu Arg Ile Val
        50                  55                  60

Met Pro Gly Ile Thr His Trp Gln Ser Pro His Met His Ala Tyr Phe
65                  70                  75                  80

Pro Ala Leu Asn Ser Met Pro Ser Leu Leu Gly Asp Met Leu Ala Asp
                85                  90                  95

Ala Ile Asn Cys Leu Gly Phe Thr Trp Ala Ser Ser Pro Ala Cys Thr
            100                 105                 110

Glu Leu Glu Ile Ile Val Met Asn Trp Leu Gly Lys Met Ile Gly Leu
        115                 120                 125

Pro Asp Ala Phe Leu His Leu Ser Ser Gln Ser Gln Gly Gly Gly Val
    130                 135                 140

Leu Gln Thr Thr Ala Ser Glu Ala Thr Leu Val Cys Leu Leu Ala Gly
145                 150                 155                 160

Arg Thr Arg Ala Ile Gln Arg Phe His Glu Arg His Pro Gly Tyr Gln
```

```
                165                 170                 175
Asp Ala Glu Ile Asn Ala Arg Leu Val Ala Tyr Cys Ser Asp Gln Ala
                180                 185                 190

His Ser Ser Val Glu Lys Ala Ala Leu Ile Gly Leu Val Arg Met Arg
                195                 200                 205

Tyr Ile Glu Ala Asp Asp Leu Ala Met Arg Gly Lys Leu Leu Arg
                210                 215                 220

Glu Ala Ile Glu Asp Asp Ile Lys Gln Gly Leu Val Pro Phe Trp Val
225                 230                 235                 240

Cys Ala Thr Leu Gly Thr Thr Gly Ser Cys Ser Phe Asp Asn Leu Glu
                245                 250                 255

Glu Ile Gly Ile Val Cys Ala Glu His His Leu Trp Leu His Val Asp
                260                 265                 270

Ala Ala Tyr Ala Gly Ser Ala Phe Ile Cys Pro Glu Phe Arg Thr Trp
                275                 280                 285

Leu Arg Gly Ile Glu Arg Ala Asp Ser Ile Ala Phe Asn Pro Ser Lys
                290                 295                 300

Trp Leu Met Val His Phe Asp Ala Thr Ala Leu Trp Val Arg Asp Ser
305                 310                 315                 320

Thr Ala Val His Arg Thr Phe Asn Val Glu Pro Leu Tyr Leu Gln His
                325                 330                 335

Glu Asn Ser Gly Val Ala Val Asp Phe Met His Trp Gln Ile Pro Leu
                340                 345                 350

Ser Arg Arg Phe Arg Ala Leu Lys Val Trp Phe Val Leu Arg Ser Tyr
                355                 360                 365

Gly Ile Lys Gly Leu Gln Arg His Ile Arg Glu Gly Val Arg Leu Ala
                370                 375                 380

Gln Lys Phe Glu Ala Leu Val Leu Ala Asp His Arg Phe Glu Leu Pro
385                 390                 395                 400

Ala Lys Arg His Leu Gly Leu Val Val Phe Arg Ile Arg Gly Asp Asn
                405                 410                 415

Glu Ile Thr Glu Lys Leu Leu Lys Arg Leu Asn His Arg Gly Asn Leu
                420                 425                 430

His Cys Ile Pro Ser Ser Leu Lys Gly Gln Tyr Val Ile Arg Phe Thr
                435                 440                 445

Ile Thr Ser Thr His Thr Thr Leu Asp Asp Ile Val Lys Asp Trp Met
                450                 455                 460

Glu Ile Arg Gln Val Ala Ser Thr Val Leu Glu Glu Met Asn Ile Thr
465                 470                 475                 480

Ile Ser Asn Arg Val Tyr Leu Lys Glu Thr Lys Glu Lys Asn Glu Ala
                485                 490                 495

Phe Gly Ser Ser Leu Leu Leu Ser Asn Ser Pro Leu Ser Pro Lys Val
                500                 505                 510

Val Asn Gly Ser Phe Ala Ala Ile Phe Asp Ala Asp Glu Phe Leu Ala
                515                 520                 525

Lys Thr Tyr Ala Gly Val Arg Ile Ala His Gln Glu Ser Pro Ser Met
                530                 535                 540

Arg Arg Arg Val Arg Gly Ile Leu Met Ser Gly Lys Gln Phe Ser Leu
545                 550                 555                 560

Asp Ser His Met Asp Val Val Gln Thr Thr Leu Asp Ala Gly Asn
                565                 570                 575

Gly Ala Thr Arg Thr Ser Thr Thr Asn Ser Tyr Gly His Thr Thr Ser
                580                 585                 590
```

```
Ala Ala Gln Ala Asn Ser Glu Arg Gln Ala Ser Ile Gln Glu Asp Asn
        595                 600                 605

Glu Glu Ser Pro Glu Glu Thr Glu Leu Leu Ser Leu Cys Arg Thr Ser
610                 615                 620

Asn Val Pro Ser Pro Glu His Ala His Ser Leu Ser Thr Pro Ser Arg
625                 630                 635                 640

Ser Cys Ser Ser Ser His Ser Leu Ile His Ser Leu Thr Gln Ser
        645                 650                 655

Ser Pro Arg Ser Ser Pro Val Asn Gln Phe Arg Pro Ile Thr Leu Cys
        660                 665                 670

Ala Val Pro Ser Gln Ser Gln Leu Ser Met Pro Leu Ala Met Pro Leu
        675                 680                 685

Pro Asn Arg Asn Val Thr Val Ser Val Asp Ser Leu Leu Asn Pro Val
690                 695                 700

Thr Thr Cys Asn Val Tyr His Gly Lys Arg Phe Leu Glu Pro Leu Glu
705                 710                 715                 720

Asn Leu Ala Gln Thr Ser Ala Ser Phe Ser Ser Ile Phe Arg Leu
            725                 730                 735

Pro Thr Pro Ile Ala Thr Pro Thr Arg Glu Ser Pro Glu Asp Pro Asp
            740                 745                 750

Trp Pro Ala Lys Thr Phe Ser Gln Leu Leu Leu Glu Arg Tyr Ser Ser
        755                 760                 765

Gln Ser Gln Ser Leu Gly Asn Asn Ser Ser Thr Glu Ser Ser Ser Leu
770                 775                 780

Ser Gly Gly Ala Thr Pro Thr Pro Thr Pro Met Ser Ser Leu Asp Glu
785                 790                 795                 800

Leu Val Thr Pro Leu Leu Leu Ser Phe Ala Ser Pro Ser Gln Pro Met
            805                 810                 815

Leu Ser Ala His Gly Ile Gly Glu Gly Gln Arg Glu Gln Gly Ser Asp
            820                 825                 830

Ser Asp Ala Thr Val Cys Ser Thr Thr Ser Ser Met Glu Ser Leu
            835                 840                 845

<210> SEQ ID NO 11
<211> LENGTH: 413
<212> TYPE: PRT
<213> ORGANISM: Solanum lycopersicum

<400> SEQUENCE: 11

Met Glu Ser Asp Ile Lys Asn Glu Thr Ser Phe Gln Glu Leu Asp Met
1               5                   10                  15

Ile Leu Thr Gln Tyr Leu Glu Thr Leu Ser Glu Arg Lys Lys Tyr His
            20                  25                  30

Ile Gly Tyr Pro Ile Asn Met Cys Tyr Glu His His Ala Thr Leu Ala
        35                  40                  45

Pro Leu Leu Gln Phe His Leu Asn Asn Cys Gly Asp Pro Phe Thr Gln
    50                  55                  60

His Pro Thr Asp Phe His Ser Lys Asp Phe Glu Val Ala Val Leu Asp
65                  70                  75                  80

Trp Phe Ala Gln Leu Trp Glu Ile Glu Lys Asp Glu Tyr Trp Gly Tyr
                85                  90                  95

Ile Thr Ser Gly Gly Thr Glu Gly Asn Leu His Gly Phe Trp Leu Gly
            100                 105                 110

Arg Arg Glu Leu Leu Pro Asn Gly Tyr Leu Tyr Ala Ser Lys Asp Ser
```

115                 120                 125
        His Tyr Ser Ile Phe Lys Ala Ala Arg Met Tyr Arg Met Glu Leu Gln
            130                 135                 140

Thr Ile Asn Thr Leu Val Asn Gly Glu Ile Asp Tyr Glu Asp Leu Gln
    145                 150                 155                 160

Ser Lys Leu Leu Val Asn Lys Asn Lys Pro Ala Ile Ile Asn Ile Asn
                        165                 170                 175

Ile Gly Thr Thr Phe Lys Gly Ala Ile Asp Asp Leu Asp Phe Val Ile
                    180                 185                 190

Gln Thr Leu Glu Asn Cys Gly Tyr Ser Asn Asp Asn Tyr Tyr Ile His
                195                 200                 205

Cys Asp Arg Ala Leu Cys Gly Leu Ile Leu Pro Phe Ile Lys His Ala
            210                 215                 220

Lys Lys Ile Thr Phe Lys Lys Pro Ile Gly Ser Ile Ser Ile Ser Gly
    225                 230                 235                 240

His Lys Phe Leu Gly Cys Pro Met Ser Cys Gly Val Gln Ile Thr Arg
                        245                 250                 255

Arg Ser Tyr Val Ser Thr Leu Ser Lys Ile Glu Tyr Ile Asn Ser Ala
                    260                 265                 270

Asp Ala Thr Ile Ser Gly Ser Arg Asn Gly Phe Thr Pro Ile Phe Leu
                275                 280                 285

Trp Tyr Cys Leu Ser Lys Lys Gly His Ala Arg Leu Gln Gln Asp Ser
            290                 295                 300

Ile Thr Cys Ile Glu Asn Ala Arg Tyr Leu Lys Asp Arg Leu Leu Glu
    305                 310                 315                 320

Ala Gly Ile Ser Val Met Leu Asn Asp Phe Ser Ile Thr Val Val Phe
                        325                 330                 335

Glu Arg Pro Cys Asp His Lys Phe Ile Arg Arg Trp Asn Leu Cys Cys
                    340                 345                 350

Leu Arg Gly Met Ala His Val Val Ile Met Pro Gly Ile Thr Arg Glu
                355                 360                 365

Thr Ile Asp Ser Phe Phe Lys Asp Leu Met Gln Glu Arg Asn Tyr Lys
            370                 375                 380

Trp Tyr Gln Asp Val Lys Ala Leu Pro Pro Cys Leu Ala Asp Asp Leu
    385                 390                 395                 400

Ala Leu Asn Cys Met Cys Ser Asn Lys Lys Met His Asn
                        405                 410

<210> SEQ ID NO 12
<211> LENGTH: 662
<212> TYPE: PRT
<213> ORGANISM: Mus musculus

<400> SEQUENCE: 12

Met Met Glu Pro Cys Glu Tyr Arg Glu Tyr Arg Glu Tyr Tyr Arg Ala
    1                   5                   10                  15

Arg Gly Lys Glu Met Val Asp Tyr Ile Ser Gln Tyr Leu Ser Thr Val
                        20                  25                  30

Arg Glu Arg Gln Val Thr Pro Asn Val Gln Pro Gly Tyr Leu Arg Ala
                    35                  40                  45

Gln Leu Pro Ala Ser Ala Pro Glu Glu Pro Asp Ser Trp Asp Ser Ile
                50                  55                  60

Phe Gly Asp Ile Glu Arg Val Ile Met Pro Gly Val Val His Trp Gln
    65                  70                  75                  80

```
Ser Pro His Met His Ala Tyr Tyr Pro Ala Leu Thr Ser Trp Pro Ser
            85                  90                  95

Leu Leu Gly Asp Met Leu Ala Asp Ala Ile Asn Cys Leu Gly Phe Thr
            100                 105                 110

Trp Ala Ser Pro Ala Cys Thr Glu Leu Glu Met Asn Ile Met Asp
        115                 120                 125

Trp Leu Ala Lys Met Leu Gly Leu Pro Glu Tyr Phe Leu His His His
130                 135                 140

Pro Ser Ser Arg Gly Gly Val Leu Gln Ser Thr Val Ser Glu Ser
145                 150                 155                 160

Thr Leu Ile Ala Leu Leu Ala Ala Arg Lys Asn Lys Ile Leu Ala Met
                165                 170                 175

Lys Ala Cys Glu Pro Asp Ala Asn Glu Ser Ser Leu Asn Ala Arg Leu
            180                 185                 190

Val Ala Tyr Thr Ser Asp Gln Ala His Ser Ser Val Glu Lys Ala Gly
            195                 200                 205

Leu Ile Ser Leu Val Lys Ile Arg Phe Leu Pro Val Asp Asp Asn Phe
        210                 215                 220

Ser Leu Arg Gly Glu Ala Leu Gln Lys Ala Ile Glu Glu Asp Lys Gln
225                 230                 235                 240

Gln Gly Leu Val Pro Val Phe Val Cys Ala Thr Leu Gly Thr Thr Gly
                245                 250                 255

Val Cys Ala Phe Asp Arg Leu Ser Glu Leu Gly Pro Ile Cys Ala Ser
            260                 265                 270

Glu Gly Leu Trp Leu His Val Asp Ala Ala Tyr Ala Gly Thr Ala Phe
            275                 280                 285

Leu Cys Pro Glu Leu Arg Gly Phe Leu Glu Gly Ile Glu Tyr Ala Asp
        290                 295                 300

Ser Phe Thr Phe Asn Pro Ser Lys Trp Met Met Val His Phe Asp Cys
305                 310                 315                 320

Thr Gly Phe Trp Val Lys Asp Lys Tyr Lys Leu Gln Gln Thr Phe Ser
                325                 330                 335

Val Asn Pro Ile Tyr Leu Arg His Ala Asn Ser Gly Ala Ala Thr Asp
            340                 345                 350

Phe Met His Trp Gln Ile Pro Leu Ser Arg Arg Phe Arg Ser Ile Lys
            355                 360                 365

Leu Trp Phe Val Ile Arg Ser Phe Gly Val Lys Asn Leu Gln Ala His
        370                 375                 380

Val Arg His Gly Thr Glu Met Ala Lys Tyr Phe Glu Ser Leu Val Arg
385                 390                 395                 400

Ser Asp Pro Ser Phe Glu Ile Pro Ala Lys Arg His Leu Gly Leu Val
                405                 410                 415

Val Phe Arg Leu Lys Gly Pro Asn Cys Leu Thr Glu Ser Val Leu Lys
            420                 425                 430

Glu Ile Ala Lys Ala Gly Gln Leu Phe Leu Ile Pro Ala Thr Ile Gln
            435                 440                 445

Asp Lys Leu Ile Ile Arg Phe Thr Val Thr Ser Gln Phe Thr Thr Lys
        450                 455                 460

Glu Asp Ile Leu Arg Asp Trp His Leu Ile Gln Glu Ala Ala Asn Leu
465                 470                 475                 480

Val Leu Ser Gln His Cys Thr Ser Gln Pro Ser Pro Arg Ala Lys Asn
                485                 490                 495

Val Ile Pro Pro Pro Pro Gly Thr Arg Gly Leu Ser Leu Glu Ser Val
```

```
            500                 505                 510
Ser Glu Gly Gly Asp Pro Ala Gln Ala Arg Lys Ile Ile Lys Gln
        515                 520                 525

Pro Gly Ala Ser Leu Ala Arg Arg Glu Gly Gly Ser Asp Leu Glu Thr
        530                 535                 540

Met Pro Asp Pro Phe Asp Asp Cys Phe Ser Glu Ala Pro Asn Thr
545                 550                 555                 560

Thr Lys His Lys Leu Ser Ser Phe Leu Phe Ser Tyr Leu Ser Val Gln
                565                 570                 575

Asn Arg Arg Lys Thr Thr Arg Ser Leu Ser Cys Asn Ser Val Pro Met
            580                 585                 590

Ser Ala Gln Lys Ser Leu Pro Ala Asp Ala Ser Leu Lys Asn Gly Gly
        595                 600                 605

Ser Phe Arg Ala Arg Ile Phe Ser Gly Phe Pro Glu Gln Met Met Met
        610                 615                 620

Met Lys Lys Gly Ala Phe Lys Lys Leu Ile Lys Phe Tyr Ser Val Pro
625                 630                 635                 640

Ser Phe Pro Glu Cys Ser Ser Gln Cys Ala Arg Gln Leu Pro Cys Cys
                645                 650                 655

Pro Leu Glu Ala Met Val
            660

<210> SEQ ID NO 13
<211> LENGTH: 246
<212> TYPE: PRT
<213> ORGANISM: Corynebacterium glutamicum

<400> SEQUENCE: 13

Met Thr Phe Thr Ile Leu Pro Ala Val Asp Val Asn Gly Gln Ala
1               5                   10                  15

Val Arg Leu Asp Gln Gly Glu Ala Gly Thr Glu Lys Ser Tyr Gly Thr
            20                  25                  30

Pro Leu Glu Ser Ala Leu Lys Trp Gln Glu Gln Gly Ala Lys Trp Leu
        35                  40                  45

His Phe Val Asp Leu Asp Ala Ala Phe Asn Arg Gly Ser Asn His Glu
    50                  55                  60

Met Met Ala Glu Ile Val Gly Lys Leu Asp Val Asp Val Glu Leu Thr
65                  70                  75                  80

Gly Gly Ile Arg Asp Asp Glu Ser Leu Glu Arg Ala Leu Ala Thr Gly
                85                  90                  95

Ala Arg Arg Val Asn Ile Gly Thr Ala Ala Leu Glu Lys Pro Glu Trp
            100                 105                 110

Ile Ala Ser Ala Ile Gln Arg Tyr Gly Glu Lys Ile Ala Val Asp Ile
        115                 120                 125

Ala Val Arg Leu Glu Asp Gly Glu Trp Arg Thr Arg Gly Asn Gly Trp
    130                 135                 140

Val Ser Asp Gly Gly Asp Leu Trp Asp Val Leu Glu Arg Leu Asp Ser
145                 150                 155                 160

Gln Gly Cys Ala Arg Phe Val Val Thr Asp Val Ser Lys Asp Gly Thr
                165                 170                 175

Leu Ser Gly Pro Asn Val Glu Leu Leu Arg Glu Val Ala Ala Ala Thr
            180                 185                 190

Asp Ala Pro Ile Val Ala Ser Gly Gly Ile Ser Val Leu Glu Asp Val
        195                 200                 205
```

Leu Glu Leu Ala Lys Tyr Gln Asp Glu Gly Ile Asp Ser Val Ile Ile
210                 215                 220

Gly Lys Ala Leu Tyr Glu His Lys Phe Thr Leu Glu Glu Ala Leu Ala
225                 230                 235                 240

Ala Val Glu Lys Leu Gly
                245

<210> SEQ ID NO 14
<211> LENGTH: 366
<212> TYPE: PRT
<213> ORGANISM: Corynebacterium glutamicum

<400> SEQUENCE: 14

Met Thr Lys Ile Thr Leu Ser Asp Leu Pro Leu Arg Glu Glu Leu Arg
1               5                   10                  15

Gly Glu His Ala Tyr Gly Ala Pro Gln Leu Asn Val Asp Ile Arg Leu
                20                  25                  30

Asn Thr Asn Glu Asn Pro Tyr Pro Pro Ser Glu Ala Leu Val Ala Asp
            35                  40                  45

Leu Val Ala Thr Val Asp Lys Ile Ala Thr Glu Leu Asn Arg Tyr Pro
    50                  55                  60

Glu Arg Asp Ala Val Glu Leu Arg Asp Glu Leu Ala Ala Tyr Ile Thr
65                  70                  75                  80

Lys Gln Thr Gly Val Ala Val Thr Arg Asp Asn Leu Trp Ala Ala Asn
                85                  90                  95

Gly Ser Asn Glu Ile Leu Gln Gln Leu Leu Gln Ala Phe Gly Gly Pro
            100                 105                 110

Gly Arg Thr Ala Leu Gly Phe Gln Pro Ser Tyr Ser Met His Pro Ile
    115                 120                 125

Leu Ala Lys Gly Thr His Thr Glu Phe Ile Ala Val Ser Arg Gly Ala
    130                 135                 140

Asp Phe Arg Ile Asp Met Asp Val Ala Leu Glu Glu Ile Arg Ala Lys
145                 150                 155                 160

Gln Pro Asp Ile Val Phe Val Thr Thr Pro Asn Asn Pro Thr Gly Asp
                165                 170                 175

Val Thr Ser Leu Asp Asp Ile Glu Arg Ile Ile Asn Val Ala Pro Gly
            180                 185                 190

Ile Val Ile Val Asp Glu Ala Tyr Ala Glu Phe Ser Pro Ser Pro Ser
    195                 200                 205

Ala Thr Thr Leu Leu Glu Lys Tyr Pro Thr Lys Leu Val Val Ser Arg
    210                 215                 220

Thr Met Ser Lys Ala Phe Asp Phe Ala Gly Gly Arg Leu Gly Tyr Phe
225                 230                 235                 240

Val Ala Asn Pro Ala Phe Ile Asp Ala Val Met Leu Val Arg Leu Pro
                245                 250                 255

Tyr His Leu Ser Ala Leu Ser Gln Ala Ala Ala Ile Val Ala Leu Arg
            260                 265                 270

His Ser Ala Asp Thr Leu Gly Thr Val Glu Lys Leu Ser Val Glu Arg
    275                 280                 285

Val Arg Val Ala Ala Arg Leu Glu Glu Leu Gly Tyr Ala Val Val Pro
    290                 295                 300

Ser Glu Ser Asn Phe Val Phe Phe Gly Asp Phe Ser Asp Gln His Ala
305                 310                 315                 320

Ala Trp Gln Ala Phe Leu Asp Arg Gly Val Leu Ile Arg Asp Val Gly
                325                 330                 335

```
            Ile Ala Gly His Leu Arg Thr Thr Ile Gly Val Pro Glu Glu Asn Asp
                            340                 345                 350

Ala Phe Leu Asp Ala Ala Ala Glu Ile Ile Lys Leu Asn Leu
                            355                 360                 365

<210> SEQ ID NO 15
<211> LENGTH: 442
<212> TYPE: PRT
<213> ORGANISM: Corynebacterium glutamicum

<400> SEQUENCE: 15

Met Leu Asn Val Thr Asp Leu Arg Gly Gln Thr Pro Ser Lys Ser Asp
1               5                   10                  15

Ile Arg Arg Ala Leu Pro Arg Gly Gly Thr Asp Val Trp Ser Val Leu
                20                  25                  30

Pro Ile Val Gln Pro Val Val Glu Asp Val Gln Asn Arg Gly Ala Glu
                35                  40                  45

Ala Ala Leu Asp Tyr Gly Glu Lys Phe Asp His Ile Arg Pro Ala Ser
            50                  55                  60

Val Arg Val Pro Ala Glu Val Ile Ala Ala Glu Asn Thr Leu Asp
65                  70                  75                  80

Pro Leu Val Arg Glu Ser Ile Glu Ser Ile Arg Arg Val Arg Lys
                85                  90                  95

Val His Ala Glu Gln Lys Pro Ala Glu His Thr Thr Glu Leu Ser Pro
                100                 105                 110

Gly Gly Thr Val Thr Glu Arg Phe Met Pro Ile Asp Arg Val Gly Leu
                115                 120                 125

Tyr Val Pro Gly Gly Asn Ala Val Tyr Pro Ser Ser Val Ile Met Asn
            130                 135                 140

Thr Val Pro Ala Gln Glu Ala Gly Val Asn Ser Leu Val Val Ala Ser
145                 150                 155                 160

Pro Pro Gln Ala Glu His Gly Gly Trp Pro His Pro Thr Ile Leu Ala
                165                 170                 175

Ala Cys Ser Ile Leu Gly Val Asp Glu Val Trp Ala Val Gly Gly Gly
                180                 185                 190

Gln Ala Val Ala Leu Leu Ala Tyr Gly Asp Asp Ala Ala Gly Leu Glu
            195                 200                 205

Pro Val Asp Met Ile Thr Gly Pro Gly Asn Ile Phe Val Thr Ala Ala
                210                 215                 220

Lys Arg Leu Val Arg Gly Val Val Gly Thr Asp Ser Glu Ala Gly Pro
225                 230                 235                 240

Thr Glu Ile Ala Val Leu Ala Asp Ala Ser Ala Asn Ala Val Asn Val
                245                 250                 255

Ala Tyr Asp Leu Ile Ser Gln Ala Glu His Asp Val Met Ala Ala Ser
                260                 265                 270

Val Leu Ile Thr Asp Ser Glu Gln Leu Ala Lys Asp Val Asn Arg Glu
                275                 280                 285

Ile Glu Ala Arg Tyr Ser Ile Thr Arg Asn Ala Glu Arg Val Ala Glu
                290                 295                 300

Ala Leu Arg Gly Ala Gln Ser Gly Ile Val Leu Val Asp Asp Ile Ser
305                 310                 315                 320

Val Gly Ile Gln Val Ala Asp Gln Tyr Ala Ala Glu His Leu Glu Ile
                325                 330                 335

His Thr Glu Asn Ala Arg Ala Val Ala Glu Gln Ile Thr Asn Ala Gly
```

```
                340                 345                 350
Ala Ile Phe Val Gly Asp Phe Ser Pro Val Leu Gly Asp Tyr Ser
            355                 360                 365

Ala Gly Ser Asn His Val Leu Pro Thr Ser Gly Ser Ala Arg Phe Ser
370                 375                 380

Ala Gly Leu Ser Thr His Met Phe Leu Arg Pro Val Asn Leu Ile Glu
385                 390                 395                 400

Tyr Asp Glu Ala Ala Leu Lys Asp Val Ser Gln Val Val Ile Asn Phe
                405                 410                 415

Ala Asn Ala Glu Asp Leu Pro Ala His Gly Glu Ala Ile Arg Ala Arg
                420                 425                 430

Phe Glu Asn Leu Pro Thr Thr Asp Glu Ala
                435                 440

<210> SEQ ID NO 16
<211> LENGTH: 87
<212> TYPE: PRT
<213> ORGANISM: Corynebacterium glutamicum

<400> SEQUENCE: 16

Val Lys Thr Phe Asp Ser Leu Tyr Glu Glu Leu Leu Asn Arg Ala Gln
1               5                   10                  15

Thr Arg Pro Glu Gly Ser Gly Thr Val Ala Ala Leu Asp Lys Gly Ile
            20                  25                  30

His His Leu Gly Lys Lys Val Ile Glu Glu Ala Gly Glu Val Trp Ile
        35                  40                  45

Ala Ala Glu Tyr Glu Thr Asp Glu Glu Leu Ala Gly Ile Ser Gln
    50                  55                  60

Leu Ile Tyr Trp Thr Gln Val Ile Met Val Ala Arg Gly Leu Lys Pro
65                  70                  75                  80

Glu Asp Ile Tyr Lys Asn Leu
                85

<210> SEQ ID NO 17
<211> LENGTH: 258
<212> TYPE: PRT
<213> ORGANISM: Corynebacterium glutamicum

<400> SEQUENCE: 17

Met Gly Val Ala Ile Arg Val Ile Pro Cys Leu Asp Val Asp Asn Gly
1               5                   10                  15

Arg Val Val Lys Gly Val Asn Phe Glu Asn Leu Arg Asp Ala Gly Asp
            20                  25                  30

Pro Val Glu Leu Ala Lys Arg Tyr Asp Glu Glu Gly Ala Asp Glu Leu
        35                  40                  45

Thr Phe Leu Asp Val Thr Ala Ser Lys His Gly Arg Gly Thr Met Leu
    50                  55                  60

Asp Val Val Arg Arg Thr Ala Asp Gln Val Phe Ile Pro Leu Thr Val
65                  70                  75                  80

Gly Gly Gly Val Arg Ser Glu Glu Asp Val Asp Gln Leu Leu Arg Ala
                85                  90                  95

Gly Ala Asp Lys Val Ser Val Asn Thr Ser Ala Ile Ala Arg Pro Glu
                100                 105                 110

Leu Leu Ser Glu Leu Ser Lys Arg Phe Gly Ala Gln Cys Ile Val Leu
            115                 120                 125

Ser Val Asp Ala Arg Arg Val Pro Glu Gly Gly Thr Pro Gln Pro Ser
```

-continued

```
                130                 135                 140
Gly Phe Glu Val Thr Thr His Gly Gly Ser Lys Ser Ala Glu Leu Asp
145                 150                 155                 160

Ala Ile Glu Trp Ala Lys Arg Gly Glu Leu Gly Val Gly Glu Ile
                165                 170                 175

Leu Leu Asn Ser Met Asp Gly Asp Thr Lys Asn Gly Phe Asp Leu
                180                 185                 190

Glu Leu Leu Glu Lys Val Arg Ala Ala Val Ser Ile Pro Val Ile Ala
                195                 200                 205

Ser Gly Gly Ala Gly Lys Ala Glu His Phe Pro Pro Ala Val Ala Ala
210                 215                 220

Gly Ala Asn Ala Val Leu Ala Ala Thr Ile Phe His Phe Arg Glu Val
225                 230                 235                 240

Thr Ile Ala Glu Val Lys Gly Ala Ile Lys Asp Ala Gly Phe Glu Val
                245                 250                 255

Arg Lys

<210> SEQ ID NO 18
<211> LENGTH: 211
<212> TYPE: PRT
<213> ORGANISM: Corynebacterium glutamicum

<400> SEQUENCE: 18

Met Thr Lys Thr Val Ala Leu Leu Asp Tyr Gly Ser Gly Asn Leu Arg
1               5                   10                  15

Ser Ala Gln Arg Ala Leu Glu Arg Ala Gly Ala Glu Val Thr Val Ser
                20                  25                  30

Ser Asp Pro Glu Val Cys Thr Asn Ala Asp Gly Leu Leu Val Pro Gly
            35                  40                  45

Val Gly Ala Phe Asp Ala Cys Met Lys Gly Leu Lys Asn Val Phe Gly
        50                  55                  60

His Arg Ile Ile Gly Gln Arg Leu Ala Gly Gly Arg Pro Val Met Gly
65                  70                  75                  80

Ile Cys Val Gly Met Gln Ile Leu Phe Asp Glu Gly Asp Glu His Gly
                85                  90                  95

Ile Lys Ser Ala Gly Cys Gly Glu Trp Pro Gly Lys Val Glu Arg Leu
                100                 105                 110

Gln Ala Glu Ile Leu Pro His Met Gly Trp Asn Thr Leu Glu Met Pro
            115                 120                 125

Thr Asn Ser Pro Met Phe Glu Gly Ile Ser Pro Asp Glu Arg Phe Tyr
        130                 135                 140

Phe Val His Ser Tyr Gly Val Arg Lys Trp Thr Leu Glu Thr Asp Asp
145                 150                 155                 160

Leu Thr Thr Pro Pro Glu Val Val Trp Ala Lys His Glu Asn Asp Arg
                165                 170                 175

Phe Val Ala Ala Val Glu Asn Gly Thr Leu Trp Ala Thr Gln Phe His
                180                 185                 190

Pro Glu Lys Ser Gly Asp Val Gly Ala Lys Leu Leu Arg Asn Trp Ile
            195                 200                 205

Asn Tyr Ile
        210

<210> SEQ ID NO 19
<211> LENGTH: 118
<212> TYPE: PRT
```

<213> ORGANISM: Corynebacterium glutamicum

<400> SEQUENCE: 19

Met Ser Asp Asn Pro Gln Glu Tyr Glu Leu Asp Trp Asp Val Glu Lys
1               5                   10                  15

Arg Leu Lys Leu Asn Asp Ala Gly Leu Val Pro Ala Ile Val Gln Ala
            20                  25                  30

Asp Gly Thr Asn Glu Val Leu Met Met Ala Trp Met Asp Thr His Ala
        35                  40                  45

Leu Ala Tyr Thr Leu Ala Thr Arg Arg Gly Thr Tyr Phe Ser Arg Ser
    50                  55                  60

Arg Asn Glu Tyr Trp Ile Lys Gly Leu Thr Ser Gly Asn Val Gln Glu
65                  70                  75                  80

Val Thr Gly Leu Ala Leu Asp Cys Asp Gly Asp Thr Val Leu Leu Thr
                85                  90                  95

Val Lys Gln Thr Gly Gly Ala Cys His Thr Gly Ala His Thr Cys Phe
            100                 105                 110

Asp Asn Asp Val Leu Leu
            115

<210> SEQ ID NO 20
<211> LENGTH: 799
<212> TYPE: PRT
<213> ORGANISM: Saccharomyces cerevisiae

<400> SEQUENCE: 20

Met Val Leu Pro Ile Leu Pro Leu Ile Asp Asp Leu Ala Ser Trp Asn
1               5                   10                  15

Ser Lys Lys Glu Tyr Val Ser Leu Val Gly Gln Val Leu Leu Asp Gly
            20                  25                  30

Ser Ser Leu Ser Asn Glu Glu Ile Leu Gln Phe Ser Lys Glu Glu Glu
        35                  40                  45

Val Pro Leu Val Ala Leu Ser Leu Pro Ser Gly Lys Phe Ser Asp Asp
    50                  55                  60

Glu Ile Ile Ala Phe Leu Asn Asn Gly Val Ser Ser Leu Phe Ile Ala
65                  70                  75                  80

Ser Gln Asp Ala Lys Thr Ala Glu His Leu Val Glu Gln Leu Asn Val
                85                  90                  95

Pro Lys Glu Arg Val Val Glu Glu Asn Gly Val Phe Ser Asn Gln
            100                 105                 110

Phe Met Val Lys Gln Lys Phe Ser Gln Asp Lys Ile Val Ser Ile Lys
            115                 120                 125

Lys Leu Ser Lys Asp Met Leu Thr Lys Glu Val Leu Gly Glu Val Arg
        130                 135                 140

Thr Asp Arg Pro Asp Gly Leu Tyr Thr Thr Leu Val Val Asp Gln Tyr
145                 150                 155                 160

Glu Arg Cys Leu Gly Leu Val Tyr Ser Ser Lys Lys Ser Ile Ala Lys
                165                 170                 175

Ala Ile Asp Leu Gly Arg Gly Val Tyr Tyr Ser Arg Ser Arg Asn Glu
            180                 185                 190

Ile Trp Ile Lys Gly Glu Thr Ser Gly Asn Gly Gln Lys Leu Leu Gln
        195                 200                 205

Ile Ser Thr Asp Cys Asp Ser Asp Ala Leu Lys Phe Ile Val Glu Gln
    210                 215                 220

Glu Asn Val Gly Phe Cys His Leu Glu Thr Met Ser Cys Phe Gly Glu

-continued

```
            225                 230                 235                 240

Phe Lys His Gly Leu Val Gly Leu Glu Ser Leu Leu Lys Gln Arg Leu
                        245                 250                 255

Gln Asp Ala Pro Glu Glu Ser Tyr Thr Arg Arg Leu Phe Asn Asp Ser
                        260                 265                 270

Ala Leu Leu Asp Ala Lys Ile Lys Glu Glu Ala Glu Leu Thr Glu
                        275                 280                 285

Ala Lys Gly Lys Lys Glu Leu Ser Trp Glu Ala Asp Leu Phe Tyr
                        290                 295                 300

Phe Ala Leu Ala Lys Leu Val Ala Asn Asp Val Ser Leu Lys Asp Val
        305                 310                 315                 320

Glu Asn Asn Leu Asn Met Lys His Leu Lys Val Thr Arg Arg Lys Gly
                        325                 330                 335

Asp Ala Lys Pro Lys Phe Val Gly Gln Pro Lys Ala Glu Glu Lys
                        340                 345                 350

Leu Thr Gly Pro Ile His Leu Asp Val Val Lys Ala Ser Asp Lys Val
                        355                 360                 365

Gly Val Gln Lys Ala Leu Ser Arg Pro Ile Gln Lys Thr Ser Glu Ile
                        370                 375                 380

Met His Leu Val Asn Pro Ile Ile Glu Asn Val Arg Asp Lys Gly Asn
        385                 390                 395                 400

Ser Ala Leu Leu Glu Tyr Thr Glu Lys Phe Asp Gly Val Lys Leu Ser
                        405                 410                 415

Asn Pro Val Leu Asn Ala Pro Phe Pro Glu Glu Tyr Phe Glu Gly Leu
                        420                 425                 430

Thr Glu Glu Met Lys Glu Ala Leu Asp Leu Ser Ile Glu Asn Val Arg
                        435                 440                 445

Lys Phe His Ala Ala Gln Leu Pro Thr Glu Thr Leu Glu Val Glu Thr
                        450                 455                 460

Gln Pro Gly Val Leu Cys Ser Arg Phe Pro Arg Pro Ile Glu Lys Val
        465                 470                 475                 480

Gly Leu Tyr Ile Pro Gly Gly Thr Ala Ile Leu Pro Ser Thr Ala Leu
                        485                 490                 495

Met Leu Gly Val Pro Ala Gln Val Ala Gln Cys Lys Glu Ile Val Phe
                        500                 505                 510

Ala Ser Pro Pro Arg Lys Ser Asp Gly Lys Val Ser Pro Glu Val Val
                        515                 520                 525

Tyr Val Ala Glu Lys Val Gly Ala Ser Lys Ile Val Leu Ala Gly Gly
                        530                 535                 540

Ala Gln Ala Val Ala Ala Met Ala Tyr Gly Thr Glu Thr Ile Pro Lys
        545                 550                 555                 560

Val Asp Lys Ile Leu Gly Pro Gly Asn Gln Phe Val Thr Ala Ala Lys
                        565                 570                 575

Met Tyr Val Gln Asn Asp Thr Gln Ala Leu Cys Ser Ile Asp Met Pro
                        580                 585                 590

Ala Gly Pro Ser Glu Val Leu Val Ile Ala Asp Glu Asp Ala Asp Val
                        595                 600                 605

Asp Phe Val Ala Ser Asp Leu Leu Ser Gln Ala Glu His Gly Ile Asp
                        610                 615                 620

Ser Gln Val Ile Leu Val Gly Val Asn Leu Ser Glu Lys Lys Ile Gln
        625                 630                 635                 640

Glu Ile Gln Asp Ala Val His Asn Gln Ala Leu Gln Leu Pro Arg Val
                        645                 650                 655
```

Asp Ile Val Arg Lys Cys Ile Ala His Ser Thr Ile Val Leu Cys Asp
            660                 665                 670

Gly Tyr Glu Glu Ala Leu Glu Met Ser Asn Gln Tyr Ala Pro Glu His
        675                 680                 685

Leu Ile Leu Gln Ile Ala Asn Ala Asn Asp Tyr Val Lys Leu Val Asp
        690                 695                 700

Asn Ala Gly Ser Val Phe Val Gly Ala Tyr Thr Pro Glu Ser Cys Gly
705                 710                 715                 720

Asp Tyr Ser Ser Gly Thr Asn His Thr Leu Pro Thr Tyr Gly Tyr Ala
                725                 730                 735

Arg Gln Tyr Ser Gly Ala Asn Thr Ala Thr Phe Gln Lys Phe Ile Thr
            740                 745                 750

Ala Gln Asn Ile Thr Pro Glu Gly Leu Glu Asn Ile Gly Arg Ala Val
        755                 760                 765

Met Cys Val Ala Lys Lys Glu Gly Leu Asp Gly His Arg Asn Ala Val
    770                 775                 780

Lys Ile Arg Met Ser Lys Leu Gly Leu Ile Pro Lys Asp Phe Gln
785                 790                 795

<210> SEQ ID NO 21
<211> LENGTH: 552
<212> TYPE: PRT
<213> ORGANISM: Saccharomyces cerevisiae

<400> SEQUENCE: 21

Met Pro Val Val His Val Ile Asp Val Glu Ser Gly Asn Leu Gln Ser
1               5                   10                  15

Leu Thr Asn Ala Ile Glu His Leu Gly Tyr Glu Val Gln Leu Val Lys
            20                  25                  30

Ser Pro Lys Asp Phe Asn Ile Ser Gly Thr Ser Arg Leu Ile Leu Pro
        35                  40                  45

Gly Val Gly Asn Tyr Gly His Phe Val Asp Asn Leu Phe Asn Arg Gly
    50                  55                  60

Phe Glu Lys Pro Ile Arg Glu Tyr Ile Glu Ser Gly Lys Pro Ile Met
65                  70                  75                  80

Gly Ile Cys Val Gly Leu Gln Ala Leu Phe Ala Gly Ser Val Glu Ser
                85                  90                  95

Pro Lys Ser Thr Gly Leu Asn Tyr Ile Asp Phe Lys Leu Ser Arg Phe
            100                 105                 110

Asp Asp Ser Glu Lys Pro Val Pro Glu Ile Gly Trp Asn Ser Cys Ile
        115                 120                 125

Pro Ser Glu Asn Leu Phe Phe Gly Leu Asp Pro Tyr Lys Arg Tyr Tyr
    130                 135                 140

Phe Val His Ser Phe Ala Ala Ile Leu Asn Ser Glu Lys Lys Lys Asn
145                 150                 155                 160

Leu Glu Asn Asp Gly Trp Lys Ile Ala Lys Ala Lys Tyr Gly Ser Glu
                165                 170                 175

Glu Phe Ile Ala Ala Val Asn Lys Asn Asn Ile Phe Ala Thr Gln Phe
            180                 185                 190

His Pro Glu Lys Ser Gly Lys Ala Gly Leu Asn Val Ile Glu Asn Phe
        195                 200                 205

Leu Lys Gln Gln Ser Pro Pro Ile Pro Asn Tyr Ser Ala Glu Glu Lys
    210                 215                 220

Glu Leu Leu Met Asn Asp Tyr Ser Asn Tyr Gly Leu Thr Arg Arg Ile

```
                225                 230                 235                 240
Ile Ala Cys Leu Asp Val Arg Thr Asn Asp Gln Gly Asp Leu Val Val
                    245                 250                 255

Thr Lys Gly Asp Gln Tyr Asp Val Arg Glu Lys Ser Asp Gly Lys Gly
                260                 265                 270

Val Arg Asn Leu Gly Lys Pro Val Gln Leu Ala Gln Lys Tyr Tyr Gln
            275                 280                 285

Gln Gly Ala Asp Glu Val Thr Phe Leu Asn Ile Thr Ser Phe Arg Asp
        290                 295                 300

Cys Pro Leu Lys Asp Thr Pro Met Leu Glu Val Leu Lys Gln Ala Ala
305                 310                 315                 320

Lys Thr Val Phe Val Pro Leu Thr Val Gly Gly Ile Lys Asp Ile
                325                 330                 335

Val Asp Val Asp Gly Thr Lys Ile Pro Ala Leu Glu Val Ala Ser Leu
            340                 345                 350

Tyr Phe Arg Ser Gly Ala Asp Lys Val Ser Ile Gly Thr Asp Ala Val
        355                 360                 365

Tyr Ala Ala Glu Lys Tyr Tyr Glu Leu Gly Asn Arg Gly Asp Gly Thr
    370                 375                 380

Ser Pro Ile Glu Thr Ile Ser Lys Ala Tyr Gly Ala Gln Ala Val Val
385                 390                 395                 400

Ile Ser Val Asp Pro Lys Arg Val Tyr Val Asn Ser Gln Ala Asp Thr
                405                 410                 415

Lys Asn Lys Val Phe Glu Thr Glu Tyr Pro Gly Pro Asn Gly Glu Lys
            420                 425                 430

Tyr Cys Trp Tyr Gln Cys Thr Ile Lys Gly Gly Arg Glu Ser Arg Asp
        435                 440                 445

Leu Gly Val Trp Glu Leu Thr Arg Ala Cys Glu Ala Leu Gly Ala Gly
    450                 455                 460

Glu Ile Leu Leu Asn Cys Ile Asp Lys Asp Gly Ser Asn Ser Gly Tyr
465                 470                 475                 480

Asp Leu Glu Leu Ile Glu His Val Lys Asp Ala Val Lys Ile Pro Val
                485                 490                 495

Ile Ala Ser Ser Gly Ala Gly Val Pro Glu His Phe Glu Glu Ala Phe
            500                 505                 510

Leu Lys Thr Arg Ala Asp Ala Cys Leu Gly Ala Gly Met Phe His Arg
        515                 520                 525

Gly Glu Phe Thr Val Asn Asp Val Lys Glu Tyr Leu Leu Glu His Gly
    530                 535                 540

Leu Lys Val Arg Met Asp Glu Glu
545                 550

<210> SEQ ID NO 22
<211> LENGTH: 281
<212> TYPE: PRT
<213> ORGANISM: Corynebacterium glutamicum (strain ATCC 13032 / DSM
      20300 / JCM 1318 / LMG 3730 / NCIMB 10025)

<400> SEQUENCE: 22

Met Leu Lys Ile Ala Val Pro Asn Lys Gly Ser Leu Ser Glu Arg Ala
1               5                   10                  15

Met Glu Ile Leu Ala Glu Ala Gly Tyr Ala Gly Arg Gly Asp Ser Lys
            20                  25                  30

Ser Leu Asn Val Phe Asp Glu Ala Asn Asn Val Glu Phe Phe Phe Leu
        35                  40                  45
```

```
Arg Pro Lys Asp Ile Ala Ile Tyr Val Ala Gly Gly Gln Leu Asp Leu
         50                  55                  60

Gly Ile Thr Gly Arg Asp Leu Ala Arg Asp Ser Gln Ala Asp Val His
 65              70                  75                  80

Glu Val Leu Ser Leu Gly Phe Gly Ser Ser Thr Phe Arg Tyr Ala Ala
                 85                  90                  95

Pro Ala Asp Glu Glu Trp Ser Ile Glu Lys Leu Asp Gly Lys Arg Ile
            100                 105                 110

Ala Thr Ser Tyr Pro Asn Leu Val Arg Asp Leu Ala Ala Arg Gly
            115                 120                 125

Leu Ser Ala Glu Val Leu Arg Leu Asp Gly Ala Val Glu Val Ser Ile
        130                 135                 140

Lys Leu Gly Val Ala Asp Ala Ile Ala Asp Val Val Ser Thr Gly Arg
145                 150                 155                 160

Thr Leu Arg Gln Gln Gly Leu Ala Pro Phe Gly Glu Val Leu Cys Thr
                    165                 170                 175

Ser Glu Ala Val Ile Val Gly Arg Lys Asp Glu Lys Val Thr Pro Glu
                180                 185                 190

Gln Gln Ile Leu Leu Arg Arg Ile Gln Gly Ile Leu His Ala Gln Asn
            195                 200                 205

Phe Leu Met Leu Asp Tyr Lys Val Asp Arg Asp Asn Leu Asp Ala Ala
210                 215                 220

Thr Ala Val Thr Pro Gly Phe Ser Gly Pro Ala Val Ser Pro Leu Ala
225                 230                 235                 240

Arg Asp Asn Trp Val Ala Val Arg Ala Met Val Pro Arg Arg Ser Ala
                245                 250                 255

Asn Ala Ile Met Asp Lys Leu Ala Gly Leu Gly Ala Glu Ala Ile Leu
                260                 265                 270

Ala Ser Glu Ile Arg Ile Ala Arg Ile
            275                 280

<210> SEQ ID NO 23
<211> LENGTH: 385
<212> TYPE: PRT
<213> ORGANISM: Saccharomyces cerevisiae

<400> SEQUENCE: 23

Met Val Phe Asp Leu Lys Arg Ile Val Arg Pro Lys Ile Tyr Asn Leu
 1               5                  10                  15

Glu Pro Tyr Arg Cys Ala Arg Asp Asp Phe Thr Glu Gly Ile Leu Leu
             20                  25                  30

Asp Ala Asn Glu Asn Ala His Gly Pro Thr Pro Val Glu Leu Ser Lys
         35                  40                  45

Thr Asn Leu His Arg Tyr Pro Asp Pro His Gln Leu Glu Phe Lys Thr
     50                  55                  60

Ala Met Thr Lys Tyr Arg Asn Lys Thr Ser Ser Tyr Ala Asn Asp Pro
 65              70                  75                  80

Glu Val Lys Pro Leu Thr Ala Asp Asn Leu Cys Leu Gly Val Gly Ser
                 85                  90                  95

Asp Glu Ser Ile Asp Ala Ile Arg Ala Cys Cys Val Pro Gly Lys
            100                 105                 110

Glu Lys Ile Leu Val Leu Pro Pro Thr Tyr Ser Met Tyr Ser Val Cys
            115                 120                 125

Ala Asn Ile Asn Asp Ile Glu Val Val Gln Cys Pro Leu Thr Val Ser
```

-continued

```
                130                 135                 140
Asp Gly Ser Phe Gln Met Asp Thr Glu Ala Val Leu Thr Ile Leu Lys
145                 150                 155                 160

Asn Asp Ser Leu Ile Lys Leu Met Phe Val Thr Ser Pro Gly Asn Pro
                165                 170                 175

Thr Gly Ala Lys Ile Lys Thr Ser Leu Ile Glu Lys Val Leu Gln Asn
            180                 185                 190

Trp Asp Asn Gly Leu Val Val Asp Glu Ala Tyr Val Asp Phe Cys
            195                 200                 205

Gly Gly Ser Thr Ala Pro Leu Val Thr Lys Tyr Pro Asn Leu Val Thr
        210                 215                 220

Leu Gln Thr Leu Ser Lys Ser Phe Gly Leu Ala Gly Ile Arg Leu Gly
225                 230                 235                 240

Met Thr Tyr Ala Thr Ala Glu Leu Ala Arg Ile Leu Asn Ala Met Lys
                245                 250                 255

Ala Pro Tyr Asn Ile Ser Ser Leu Ala Ser Glu Tyr Ala Leu Lys Ala
                260                 265                 270

Val Gln Asp Ser Asn Leu Lys Lys Met Glu Ala Thr Ser Lys Ile Ile
            275                 280                 285

Asn Glu Glu Lys Met Arg Leu Leu Lys Glu Leu Thr Ala Leu Asp Tyr
        290                 295                 300

Val Asp Asp Gln Tyr Val Gly Gly Leu Asp Ala Asn Phe Leu Leu Ile
305                 310                 315                 320

Arg Ile Asn Gly Gly Asp Asn Val Leu Ala Lys Lys Leu Tyr Tyr Gln
                325                 330                 335

Leu Ala Thr Gln Ser Gly Val Val Arg Phe Arg Gly Asn Glu Leu
            340                 345                 350

Gly Cys Ser Gly Cys Leu Arg Ile Thr Val Gly Thr His Glu Glu Asn
        355                 360                 365

Thr His Leu Ile Lys Tyr Phe Lys Glu Thr Leu Tyr Lys Leu Ala Asn
    370                 375                 380

Glu
385

<210> SEQ ID NO 24
<211> LENGTH: 220
<212> TYPE: PRT
<213> ORGANISM: Saccharomyces cerevisiae

<400> SEQUENCE: 24

Met Thr Glu Gln Lys Ala Leu Val Lys Arg Ile Thr Asn Glu Thr Lys
1               5                   10                  15

Ile Gln Ile Ala Ile Ser Leu Lys Gly Gly Pro Leu Ala Ile Glu His
            20                  25                  30

Ser Ile Phe Pro Glu Lys Glu Ala Glu Ala Val Ala Glu Gln Ala Thr
        35                  40                  45

Gln Ser Gln Val Ile Asn Val His Thr Gly Ile Gly Phe Leu Asp His
    50                  55                  60

Met Ile His Ala Leu Ala Lys His Ser Gly Trp Ser Leu Ile Val Glu
65                  70                  75                  80

Cys Ile Gly Asp Leu His Ile Asp Asp His His Thr Thr Glu Asp Cys
                85                  90                  95

Gly Ile Ala Leu Gly Gln Ala Phe Lys Glu Ala Leu Gly Ala Val Arg
            100                 105                 110
```

```
Gly Val Lys Arg Phe Gly Ser Gly Phe Ala Pro Leu Asp Glu Ala Leu
            115                 120                 125

Ser Arg Ala Val Val Asp Leu Ser Asn Arg Pro Tyr Ala Val Val Glu
130                 135                 140

Leu Gly Leu Gln Arg Glu Lys Val Gly Asp Leu Ser Cys Glu Met Ile
145                 150                 155                 160

Pro His Phe Leu Glu Ser Phe Ala Glu Ala Ser Arg Ile Thr Leu His
                165                 170                 175

Val Asp Cys Leu Arg Gly Lys Asn Asp His His Arg Ser Glu Ser Ala
            180                 185                 190

Phe Lys Ala Leu Ala Val Ala Ile Arg Glu Ala Thr Ser Pro Asn Gly
            195                 200                 205

Thr Asn Asp Val Pro Ser Thr Lys Gly Val Leu Met
210                 215                 220

<210> SEQ ID NO 25
<211> LENGTH: 335
<212> TYPE: PRT
<213> ORGANISM: Saccharomyces cerevisiae

<400> SEQUENCE: 25

Met His Ser His His Ser His Ser Gly Asp Tyr Ser Ala His Gly Thr
1               5                   10                  15

Asp Pro Leu Asp Ser Val Val Asp Gln Val Val Asn Leu Asn Phe His
            20                  25                  30

Thr Tyr Cys Leu Thr Glu His Ile Pro Arg Ile Glu Ala Lys Phe Ile
            35                  40                  45

Tyr Pro Glu Glu Gln Ser Leu Gly Lys Asn Pro Glu Glu Val Ile Ser
50                  55                  60

Lys Leu Glu Thr Ser Phe Lys Asn Phe Met Ser His Ala Gln Glu Ile
65                  70                  75                  80

Lys Thr Arg Tyr Ala Asp Arg Pro Asp Val Arg Thr Lys Phe Ile Ile
                85                  90                  95

Gly Met Glu Ile Glu Ser Cys Asp Met Ala His Ile Glu Tyr Ala Lys
            100                 105                 110

Arg Leu Met Lys Glu Asn Asn Asp Thr Leu Lys Phe Cys Val Gly Ser
            115                 120                 125

Val His His Val Asn Gly Ile Pro Ile Asp Phe Asp Gln Gln Gln Trp
130                 135                 140

Tyr Asn Ser Leu His Ser Phe Asn Asp Asn Leu Lys Asp Phe Leu Leu
145                 150                 155                 160

Ser Tyr Phe Gln Ser Gln Tyr Glu Met Leu Ile Asn Ile Lys Pro Leu
                165                 170                 175

Val Val Gly His Phe Asp Leu Tyr Lys Leu Phe Leu Pro Asn Asp Met
            180                 185                 190

Leu Val Asn Gln Lys Ser Gly Asn Cys Asn Glu Glu Thr Gly Val Pro
            195                 200                 205

Val Ala Ser Leu Asp Val Ile Ser Glu Trp Pro Glu Ile Tyr Asp Ala
210                 215                 220

Val Val Arg Asn Leu Gln Phe Ile Asp Ser Tyr Gly Gly Ala Ile Glu
225                 230                 235                 240

Ile Asn Thr Ser Ala Leu Arg Lys Gly Leu Glu Glu Pro Tyr Pro Ser
                245                 250                 255

Lys Thr Leu Cys Asn Leu Val Lys Lys His Cys Gly Ser Arg Phe Val
            260                 265                 270
```

```
Leu Ser Asp Asp Ala His Gly Val Ala Gln Val Gly Val Cys Tyr Asp
            275                 280                 285

Lys Val Lys Lys Tyr Ile Val Asp Val Leu Gln Leu Glu Tyr Ile Cys
        290                 295                 300

Tyr Leu Glu Glu Ser Gln Ser Pro Glu Asn Val Leu Thr Val Lys Arg
305                 310                 315                 320

Leu Pro Ile Ser Gln Phe Val Asn Asp Pro Phe Trp Ala Asn Ile
                325                 330                 335

<210> SEQ ID NO 26
<211> LENGTH: 514
<212> TYPE: PRT
<213> ORGANISM: Artificial
<220> FEATURE:
<223> OTHER INFORMATION: Codon-optimized and/or mutated sequence

<400> SEQUENCE: 26

Met Ser Thr Asn Thr Thr Pro Ser Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Ala Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Thr Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
    290                 295                 300
```

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Asp Gly Phe Asn Pro
            325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
            355                 360                 365

Gly Arg Arg Val Thr Glu Ile Ala Val Val Phe Lys Asp Ala Pro His
370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
            420                 425                 430

Ser Tyr Ser Glu Ser Phe Thr Glu Glu Ser Pro Glu Ala Tyr Glu Arg
            435                 440                 445

Leu Ile Leu Asp Ala Leu Leu Asp Glu Ser Ser Leu Phe Pro Thr Asn
450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495

Pro Lys Ser Ala Asp Glu Met Leu Ser Arg Asn Gly His Thr Trp Arg
            500                 505                 510

Arg Pro

<210> SEQ ID NO 27
<211> LENGTH: 680
<212> TYPE: PRT
<213> ORGANISM: Saccharomyces cerevisiae (strain ATCC 204508 / S288c)
      (Baker's yeast)

<400> SEQUENCE: 27

Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
                20                  25                  30

Ala Pro Leu Gly Met Ala Pro Ala Ala His Val Leu Trp Ser Gln Met
            35                  40                  45

Arg Met Asn Pro Thr Asn Pro Asp Trp Ile Asn Arg Asp Arg Phe Val
        50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
            115                 120                 125

Ala Met Ala Gln Ala Asn Leu Ala Ala Thr Tyr Asn Lys Pro Gly Phe
        130                 135                 140

Thr Leu Ser Asp Asn Tyr Thr Tyr Val Phe Leu Gly Asp Gly Cys Leu

```
            145                 150                 155                 160
Gln Glu Gly Ile Ser Ser Glu Ala Ser Ser Leu Ala Gly His Leu Lys
                165                 170                 175
Leu Gly Asn Leu Ile Ala Ile Tyr Asp Asp Asn Lys Ile Thr Ile Asp
                180                 185                 190
Gly Ala Thr Ser Ile Ser Phe Asp Glu Asp Val Ala Lys Arg Tyr Glu
                195                 200                 205
Ala Tyr Gly Trp Glu Val Leu Tyr Val Glu Asn Gly Asn Glu Asp Leu
            210                 215                 220
Ala Gly Ile Ala Lys Ala Ile Ala Gln Ala Lys Leu Ser Lys Asp Lys
225                 230                 235                 240
Pro Thr Leu Ile Lys Met Thr Thr Thr Ile Gly Tyr Gly Ser Leu His
                245                 250                 255
Ala Gly Ser His Ser Val His Gly Ala Pro Leu Lys Ala Asp Asp Val
                260                 265                 270
Lys Gln Leu Lys Ser Lys Phe Gly Phe Asn Pro Asp Lys Ser Phe Val
                275                 280                 285
Val Pro Gln Glu Val Tyr Asp His Tyr Gln Lys Thr Ile Leu Lys Pro
            290                 295                 300
Gly Val Glu Ala Asn Asn Lys Trp Asn Lys Leu Phe Ser Glu Tyr Gln
305                 310                 315                 320
Lys Lys Phe Pro Glu Leu Gly Ala Glu Leu Ala Arg Arg Leu Ser Gly
                325                 330                 335
Gln Leu Pro Ala Asn Trp Glu Ser Lys Leu Pro Thr Tyr Thr Ala Lys
                340                 345                 350
Asp Ser Ala Val Ala Thr Arg Lys Leu Ser Glu Thr Val Leu Glu Asp
            355                 360                 365
Val Tyr Asn Gln Leu Pro Glu Leu Ile Gly Gly Ser Ala Asp Leu Thr
            370                 375                 380
Pro Ser Asn Leu Thr Arg Trp Lys Glu Ala Leu Asp Phe Gln Pro Pro
385                 390                 395                 400
Ser Ser Gly Ser Gly Asn Tyr Ser Gly Arg Tyr Ile Arg Tyr Gly Ile
                405                 410                 415
Arg Glu His Ala Met Gly Ala Ile Met Asn Gly Ile Ser Ala Phe Gly
                420                 425                 430
Ala Asn Tyr Lys Pro Tyr Gly Gly Thr Phe Leu Asn Phe Val Ser Tyr
                435                 440                 445
Ala Ala Gly Ala Val Arg Leu Ser Ala Leu Ser Gly His Pro Val Ile
            450                 455                 460
Trp Val Ala Thr His Asp Ser Ile Gly Val Gly Glu Asp Gly Pro Thr
465                 470                 475                 480
His Gln Pro Ile Glu Thr Leu Ala His Phe Arg Ser Leu Pro Asn Ile
                485                 490                 495
Gln Val Trp Arg Pro Ala Asp Gly Asn Glu Val Ser Ala Ala Tyr Lys
                500                 505                 510
Asn Ser Leu Glu Ser Lys His Thr Pro Ser Ile Ile Ala Leu Ser Arg
            515                 520                 525
Gln Asn Leu Pro Gln Leu Glu Gly Ser Ser Ile Glu Ser Ala Ser Lys
            530                 535                 540
Gly Gly Tyr Val Leu Gln Asp Val Ala Asn Pro Asp Ile Ile Leu Val
545                 550                 555                 560
Ala Thr Gly Ser Glu Val Ser Leu Ser Val Glu Ala Ala Lys Thr Leu
                565                 570                 575
```

-continued

```
Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
    610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
            645                 650                 655

Ala Glu Arg Ala Gln Lys Thr Ile Ala Phe Tyr Lys Gly Asp Lys Leu
        660                 665                 670

Ile Ser Pro Leu Lys Lys Ala Phe
    675                 680

<210> SEQ ID NO 28
<211> LENGTH: 496
<212> TYPE: PRT
<213> ORGANISM: Saccharomyces cerevisiae (strain ATCC 204508 / S288c)
      (Baker's yeast)

<400> SEQUENCE: 28

Met Ser Met Ser Asn Ile Val Val Phe Gly Gly Asp Ser His Pro Glu
1               5                   10                  15

Leu Val Thr Lys Ile Cys Glu Asn Leu Asp Ile His Pro Ser Lys Val
            20                  25                  30

Glu Leu Gly Lys Phe Ser Asn Gly Glu Thr Asn Ile Ala Leu Arg Glu
        35                  40                  45

Ser Val Arg Glu Lys Asp Val Tyr Ile Ile Gln Ser Gly Cys Gly Gln
    50                  55                  60

Val Asn Asp Thr Phe Met Gln Leu Leu Ile Leu Ile Ser Ala Cys Lys
65                  70                  75                  80

Ser Ala Ser Ala Ser Arg Val Thr Ala Val Met Pro Tyr Leu Cys Tyr
            85                  90                  95

Ser Arg Gln Pro Asp Ile Pro Tyr Thr Ala Lys Gly Ala Pro Ile Ile
        100                 105                 110

Ser Lys Pro Lys Glu Asn Tyr Thr Phe Glu Ser His Pro Gly Thr Pro
    115                 120                 125

Val Ser Ser Ser Leu Met Thr Gln Arg Pro Gly Ala Glu Ser Ser Leu
130                 135                 140

Lys Ser Leu Asp Ser Ala Ile Arg Ser Thr Ile Asn Leu Glu Asn Pro
145                 150                 155                 160

Gln Pro Ile Arg Thr Pro Asn Ser Ser Ala Thr Ala Asn Asn Asn Phe
            165                 170                 175

Asp Ile Lys Lys Thr Leu Ser Phe Ser Arg Ile Pro Met Ile Pro Gly
        180                 185                 190

Gly Lys Leu Gln Asn Thr Ser Asn Ser Thr Asp Ala Gly Glu Leu Phe
    195                 200                 205

Asn Ala Gln Asn Ala Gly Tyr Lys Leu Trp Val Val Gln Ala Gly Thr
210                 215                 220

Leu Ile Ala His Leu Leu Ser Ala Ala Gly Ala Asp His Val Ile Thr
225                 230                 235                 240

Met Asp Leu His Asp Pro Gln Phe Pro Gly Phe Phe Asp Ile Pro Val
            245                 250                 255
```

```
Asp Asn Leu Tyr Cys Lys Pro Ile Ala Gln Asn Tyr Ile Gln His Arg
            260                 265                 270

Ile Pro Asp Tyr Gln Asp Ala Val Ile Val Ser Pro Asp Ala Gly Gly
        275                 280                 285

Ala Lys Arg Ala Thr Ala Ile Ala Asp Ala Leu Glu Leu Ser Phe Ala
    290                 295                 300

Leu Ile His Lys Glu Arg Arg Ser Gln Leu Leu Lys Gly Pro Pro Asp
305                 310                 315                 320

Ala Thr Leu Thr Ser Gly Gly Ser Leu Pro Val Ser Pro Arg Pro Leu
                325                 330                 335

Val Thr Thr Leu Val Ser Ser Gln Asn Thr Thr Ser Ser Gly Ala Thr
            340                 345                 350

Gly Val Ala Ala Leu Glu Met Lys Lys Thr Thr Ser Thr Ser Ser Thr
        355                 360                 365

Ser Ser Gln Ser Ser Asn Ser Ser Lys Phe Val Gln Thr Thr Met Leu
    370                 375                 380

Val Gly Asp Val Arg Asn Lys Val Cys Ile Ile Val Asp Asp Leu Val
385                 390                 395                 400

Asp Thr Ser Tyr Thr Ile Thr Arg Ala Ala Lys Leu Leu Lys Asp Gln
                405                 410                 415

Gly Ser Thr Lys Val Tyr Ala Leu Ile Thr His Gly Val Phe Ser Gly
            420                 425                 430

Asp Ala Leu Glu Arg Ile Gly Gln Ser Ser Ile Asp Lys Leu Ile Ile
        435                 440                 445

Ser Asn Thr Val Pro Gln Asp Arg Thr Leu Gln Tyr Leu Gly Lys Asp
    450                 455                 460

Arg Val Asp Val Ile Asp Val Ser Cys Ile Ile Gly Glu Ala Ile Arg
465                 470                 475                 480

Arg Ile His Asn Gly Glu Ser Ile Ser Met Leu Phe Glu His Gly Trp
                485                 490                 495
```

<210> SEQ ID NO 29
<211> LENGTH: 2397
<212> TYPE: DNA
<213> ORGANISM: Saccharomyces cerevisiae

<400> SEQUENCE: 29

```
atggttttgc cgattctacc gttaattgat gatctggcct catggaatag taagaaggaa      60
tacgtttcac ttgttggtca ggtacttttg gatggctcga gcctgagtaa tgaagagatt     120
ctccagttct ccaaagagga agaagttcca ttggtggctt gtccttgcc aagtggtaaa      180 ttcagcgatg atgaaatcat tgccttcttg aacaacggag tttcttctct gttcattgct     240
agccaagatc taaaacagc cgaacacttg gttgaacaat gaatgtacc aaaggagcgt       300 gttgttgtgg aagagaacgg tgttttctcc aatcaattca tggtaaaaca aaaattctcg    360
caagataaaa ttgtgtccat aaagaaatta agcaaggata tgttgaccaa agaagtgctt    420
ggtgaagtac gtacagaccg tcctgacggt ttatatacca ccctagttgt cgaccaatat    480
gagcgttgtc tagggttggt gtattcttcg aagaaatcta tagcaaaggc catcgatttg    540
ggtcgtggcg tttattattc tcgttctagg aatgaaatct ggatcaaggg tgaaacttct    600
ggcaatggcc aaaagctttt acaaatctct actgactgtg attcggatgc cttaaagttt    660
atcgttgaac aagaaacgt tggattttgc cacttggaga ccatgtcttg ctttggtgaa    720
ttcaagcatg gtttggtggg gctagaatct ttactaaaac aaaggctaca ggacgctcca    780
```

```
gaggaatctt atactagaag actattcaac gactctgcat tgttagatgc caagatcaag    840
gaagaagctg aagaactgac tgaggcaaag ggtaagaagg agctttcttg ggaggctgcc    900
gatttgttct actttgcact ggccaaatta gtggccaacg atgtttcatt gaaggacgtc    960
gagaataatc tgaatatgaa gcatctgaag gttacaagac ggaaaggtga tgctaagcca   1020
aagtttgttg acaaccaaa ggctgaagaa gaaaaactga ccggtccaat tcacttggac   1080
gtggtgaagg cttccgacaa agttggtgtg cagaaggctt tgagcagacc aatccaaaag   1140
acttctgaaa ttatgcattt agtcaatccg atcatcgaaa atgttagaga caaaggtaac   1200
tctgcccttt tggagtacac agaaaagttt gatggtgtaa aattatccaa tcctgttctt   1260
aatgctccat tcccagaaga atactttgaa ggtttaaccg aggaaatgaa ggaagctttg   1320
gaccttttcaa ttgaaaacgt ccgcaaattc catgctgctc aattgccaac agagactctt   1380
gaagttgaaa cccaacctgg tgtcttgtgt tccagattcc ctcgtcctat tgaaaaagtt   1440
ggtttgtata tccctggtgg cactgccatt ttaccaagta ctgcattaat gcttggtgtt   1500
ccagcacaag ttgcccaatg taaggagatt gtgtttgcat ctccaccaag aaaatctgat   1560
ggtaaagttt cacccgaagt tgtttatgtc gcagaaaaag ttggcgcttc caagattgtt   1620
ctagctggtg gtgcccaagc cgttgctgct atggcttacg gacagaaaac tattcctaaa   1680
gtggataaga tcttgggtcc aggtaatcaa tttgtgactg ccgccaaaat gtatgttcaa   1740
aatgacactc aagctctatg ttccattgat atgccagctg gcccaagtga agttttggtt   1800
attgccgatg aagatgccga tgtggatttt gttgcaagtg atttgctatc gcaagctgaa   1860
cacggtattg actcccaagt tatccttgtt ggtgttaact tgagcgaaaa gaaaattcaa   1920
gagattcaag atgctgtcca caatcaagct ttacaactgc cacgtgtgga tattgttcgt   1980
aaatgtattg ctcacagtac gatcgttctt tgtgacggtt acgaagaagc ccttgaaatg   2040
tccaaccaat atgcaccaga acatttgatt ctacaaatcg ccaatgctaa cgattatgtt   2100
aaattggttg acaatgcagg gtccgtattt gtgggtgctt acactccaga atcgtgcggt   2160
gactattcaa gtggtactaa ccatacatta ccaacctatg gttacgctag gcagtacagt   2220
ggtgccaaca ctgcaacctt ccaaaagttt atcactgccc aaaacattac ccctgaaggt   2280
ttagaaaaca tcggtagagc tgttatgtgc gttgccaaga aggagggtct agacggtcac   2340
agaaacgctg tgaaaatcag aatgagtaag cttgggttga tcccaaagga tttccag     2397
```

<210> SEQ ID NO 30
<211> LENGTH: 843
<212> TYPE: DNA
<213> ORGANISM: Corynebacterium glutamicum

<400> SEQUENCE: 30

```
atgttgaaaa tcgctgtccc aaacaagggc tcgctgtccg agcgcgccat ggaaatcctc     60
gccgaagcag gctacgcagg ccgtggagat tccaaatccc tcaacgtttt tgatgaagca    120
aacaacgttg aattcttctt ccttcgccct aaagatatcg ccatctacgt tgcaggtggc    180
cagctcgatt tgggtatcac cggccgcgac cttgctcgcg attcccaggc tgatgtccac    240
gaagttcttt ccctcggctt cggttcctcc accttccgtt acgcagcacc agctgatgaa    300
gagtggagca tcgaaaagct cgacggcaag cgcatcgcta cctcttaccc caaccttgtt    360
cgcgatgacc tcgcagcacg tgggctttcc gctgaggtgc tccgcctcga cggtgcagta    420
gaggtatcca tcaagcttgg tgtcgcagat gccatcgccg atgttgtatc caccggccgc    480
acgctgcgtc agcaaggtct tgcacctttc ggcgaggttc tgtgcacctc tgaggctgtc    540
```

```
attgttggcc gcaaggatga aaaggtcacc ccagagcagc agatcctgct tcgccgcatc      600
cagggaattt tgcacgcgca gaacttcctc atgctggatt acaacgtcga ccgcgacaac      660
ctggacgctg ccactgcagt aaccccaggc ctatccggcc caacggtatc cccactggca      720
cgcgacaact gggttgctgt acgcgccatg gtgccacgca ggtcagctaa cgccatcatg      780
gataagcttg ctggactcgg cgctgaagcc atcctggctt ctgaaatccg catcgcccgc      840
atc                                                                    843
```

<210> SEQ ID NO 31
<211> LENGTH: 261
<212> TYPE: PRT
<213> ORGANISM: Saccharomyces cerevisiae (strain ATCC 204508 / S288c)
      (Baker's yeast)

<400> SEQUENCE: 31

```
Met Thr Lys Phe Ile Gly Cys Ile Asp Leu His Asn Gly Glu Val Lys
1               5                   10                  15

Gln Ile Val Gly Gly Thr Leu Thr Ser Lys Lys Glu Asp Val Pro Lys
            20                  25                  30

Thr Asn Phe Val Ser Gln His Pro Ser Ser Tyr Tyr Ala Lys Leu Tyr
        35                  40                  45

Lys Asp Arg Asp Val Gln Gly Cys His Val Ile Lys Leu Gly Pro Asn
    50                  55                  60

Asn Asp Asp Ala Ala Arg Glu Ala Leu Gln Glu Ser Pro Gln Phe Leu
65                  70                  75                  80

Gln Val Gly Gly Gly Ile Asn Asp Thr Asn Cys Leu Glu Trp Leu Lys
                85                  90                  95

Trp Ala Ser Lys Val Ile Val Thr Ser Trp Leu Phe Thr Lys Glu Gly
            100                 105                 110

His Phe Gln Leu Lys Arg Leu Glu Arg Leu Thr Glu Leu Cys Gly Lys
        115                 120                 125

Asp Arg Ile Val Val Asp Leu Ser Cys Arg Lys Thr Gln Asp Gly Arg
    130                 135                 140

Trp Ile Val Ala Met Asn Lys Trp Gln Thr Leu Thr Asp Leu Glu Leu
145                 150                 155                 160

Asn Ala Asp Thr Phe Arg Glu Leu Arg Lys Tyr Thr Asn Glu Phe Leu
                165                 170                 175

Ile His Ala Ala Asp Val Glu Gly Leu Cys Gly Gly Ile Asp Glu Leu
            180                 185                 190

Leu Val Ser Lys Leu Phe Glu Trp Thr Lys Asp Tyr Asp Asp Leu Lys
        195                 200                 205

Ile Val Tyr Ala Gly Gly Ala Lys Ser Val Asp Asp Leu Lys Leu Val
    210                 215                 220

Asp Glu Leu Ser His Gly Lys Val Asp Leu Thr Phe Gly Ser Ser Leu
225                 230                 235                 240

Asp Ile Phe Gly Gly Asn Leu Val Lys Phe Glu Asp Cys Cys Arg Trp
                245                 250                 255

Asn Glu Lys Gln Gly
            260
```

<210> SEQ ID NO 32
<211> LENGTH: 248
<212> TYPE: PRT
<213> ORGANISM: Artificial
<220> FEATURE:

<223> OTHER INFORMATION: Codon-optimized and/or mutated sequence

<400> SEQUENCE: 32

```
Met Ala Arg Thr Phe Phe Val Gly Gly Asn Phe Lys Leu Asn Gly Ser
1               5                   10                  15

Lys Gln Ser Ile Lys Glu Ile Val Glu Arg Leu Asn Thr Ala Ser Ile
            20                  25                  30

Pro Glu Asn Val Glu Val Val Ile Cys Pro Pro Ala Thr Tyr Leu Asp
        35                  40                  45

Tyr Ser Val Ser Leu Val Lys Lys Pro Gln Val Thr Val Gly Ala Gln
50                  55                  60

Asn Ala Tyr Leu Lys Ala Ser Gly Ala Phe Thr Gly Glu Asn Ser Val
65                  70                  75                  80

Asp Gln Ile Lys Asp Val Gly Ala Lys Trp Val Ile Leu Gly His Ser
                85                  90                  95

Glu Arg Arg Ser Tyr Phe His Glu Asp Asp Lys Phe Ile Ala Asp Lys
            100                 105                 110

Thr Lys Phe Ala Leu Gly Gln Gly Val Gly Val Ile Leu Cys Ile Gly
        115                 120                 125

Glu Thr Leu Glu Glu Lys Lys Ala Gly Lys Thr Leu Asp Val Val Glu
130                 135                 140

Arg Gln Leu Asn Ala Val Leu Glu Glu Val Lys Asp Trp Thr Asn Val
145                 150                 155                 160

Val Val Ala Tyr Glu Pro Val Trp Ala Val Gly Thr Gly Leu Ala Ala
                165                 170                 175

Thr Pro Glu Asp Ala Gln Asp Ile His Ala Ser Ile Arg Lys Phe Leu
            180                 185                 190

Ala Ser Lys Leu Gly Asp Lys Ala Ala Ser Glu Leu Arg Ile Leu Tyr
        195                 200                 205

Gly Gly Ser Ala Asn Gly Ser Asn Ala Val Thr Phe Lys Asp Lys Ala
210                 215                 220

Asp Val Asp Gly Phe Leu Val Gly Gly Ala Ser Leu Lys Pro Glu Phe
225                 230                 235                 240

Val Asp Ile Ile Asn Ser Arg Asn
                245
```

<210> SEQ ID NO 33
<211> LENGTH: 408
<212> TYPE: PRT
<213> ORGANISM: Pseudomonas rhizosphaerae

<400> SEQUENCE: 33

```
Met Thr Leu Ser Thr Ala Asp Thr His Arg Leu Asp Asp Phe Trp Gln
1               5                   10                  15

His Cys Leu Lys His Gln Phe Phe Asn Ile Gly Tyr Pro Glu Asn Ala
            20                  25                  30

Asp Phe Asp Tyr Ser Ala Leu Glu Arg Phe Leu Arg Phe Ser Ile Asn
        35                  40                  45

Asn Cys Gly Asp Trp Ser Glu His Ser Asn Tyr Val Leu Asn Ser Phe
50                  55                  60

Asp Phe Glu Lys Glu Val Met Ala Tyr Phe Ala Asp Leu Phe Glu Ile
65                  70                  75                  80

Pro Arg Glu Asp Ser Trp Gly Tyr Val Thr Asn Gly Gly Thr Glu Gly
                85                  90                  95

Asn Met Phe Gly Cys Tyr Leu Ala Arg Glu Leu Phe Pro Asp Gly Thr
```

```
              100                 105                 110
Leu Tyr Tyr Ser Lys Asp Thr His Tyr Ser Val Ala Lys Ile Val Lys
            115                 120                 125

Leu Leu Arg Ile Lys Cys Arg Ala Val Asn Ala Leu Pro Thr Gly Glu
        130                 135                 140

Ile Asp Tyr Asp Asp Leu Leu Ala Lys Ile Ala Ala Asp Gly Glu Arg
145                 150                 155                 160

His Pro Ile Ile Phe Ala Asn Ile Gly Thr Thr Met Arg Gly Ala Val
                165                 170                 175

Asp Asp Ile Ala Val Ile Gln Gln Arg Leu Gln Asp Ala Gly Ile Ala
            180                 185                 190

Arg Arg Asp Tyr Tyr Leu His Ala Asp Ala Ala Leu Ser Gly Met Ile
        195                 200                 205

Leu Pro Phe Val Asp Ala Pro Gln Pro Phe Thr Phe Ala Asp Gly Ile
    210                 215                 220

Asp Ser Ile Cys Val Ser Gly His Lys Met Ile Gly Ser Pro Ile Pro
225                 230                 235                 240

Cys Gly Ile Val Val Ala Lys Arg Arg Asn Val Ala Arg Ile Ser Val
                245                 250                 255

Glu Val Asp Tyr Ile Ser Ala Ser Asp Lys Thr Ile Ser Gly Ser Arg
            260                 265                 270

Asn Gly His Thr Pro Met Ile Met Trp Ala Ala Leu Arg Ser His Ser
        275                 280                 285

Ser Ala Gln Trp Arg Arg Arg Val Glu Arg Ser Leu Ala Ala Ala Gln
    290                 295                 300

Tyr Ala Val Asn Arg Leu Gln Ala Gly Gly Val Lys Ala Trp Arg Asn
305                 310                 315                 320

Pro Asn Ser Ile Thr Val Val Phe Pro Cys Pro Ser Ala Asp Ile Ala
                325                 330                 335

Arg Lys Tyr Gly Leu Ala Thr Ser Gly Asp Thr Ala His Leu Ile Thr
            340                 345                 350

Thr Pro His His Arg Asp Asn Arg Ala Ile Asp Ala Leu Ile Asp Glu
        355                 360                 365

Val Ile Ala Asp Ala Arg Pro Glu Val Trp Arg Ala Thr Leu Gln Arg
    370                 375                 380

Ser Trp Gln Gly Ser Ala Gln Arg Leu Pro Arg Thr Ala Ser Trp Asn
385                 390                 395                 400

Gln Ala Ala Gly Leu Gly Arg Phe
                405

<210> SEQ ID NO 34
<211> LENGTH: 427
<212> TYPE: PRT
<213> ORGANISM: Pseudomonas putida (Arthrobacter siderocapsulatus)

<400> SEQUENCE: 34

Met Thr Phe Ser Pro Ala Asp His Lys Arg Leu Glu Ala Phe Trp Gln
1               5                   10                  15

Tyr Cys Leu Thr His Gln Tyr Phe Asn Val Gly Tyr Pro Glu Ser Ala
            20                  25                  30

Asp Phe Asp Tyr Ser Leu Leu His Arg Phe Met Arg Phe Ser Ile Asn
        35                  40                  45

Asn Cys Gly Asp Trp Asn Glu Pro Ser Asn Tyr Leu Leu Asn Ser Phe
    50                  55                  60
```

```
Asp Phe Glu Arg Glu Val Met Arg Phe Phe Ala Glu Leu Phe His Ile
 65                  70                  75                  80

Pro Phe Glu Asp Ser Trp Gly Tyr Val Thr Asn Gly Gly Thr Glu Gly
                 85                  90                  95

Asn Met Phe Gly Cys Tyr Leu Ala Arg Glu Leu Phe Pro Asp Ala Thr
            100                 105                 110

Leu Tyr Tyr Ser Lys Asp Thr His Tyr Ser Val Ala Lys Ile Val Arg
        115                 120                 125

Leu Leu Arg Ile Lys Ala Gln Val Val Glu Ser Gln Ala Asn Gly Glu
    130                 135                 140

Met Asp Tyr Asp Leu Val Ala Arg Ile Ala Ala Asp Gly Glu Arg
145                 150                 155                 160

His Pro Ile Ile Phe Ala Asn Ile Gly Thr Thr Leu Arg Gly Ala Thr
                165                 170                 175

Asp Asn Ile Ala Val Ile Gln Gln Arg Leu Ala Gln Ala Gly Ile Arg
            180                 185                 190

Arg Glu Asp Tyr Tyr Leu His Ala Asp Ala Ala Leu Ser Gly Met Ile
        195                 200                 205

Leu Pro Phe Val Asp Ala Pro Glu Pro Tyr Ser Phe Ala Asp Gly Ile
    210                 215                 220

Asp Ser Ile Cys Val Ser Gly His Lys Met Ile Gly Ser Pro Met Pro
225                 230                 235                 240

Cys Gly Ile Val Val Ala Arg Arg His Asn Val Glu Arg Ile Ser Val
                245                 250                 255

Glu Ile Asp Tyr Ile Ser Ala Arg Asp Gln Thr Ile Ser Gly Ser Arg
            260                 265                 270

Asn Gly His Thr Pro Leu Met Met Trp Ala Ala Leu Cys Ser Arg Ser
        275                 280                 285

Arg Glu Asp Trp Arg Ala Arg Ile Gln Arg Cys Leu Asp Leu Ala Gln
    290                 295                 300

His Ala Val Asp Arg Leu Arg Ala Ala Gly Ile Glu Ala Trp Arg Asn
305                 310                 315                 320

Pro Asn Ser Ile Thr Val Val Phe Pro Cys Pro Ser Ala Ser Val Trp
                325                 330                 335

Lys Arg His Cys Leu Ala Thr Ser Gly Asp Thr Ala His Leu Ile Thr
            340                 345                 350

Thr Ala His His Gln Asp Ser Thr Gln Ile Asp Ala Leu Leu Asp Glu
        355                 360                 365

Leu Ile Ala Asp Leu Lys Ala Arg Thr Arg Tyr Pro Leu Gln Ala Pro
    370                 375                 380

Leu Val Glu Gly Leu Gly Ser Arg Thr Arg Val Tyr Ser Thr Ala Gly
385                 390                 395                 400

Gln Pro Arg Pro Glu Pro Leu Pro Asp His Ala Arg Pro Ala Arg Asp
                405                 410                 415

Ser Gly Leu Ala Arg Leu Lys Asp Ser Glu Ile
            420                 425

<210> SEQ ID NO 35
<211> LENGTH: 378
<212> TYPE: PRT
<213> ORGANISM: Citrobacter pasteurii

<400> SEQUENCE: 35

Met Thr Leu Ser Ile Val Asp Gln Asn Lys Leu Asp Ala Phe Trp Ser
1               5                   10                  15
```

Tyr Cys Val Lys Asn Gln Tyr Phe Asn Ile Gly Tyr Pro Glu Ser Ala
            20                  25                  30

Asp Phe Asp Tyr Thr Ile Leu Glu Arg Phe Met Arg Phe Ser Ile Asn
        35                  40                  45

Asn Cys Gly Asp Trp Gly Glu Tyr Cys Asn Tyr Leu Leu Asn Ser Phe
50                  55                  60

Asp Phe Glu Lys Glu Val Met Glu Tyr Phe Ala Arg Ile Phe Lys Ile
65                  70                  75                  80

Pro Phe Glu Glu Ser Trp Gly Tyr Val Thr Asn Gly Thr Glu Gly
                85                  90                  95

Asn Met Phe Gly Cys Tyr Leu Gly Arg Glu Leu Phe Pro Glu Gly Thr
            100                 105                 110

Leu Tyr Tyr Ser Lys Asp Thr His Tyr Ser Val Ala Lys Ile Val Lys
        115                 120                 125

Leu Leu Arg Ile Lys Ser Ser Leu Val Glu Ser Gln Pro Asn Gly Glu
    130                 135                 140

Met Asp Tyr Asp Asp Leu Ile Arg Lys Ile Gln Arg Asp Asn Glu Glu
145                 150                 155                 160

His Pro Ile Ile Phe Ala Asn Ile Gly Thr Thr Val Arg Gly Ala Ile
                165                 170                 175

Asp Asn Ile Ala Glu Ile Gln Gln Arg Ile Gly Gln Leu Gly Ile Lys
            180                 185                 190

Arg Asp Asp Tyr Tyr Leu His Ala Asp Ala Ala Leu Ser Gly Met Ile
        195                 200                 205

Leu Pro Phe Val Asn Asp Pro Gln Pro Phe Asn Phe Ala Asp Gly Ile
    210                 215                 220

Asp Ser Ile Gly Val Ser Gly His Lys Met Ile Gly Ser Pro Ile Pro
225                 230                 235                 240

Cys Gly Ile Val Val Ala Lys Arg Lys Asn Val Asp Arg Ile Ser Val
                245                 250                 255

Glu Ile Asp Tyr Ile Ser Ala His Asp Lys Thr Ile Ser Gly Ser Arg
            260                 265                 270

Asn Gly His Thr Pro Leu Met Met Trp Glu Ala Ile Arg Ser His Ser
        275                 280                 285

Trp Ser Asp Trp Gln Arg Arg Ile Glu His Ser Leu Asn Met Ala Gln
    290                 295                 300

Tyr Ala Val Asp Arg Leu Gln Ala Ala Gly Ile Asp Ala Trp Arg Asn
305                 310                 315                 320

Lys Asn Ser Ile Thr Val Phe Pro Cys Pro Ser Glu Ala Val Trp
                325                 330                 335

Lys Lys His Cys Leu Ala Thr Ser Gly Asp Ile Ala His Leu Ile Thr
            340                 345                 350

Thr Ala His His Leu Asp Ser Ser Lys Ile Asp Glu Leu Ile Asp Asp
        355                 360                 365

Val Ile Ala Asp Leu Asn Gln Gln Ala Ala
    370                 375

<210> SEQ ID NO 36
<211> LENGTH: 387
<212> TYPE: PRT
<213> ORGANISM: Chromobacterium haemolyticum

<400> SEQUENCE: 36

Met Ser Leu Ser Ser Leu Asp Gln Asn Arg Ile Glu Ser Phe Trp Gln

```
            1               5                    10                      15
        Tyr Cys Leu Gln His Gln Tyr Phe Asn Leu Ala Tyr Pro Glu Ser Ala
                        20                  25                  30
        Asp Phe Asp Tyr Thr Pro Leu His Arg Phe Leu Arg Phe Ser Ile Asn
                        35                  40                  45
        Asn Cys Gly Asp Trp Asn Glu Ser Ser Asn Tyr Leu Leu Asn Ser Phe
                50                  55                  60
        Asp Phe Glu Arg Glu Val Met His Phe Phe Ala Glu Leu Phe His Ile
        65                  70                  75                  80
        Pro Phe Asp Glu Ser Trp Gly Tyr Val Thr Asn Gly Gly Thr Glu Gly
                        85                  90                  95
        Asn Met Phe Gly Cys Tyr Leu Ala Arg Glu Leu Phe Pro Asp Ala Thr
                        100                 105                 110
        Leu Tyr Tyr Ser Lys Asp Ser His Tyr Ser Val Ala Lys Ile Ile Lys
                        115                 120                 125
        Leu Leu Arg Ile Lys Ser Arg Ala Val Asp Ser Leu Pro Ser Gly Glu
                        130                 135                 140
        Ile Asp Tyr Asp Asp Leu Val Ala Lys Ile Gln Gln Asp Gln Glu Arg
        145                 150                 155                 160
        His Pro Ile Val Phe Val Asn Val Gly Thr Thr Met Lys Gly Ala Val
                            165                 170                 175
        Asp Asp Ile Gly Ile Ile Gln Asp Lys Leu Ala Gln Ala Gly Ile Pro
                    180                 185                 190
        Arg Arg Asp Tyr Tyr Leu His Ala Asp Ala Ala Leu Ser Gly Met Ile
                    195                 200                 205
        Leu Pro Phe Val Asp Ala Pro Gln Pro Tyr Ser Phe Ala Asp Gly Ile
                    210                 215                 220
        Asp Ser Ile Ser Val Ser Gly His Lys Met Ile Gly Ser Pro Met Pro
        225                 230                 235                 240
        Cys Gly Ile Val Leu Ala Lys Arg Ser Asn Val Ser Arg Ile Ser Val
                            245                 250                 255
        Glu Ile Asp Tyr Ile Ser Ala Arg Asp Gln Thr Ile Ser Gly Ser Arg
                    260                 265                 270
        Asn Gly His Thr Pro Met Met Leu Trp Ala Ala Ile Lys Ser Arg Pro
                    275                 280                 285
        Leu Ala Glu Trp Arg Arg Lys Val Arg His Cys Leu Asp Met Ala Gln
                    290                 295                 300
        Tyr Ala Ile Asp Arg Phe Arg Ala Ala Gly Ile Gln Ala Trp Arg Cys
        305                 310                 315                 320
        Gln Asn Ser Ile Thr Val Val Phe Pro Ser Pro Ser Glu Pro Val Cys
                            325                 330                 335
        Asp Lys His Gly Leu Ala Arg Ser Gly Gly Ala Ala His Leu Ile Thr
                    340                 345                 350
        Thr Pro His His His Asp Ser Gln Arg Leu Asp Arg Leu Ile Asp Asp
                    355                 360                 365
        Ile Ile Gln Asp Leu Gly Ala Val Thr Ala Pro Ala Gly Ala Ala Met
        370                 375                 380
        Ser Ala Ala
        385

<210> SEQ ID NO 37
<211> LENGTH: 311
<212> TYPE: PRT
<213> ORGANISM: Lactobacillus reuteri
```

<400> SEQUENCE: 37

| | | | | | | | | | | | | | | |
|---|---|---|---|---|---|---|---|---|---|---|---|---|---|---|
| Met | Ser | Glu | Leu | Asp | Thr | Lys | Leu | His | Lys | Leu | Gly | Val | Asp | Arg | Ile |
| 1 | | | | 5 | | | | | 10 | | | | | 15 | |
| Ala | Ile | Ser | Pro | Tyr | Lys | Gln | Trp | Ser | Arg | Gly | Tyr | Met | Glu | Pro | Gly |
| | | | 20 | | | | | 25 | | | | | 30 | | |
| Asn | Ile | Gly | Asn | Gly | Tyr | Val | Thr | Gly | Leu | Lys | Val | Asp | Ala | Gly | Val |
| | | | | 35 | | | | | 40 | | | | | 45 | |
| Arg | Asp | Lys | Thr | Asp | Asp | Glu | Val | Leu | Asp | Gly | Ile | Val | Ser | Tyr | Asp |
| | 50 | | | | | 55 | | | | | 60 | | | | |
| Arg | Ala | Glu | Thr | Lys | Asn | Ala | Tyr | Ile | Gly | Gln | Ile | Asn | Met | Thr | Thr |
| 65 | | | | | 70 | | | | | 75 | | | | | 80 |
| Ala | Ser | Ser | Phe | Thr | Gly | Pro | Gln | Gly | His | Cys | Ile | Gly | Tyr | Asp | Leu |
| | | | | 85 | | | | | 90 | | | | | 95 | |
| Leu | Arg | Asn | Pro | Glu | Val | Asp | Thr | Ala | Glu | Pro | Leu | Phe | Thr | Val | Lys |
| | | | 100 | | | | | 105 | | | | | 110 | | |
| Gln | Trp | Asp | Gly | Ser | Glu | Leu | Pro | Ile | Tyr | Asp | Ala | Lys | Pro | Leu | Gln |
| | | | 115 | | | | | 120 | | | | | 125 | | |
| Asp | Ser | Leu | Val | Glu | Tyr | Phe | Gly | Thr | Asn | Asn | Arg | Arg | His | Tyr | |
| | 130 | | | | | 135 | | | | | 140 | | | | |
| Pro | Ala | Pro | Gly | Ser | Phe | Ile | Val | Cys | Ala | Asn | Lys | Gly | Val | Thr | Ala |
| 145 | | | | | 150 | | | | | 155 | | | | | 160 |
| Glu | Arg | Pro | Met | Asn | Asp | Ser | Asp | Met | Lys | Pro | Gly | Gln | Gly | Tyr | Gly |
| | | | | 165 | | | | | 170 | | | | | 175 | |
| Val | Trp | Ser | Ala | Ile | Ala | Leu | Ser | Phe | Ala | Lys | Asp | Pro | Ala | Lys | Asp |
| | | | 180 | | | | | 185 | | | | | 190 | | |
| Ser | Ser | Met | Phe | Ile | Glu | Asp | Ala | Gly | Val | Trp | Glu | Thr | Pro | Asn | Glu |
| | | | 195 | | | | | 200 | | | | | 205 | | |
| Asp | Glu | Leu | Ile | Glu | Tyr | Leu | Lys | Gly | Arg | Arg | Lys | Ala | Ile | Ala | Lys |
| | 210 | | | | | 215 | | | | | 220 | | | | |
| Ser | Ile | Ala | Glu | Cys | Gly | Gln | Asp | Ala | Asn | Thr | Ser | Phe | Lys | Gly | Ser |
| 225 | | | | | 230 | | | | | 235 | | | | | 240 |
| Trp | Ile | Gly | Phe | Ala | His | Ala | Met | Met | Glu | Pro | Gly | Gln | Ile | Gly | Asn |
| | | | | 245 | | | | | 250 | | | | | 255 | |
| Ala | Ile | Thr | Val | Ala | Pro | Tyr | Ile | Ser | Met | Pro | Val | Asp | Ser | Ile | Pro |
| | | | 260 | | | | | 265 | | | | | 270 | | |
| Gly | Gly | Ser | Ile | Leu | Thr | Pro | Asp | Thr | Asp | Met | Asp | Ile | Met | Glu | Asn |
| | | | 275 | | | | | 280 | | | | | 285 | | |
| Leu | Thr | Met | Pro | Glu | Trp | Leu | Asp | Lys | Met | Glu | Tyr | Lys | Ser | Leu | Thr |
| | 290 | | | | | 295 | | | | | 300 | | | | |
| Ala | Asn | Gly | Ala | Ile | Lys | Tyr | | | | | | | | | |
| 305 | | | | | 310 | | | | | | | | | | |

<210> SEQ ID NO 38
<211> LENGTH: 390
<212> TYPE: PRT
<213> ORGANISM: Aeromonas salmonicida subsp. pectinolytica 34mel

<400> SEQUENCE: 38

| | | | | | | | | | | | | | | |
|---|---|---|---|---|---|---|---|---|---|---|---|---|---|---|
| Met | Cys | Arg | His | Ala | Cys | Ile | Ala | Leu | Ala | Met | Gly | Met | Ile | Met | Gly |
| 1 | | | | 5 | | | | | 10 | | | | | 15 | |
| Leu | Ser | Ser | Glu | Asp | Ala | Gly | Lys | Ile | Glu | Ser | Phe | Trp | Arg | Tyr | Cys |
| | | | 20 | | | | | 25 | | | | | 30 | | |
| Val | Gln | His | Gln | Tyr | Phe | Asn | Ile | Gly | Tyr | Pro | Glu | Ala | Ala | Asp | Phe |
| | | | | 35 | | | | | 40 | | | | | 45 | |

```
Asp Tyr Ser Ala Leu Asn Arg Phe Leu Asn Phe Ser Ile Asn Asn Cys
        50                  55                  60

Gly Asp Trp Ser Gln Gln Ser Asn Tyr Leu Leu Asn Ser Phe Asp Phe
 65                  70                  75                  80

Glu Arg Glu Val Met Gln Phe Phe Ala Thr Leu Phe Cys Ile Pro Phe
                 85                  90                  95

Glu Gln Ser Trp Gly Tyr Val Thr Asn Gly Gly Thr Glu Gly Asn Met
                100                 105                 110

Phe Gly Cys Tyr Leu Ala Arg Glu Leu Phe Pro Glu Ala Thr Leu Tyr
            115                 120                 125

Tyr Ser Lys Asp Thr His Tyr Ser Val Ala Lys Ile Ile Arg Leu Leu
        130                 135                 140

Arg Val Lys Ser Cys Met Val Asp Ser Leu Pro Asn Gly Glu Met Asn
145                 150                 155                 160

Tyr Asp Asp Leu Ile Asn Arg Ile Arg Leu Asp Gly Glu Arg His Pro
                165                 170                 175

Ile Ile Phe Ala Asn Ile Gly Thr Thr Met Thr Gly Ala Thr Asp Asn
            180                 185                 190

Ile Ala Thr Ile Gln Arg Arg Leu Lys Lys Ile Gly Ile Thr Lys Gly
        195                 200                 205

Asp Tyr Tyr Leu His Ala Asp Ala Ala Leu Ser Gly Met Ile Leu Pro
    210                 215                 220

Phe Ile Asp Asn Pro Gln Pro Phe Ser Phe Ala Asp Gly Val Asp Ser
225                 230                 235                 240

Ile Ser Val Ser Gly His Lys Met Ile Gly Ser Pro Ile Pro Cys Gly
                245                 250                 255

Ile Val Leu Ala Arg Arg Lys His Val Glu His Val Ser Val Glu Ile
            260                 265                 270

Asp Tyr Ile Ser Ala Cys Asp Gln Thr Ile Ser Gly Ser Arg Asn Gly
        275                 280                 285

Tyr Thr Pro Leu Leu Leu Trp Met Ala Ile Lys Ser Arg Ser Phe Ser
    290                 295                 300

Asp Trp Arg Gln Arg Thr Gln His Cys Leu Asp Met Ala Gln Tyr Val
305                 310                 315                 320

Ile Glu Arg Phe His Ala Lys Gly Ile His Ala Trp Arg Asn Pro Asn
                325                 330                 335

Ser Ile Thr Val Val Phe Pro Lys Pro Ala Asp His Ile Trp Lys Lys
            340                 345                 350

His Cys Leu Ala Thr Ser Gly Lys Ile Ser His Ile Ile Thr Met Pro
        355                 360                 365

His His Thr Gly Lys Glu Thr Leu Asp Arg Val Ile Asn Asp Ile Ala
    370                 375                 380

Leu Asp Arg Glu Pro Lys
385                 390

<210> SEQ ID NO 39
<211> LENGTH: 378
<212> TYPE: PRT
<213> ORGANISM: Morganella psychrotolerans

<400> SEQUENCE: 39

Met Thr Leu Ser Ile Asn Asp Gln Asn Lys Leu Asp Ala Phe Trp Ala
 1               5                  10                  15

Tyr Cys Val Lys Asn Gln Tyr Phe Asn Ile Gly Tyr Pro Glu Ser Ala
```

```
            20                  25                  30
Asp Phe Asp Tyr Thr Asn Leu Glu Arg Phe Leu Arg Phe Ser Ile Asn
         35                  40                  45

Asn Cys Gly Asp Trp Gly Tyr Cys Asn Tyr Leu Leu Asn Ser Phe
 50                  55                  60

Asp Phe Glu Lys Glu Val Met Glu Tyr Phe Ala Asp Leu Phe Lys Ile
 65                  70                  75                  80

Pro Phe Glu Lys Ser Trp Gly Tyr Val Thr Asn Gly Gly Thr Glu Gly
                 85                  90                  95

Asn Met Phe Gly Cys Tyr Leu Gly Arg Glu Ile Phe Pro Asp Gly Thr
             100                 105                 110

Leu Tyr Tyr Ser Lys Asp Thr His Tyr Ser Val Ala Lys Ile Val Lys
             115                 120                 125

Leu Leu Arg Ile Lys Ser Gln Val Val Glu Ala Gln Pro Asn Gly Glu
             130                 135                 140

Ile Asp Tyr Asp Asp Leu Met Lys Lys Ile Ala Ala Asp Lys Glu Ala
145                 150                 155                 160

His Pro Ile Ile Phe Ala Asn Ile Gly Thr Thr Val Arg Gly Ala Ile
                 165                 170                 175

Asp Asp Ile Thr Glu Ile Gln Lys Arg Met Lys Ala Ala Gly Ile Lys
             180                 185                 190

Arg Glu Asp Tyr Tyr Leu His Ala Asp Ala Ala Leu Ser Gly Met Ile
             195                 200                 205

Leu Pro Phe Val Asp Glu Pro Gln Ala Phe Thr Phe Ala Asp Gly Ile
 210                 215                 220

Asp Ser Ile Gly Val Ser Gly His Lys Met Ile Gly Ser Pro Ile Pro
225                 230                 235                 240

Cys Gly Ile Val Val Ala Lys Lys Glu Asn Val Asp Arg Ile Ser Val
                 245                 250                 255

Glu Ile Asp Tyr Ile Ser Ala His Asp Lys Thr Ile Thr Gly Ser Arg
             260                 265                 270

Asn Gly His Thr Pro Leu Met Leu Trp Glu Ala Val Arg Ala His Ser
             275                 280                 285

Thr Glu Asp Trp Lys Arg Arg Ile Gly Arg Ser Leu Asp Met Ala Gln
 290                 295                 300

Tyr Ala Val Asp Arg Leu Gln Lys Ala Gly Ile Asn Ala Trp Arg Asn
305                 310                 315                 320

Lys Asn Ser Ile Thr Val Val Phe Pro Cys Pro Ser Glu Arg Val Trp
                 325                 330                 335

Lys Glu His Cys Leu Ala Thr Ser Gly Asn Asp Ala His Leu Ile Thr
             340                 345                 350

Thr Ala His His Leu Asp Thr Ala Gln Ile Asp Ala Leu Ile Asp Asp
             355                 360                 365

Val Ile Ala Asp Ala Lys Leu His Ala Ala
         370                 375

<210> SEQ ID NO 40
<211> LENGTH: 311
<212> TYPE: PRT
<213> ORGANISM: Lactobacillus fructivorans

<400> SEQUENCE: 40

Met Ala Lys Ile Asp Lys Ile Leu Asn Gln Glu Gly Ile Asp Arg Ile
1               5                   10                  15
```

-continued

Ala Ile Asn Pro Tyr Gln Lys Tyr Ser Arg Gly Tyr Met Glu Pro Gly
            20                  25                  30

Asn Leu Gly Gly Gly Tyr Val Thr Gly Leu Lys Val Asp Ala Gly Thr
        35                  40                  45

Arg Glu Lys Thr Asp Asp Ser Met Leu Asp Gly Ile Val Ser Tyr Asp
    50                  55                  60

Arg Ala Glu Cys Lys Asn Ala Tyr Ile Gly Gln Ile Asn Met Met Thr
65                  70                  75                  80

Ala Ser Ser Phe Thr Gly Val Gln Gly His Ile Leu Gly Tyr Asp Leu
                85                  90                  95

Leu Arg Asn Pro Ala Val Asp Lys Ala Gln Pro Leu Phe Tyr Glu Thr
            100                 105                 110

Gln Trp Asp Gly Ser Lys Leu Pro Ile Tyr Asp Gly Lys Pro Leu Gln
        115                 120                 125

Asp Ser Leu Val Glu Phe Phe Gly Thr Ala Asp Asn Arg Arg His Tyr
    130                 135                 140

Pro Ala Pro Gly Ser Phe Ile Val Cys Ala Asn Lys Gly Val Thr Ala
145                 150                 155                 160

Glu Arg Pro Leu Glu Asp Arg Pro Leu Asn Pro Gly Glu Ala Tyr Gly
                165                 170                 175

Val Trp Ser Ala Ile Ala Ile Ser Ile Ala Lys Asp Pro Val His Asn
            180                 185                 190

Ser Ser Met Phe Ile Glu Asp Ala Gly Thr Trp Asn Thr Pro Asn Glu
        195                 200                 205

Asp Asp Leu Asn Glu Phe Leu Tyr His Arg Arg Glu Ala Ile Ala Arg
    210                 215                 220

Ser Ile Ala Gln Cys Gly Gln Asp Ala Ser Thr Ser Phe Ala Ser Ser
225                 230                 235                 240

Trp Ile Gly Phe Ala His Val Met Met Lys Pro Gly Glu Ile Gly Asn
                245                 250                 255

Ala Ile Thr Val Gly Pro Tyr Phe Ser Met Pro Val Asp Ala Val Pro
            260                 265                 270

Gly Gly Ser Ile Leu Thr Pro Asp Val Asp Met Asn Ile Met Glu Asp
        275                 280                 285

Leu Ser Leu Pro Glu Trp Leu Glu Lys Met Gly Tyr Gln Ser Ile Val
    290                 295                 300

Glu Asn Gln Asp Ile Gln Tyr
305                 310

<210> SEQ ID NO 41
<211> LENGTH: 315
<212> TYPE: PRT
<213> ORGANISM: Escherichia coli (strain K12)

<400> SEQUENCE: 41

Met Pro Asp Met Lys Leu Phe Ala Gly Asn Ala Thr Pro Glu Leu Ala
1               5                   10                  15

Gln Arg Ile Ala Asn Arg Leu Tyr Thr Ser Leu Gly Asp Ala Ala Val
            20                  25                  30

Gly Arg Phe Ser Asp Gly Glu Val Ser Val Gln Ile Asn Glu Asn Val
        35                  40                  45

Arg Gly Gly Asp Ile Phe Ile Ile Gln Ser Thr Cys Ala Pro Thr Asn
    50                  55                  60

Asp Asn Leu Met Glu Leu Val Val Met Val Asp Ala Leu Arg Arg Ala
65                  70                  75                  80

```
Ser Ala Gly Arg Ile Thr Ala Val Ile Pro Tyr Phe Gly Tyr Ala Arg
                85                  90                  95

Gln Asp Arg Arg Val Arg Ser Ala Arg Val Pro Ile Thr Ala Lys Val
            100                 105                 110

Val Ala Asp Phe Leu Ser Ser Val Gly Val Asp Arg Val Leu Thr Val
        115                 120                 125

Asp Leu His Ala Glu Gln Ile Gln Gly Phe Phe Asp Val Pro Val Asp
    130                 135                 140

Asn Val Phe Gly Ser Pro Ile Leu Leu Glu Asp Met Leu Gln Leu Asn
145                 150                 155                 160

Leu Asp Asn Pro Ile Val Val Ser Pro Asp Ile Gly Gly Val Val Arg
                165                 170                 175

Ala Arg Ala Ile Ala Lys Leu Leu Asn Asp Thr Asp Met Ala Ile Ile
            180                 185                 190

Asp Lys Arg Arg Pro Arg Ala Asn Val Ser Gln Val Met His Ile Ile
        195                 200                 205

Gly Asp Val Ala Gly Arg Asp Cys Val Leu Val Asp Asp Met Ile Asp
    210                 215                 220

Thr Gly Gly Thr Leu Cys Lys Ala Ala Glu Ala Leu Lys Glu Arg Gly
225                 230                 235                 240

Ala Lys Arg Val Phe Ala Tyr Ala Thr His Pro Ile Phe Ser Gly Asn
                245                 250                 255

Ala Ala Asn Asn Leu Arg Asn Ser Val Ile Asp Glu Val Val Val Cys
            260                 265                 270

Asp Thr Ile Pro Leu Ser Asp Glu Ile Lys Ser Leu Pro Asn Val Arg
        275                 280                 285

Thr Leu Thr Leu Ser Gly Met Leu Ala Glu Ala Ile Arg Arg Ile Ser
    290                 295                 300

Asn Glu Glu Ser Ile Ser Ala Met Phe Glu His
305                 310                 315

<210> SEQ ID NO 42
<211> LENGTH: 337
<212> TYPE: PRT
<213> ORGANISM: Arabidopsis thaliana (Mouse-ear cress)

<400> SEQUENCE: 42

Met Ser Glu Asn Ala Ala Asn Asn Ile Met Glu Thr Lys Ile Cys Thr
1               5                   10                  15

Asp Ala Ile Val Ser Glu Leu Gln Lys Lys Val His Leu Phe Tyr
            20                  25                  30

Cys Leu Glu Cys Glu Glu Leu Ala Arg Asn Ile Ala Ala Glu Ser Asp
        35                  40                  45

His Ile Thr Leu Gln Ser Ile Asn Trp Arg Ser Phe Ala Asp Gly Phe
    50                  55                  60

Pro Asn Leu Phe Ile Asn Asn Ala His Asp Ile Arg Gly Gln His Val
65                  70                  75                  80

Ala Phe Leu Ala Ser Phe Ser Ser Pro Ala Val Ile Phe Glu Gln Ile
                85                  90                  95

Ser Val Ile Tyr Leu Leu Pro Arg Leu Phe Val Ala Ser Phe Thr Leu
            100                 105                 110

Val Leu Pro Phe Phe Pro Thr Gly Ser Phe Glu Arg Met Glu Glu Glu
        115                 120                 125

Gly Asp Val Ala Thr Ala Phe Thr Met Ala Arg Ile Val Ser Asn Ile
```

```
            130                 135                 140
Pro Ile Ser Arg Gly Gly Pro Thr Ser Val Val Ile Tyr Asp Ile His
145                 150                 155                 160

Ala Leu Gln Glu Arg Phe Tyr Phe Ala Asp Gln Val Leu Pro Leu Phe
                165                 170                 175

Glu Thr Gly Ile Pro Leu Leu Thr Lys Arg Leu Gln Gln Leu Pro Glu
            180                 185                 190

Thr Glu Lys Val Ile Val Ala Phe Pro Asp Asp Gly Ala Trp Lys Arg
        195                 200                 205

Phe His Lys Leu Leu Asp His Tyr Pro Thr Val Val Cys Thr Lys Val
    210                 215                 220

Arg Glu Gly Asp Lys Arg Ile Val Arg Leu Lys Gly Asn Pro Ala
225                 230                 235                 240

Gly Cys His Val Val Ile Val Asp Asp Leu Val Gln Ser Gly Gly Thr
                245                 250                 255

Leu Ile Glu Cys Gln Lys Val Leu Ala Ala His Gly Ala Val Lys Val
            260                 265                 270

Ser Ala Tyr Val Thr His Gly Val Phe Pro Lys Ser Ser Trp Glu Arg
        275                 280                 285

Phe Thr His Lys Lys Asn Gly Leu Glu Glu Ala Phe Ala Tyr Phe Trp
    290                 295                 300

Ile Thr Asp Ser Cys Pro Gln Thr Val Lys Ala Ile Gly Asn Lys Ala
305                 310                 315                 320

Pro Phe Glu Val Leu Ser Leu Ala Gly Ser Ile Ala Asp Ala Leu Gln
                325                 330                 335

Ile

<210> SEQ ID NO 43
<211> LENGTH: 318
<212> TYPE: PRT
<213> ORGANISM: Saccharomyces cerevisiae (strain ATCC 204508 / S288c)
      (Baker's yeast)

<400> SEQUENCE: 43

Met Ser Thr Asn Ser Ile Lys Leu Leu Ala Gly Asn Ser His Pro Gly
1               5                   10                  15

Leu Ala Glu Leu Ile Ser Gln Arg Leu Gly Val Pro Leu Ser Lys Val
            20                  25                  30

Gly Val Tyr Gln Tyr Ser Asn Lys Glu Thr Ser Val Thr Ile Gly Glu
        35                  40                  45

Ser Ile Arg Asp Glu Asp Val Tyr Ile Ile Gln Thr Gly Tyr Gly Glu
    50                  55                  60

His Glu Ile Asn Asp Phe Leu Met Glu Leu Leu Ile Leu Ile His Ala
65                  70                  75                  80

Cys Lys Thr Ala Ser Val Arg Arg Ile Thr Ala Val Ile Pro Asn Phe
                85                  90                  95

Pro Tyr Ala Arg Gln Asp Lys Lys Asp Lys Ser Arg Ala Pro Ile Thr
            100                 105                 110

Ala Lys Leu Ile Ala Asn Leu Leu Glu Thr Ala Gly Cys Asp His Val
        115                 120                 125

Ile Thr Met Asp Leu His Ala Ser Gln Ile Gln Gly Phe Phe His Ile
    130                 135                 140

Pro Val Asp Asn Leu Tyr Gly Glu Pro Ser Val Leu Asn Tyr Ile Arg
145                 150                 155                 160
```

```
Thr Lys Thr Asp Phe Asn Asn Ala Ile Leu Val Ser Pro Asp Ala Gly
            165                 170                 175

Gly Ala Lys Arg Val Ala Ser Leu Ala Asp Lys Leu Asp Met Asn Phe
        180                 185                 190

Ala Leu Ile His Lys Glu Arg Gln Lys Ala Asn Glu Val Ser Arg Met
        195                 200                 205

Leu Leu Val Gly Asp Val Ala Gly Lys Ser Cys Leu Leu Ile Asp Asp
    210                 215                 220

Met Ala Asp Thr Cys Gly Thr Leu Val Lys Ala Cys Asp Thr Leu Met
225                 230                 235                 240

Asp His Gly Ala Lys Glu Val Ile Ala Ile Val Thr His Gly Ile Phe
                245                 250                 255

Ser Gly Ser Ala Arg Glu Lys Leu Ile Asn Ser Arg Leu Ser Arg Ile
            260                 265                 270

Val Cys Thr Asn Thr Val Pro Val Asp Leu Asp Leu Asp Ile Val Asp
        275                 280                 285

Gln Val Asp Ile Ser Pro Thr Ile Ala Glu Ala Ile Arg Arg Leu His
    290                 295                 300

Asn Gly Glu Ser Val Ser Tyr Leu Phe Thr His Ala Pro Val
305                 310                 315

<210> SEQ ID NO 44
<211> LENGTH: 427
<212> TYPE: PRT
<213> ORGANISM: Saccharomyces cerevisiae (strain ATCC 204508 / S288c)
      (Baker's yeast)

<400> SEQUENCE: 44

Met Arg Lys Cys Lys Ile Phe Val Gly Asn Ser His Pro Glu Leu Gly
1               5                   10                  15

Asn Met Val Cys Gln Arg Leu Gly Ile Glu Pro Ala Pro Cys Thr Leu
            20                  25                  30

Lys Lys Phe Ala Asn Gly Glu Thr Ser Val Gln Ile Gly Val Ser Val
        35                  40                  45

Arg Asp Glu Asp Val Tyr Val Ile Gln Ser Gly Ser Pro Ser Ile Asn
    50                  55                  60

Asp Asp Ile Met Glu Leu Leu Ile Leu Val Ser Ala Cys Arg Gly Gly
65                  70                  75                  80

Ser Ala Arg Lys Ile Thr Ala Val Ile Pro Gln Phe Pro Tyr Ser Lys
                85                  90                  95

Gln Cys Lys Met Lys Arg His Arg Gly Ala Ile Thr Ala Arg Met Leu
            100                 105                 110

Ala Asn Leu Leu Val Met Ala Gly Ala Asp His Val Val Ser Met Asp
        115                 120                 125

Leu His Ala Ser Gln Met Gln Gly Phe Phe Thr Lys Pro Val Asp Asn
    130                 135                 140

Leu Tyr Gly Gly Pro Ser Leu Ala Lys Trp Ile Arg Glu Asn Val Glu
145                 150                 155                 160

Asp Tyr Glu Asp Ala Val Val Val Ser Lys Asn Pro Gly Gly Thr Lys
                165                 170                 175

Arg Val Thr Ala Leu Ala Asp Ser Leu Lys Ile Asn Phe Ala Met Ile
            180                 185                 190

His Thr Asp Arg Arg Arg Ser Lys Asp Leu Tyr Ser Gln Asn Lys Asp
        195                 200                 205

Leu Gln Gln Leu Lys Leu Arg Lys Gln Ser Met Leu Arg Lys Asn Arg
```

```
                210                 215                 220
Pro Ile Ile Arg Gln Gly Asp His Pro Asn Glu Glu Asn Ile Ile
225                 230                 235                 240

Leu Ser Asn Gly Ile Gln Thr Ala Arg Ile Arg Asn Gly His Val Ile
                245                 250                 255

Gly Asp Asp Glu Ala Asp Asp Glu Asp Ala Ile Leu Glu Ser Asp
            260                 265                 270

Ser Glu Leu His Ser Ile Asp Gly Leu Asp Ser His Gly Leu Gly Gly
            275                 280                 285

Thr Tyr Asp Ala Val Asp Ser Glu Asp Glu Glu Ile Pro Val Leu
            290                 295                 300

Tyr Arg Glu Gln Leu Ile Thr Leu Val Gly Asn Val Arg Gly Arg Ser
305                 310                 315                 320

Ala Ile Ile Leu Asp Asp Met Ile Asp Arg Pro Gly Ser Phe Ile Ser
                325                 330                 335

Ala Ala Glu His Leu Val Gln Asn Cys Gly Ala Lys Lys Val Tyr Val
            340                 345                 350

Val Ala Thr His Gly Ile Phe Thr Gly Asp Cys Leu Glu Glu Leu Glu
            355                 360                 365

Lys Ser Asp Ala Ile Asp Thr Ile Val Val Thr Asn Thr Tyr Pro Ile
370                 375                 380

Ser Gly Glu Arg Ile Ala Gly Ser Lys Lys Leu Val Thr Ile Asp Val
385                 390                 395                 400

Ser Pro Ile Phe Ala Glu Cys Ile Arg Arg Asp His Tyr Gly Glu Ser
                405                 410                 415

Ile Ser Val Leu Phe Asp Ser Leu Ala Ala Leu
                420                 425

<210> SEQ ID NO 45
<211> LENGTH: 320
<212> TYPE: PRT
<213> ORGANISM: Saccharomyces cerevisiae (strain ATCC 204508 / S288c)
      (Baker's yeast)

<400> SEQUENCE: 45

Met Pro Thr Asn Ser Ile Lys Leu Leu Ala Pro Asp Val His Arg Gly
1               5                   10                  15

Leu Ala Glu Leu Val Ala Lys Arg Leu Gly Leu Gln Leu Thr Ser Ser
            20                  25                  30

Lys Leu Lys Arg Asp Pro Thr Gly Glu Val Ser Phe Ser Ile Gly Glu
        35                  40                  45

Ser Val Arg Asp Gln Asp Ile Phe Ile Ile Thr Gln Ile Gly Ser Gly
    50                  55                  60

Val Val Asn Asp Arg Val Leu Glu Leu Leu Met Ile Asn Ala Ser
65                  70                  75                  80

Lys Thr Ala Ser Ala Arg Arg Ile Thr Ala Ile Ile Pro Asn Phe Pro
                85                  90                  95

Tyr Ala Arg Gln Asp Arg Lys Asp Lys Ser Arg Ala Pro Ile Thr Ala
            100                 105                 110

Lys Leu Met Ala Asp Met Leu Thr Thr Ala Gly Cys Asp His Val Ile
        115                 120                 125

Thr Met Asp Leu His Ala Ser Gln Ile Gln Gly Phe Phe Asp Val Pro
    130                 135                 140

Val Asp Asn Leu Tyr Ala Glu Pro Ser Val Val Arg Tyr Ile Lys Glu
145                 150                 155                 160
```

```
Asn Val Asn Tyr Met Asp Ser Ile Ile Ser Pro Asp Ala Gly Gly
            165                 170                 175

Ala Lys Arg Ala Ala Thr Leu Ala Asp Arg Leu Asp Leu Asn Phe Ala
        180                 185                 190

Leu Ile His Lys Glu Arg Ala Arg Ala Asn Glu Val Ser Arg Met Val
            195                 200                 205

Leu Val Gly Asp Val Thr Asp Lys Ile Cys Ile Ile Val Asp Asp Met
        210                 215                 220

Ala Asp Thr Cys Gly Thr Leu Ala Lys Ala Ala Glu Ile Leu Leu Glu
225                 230                 235                 240

Asn Arg Ala Lys Ser Val Ile Ala Ile Val Thr His Gly Val Leu Ser
            245                 250                 255

Gly Arg Ala Ile Glu Asn Ile Asn Asn Ser Lys Leu Asp Arg Val Val
        260                 265                 270

Cys Thr Asn Thr Val Pro Phe Glu Glu Lys Ile Lys Lys Cys Pro Lys
    275                 280                 285

Leu Ala Val Ile Asp Ile Ser Ser Val Leu Ala Glu Ser Ile Arg Arg
        290                 295                 300

Leu His Asn Gly Glu Ser Ile Ser Tyr Leu Phe Lys Asn Tyr Pro Leu
305                 310                 315                 320

<210> SEQ ID NO 46
<211> LENGTH: 335
<212> TYPE: PRT
<213> ORGANISM: Saccharomyces cerevisiae (strain ATCC 204508 / S288c)
      (Baker's yeast)

<400> SEQUENCE: 46

Met Ser Glu Pro Ala Gln Lys Lys Gln Lys Val Ala Asn Asn Ser Leu
1               5                   10                  15

Glu Gln Leu Lys Ala Ser Gly Thr Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
    50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
            85                  90                  95

Ile Leu Lys Ile Val Pro Gly Arg Val Ser Thr Glu Val Asp Ala Arg
        100                 105                 110

Leu Ser Phe Asp Thr Gln Ala Thr Ile Glu Lys Ala Arg His Ile Ile
    115                 120                 125

Lys Leu Phe Glu Gln Glu Gly Val Ser Lys Glu Arg Val Leu Ile Lys
130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
            165                 170                 175

Ala Val Ala Cys Ala Glu Ala Gln Val Thr Leu Ile Ser Pro Phe Val
        180                 185                 190

Gly Arg Ile Leu Asp Trp Tyr Lys Ser Ser Thr Gly Lys Asp Tyr Lys
    195                 200                 205
```

```
Gly Glu Ala Asp Pro Gly Val Ile Ser Val Lys Lys Ile Tyr Asn Tyr
    210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
                260                 265                 270

Arg Val Leu Asp Pro Val Ser Ala Lys Lys Glu Ala Gly Asp Lys Ile
                275                 280                 285

Ser Tyr Ile Ser Asp Glu Ser Lys Phe Arg Phe Asp Leu Asn Glu Asp
290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335
```

<210> SEQ ID NO 47
<211> LENGTH: 603
<212> TYPE: PRT
<213> ORGANISM: Saccharomyces cerevisiae (strain ATCC 204508 / S288c) (Baker's yeast)

<400> SEQUENCE: 47

```
Met Pro Arg Asn Pro Leu Lys Lys Glu Tyr Trp Ala Asp Val Val Asp
1               5                   10                  15

Gly Phe Lys Pro Ala Thr Ser Pro Ala Phe Glu Asn Glu Lys Glu Ser
                20                  25                  30

Thr Thr Phe Val Thr Glu Leu Thr Ser Lys Thr Asp Ser Ala Phe Pro
            35                  40                  45

Leu Ser Ser Lys Asp Ser Pro Gly Ile Asn Gln Thr Thr Asn Asp Ile
50                  55                  60

Thr Ser Ser Asp Arg Phe Arg Arg Asn Glu Asp Thr Glu Gln Glu Asp
65                  70                  75                  80

Ile Asn Asn Thr Asn Leu Ser Lys Asp Leu Ser Val Arg His Leu Leu
                85                  90                  95

Thr Leu Ala Val Gly Gly Ala Ile Gly Thr Gly Leu Tyr Val Asn Thr
            100                 105                 110

Gly Ala Ala Leu Ser Thr Gly Gly Pro Ala Ser Leu Val Ile Asp Trp
            115                 120                 125

Val Ile Ile Ser Thr Cys Leu Phe Thr Val Ile Asn Ser Leu Gly Glu
130                 135                 140

Leu Ser Ala Ala Phe Pro Val Val Gly Gly Phe Asn Val Tyr Ser Met
145                 150                 155                 160

Arg Phe Ile Glu Pro Ser Phe Ala Phe Ala Val Asn Leu Asn Tyr Leu
                165                 170                 175

Ala Gln Trp Leu Val Leu Leu Pro Leu Glu Leu Val Ala Ala Ser Ile
            180                 185                 190

Thr Ile Lys Tyr Trp Asn Asp Lys Ile Asn Ser Asp Ala Trp Val Ala
            195                 200                 205

Ile Phe Tyr Ala Thr Ile Ala Leu Ala Asn Met Leu Asp Val Lys Ser
            210                 215                 220

Phe Gly Glu Thr Glu Phe Val Leu Ser Met Ile Lys Ile Leu Ser Ile
225                 230                 235                 240

Ile Gly Phe Thr Ile Leu Gly Ile Val Leu Ser Cys Gly Gly Gly Pro
```

```
                    245                 250                 255
His Gly Gly Tyr Ile Gly Gly Lys Tyr Trp His Asp Pro Gly Ala Phe
            260                 265                 270

Val Gly His Ser Ser Gly Thr Gln Phe Lys Gly Leu Cys Ser Val Phe
            275                 280                 285

Val Thr Ala Ala Phe Ser Tyr Ser Gly Ile Glu Met Thr Ala Val Ser
            290                 295                 300

Ala Ala Glu Ser Lys Asn Pro Arg Glu Thr Ile Pro Lys Ala Ala Lys
305                 310                 315                 320

Arg Thr Phe Trp Leu Ile Thr Ala Ser Tyr Val Thr Ile Leu Thr Leu
                325                 330                 335

Ile Gly Cys Leu Val Pro Ser Asn Asp Pro Arg Leu Leu Asn Gly Ser
            340                 345                 350

Ser Ser Val Asp Ala Ala Ser Ser Pro Leu Val Ile Ala Ile Glu Asn
            355                 360                 365

Gly Gly Ile Lys Gly Leu Pro Ser Leu Met Asn Ala Ile Ile Leu Ile
            370                 375                 380

Ala Val Val Ser Val Ala Asn Ser Ala Val Tyr Ala Cys Ser Arg Cys
385                 390                 395                 400

Met Val Ala Met Ala His Ile Gly Asn Leu Pro Lys Phe Leu Asn Arg
                405                 410                 415

Val Asp Lys Arg Gly Arg Pro Met Asn Ala Ile Leu Leu Thr Leu Phe
            420                 425                 430

Phe Gly Leu Leu Ser Phe Val Ala Ala Ser Asp Lys Gln Ala Glu Val
            435                 440                 445

Phe Thr Trp Leu Ser Ala Leu Ser Gly Leu Ser Thr Ile Phe Cys Trp
            450                 455                 460

Met Ala Ile Asn Leu Ser His Ile Arg Phe Arg Gln Ala Met Lys Val
465                 470                 475                 480

Gln Glu Arg Ser Leu Asp Glu Leu Pro Phe Ile Ser Gln Thr Gly Val
                485                 490                 495

Lys Gly Ser Trp Tyr Gly Phe Ile Val Leu Phe Leu Val Leu Ile Ala
            500                 505                 510

Ser Phe Trp Thr Ser Leu Phe Pro Leu Gly Gly Ser Gly Ala Ser Ala
            515                 520                 525

Glu Ser Phe Phe Glu Gly Tyr Leu Ser Phe Pro Ile Leu Ile Val Cys
            530                 535                 540

Tyr Val Gly His Lys Leu Tyr Thr Arg Asn Trp Thr Leu Met Val Lys
545                 550                 555                 560

Leu Glu Asp Met Asp Leu Asp Thr Gly Arg Lys Gln Val Asp Leu Thr
                565                 570                 575

Leu Arg Arg Glu Glu Met Arg Ile Glu Arg Glu Thr Leu Ala Lys Arg
            580                 585                 590

Ser Phe Val Thr Arg Phe Leu His Phe Trp Cys
            595                 600
```

<210> SEQ ID NO 48
<211> LENGTH: 417
<212> TYPE: PRT
<213> ORGANISM: Schizosaccharomyces pombe (strain 972 / ATCC 24843)
      (Fission yeast)

<400> SEQUENCE: 48

```
Met Ala Leu Leu Pro Phe Phe Asp Leu Thr Asn Phe Glu Ser Asp Ala
1               5                   10                  15
```

```
Ser Glu Glu Leu Gly Trp Leu Lys Tyr Val Gly Arg Val Gln Thr Arg
            20                  25                  30

Val Phe Pro Gln His Phe Lys Asp Asn Leu Glu Lys Val Arg Lys Ile
            35                  40                  45

Ser Glu Thr Ile Asp Val Ile Val Asp Thr Thr Ala Glu Leu Gly Pro
 50                  55                  60

Glu Ala Cys Val Asn Leu Leu Asn Ala Gly Ala Leu Ala Ile Leu Val
 65                  70                  75                  80

Asn Glu Glu Met Leu Asn Glu Leu Ala Asp Ile Ser Pro Asn Arg Leu
                 85                  90                  95

Val Leu Lys Thr Asp Thr Thr Asp Ile Gly Lys Ile Glu Lys Leu Ser
            100                 105                 110

Gln Val Ala Gly Ser Ile Gln Trp Ile Gly Ser Ala Glu Asn Tyr Pro
            115                 120                 125

Pro Asp Phe Phe Glu Arg Ala Ser Lys Ile Ile His Lys Ala Val Met
130                 135                 140

Pro Glu Gly Gly Gly Arg Thr Leu Tyr Leu Glu Phe Pro Glu Gln Pro
145                 150                 155                 160

Ser Met Glu Val Leu Lys Ser Phe Ser Val His Ser Val Val Pro Val
            165                 170                 175

Leu Ser Ser Ser Phe Leu Thr Val Lys Pro Ala Glu Glu Pro Lys Lys
            180                 185                 190

Leu Ser Leu Ala Asp Leu Ile Leu Ile Ser Ala Asn Thr Asp Arg Glu
            195                 200                 205

Asp Gly Leu Phe Ser Thr Leu Val Val Asn Glu Leu Gly Ile Ala Leu
            210                 215                 220

Gly Leu Val Tyr Ser Ser Lys Glu Ser Val Ala Glu Ser Leu Lys Thr
225                 230                 235                 240

Gly Thr Gly Val Tyr Gln Ser Arg Lys Arg Gly Leu Trp Tyr Lys Gly
            245                 250                 255

Ala Ser Ser Gly Ala Val Gln His Leu Ile His Ile Asp Val Asp Cys
            260                 265                 270

Asp Glu Asp Cys Leu Arg Phe Val Val Tyr Gln Thr Gly Lys Gly Phe
            275                 280                 285

Cys His Leu Asp Thr Leu His Cys Phe Gly Gln Ala Ser Gly Leu Cys
            290                 295                 300

Gln Leu Glu Lys Thr Leu Ile Asp Arg Lys Asn Asn Ala Pro Glu Gly
305                 310                 315                 320

Ser Tyr Thr Ala Arg Leu Phe Ser Asp Pro Lys Leu Leu Arg Ala Lys
            325                 330                 335

Ile Met Glu Glu Ala Glu Leu Cys Asp Ala Thr Thr Lys Glu Asn
            340                 345                 350

Val Ile Trp Glu Met Ala Asp Leu Met Tyr Phe Ala Ile Thr Arg Cys
            355                 360                 365

Val Gly Ser Gly Val Ser Leu Asn Asp Ile Ser Arg His Leu Asp Leu
            370                 375                 380

Lys His Arg Lys Val Thr Arg Arg Lys Gly Asp Ala Lys Val Ala Trp
385                 390                 395                 400

Gln Glu Lys Leu Lys Asp Lys Gly Val Ala Asn Thr Ser Tyr Thr
                405                 410                 415

Ala
```

```
<210> SEQ ID NO 49
<211> LENGTH: 316
<212> TYPE: PRT
<213> ORGANISM: Oenococcus oeni (Leuconostoc oenos)

<400> SEQUENCE: 49
```

Met Ser Glu Phe Asp Lys Lys Leu Asn Thr Leu Gly Val Asp Arg Ile
1               5                   10                  15

Ser Val Ser Pro Tyr Lys Lys Trp Ser Arg Gly Tyr Leu Glu Pro Gly
            20                  25                  30

Asn Val Gly Asn Gly Tyr Val Ser Gly Leu Lys Val Asp Ala Gly Val
        35                  40                  45

Ile Asp Lys Thr Asp Asp Met Ile Leu Asp Gly Ile Val Ser Tyr Asp
50                  55                  60

Arg Ala Glu Thr Lys Asn Ala Tyr Ile Gly Gln Ile Asn Met Thr Thr
65                  70                  75                  80

Ala Ser Ser Phe Ser Gly Val Gly Gly Thr Val Leu Gly Tyr Asp Ile
                85                  90                  95

Leu Arg Asn Pro Glu Val Asp Lys Ala Lys Pro Leu Phe Thr Glu Lys
            100                 105                 110

Gln Trp Asp Gly Ser Glu Leu Pro Ile Tyr Asp Ala Lys Pro Leu Gln
        115                 120                 125

Asp Thr Leu Val Glu Tyr Phe Gly Thr Lys Asp Met Arg His Tyr
130                 135                 140

Pro Ala Pro Gly Ala Phe Val Cys Cys Ala Asn Lys Gly Val Thr Ala
145                 150                 155                 160

Glu Arg Pro Lys Asn Asp Ala Asp Met Lys Pro Gly Gln Gly Tyr Gly
                165                 170                 175

Val Trp Ser Ala Ile Ala Ile Ser Phe Ala Lys Asp Pro Thr Lys Tyr
            180                 185                 190

Ser Ser Met Tyr Val Glu Asp Ala Gly Val Trp Glu Thr Pro Asn Glu
        195                 200                 205

Asp Glu Leu Ile Glu Tyr Leu Lys Gly Arg Arg Asn Ala Met Ala Lys
210                 215                 220

Ser Ile Ala Ala Cys Gly Glu Asn Thr Ala Ala Glu Asn Gly Gly Ala
225                 230                 235                 240

Val Phe Thr Ser Ser Trp Ile Gly Phe Ala His Ala Met Met Lys Pro
                245                 250                 255

Gly Gln Val Gly Asn Ala Ile Thr Val Ala Pro Tyr Ile Ala Met Pro
            260                 265                 270

Val Asp Ser Ile Pro Gly Gly Ser Ile Leu Thr Pro Thr Asp Met
        275                 280                 285

Asp Ile Met Gln Asn Leu Thr Met Pro Glu Trp Leu Asp Lys Met Gly
290                 295                 300

Tyr Gln Pro Leu Thr Lys Gly Gly Asn Ile Asn Tyr
305                 310                 315

```
<210> SEQ ID NO 50
<211> LENGTH: 283
<212> TYPE: PRT
<213> ORGANISM: Lactobacillus aviarius subsp. aviarius DSM 20655

<400> SEQUENCE: 50
```

Met Glu Pro Gly Asn Ile Gly Asn Gly Tyr Val Thr Gly Leu Lys Val
1               5                   10                  15

Asp Ala Gly Val Arg Asp Lys Thr Asp Asp Val Leu Asp Gly Ile

```
            20                  25                  30
Val Ser Tyr Asp Arg Ala Glu Thr Lys Asn Ala Tyr Ile Gly Gln Ile
        35                  40                  45

Asn Met Thr Thr Ala Ser Ser Phe Thr Gly Pro Gln Gly His Val Val
    50                  55                  60

Gly Tyr Asp Ile Leu Arg Asn Pro Glu Val Asp Lys Val Lys Pro Leu
65                  70                  75                  80

Phe Val Glu Lys Gln Trp Asp Gly Ser Asp Leu Pro Ile Tyr Asp Ala
                85                  90                  95

Lys Pro Leu Gln Asp Ala Leu Val Glu Tyr Phe Gly Met Glu Gln Glu
            100                 105                 110

Arg Arg His Tyr Pro Ala Pro Gly Ser Phe Ile Val Cys Ala Asn Lys
        115                 120                 125

Gly Val Thr Ala Glu Arg Pro Lys Ala Asp Glu Pro Leu Lys Pro Gly
    130                 135                 140

Gln Gly Tyr Gly Val Trp Ser Ala Ile Ala Ile Ser Phe Ala Lys Asp
145                 150                 155                 160

Pro Ser Lys Asn Ser Ser Met Phe Ile Glu Asp Ala Gly Val Trp Glu
                165                 170                 175

Thr Pro Asn Glu Asp Glu Leu Ile Glu Tyr Leu Asn Gly Arg Arg Lys
            180                 185                 190

Ala Ile Ala Lys Ser Ile Ala Glu Cys Gly Gln Asp Ala Asp Thr Ala
        195                 200                 205

Phe Glu Ser Ser Trp Ile Gly Phe Ala His Val Met Met Lys Pro Gly
    210                 215                 220

Gln Ile Gly Asn Ala Ile Thr Val Gly Pro Tyr Phe Ser Leu Pro Val
225                 230                 235                 240

Asp Ser Ile Pro Asn Gly Ser Ile Leu Thr Pro Asp Lys Asp Met Glu
                245                 250                 255

Ile Met Glu Asn Leu Ser Leu Pro Glu Trp Leu Asp Lys Met Gly Tyr
            260                 265                 270

Glu Ser Leu Val Lys Lys Asn Asn Val Thr Tyr
        275                 280

<210> SEQ ID NO 51
<211> LENGTH: 387
<212> TYPE: PRT
<213> ORGANISM: Chromobacterium sp. LK1

<400> SEQUENCE: 51

Met Ser Leu Ser Pro Leu Asp Gln Asn Arg Ile Glu Ser Phe Trp Gln
1               5                   10                  15

Tyr Cys Leu Gln His Gln Tyr Phe Asn Leu Ala Tyr Pro Glu Ser Ala
            20                  25                  30

Asp Phe Asp Tyr Ala Pro Leu His Arg Phe Leu Arg Phe Ser Ile Asn
        35                  40                  45

Asn Cys Gly Asp Trp Asn Glu Ser Ser Asn Tyr Leu Leu Asn Ser Phe
    50                  55                  60

Asp Phe Glu Arg Glu Val Met His Phe Ala Glu Leu Phe His Ile
65                  70                  75                  80

Pro Phe Asp Glu Ser Trp Gly Tyr Val Thr Asn Gly Thr Glu Gly
                85                  90                  95

Asn Met Phe Gly Cys Tyr Leu Ala Arg Glu Leu Phe Pro Asp Ala Thr
            100                 105                 110
```

```
Leu Tyr Tyr Ser Lys Asp Ser His Tyr Ser Val Ala Lys Ile Ile Lys
            115                 120                 125

Leu Leu Arg Ile Lys Ser Arg Ala Val Asp Ser Leu Pro Ser Gly Glu
    130                 135                 140

Ile Asp Tyr Asp Asp Leu Val Ala Lys Ile Gln Gln Asp Gln Glu Arg
145                 150                 155                 160

His Pro Ile Val Phe Val Asn Val Gly Thr Thr Met Lys Gly Ala Val
                165                 170                 175

Asp Asp Ile Gly Val Ile Gln His Lys Leu Ala Glu Ala Gly Ile Pro
            180                 185                 190

Arg Gln Asp Tyr Tyr Leu His Ala Asp Ala Ala Leu Ser Gly Met Ile
    195                 200                 205

Leu Pro Phe Val Asp Ala Pro Gln Pro Tyr Ser Phe Ala Asp Gly Ile
    210                 215                 220

Asp Ser Ile Ser Val Ser Gly His Lys Met Ile Gly Ser Pro Met Pro
225                 230                 235                 240

Cys Gly Ile Val Leu Ala Lys Arg Ser Asn Val Ser Arg Ile Ser Val
                245                 250                 255

Glu Ile Asp Tyr Ile Ser Ala Lys Asp Gln Thr Ile Ser Gly Ser Arg
                260                 265                 270

Asn Gly His Thr Pro Met Met Leu Trp Ala Ala Ile Lys Ser Arg Pro
            275                 280                 285

Leu Ala Glu Trp Arg Arg Lys Val Arg His Cys Leu Asp Met Ala Gln
    290                 295                 300

Tyr Ala Ile Asp Arg Leu Gln Ala Ala Gly Ile Gln Ala Trp Arg Cys
305                 310                 315                 320

Lys Asn Ser Ile Thr Val Val Phe Pro Ser Pro Ser Glu Pro Val Cys
                325                 330                 335

Asp Lys His Gly Leu Ala Arg Ser Gly Gly Thr Ala His Leu Ile Thr
            340                 345                 350

Thr Pro His His His Asp Ser Gln Arg Leu Asp Arg Leu Leu Asp Asp
    355                 360                 365

Ile Val Gln Asp Leu Gly Ala Met Thr Ala Pro Ala Gly Ala Thr Met
370                 375                 380

Ser Ala Ala
385

<210> SEQ ID NO 52
<211> LENGTH: 1149
<212> TYPE: DNA
<213> ORGANISM: Artificial
<220> FEATURE:
<223> OTHER INFORMATION: Codon-optimized and/or mutated sequence

<400> SEQUENCE: 52
atgattctgt cccccgccga ccaagaaaga attgagacct tctggaatta ctgcctgaaa      60
catcagtact ttaacattgg ttaccctgag tctgccgact cgattactc cgccctgttt     120 cggttcttca aattttctat taacaactgc ggcgactgga aggactactc caactacgcc     180
ctgaactcct tgactttga aaggacgtt atggcttatt cgctgagat ctttcagatc       240 cccttcgaag agtcgtgggg atatgtcacc aatggtggca cagaaggcaa catgtttggt     300
tgttaccttg caagagagct ctttagcgat tcgaccctct actactctaa ggatacacac     360
tattccgtgg gcaagatcgc caagcttctt cagatgaaat cgtgcgtcat cgaatcgctc     420
gacaacggcg aaattgacta cgacgacctc attcacaaga tcaagacaaa taaggaatcg     480
```

```
catcctatca tctttgccaa cattggtaca actatgactg cgctattga cgacattgag    540
atgatccagg agcgactcgc tcagatcgga attatgcgac gagattacta catccacgct    600
gacgcagccc tgtctggtat gattctgcct ttcgtcgacc atcctcaggc cttctctttt    660
gctcatggta tcgatagcat ctgcgtgtcg ggacataaga tgatcggatc ccctattcct    720
tgtggtattg tcgtcgctaa gcggcagaat gtggagcgaa tttccgtgga cgtggattac    780
atctctacac gagatcaaac tatttctggt tctcgaaacg ccataccgt gctgctgatg    840
tgggcagcca tccgttcgca gaccaacctc cagagacgac aacgaatcca gcactgtctg    900
aaaatggctc agtatgctgt cgatcgattt caagctgtcg gaatccctgc ctggcgaaac    960
cccaattcca tcactgtcgt ttttccctgt ccttctgagc acatttggaa gaagcactac   1020
ctggcaacat ctggcaacat ggctcacctt atcaccacag cccaccaccg agatacgcga   1080
cagattgact ctctcatcga tgacgtcatt tttgatcttc aaggtgcttc caagcgaacc   1140
gtcggcttc                                                           1149
```

<210> SEQ ID NO 53
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 53

```
atggatctcg tcaaccatct gaccgaccgt ctcctgttcg ctatcccaa aaagggtcgg      60
ctctattcca agtctgtgtc gatcctcaac ggagctgaca ttacgtttca tcgatctcaa    120
cggctggata ttgctctctc cacgtccctg cctgtcgccc tgattttcct gcctgccgct    180
gacattccca ctttcgtggg cgagggtaag tgtgacctcg gtatcaccgg tgtcgatcag    240
gtgagagagt ctgacgtcga cgtggacctg gccatcgatc tgcagttcgg aaactgcaag    300
cttcaggtgc aggtgcctgt gaacggtgag tacaagaagc ctgagcagct gatcggtaag    360
accatcgtca catcctttgt taagctggca gagaaatact ttgctgacct ggagggcact    420
accgtcgaga agatgaccac ccgaatcaaa ttcgtttcgg ttctgtcga ggcttcctgc    480
gctctgggca tcggtgacgc cattgtcgac cttgttgagt ctggagagac catgagagcc    540
gctggactgg tggacattgc caccgttctg tcgacttcgg cctaccttat cgagtctaag    600
aaccccaaga gcgacaagtc cctgatcgca actattaaga gcagaattga gggtgttatg    660
acagcacagc ggtttgtgtc ctgcatctat aatgctcccg aggataaact cccgaactg    720
ctcaaggtta cgcccggcag acgagccccc accatcagca agatcgacga tgagggttgg    780
gtcgccgttt cgtctatgat cgagagaaag acaaagggag tggtcctgga cgagcttaag    840
cgactgggtg cctctgacat tatggtcttt gagatttcca actgcagagt c             891
```

<210> SEQ ID NO 54
<211> LENGTH: 1149
<212> TYPE: DNA
<213> ORGANISM: Artificial
<220> FEATURE:
<223> OTHER INFORMATION: Codon-optimized and/or mutated sequence

<400> SEQUENCE: 54

```
atgattcttt caccggcgga tcaggaacgc attgagacct tctggaacta ctgcctgaaa     60
caccagtact tcaatatcgg ctatccagaa tcagcagatt tcgattacag cgcgctgttc    120
```

```
cgtttcttca aattttcgat aaataactgc ggagactgga aggactattc gaattacgcc      180
ttaaattcat ttgatttcga gaaagatgtg atggcctact tcgctgaaat ctttcaaatt      240
ccgttcgaag aatcatgggg ctatgtaaca aacggcggta ctgagggaaa catgtttggc      300
tgttatctgg caagagaact cttttccgat tcaaccctgt actattcaaa agatacacac      360
tattcagtcg gcaaaattgc gaaattactt caaatgaaaa gttgtgtcat tgagagttta      420
gataacggcg aaatcgacta tgatgattta atacataaaa ttaaaacaaa taagaaatca      480
catccaatca tatttgcgaa tatcggaact acaatgacgg gagctattga cgacatcgag      540
atgatacaag agagattagc acaaattgga attatgcgcc gcgattacta tattcacgca      600
gacgcggcct tgtcagggat gatacttcct tttgttgatc acccgcaggc attttctttc      660
gcgcatggta tcgatagcat ctgtgtttca ggacataaaa tgattgggag cccgatccca      720
tgtggtattg tcgtagcgaa aagacagaat gtcgaaagaa taagcgttga tgtggattac      780
attagcacac gcgaccagac aattagcggc tcacgtaacg gacatacagt cctgttaatg      840
tgggctgcta ttagatccca aactaattta caaagaagac aacgcatcca acattgcctt      900
aaaatggcac agtacgcggt agacagattt caagctgttg aattccggc gtggagaaac      960 ccgaattcaa ttactgtagt cttccgtgc ccttcggaac atatttggaa gaagcattat     1020
ttagcgacga gcgggaacat ggcccatctt atcacgacgg ctcaccacag agatacacgt     1080
caaattgatt ctttgattga tgatgtaatt ttcgatctgc aaggagccag taagagaacc     1140
gtgggattt                                                            1149
```

<210> SEQ ID NO 55
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 55

```
atggatttag ttaatcactt gaccgataga ttattgtttg cgattcctaa aaaaggtcgg       60
ctttactcca aaagcgtgag cattttaaat ggcgcagata ttacctttca tagatctcag      120
cgtctggata tagcgctctc cacaagcctg ccggtggcgc ttatattctt accggcggca      180
gacatcccta ctttcgtggg ggaaggaaag tgcgacctcg aatcacagg agtgagatcaa      240 gttcgcgaat cggatgtaga tgttgacctt gccatcgatt tacaatttgg aaattgcaag      300
ctccaagttc aggtacctgt gaacggagaa tataagaagc cggaacagtt aattggcaaa      360
actattgtca cttcttttgt aaagctggcg aaaaatatt tcgcggactt ggaaggtaca      420
accgtcgaaa aaatgactac acggatcaaa tttgtaagcg ggtctgttga agcaagctgc      480
gctctgggta ttggtgacgc gatagtggac ctggtggaaa gtggggaaac gatgcgagca      540
gcaggattgg tagatatcgc tacagtgtta tcaactagtg cataccctgat agaatccaaa      600 aaccctaaat cggataaatc gcttatcgcc acaataaaat cacgcattga aggagtaatg      660
acggctcaac gatttgtgtc ctgcatatat aacgctcctg aggataaatt gccggagctg      720
ctgaaggtga caccgggccg agagccccg accataagca aaatagacga cgagggctgg      780
gttgccgtaa gcagtatgat cgaacgcaag acgaagggag tagttttgga cgaacttaag      840
cgcttagggg catccgatat aatggtgttt gaaattagca actgtagagt c              891
```

<210> SEQ ID NO 56
<211> LENGTH: 1149

| <212> TYPE: DNA
| <213> ORGANISM: Artificial
| <220> FEATURE:
| <223> OTHER INFORMATION: Codon-optimized and/or mutated sequence

<400> SEQUENCE: 56

```
atgatcctat ctcctgctga ccaagaaaga attgaaacct tttggaacta ctgtttgaaa      60
catcaatact tcaacatcgg ttaccctgag agcgcagact ttgactatag tgcattattt     120
agattttca aattctctat taacaactgc ggagactgga agattactc caattacgct       180
ttaaactcct ttgattttga aaggatgtg atggcatact tgcagaaat attccaaatt       240
cctttcgaag aaagctgggg atacgttaca aatggtggta cagaaggtaa catgttcggt     300
tgttacttag cgagagaatt gttcagtgac tccacattgt attatagcaa agacactcat     360
tactcagtag gtaagattgc caaacttttg caaatgaagt catgcgtcat agaatcttta     420
gacaatgggg aaatagacta cgatgatctg atccataaga ttaaaactaa caaggaaagc     480
catccaatca tattcgcaaa tattggaaca acaatgacag gagcaatcga cgacatcgaa     540
atgatacaag aaagattagc ccaaataggc ataatgcgta gagactatta catacatgct     600
gacgcagcat tgagtggtat gattttgcct tttgtcgatc acccacaggc gttcagtttt     660
gctcatggta tcgatagtat atgtgtctcc ggacacaaga tgattggctc accgattcca     720
tgcggcattg ttgttgcaaa aagacagaac gtcgaaagaa ttagtgtgga cgtcgactat     780
atatcaacca gagaccaaac cattagcggt tcaagaaatg gccacacagt acttctgatg     840
tgggccgcga ttcgtagtca aacgaactta caaagaaggc aaagaattca acattgttta     900
aagatggcgc aatacgccgt cgacagattt caggctgtag gtatacctgc gtggagaaat     960
ccaaattcaa ttaccgtggt tttccatgt ccttctgaac atatctggaa aaaacattac    1020
ttagccacta gcggtaacat ggcacaccta atcactaccg cccatcatag agatacaaga    1080
caaattgatt ccttaattga tgatgtcatt tttgacttac agggagcttc taagaggacc    1140
gttggttttc                                                          1149
```

<210> SEQ ID NO 57
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 57

```
atggatttgg tcaaccacct tactgacagg cttttgttcg ccattccaaa gaaaggcagg      60
ttatactcca aatctgtttc aatactaaat ggagcagaca ttacttttca tcgtagccag     120
agactagata ttgctttatc aacctcactt ccagtagcac ttatttttt acccgcagca     180
gatataccaa catttgtagg tgagggtaag tgtgatttag gtattacagg ggttgaccaa     240
gttagagaaa gcgatgtcga tgtagacctt gctatcgact gcagttcgg aaattgcaag     300
ttacaagtgc aggtgccagt taatggcgag tataagaagc cggaacagtt aataggaaaa     360
acaatagtta cctcttttgt gaagttagct gaaaaatact tgccgacttt agaaggtacg     420
actgtggaaa aatgacaac aagaattaag tttgttagtg gttctgtcga agcatcctgc     480
gcactaggaa ttggtgatgc tattgtagac ttagtagaga gtggagaaac aatgagggcc     540
gcaggttttgg tagatattgc taccgtatta tcaacatccg catatcttat tgagtctaaa     600
aatcctaaat ccgacaaaag tttgatcgct actataaagt caaggattga gggtgtcatg     660
```

| | |
|---|---|
| acagctcaga gatttgtatc atgcatctat aatgctcccg aagacaagct gcctgaatta | 720 |
| ctaaaggtaa caccgggaag aagggcacca actatcagca agattgatga tgaaggatgg | 780 |
| gtcgccgttt catcaatgat tgaaagaaag acaaaaggtg tggttcttga cgaacttaaa | 840 |
| cgtttgggag ccagtgatat catggtcttc gaaatttcta attgccgtgt g | 891 |

<210> SEQ ID NO 58
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 58

| | |
|---|---|
| atgctggaca acacaagact gcgaattgcc atccagaagt ctggtagact cagcgatgat | 60 |
| tccagagagc ttctggcccg ttgtggcatt aaaatcaacc ttcatactca gcggctcatc | 120 |
| gccatggccg aaaacatgcc tatcgatatt cttagagtcc gagatgatga catccctgga | 180 |
| ctggtcatgg acggcgtcgt cgatctgggt attattggcg aaaacgtgct cgaggaagag | 240 |
| ctcctcaacc gacgtgccca gggagaggat ccccgatacc tcaccctccg aagactcgac | 300 |
| ttcggaggct gccgactctc gcttgccacc cccgtcgacg aggcttggga cggacctgcc | 360 |
| gcccttgatg gtaagcgaat tgccacctct tacccccacc tgctcaagcg ttacctggat | 420 |
| cagaagggag tctcgttcaa gtcgtgcctg cttaacggta gcgtcgaggt ggctccccga | 480 |
| gctggcctcg ccgacgccat ttgtgatctg gtctccactg gcgccaccct cgaagccaat | 540 |
| ggtcttcggg aggttgaggt gatttaccga tccaaggctt gtctcattca gcgagatggc | 600 |
| gagatggccc aatccaaact gattgacaag ctcctgaccc gaattcaggg agtgatccag | 660 |
| gcccgagaat cgaagtacat catgatgcac gccccttccg aacgactcga ggaggtcatc | 720 |
| gccctgcttc ccggcgctga gcgtcccacc attcttcccc tggctggtga gcaacagcga | 780 |
| gttgccatgc acatggtttc ctcggaaact ctttttttggg agacaatgga gaagctcaag | 840 |
| gccctcggcg cctcgtctat cctcgtcctt cctatcgaga agatgatgga g | 891 |

<210> SEQ ID NO 59
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 59

| | |
|---|---|
| atgttggata cacacgcct gagaatagcc attcagaagt ctggtagatt gtcagacgat | 60 |
| agtcgggaat gctggctcg gtgtggaatt aagattaacc tgcatacgca gcgcctgatc | 120 |
| gcgatggctg aaaatatgcc aattgatatt cttcgtgtga gagacgatga tattccaggt | 180 |
| ttagtaatgg atggcgttgt cgatcttggc atcataggag aaaatgttct ggaggaggaa | 240 |
| ttattgaacc ggcgcgcaca gggcgaggat cctcgatatt taacattacg cgactggac | 300 |
| tttggtggat gccggttgag cttagcgacg ccagtcgacg aggcttggga tggaccggct | 360 |
| gctttggatg gaaaacgtat tgcgacctca taccctcatc tgttaaaacg ctatcttgac | 420 |
| cagaaaggag tatcctttaa atcatgtctg ctgaatggat ctgtggaggt ggcccctcgt | 480 |
| gcaggattgg ccgatgccat ctgcgatctt gtgagcacag gtgcaactct tgaggcaaat | 540 |
| gggctcagag aagtcgaagt aatttaccgt agcaaagctt gcctgatcca gcgcgatgga | 600 |
| gaaatggcgc agtctaagtt aattgacaaa ttgctgactc gaatacaagg agttatccaa | 660 |

| | |
|---|---|
| gctagagaat ctaaatacat catgatgcat gctccatctg agcgactgga ggaagtaatt | 720 |
| gcgcttcttc ctggggcgga aagaccgact atcttgccgt tagcaggtga acaacagcgg | 780 |
| gttgccatgc acatggtttc ctctgaaact ctgttttggg aaaccatgga aaaactgaaa | 840 |
| gcgttgggag cgtcctctat ccttgttctt cctatcgaga aatgatggaa | 891 |

<210> SEQ ID NO 60
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 60

| | |
|---|---|
| atgctggaca atacaagatt aagaatagca atacagaaat caggtagact gtcagacgat | 60 |
| agccgtgagc ttttagccag atgtggcata aaaattaatt tgcacacaca aaggcttatt | 120 |
| gccatggccg aaaatatgcc gatagacata ttaagagtga gatgatgatga tacccggg | 180 |
| ttggttatgg atggtgttgt cgatttgggt atcattggtg agaacgtgtt ggaagaagaa | 240 |
| ctgttaaaca aagagctca gggagaggac cccagatatt aactttaag gcgtctggat | 300 |
| tttggtggtt gtcgtctttc cttagccaca ccagtagacg aagcttggga tggtccagca | 360 |
| gcactagacg gtaaaggat tgcgacatcc tacccacatt tgctaaagcg ttatttggac | 420 |
| caaaaaggcg tttcttttaa gtcttgtcta ttaaatggct cagtagaagt ggctcctaga | 480 |
| gctggtctgg ctgatgcaat ctgtgattta gtgtctacag gtgcaacact agaagctaac | 540 |
| ggcttaagag aagtggaggt catttatagg tcaaaggctt gtttgatcca agagacgga | 600 |
| gaaatggccc aatcaaaatt aattgataaa ctgcttacta gaattcaagg tgtgatccaa | 660 |
| gcaagagaat ccaaatatat catgatgcat gcaccgtcag agcgtctgga ggaggtgatc | 720 |
| gccttgttac caggtgcgga aagaccaacg attttgcccc ttgctggtga acaacaaaga | 780 |
| gtggccatgc acatggtatc ctctgaaacg ttattctggg agacgatgga aaaattaaag | 840 |
| gcattaggtg caagttctat attagtactg ccaatagaaa agatgatgga g | 891 |

<210> SEQ ID NO 61
<211> LENGTH: 1149
<212> TYPE: DNA
<213> ORGANISM: Artificial
<220> FEATURE:
<223> OTHER INFORMATION: Codon-optimized and/or mutated sequence

<400> SEQUENCE: 61

| | |
|---|---|
| atgatcctta gccctgccga ccaagaacgt atcgaaactt tctggaacta ctgcttgaaa | 60 |
| catcagtact ttaacatcgg atatccggag tctgccgact ttgactacag cgcactttc | 120 |
| cgattcttca agttctcaat caacaattgc ggtgactgga aggattattc caactacgcc | 180 |
| ctgaactctt tcgatttcga aaagatgta atggcatatt tcgcagagat cttccagatt | 240 |
| cccttgaag aatcgtgggg ctacgtcacc aatggcggca ccgaaggcaa tatgttcgga | 300 |
| tgttacctgg ctcgcgaact cttttccgat tccacacttt attattcgaa ggatacccac | 360 |
| tactcggtgg gcaaaatcgc aaagctcctc cagatgaagt cctgtgttat cgaatctctt | 420 |
| gataacggtg aaatcgacta cgacgatttg attcataaaa tcaaaaccaa caaggagtct | 480 |
| catccaatta tttttgctaa cattggaacc accatgacgg cgctattga cgatatcgaa | 540 |
| atgattcagg aacgcttggc ccagatcgga atcatgcgtc gagattacta tattcatgct | 600 |

```
gatgccgcac tgtcgggtat gatcctccca ttcgtcgatc atccgcaagc ctttccttc      660 gcgcatggta tcgatagcat ctgtgtttcc ggccataaga tgattggctc gcccatcccc      720
tgcggcattg tggtggcaaa gcgccagaat gtcgagcgca tctccgtgga tgtggattat      780
atctctaccc gcgatcaaac catctcgggc tcccgcaacg gtcatactgt cttgctgatg      840
tgggcggcaa tccgttcaca aacgaacctc cagcgtcgcc agcgcatcca gcactgtctg      900
aaaatggcac aatacgcagt ggatcgcttt caagcagtcg gaattccagc atggcgcaac      960
ccgaactcca tcaccgttgt gttcccatgc ccgagcgaac acatctggaa gaagcactac     1020
ctggctacca gcggcaacat ggcccacctt atcaccactg cacatcaccg tgatactcgt     1080
cagatcgact cgctgatcga cgatgtgatc ttcgatctgc aaggtgcaag caaacgtact     1140
gtcggtttc                                                            1149

<210> SEQ ID NO 62
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 62
atgttggata cacacgcct gcgcatcgct atccagaagt caggtcgtct gtcggacgac        60
tcccgcgagc tcctcgctcg ctgtggcatt aaaatcaacc tgcatacccca acgcctgatt      120 gcgatggctg agaacatgcc tatcgacatc cttcgtgtcc gcgatgatga cattccaggt      180
cttgtgatgg atggcgttgt cgacttgggc atcattggcg aaaacgtgct cgaggaagaa      240
ttgctgaatc gccgagcgca aggcgaggac cctcgctatc tgaccctccg tcgactggat      300
tttggtggct gccgcctctc tttggcaact ccggtggacg aggcatggga tggtcctgcc      360
gcccttgatg gtaaacgcat cgccacttct tacccccact tgttgaaacg ctatttggat      420
caaaaaggcg tttcttttaa gagctgtttg cttaacggct cagtggaggt cgctcctcgc      480
gccggactgg cagatgctat ctgtgacctt gtttctaccg gtgctacctt ggaagccaac      540
ggattgcgcg aggttgaagt catctaccgc tccaaggcgt gcctcattca gcgagatggt      600
gaaatggccc agtccaagct tatcgataaa ctgttgactc gcattcaggg cgtgattcag      660
gcgcgcgaat cgaaatatat catgatgcac gcgccttctg aacgcctgga agaagtgatt      720
gcactgctcc ctggagccga gcgcccaacc atcctgcctc tcgcgggtga gcaacaacgt      780
gtcgccatgc acatggtctc gtctgaaaca ctgttctggg agaccatgga gaaacttaaa      840
gcactgggcg cgtcctcaat ccttgtcctg cccattgaaa agatgatgga a                891

<210> SEQ ID NO 63
<211> LENGTH: 1161
<212> TYPE: DNA
<213> ORGANISM: Artificial
<220> FEATURE:
<223> OTHER INFORMATION: Codon-optimized and/or mutated sequence

<400> SEQUENCE: 63
atgtccctgt ctccctgga tcagaatcga attgagtcct tttggcagta ctgtctccag        60
caccaatact ttaacctcgc ttaccccgag tcggccgatt tgactacgc ccctctgcac       120 cgattcctgc gattctccat caataactgc ggcgattgga acgagagctc caactacctc      180
cttaactcgt tcgacttcga gcgggaggtg atgcatttct tcgccgagct cttccatatt      240
cccttcgacg aaagctgggg ctacgtgacc aacggaggca ccgagggcaa tatgtttggt      300
```

```
tgctacctcg cccgagaact ctttcctgac gcaactctct actacagcaa ggacagccat    360
tactctgtgg ctaagatcat taagctgctg cgaatcaaaa gcagagcagt ggactccctg    420
ccctcgggtg agattgatta cgacgacctc gtggcaaaaa tccagcagga tcaggagcgg    480
caccctatcg tctttgtgaa cgtcggcaca accatgaagg cgccgtcga tgacatcgga    540 gtcattcagc acaagcttgc tgaagccggc attccccggc aggactatta tctgcacgca    600
gatgctgctc tgtcgggcat gattcttccc tttgttgatg cccccagcc ctacagcttt    660 gccgacggaa tcgactcgat ctccgtgtcg ggacacaaga tgatcggatc ccccatgccc    720
tgcggtattg tcctggctaa gcgttccaac gtctcgcgaa tttcggtcga gattgactac    780
atctctgcta aggaccagac catcagcggt cccggaacg tcacacccc catgatgctg    840 tgggccgcca tcaaatctcg acctctggct gagtggcgtc gtaaggtgcg cactgcctg    900 gatatggcac agtatgctat cgatcgactg caggccgccg gtattcaggc ttggcgatgc    960
aagaacagca ttacggttgt tttcccttcg ccatctgagc ccgtctgcga taagcatggc   1020
ctcgcacgat ctggtggtac agctcacctg attaccacgc tcatcacca tgacagccaa   1080 cgactggacc ggcttctgga cgatatcgtt caggacctgg gagccatgac ggctcctgct   1140
ggcgctacca tgagcgccgc t                                              1161

<210> SEQ ID NO 64
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 64
atgctcaaga ttgcagtccc caacaagggt tcgctctccg agagagccat ggagattctg     60
gccgaggccg gctacgccgg cagaggagac tctaagtccc tcaacgtttt cgacgaggcc    120
aacaacgtcg agttcttctt cctccgaccc aaggatattg ctatctacgt tgccggtggc    180
cagctggatc tcggaatcac tggtagagac ctggcccgag attctcaagc cgatgtccac    240
gaagtcctgt ctctgggatt cggctcttcg acattccgat acgcagcccc tgctgacgag    300
gagtggtcga tcgagaagct cgatggcaag cgaatcgcca ccagctatcc aaatctggtt    360
cgagacgacc ttgcagcccg aggactctcg gctgaggtgc tgcgtctcga tggcgccgtc    420
gaggtctcca tcaagcttgg tgttgccgac gctattgctg acgtcgtctc cacgggccga    480
acactgcgac agcaaggtct tgcccctttc ggtgaggtgc tctgcacgtc cgaggccgtc    540
attgtcggac gaaaggatga aaggtcact cctgaacaac agattctgct gcgtcgaatc    600
cagggtattc tgcatgctca gaacttcctc atgctcgatt acaaggtcga ccgggataac    660
ctcgatgccg ctactgccgt cactcccggc ttttctggac ctgccgtctc tcccctcgct    720
cgagacaact gggttgcagt cagagccatg gtgcctagaa gatctgctaa cgctattatg    780
gataagctcg ctggcctggg cgccgaagct atcctggcaa gcgagatcag aattgctcga    840
atc                                                                  843

<210> SEQ ID NO 65
<211> LENGTH: 1161
<212> TYPE: DNA
<213> ORGANISM: Artificial
<220> FEATURE:
<223> OTHER INFORMATION: Codon-optimized and/or mutated sequence
```

```
<400> SEQUENCE: 65
atgtctctaa gtcccttgga ccagaatagg atcgaatctt tttggcaata ttgcttgcag      60
caccaatatt tcaacctggc ctatcctgaa agtgctgatt tcgattacgc acctcttcac     120
agattcttga ggttctctat taataattgc ggtgactgga acgaatcttc aaactacctt     180
ttaaattcct ttgattttga aagggaagtt atgcacttct tcgccgaatt attccacatt     240
ccatttgatg aatcttgggg ctatgtcacc aacggtggta ctgaaggcaa tatgttcgga     300
tgttatcttg cacgtgaatt gtttccagat gctactcttt actactccaa agactcacat     360
tattcagttg ccaagattat taaactgctt aggattaaat ctagagctgt ggacagtctg     420
ccgagtggag aaattgacta cgacgacttg gtggcgaaga tacagcaaga tcaagaacgt     480
catccgatcg ttttcgtcaa cgtcggcaca caatgaagg gagcagtgga cgatataggc      540
gtgattcagc acaaattggc tgaggcaggc atacctcgtc aagattacta tttacatgcc     600
gacgcggcac tttctggcat gatactacca tttgttgatg ctcctcaacc atattctttt     660
gctgatggaa tcgatagcat atctgtatca gggcataaga tgataggttc cccaatgccg     720
tgtggtattg tgttggcgaa gagatctaac gttagcagaa tatctgttga aatagattac     780
atttcagcta aagatcaaac aattagtggt agtagaaacg ccatacacc aatgatgttg      840 tgggcagcca taaaaagcag accgttagcc gagtggaggc gtaaggttcg tcattgcttg     900
gatatggctc agtatgctat agatcgtctt caagccgctg gcattcaagc ttggagatgt     960
aaaaactcca tcactgtcgt tttcccttct ccatccgaac ctgtctgtga caaacacggc    1020
ctagccagaa gtggtggtac tgcacacctg attactacgc cacatcacca tgattctcag    1080
agattagata ggctacttga tgatatcgtt caggatttgg gcgctatgac tgctccagct    1140
ggtgcgacaa tgagcgcagc t                                              1161

<210> SEQ ID NO 66
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 66
atgctgaaaa tagcggtgcc taataagggt tctttatcag aaagagcaat ggaaatacta      60
gctgaagctg gttacgccgg tagggggtgat tctaaatcct tgaacgtgtt cgacgaagca     120
aataatgtag agtttttctt cttgaggccc aaagatattg ctatatatgt tgccggtggt     180
caattagatt taggtattac aggcagagat ttagctaggg attcccaggc agacgtgcat     240
gaagtcttat ctttaggatt cggtagttct acattcaggt acgcagctcc tgcagatgaa     300
gaatggagca ttgaaaaact agatgggaag agaatcgcaa catcctatcc taacctagtt     360
agagatgact tggccgcacg tggtctatca gccgaagttt tgcgtttaga tggtgcagtt     420
gaagtatcta ttaaattagg cgtggctgat gctattgcag atgtagtctc aacaggtcgt     480
acattaagac aacaaggatt ggctcccttc ggggaagttt tgtgtacctc agaagcagtc     540
attgttggca ggaagatga aaagttaca ccggaacagc aaattttatt aagaagaatt       600
cagggcatac tacatgcgca aaattttta atgctagatt ataaggtgga tagagacaac      660
ttggatgcag ctaccgcagt aacacctggt ttttcaggcc cagcagtttc tcctctggcc     720
agagacaatt gggtcgctgt tagagcaatg gtgcctcgta ggagcgcgaa tgccataatg     780
gataagctag ctggtttagg agcagaagcc attttggctt ctgagatcag aatcgcaagg     840
```

```
att                                                            843
```

<210> SEQ ID NO 67
<211> LENGTH: 1161
<212> TYPE: DNA
<213> ORGANISM: Artificial
<220> FEATURE:
<223> OTHER INFORMATION: Codon-optimized and/or mutated sequence

<400> SEQUENCE: 67

```
atgagccttt cccctttgga tcaaaatcgc attgagtctt tttggcaata ctgtttacag    60
caccaatact tcaaccttgc gtatccggag tccgcagatt ttgattatgc accgcttcac   120
cggtttctgc gttttttctat aaacaactgc ggggactgga atgaatcgtc taactatttg   180
ctcaattcat ttgacttcga acgtgaagtc atgcatttct tcgcagagct ttttcatatt   240
cctttcgacg agagttgggg gtacgtaacg aatggcggaa ccgaaggaaa catgtttgga   300
tgctaccttg cacggggaatt gtttcctgac gctacattat attacagcaa agatagccat   360
tatagcgtcg ctaaaatcat caaattgctt agaataaaaa gcagagcggt tgatagcctt   420
ccgtccggcg agatagatta cgatgatctt gtagccaaaa ttcagcaaga ccaagaacgg   480
catccaattg tttttgtaaa cgtcggaaca accatgaaag gtgccgtcga cgatattggt   540
gtcattcaac ataagctggc agaggcagga attccgcgtc aagattatta tctgcatgct   600
gacgcagcat atcaggcat gatactgccg tttgtggacg ctccgcagcc gtactcattt   660
gctgacggta tcgattccat ttccgtctct ggccacaaaa tgattgggag cccgatgcca   720
tgtggtatag tactcgccaa acgctcaaac gtgagcagaa tttccgtcga aattgactat   780
atcagcgcga aggatcagac aattagtggt tctagaaatg gtcatacgcc gatgatgttg   840
tgggcagcga tcaaatccag acctttggct gaatggcgaa gaaaagtgcg tcattgtctg   900
gatatggctc aatatgctat agaccggctg caagctgcag gcatccaggc ctggcggtgt   960
aaaaactcaa ttactgtagt ctttccttcg ccgtccgaac cagtatgtga caaacatggg  1020
ttagccagat ctggcggcac ggcgcatctg attacaacgc ctcatcatca cgattcacaa  1080
cggttagatc ggcttttaga tgatatcgtg caggacctgg gtgcaatgac ggcaccggcg  1140
ggagccacaa tgagtgcagc c                                             1161
```

<210> SEQ ID NO 68
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 68

```
atgttaaaaa tagcagtacc taataaagga tctttgagcg aaagagctat ggaaatcttg    60
gcagaagccg gctatgcagg tcgtggcgat agcaaaagcc tgaatgtatt tgatgaagct   120
aataacgtcg agttttttctt tttgcggcca aaagatattg ctatttatgt ggcaggtggg   180
caactggacc ttggcatcac cggcagagac cttgctagag atagtcaggc cgatgtgcac   240
gaagtattaa gcttaggctt cggatcctct acttttcgct atgcggcccc tgctgatgaa   300
gaatggtcca ttgagaagct tgatggaaag cggatcgcga catcttatcc gaatcttgta   360
cgggatgatt tggcagctcg cggattgtct gcagaagtct taagacttga tggagcggtc   420
gaagtgtcta tcaagcttgg ggttgcggac gctattgcga tgtagtctc tacaggccgt   480
```

| | |
|---|---|
| acattgcgtc aacaagggct cgccccattc ggcgaagtgc tttgcacatc cgaagccgtg | 540 |
| atcgtaggca gaaaagatga aaaagttact ccggaacagc aaatactgtt gcgaagaatt | 600 |
| caagggatcc tgcatgctca gaattttta atgttagact ataaagtcga tcgcgataac | 660 |
| ttagatgcgg caacgccgt tacgccgggg ttttcaggtc ctgctgtttc gccacttgct | 720 |
| cgcgataact gggttgcggt aagagctatg gttccgcgca gatcagctaa tgcaatcatg | 780 |
| gataagctgg ctggacttgg cgctgaagcc attctcgctt cagagattcg tattgcccgc | 840 |
| atc | 843 |

<210> SEQ ID NO 69
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 69

| | |
|---|---|
| atgtccgaat tggacgccaa acttaacaaa cttggggttg atagaattgc gatttccccg | 60 |
| tacaaacaat ggacgagagg atacatggaa ccggggaata tcggaaacgg ctacgttaca | 120 |
| ggacttaaag ttgatgcagg agttcgcgac aaaagtgacg atgacgttct tgatggaatc | 180 |
| gtcagttacg accgcgctga acaaaaaac gcttatattg acaaatcaa tatgacaaca | 240 |
| gcgagttctt ttacgggcgt gcaaggacgc gtaataggat atgatatctt gcgcagtcct | 300 |
| gaggtagaca aagcaaaacc gctgtttacg gaaacgcagt gggacggctc agagcttcct | 360 |
| atttatgatg caaaaccttt gcaagatgct tggttgagt attttgggac agaacaagat | 420 |
| agaagacatt atcctgctcc gggatccttc atcgtgtgtg ccaataaagg agtgacagca | 480 |
| gaaagaccaa aaatgatgc tgacatgaaa ccaggccagg gtatggagt ttggtctgca | 540 |
| attgctatct cttttgccaa agatccgact aaagattctt cgatgtttgt agaggatgca | 600 |
| ggagtgtggg agacaccgaa tgaggatgag cttctggagt acctggaggg tagacgtaaa | 660 |
| gcgatggcta atcaattgc ggaatgcggc caagatgcac atgctagctt tgaaagcagc | 720 |
| tggatcggtt ttgcatacac gatgatgaa ccgggccaga taggtaacgc gattactgtc | 780 |
| gcaccttatg tctcactgcc gatcgatagc atcccgggag gatcaatctt gacccccggac | 840 |
| aaagacatgg agattatgga gaatttaaca atgccggaat ggttagaaaa gatgggatat | 900 |
| aagtccctca gcgcgaataa cgccttgaag tat | 933 |

<210> SEQ ID NO 70
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 70

| | |
|---|---|
| atgtctgaac ttgatgcaaa actaaacaaa cttggggtcg atagaatcgc tatatctcca | 60 |
| tacaagcaat ggacccgtgg ttatatggaa cccgaaata taggtaatgg atatgtaact | 120 |
| gggctgaagg ttgatgccgg tgtaagagac aaaagcgatg acgacgtgct ggacggtata | 180 |
| gtctcttatg atagggccga gactaagaac gcttacatcg ccagattaa tatgactact | 240 |
| gcatcttctt ttacaggtgt gcaaggacgt gtaataggat acgatattct aagaagccca | 300 |
| gaagttgaca aggcaaaacc gctattcaca gaaactcaat gggacggctc tgaactaccg | 360 |
| atctacgatg ctaaacctct acaagatgct ttagttgaat acttcggtac ggagcaagat | 420 |

```
aggcgtcact acccagcccc aggtagtttc attgtttgtg ctaataaggg tgttacagca    480
gaacgtccaa aaaacgatgc cgatatgaaa cctggtcaag gatatggggt ctggtctgcg    540
attgctattt ctttcgctaa ggacccaact aaagattctt ccatgttcgt tgaggacgca    600
ggcgtatggg agactccgaa tgaagatgaa ttgcttgaat acctagaagg taggcgtaag    660
gctatggcta agtcaatagc tgaatgtggt caagacgcgc atgcaagttt cgaatccagc    720
tggataggtt ttgcttacac aatgatgaaa cccggtcaaa tcgggaacgc cattacggtc    780
gccccttacg taagtttgcc tattgacagt ataccaggag gttctattct tactcccgat    840
aaagatatgg aaattatgga aacttaact atgccgagt ggttggaaaa gatggggtat     900
aaatctctgt ccgctaataa tgctttgaag tac                                 933

<210> SEQ ID NO 71
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 71
atgagcgaat tggacgcaaa actcaacaaa ctgggtgtgg atcgcatcgc aatcagccca     60
tacaagcagt ggacccgcgg ttatatggaa cccggtaaca tcggcaatgg ctacgtcact    120
ggacttaaag ttgacgcagg tgttcgtgat aaaagcgacg acgatgtgct ggatggaatc    180
gttagctatg accgagcaga gaccaaaaat gcatatatcg acagatcaa tatgactacc     240 gctagctcct ttaccggagt gcagggacgt gtgattggct acgatatcct ccgctcgcct    300
gaggttgata aagccaaacc actcttcacc gaaacccagt gggatggctc cgaactgcca    360
atctacgatg cgaagcctct gcaggacgcc ctcgtcgaat attttggaac cgagcaggat    420
cgccgtcact atcccgcacc gggttccttc attgtgtgtg caaacaaagg cgtcaccgct    480
gagcgcccta aaaacgatgc agacatgaaa ccgggtcaag gatatggcgt tggtccgcg    540 atcgccatct cgtttgccaa agacccaacc aaggactcat ccatgtttgt cgaggacgcc    600
ggagtgtggg agaccccaaa cgaggacgag ctcctggaat acctcgaggg ccgccgcaaa    660
gcgatggcaa agtcaattgc ggaatgcggt caggatgcgc acgcgtcttt tgaatcttcc    720
tggatcggat cgcatacac gatgatgaaa cccggtcaaa tcggcaacgc gatcactgtc    780
gccccttacg tctcactccc gattgacagc atcccgggtg gatcaatcct gaccccagac    840
aaggatatgg aaatcatgga gaatttgacg atgcccgagt ggttggaaaa gatgggctac    900
aagagcctgt ccgcgaacaa cgcgttgaag tat                                 933

<210> SEQ ID NO 72
<211> LENGTH: 1149
<212> TYPE: DNA
<213> ORGANISM: Artificial
<220> FEATURE:
<223> OTHER INFORMATION: Codon-optimized and/or mutated sequence

<400> SEQUENCE: 72
atgattctgt cacctgctga ccaagaacgt atcgaaacat tctggaatta ctgcttgaag     60
caccagtact tcaacattgg ttatcctgag tcggctgact tcgattactc cgccttgttt    120
cgtttcttca aattcagcat caacaattgt ggcgattgga aggattactc caactacgcg    180
ctgaactcgt tcgatttcga aaaggatgtc atggcctatt ttgctgagat tttccaaatc    240
```

```
ccgttcgagg aatcgtgggg ttacgtcacg aatggtggta ccgagggcaa tatgtttggc        300
tgttacctcg ctcgcgaact gttctccgat tccaccctgt actactccaa agatactcat        360
tattccgttg gcaagatcgc aaaactgttg cagatgaagt cctgcgtcat cgagtctctg        420
gataacggcg aaattgatta cgatgacctg attcataaga tcaaaaccaa taaggagtcc        480
cacccaatca ttttcgcgaa tattggtacg accatgaccg gtgctattga tgacattgag        540
atgatccaag aacgcctggc acagattgga atcatgcgac gcgattatta tattcatgca        600
gacgcggcgt tgtcaggcat gatcctccct tttgtggatc accccaggc ctttagcttt         660 gcacatggca ttgactccat ctgcgtgtcg ggccacaaaa tgatcggctc accaatcccg        720
tgtggtatcg tggtcgcaaa acgccaaaat gttgagcgca tttcagttga tgtagattac        780
atctccaccc gagatcaaac tatctccggc tcccgaaacg gtcacactgt gcttctgatg        840
tgggcagcga tccgctcaca aaccaatctg cagcgccgtc agcgtatcca gcactgcctt        900
aaaatggctc agtacgctgt agaccgcttc caggctgtgg gtatcccagc atggcgcaac        960
ccaaactcca tcaccgtcgt cttcccatgc ccgagcgaac atatctggaa gaagcactac       1020
cttgccactt ccggtaacat ggctcatctg attactaccg cgcaccatcg agatacccgt       1080
caaatcgact ccctgattga cgatgttatt ttcgacttgc aaggcgcgtc aaaacgcacg       1140
gtcggcttc                                                              1149

<210> SEQ ID NO 73
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 73
atggatctgg ttaaccactt gaccgatcgt ttgctctttg ccatcccgaa gaagggtcgc         60
ctctactcga gtcggtgtc cattctcaac ggcgccgata tcactttcca ccgctcccaa         120
cgactcgaca ttgcactgtc tacttctctg ccagtcgcac ttatcttctt gccagctgct        180
gacatcccaa cctttgttgg tgaaggtaaa tgtgacctgg gtatcactgg agttgatcag        240
gtgcgcgaga gcgacgtcga cgtcgatctt gcgatcgatc ttcaattcgg caactgcaag        300
cttcaggtac aagtcccggt caatggcgag tacaagaaac cagagcaact catcggcaag        360
accattgtca cttccttcgt taagcttgct gaaaagtatt tcgctgacct ggaaggaacc        420
acagtggaga aaatgaccac acgtattaag ttcgtttcgg ctcggttgaa ggcgtcctgc        480
gctttgggca ttggcgatgc aatcgttgat ttggtagagt ccggcgagac catgcgtgct        540
gcaggtctgg tcgatatcgc tactgttctg tccactagcg cttatttgat tgaaagcaag        600
aacccaaaga gcgacaagag cctgatcgca actatcaagt ctcgtatcga gggcgtgatg        660
acggcccagc gcttcgtgtc atgcatctac aacgcgcccg aagacaagct gcctgagctc        720
ttgaaagtga cccaggccg tcgtgcgcct acaatttcca aaatcgacga cgagggttgg         780
gttgcagtgt cgtcaatgat cgaacgcaaa acaaagggtg tggtactgga tgaacttaag        840
cgcctcggag cctcagatat tatggtcttc gaaatcagca actgccgtgt t                891

<210> SEQ ID NO 74
<211> LENGTH: 404
<212> TYPE: PRT
<213> ORGANISM: Artificial
<220> FEATURE:
<223> OTHER INFORMATION: Codon-optimized and/or mutated sequence
```

<400> SEQUENCE: 74

```
Met Thr Leu Ser Pro Ala Asp Gln Arg Lys Leu Glu Gly Phe Trp Gln
1               5                   10                  15

His Cys Val Thr His Gln Tyr Phe Asn Ile Gly Tyr Pro Glu Ser Ala
            20                  25                  30

Asp Phe Asp Tyr Ser Gln Leu His Arg Phe Leu Gln Phe Ser Ile Asn
        35                  40                  45

Asn Cys Gly Asp Trp Asn Glu Tyr Ser Asn Tyr Leu Leu Asn Ser Phe
50                  55                  60

Asp Phe Glu Lys Asp Val Met Thr Tyr Phe Ala Glu Leu Phe Asn Ile
65                  70                  75                  80

Ala Leu Glu Asp Ser Trp Gly Tyr Val Thr Asn Gly Gly Thr Glu Gly
                85                  90                  95

Asn Met Phe Gly Cys Tyr Leu Gly Arg Glu Leu Phe Pro Asp Gly Thr
            100                 105                 110

Leu Tyr Tyr Ser Lys Asp Thr His Tyr Ser Val Ala Lys Ile Val Lys
        115                 120                 125

Leu Leu Arg Ile Lys Cys Arg Ala Val Glu Ser Leu Pro Asn Gly Glu
130                 135                 140

Ile Asp Tyr Asp Asp Leu Met Ala Lys Ile Thr Ala Asp Gln Glu Arg
145                 150                 155                 160

His Pro Ile Ile Phe Ala Asn Ile Gly Thr Thr Met Arg Gly Ala Val
                165                 170                 175

Asp Asn Ile Val Thr Ile Gln Gln Arg Leu Gln Gln Ala Gly Ile Ala
            180                 185                 190

Arg His Asp Tyr Tyr Leu His Ala Asp Ala Ala Leu Ser Gly Met Ile
        195                 200                 205

Leu Pro Phe Val Asp His Pro Gln Pro Phe Ser Phe Ala Asp Gly Ile
210                 215                 220

Asp Ser Ile Cys Val Ser Gly His Lys Met Ile Gly Ser Pro Ile Pro
225                 230                 235                 240

Cys Gly Ile Val Val Ala Lys Arg Asn Asn Val Ala Arg Ile Ser Val
                245                 250                 255

Glu Val Asp Tyr Ile Arg Ala His Asp Lys Thr Ile Ser Gly Ser Arg
            260                 265                 270

Asn Gly His Thr Pro Leu Met Met Trp Ala Ala Leu Arg Ser Tyr Ser
        275                 280                 285

Trp Ala Glu Trp Arg His Arg Ile Lys His Ser Leu Asp Thr Ala Gln
290                 295                 300

Tyr Ala Val Asp Arg Phe Gln Ala Ser Gly Ile Asp Ala Trp Arg Asn
305                 310                 315                 320

Glu Asn Ser Ile Thr Val Val Phe Pro Cys Pro Ser Glu Arg Ile Ala
                325                 330                 335

Thr Lys Tyr Cys Leu Ala Thr Ser Gly Asn Ser Ala His Leu Ile Thr
            340                 345                 350

Thr Pro His His His Asp Cys Ser Met Ile Asp Ala Leu Ile Asp Glu
        355                 360                 365

Val Val Ala Glu Ala Gln Leu Asn Thr Leu Arg Ser Lys Arg Ala Phe
370                 375                 380

Thr Asp Gln Thr Val Val Glu Arg Leu Pro Ala Ala Ser Phe Asn Leu
385                 390                 395                 400

Arg Thr His Tyr
```

<210> SEQ ID NO 75
<211> LENGTH: 1002
<212> TYPE: DNA
<213> ORGANISM: Artificial
<220> FEATURE:
<223> OTHER INFORMATION: Codon-optimized and/or mutated sequence

<400> SEQUENCE: 75

```
atgcagaaat atgaatacga tcctaagtgg gtaatcaata atgcgatttc aagcgagcgt      60
gagttttgca ccggctacca aaaccccggc gcgtctggaa atggctatgt cacgactatt     120
aagctttcta cgggtctcgt ggacattacc ccttgggaaa aagtccaggc catgagcgag     180
catgaggtta ttaagttcga tcgcggttgc tctaatattg ttagctatga tcgttgtgaa     240
tgtaatgacg cctatattgg cgcaatcaac atgttgactg cctcctcctt ctctggtctg     300
caaggcgtca tttggggtta cgatatcgct gtagtggaga acctgcggag ccggaagctt     360
tacgatcaaa gtggccgagc ggcgacccg aattcggaat attccacgcc ggtttattct     420
attgagccgc tgctcaacgc aacggagcgc cttttcggcc atgcggagcc tggcaagcgt     480
cgctttaatc ccatcccggg atccatggtg gtctgtgcaa ataaatctgc cacttcagac     540
cctagctcag atgtaaaaga gggctgggct ttttctgtca tctcccttgc aattcttgag     600
aaccggaata gcggatcaaa tctcttcatt gaagactgcg acattattga tatcaataat     660
ccagacggta cccgtaagac taagaggat gtcaaagcga tgctcgacac gacccttcgc     720
aaggtcacgg aatgcacggt attgtgtggt ctcgaccaac acatcaagta caaagagatt     780
ttcatcggat acaaggtgat taagttcaac gagaagcaag taggttgtgc gctcgcgtgt     840
gcaccgtacg tgacgcttgc acggaatgca gtgcctcagg gaatgaaacc gtcgaaactg     900
acggacatga acatttctca atgggagaac gctctgaatc tgcaaccccct ggagaagatt     960
gaaaaatcaa agatcggcat tttgggaatg ggtgtgcttg ac                       1002
```

<210> SEQ ID NO 76
<211> LENGTH: 1047
<212> TYPE: DNA
<213> ORGANISM: Artificial
<220> FEATURE:
<223> OTHER INFORMATION: Codon-optimized and/or mutated sequence

<400> SEQUENCE: 76

```
atgactctgc actcacggta ttctaaattg aaaggtgaga caaaatgca aaagtacgag      60
tacgacccaa agtgggttat caacaacgca atctcgtccg aacgggaatt ttgtaccggc     120
tatcagaacc caggtgctag cggcaacggc tatgttacta ctattaaact gtcaacgggc     180
ttggtagata ttacgccatg ggagaaggtg caggcaatgt ccgagcacga agtgattaag     240
ttcgaccggg gatgcagcaa cattgtctct tacgaccggt gtgaatgtaa tgatgcttac     300
attggagcca ttaacatgct gactgcttct tctttctcgg gactgcaggg agtcatctgg     360
ggttatgata tcgcagtcgt ggaaaatctg cgttcgcgga agctctacga tcaaaaatgg     420
ccttccggcg atccaaattc ggaatattct acgcctgtgt attcgattga gccgttgttg     480
aatgccactg aacggctctt cggtcacgcg gagccaggaa agcgccgttt taacccaatc     540
cctggatcaa tggtggtgtg tgcgaacaag tcagctacct cggatccgtc ttcggacgtt     600
aaggagggat gggcattttc agttattagc ctcgctatcc ttgagaatcg caactctggt     660
agcaatctgt ttatcgaaga ctgtgatatt atcgacatta caatcccga tggtactcgc     720
```

| | |
|---|---|
| aaaaccaaag aggatgtgaa ggctatgttg ataccactt tgcgcaaagt acgggagtgt | 780 |
| acggttctct gcggtcttga ccagcatatt aagtataaag aaatcttcat tggctataaa | 840 |
| gtcattaaat tcaacgagaa gcaagtggga tgcgctcttg cctgcgcgcc ctatgttact | 900 |
| ctcgcacgta atgctgtacc gcaaggaatg aaaccgtcca agctcactga tatgaacatt | 960 |
| tcacagtggg aaaatgcact gaacttgcag ccactggaaa agattgaaaa gtcgaaaatc | 1020 |
| ggcattcttg aatgggagt gctcgat | 1047 |

```
<210> SEQ ID NO 77
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 77
```

| | |
|---|---|
| atgagcgaac tcgacgcaaa actgaataaa ctcggagtag accggatcgc gatttccccg | 60 |
| tataagcaat ggacgcgggg atacatggag ccaggtaaca tcggaaatgg ttacgtgacg | 120 |
| ggacttaagg tagatgctgg tgtacgcgat aaatccgatg atgatgtatt ggacggtatt | 180 |
| gtcagctatg accgggcgga gacgaaaaac gcctacatcg gccaaatcaa catgaccact | 240 |
| gcatcgtcat ttactggcgt ccagggccgg gtgattggat acgacatcct tcgctcccct | 300 |
| gaggtagaca aggcgaagcc gctgttcacg gagacgcaat gggatggttc agaacttccg | 360 |
| atttatgacg cgaaaccgct tcaagacgct cttgtagagt attttggcac cgagcaagat | 420 |
| cgtcgccatt acccagcacc aggatccttc attgtttgtg ctaataaggg tgtaaccgca | 480 |
| gagcggccta agaacgacgc agacatgaag cctggccagg gctacggcgt atggtcagcg | 540 |
| attgccatta gctttgcaaa ggatcccacc aaagattctt caatgtttgt agaagatgca | 600 |
| ggagtctggg agactccgaa cgaagatgag ctcctggaat accttgaggg acggcgtaag | 660 |
| gcgatggcaa agtctatcgc ggagtgtggt caggacgcac atgcgtcctt tgaatcgtcg | 720 |
| tggattggct cgcgtatac gatgatggag cccggccaaa tcggcaacgc tattactgtg | 780 |
| gcccccctatg tttctttgcc cattgacagc atcccgggag aagcatcct acccccggat | 840 |
| aaagatatgg aaattatgga gaacctcacg atgcccgaat ggctggagaa aatgggatac | 900 |
| aagtctctca gcgctaacaa cgcacttaaa tat | 933 |

```
<210> SEQ ID NO 78
<211> LENGTH: 1149
<212> TYPE: DNA
<213> ORGANISM: Artificial
<220> FEATURE:
<223> OTHER INFORMATION: Codon-optimized and/or mutated sequence

<400> SEQUENCE: 78
```

| | |
|---|---|
| atgattttgt ctccagccga ccaggaacgt atcgagactt tctggaatta ttgcctgaaa | 60 |
| catcagtact ttaacatcgg ctaccccgaa tcagccgact tgactactc tgcactgttc | 120 |
| cgtttcttta gtttttccat taacaactgc ggagactgga aggactattc aaactatgcc | 180 |
| cttaacagct tcgacttcga gaaagacgtc atggcgtact ttgctgagat ttttcaaatc | 240 |
| ccctttgaag agtcttgggg atacgtgact aatggcggca ctgagggcaa atatgtttggt | 300 |
| tgctacctcg cccgtgagtt gttctccgat tctacgcttt attattcgaa ggacacgcat | 360 |
| tatagcgtcg gcaaaatcgc caagctgctc caaatgaaat cctgcgttat cgagtccctc | 420 |
| gacaatggcg aaatcgacta tgacgacttg attcataaaa ttaaaacgaa taaggagtcc | 480 |

```
cacccgatta ttttcgctaa tatcggtacc actatgacgg gtgcaattga tgatattgaa    540
atgattcaag aacgtctggc tcagatcggc attatgcggc gggactacta tattcacgcg    600
gacgcagctc tttctggcat gatccttccc ttcgtcgatc atccacaagc gttttccttc    660
gcacatggca tcgattcaat ttgtgtttcg ggccataaga tgattggaag cccaattcca    720
tgtggcattg tcgtagctaa acgccaaaac gtggaacgta tctcagtaga tgtggattat    780
atcagcactc gtgaccaaac catctcgggt tcccggaatg acacaccgt gttgctcatg     840 tgggcggcaa tccggtcgca gaccaatttg caacgtcggc agcggatcca acattgcctg    900
aagatggctc agtacgcagt cgatcggttt caagcagtag gtattcctgc atggcggaac    960
ccgaatagca tcacggttgt gttcccatgt ccttctgaac acatctggaa aaaacactat   1020
ctcgcgactt cgggcaatat ggctcatctc atcactaccg ctcatcatcg cgatactcgt   1080
cagattgatt cgctgatcga cgacgtgatc tttgatttgc agggtgcgtc caaacggacc   1140
gtgggatttt                                                          1149

<210> SEQ ID NO 79
<211> LENGTH: 2541
<212> TYPE: DNA
<213> ORGANISM: Artificial
<220> FEATURE:
<223> OTHER INFORMATION: Codon-optimized and/or mutated sequence

<400> SEQUENCE: 79
atggatttca aggagtaccg ccagcgcgga aaggagatgg tcgattatat tgccgactac     60
cttgagaata ttcgcgagcg cgcgtcttc cccgatgtaa gcccgggcta tgcgtcag     120 ctcttgcccg aatcagcgcc gatcgaagga gagccgtggc cgaagatctt cagcgatgta    180
gagcgcattg taatgccagg aatcacgcac tggcagtccc cgcatatgca tgcctatttc    240
ccagccttga attcaatgcc ctccctcctc ggagatatgt tggccgatgc gattaactgt    300
ctgggcttca cctgggcatc aagccccgca tgcactgagt tggagatcat cgtcatgaat    360 tggtttgggca agatgattgg cctgcccgac gcattcctgc acctgtcgtc ccaatcacaa    420
ggtggtggcg tcctccagac tactgctagc gaggccactt tggtgtgcct gctggcagga    480
cggactcgtg caatccaacg tttccatgag cggcatcctg gttaccaaga cgcggaaatt    540
aacgcgcggc ttgttgctta ttgctccgac caagcacatt cgtcggtgga aaggcagct    600 ttgatcggac ttgtccgtat gcgctatatc gaggctgacg atgacttggc catgcgtggt    660
aagctgctgc gggaggcgat tgaggacgat attaaacaag gattggtgcc attctgggtc    720
tgcgctactc ttggcaccac cggttcttgt agctttgaca atttggagga aattggaatt    780
gtttgcgctg agcaccactt gtggcttcac gtagatgcgg catacgcggg tagcgctttc    840
atttgccctg agtttcggac gtggttgcgg ggcatcgaac gtgccgactc gattgctttc    900 aaccctcga aatggctgat ggtccactt gacgccactg ctctttgggt gcgggatagc    960
accgcggtcc atcgcactt caacgtcgaa ccctctacc tccaacatga aaactcaggt    1020
gttgctgttg atttcatgca ttggcaaatc ccctgtcgc ggcggtttcg tgctttgaaa    1080
gtgtggttcg tattgcgctc ttacggtatt aaaggactgc aacggcatat ccgcgaaggt    1140
gttcgcctgg cgcagaaatt tgaagccctc gtcctggccg atcaccgttt cgagctgcca    1200
gcaaaacgcc accttggcct ggtggtattc cgtatccgcg cgacaatga gatcactgaa    1260 aaattgctta agcgtcttaa ccaccgtggc aacctccact gcatcccatc gtccctcaag    1320
```

```
ggtcaatatg ttattcgctt caccatcacc tcaacccaca cgacgctcga tgatattgta    1380
aaggattgga tggagatccg ccaggtagcg tccacggtac tggaggaaat gaatattact    1440
atttcgaatc gtgtttacct gaaggaaacg aaagagaaga acgaagcctt cggatcgtct    1500
ctgctgctct ctaactcacc tctgtctccg aaagtggtca acggttcctt cgcagcaatc    1560
ttcgacgcgg acgaattcct cgctaaaacg tatgccggcg tgcgtattgc tcatcaggag    1620
tcaccctcca tgcgccgtcg tgtgcgcggc attctgatga gcggcaagca gttctccctg    1680
gattcccaca tggacgtcgt ggtgcaaacg acgctcgacg ctggaaacgg agcaacgcgt    1740
acttctacta ctaactcgta tggtcacacc acttccgccg cacaggccaa ttcagagcgg    1800
caggcttcta tccaggaaga taacgaggaa agcccagagg agactgaact tttgtcgctt    1860
tgccgtacct caaacgttcc cagccccgaa catgcacact ccttgtctac gccatcccgc    1920
tcatgctcgt ccagctctca ttcgttgatc cattcactta cccagtcgtc tccgcggtca    1980
agcccggtta atcagtttcg gcctattacc ctctgcgccg tacctcccca atcccagctg    2040
tccatgccgc ttgcaatgcc tttgccgaac cgcaacgtca ctgtttcggt agattcactg    2100
ctcaacccag ttacgacttg caatgtgtac cacggcaaac gttttctcga acccctcgag    2160
aacttggccc aaacctctgc atctttctcc tcttctattt tccggctgcc cacccccatt    2220
gccactccca ctcgggagag cccggaggat cccgactggc cagcgaagac tttctctcaa    2280
ctcttgttgg aacggtatag cagccaaagc caatcgctgg gaaataattc ctctacggaa    2340
tcaagcagct tgtccggcgg tgccaccccg acgccgacgc caatgtcgtc acttgacgaa    2400
ctcgtaacgc ctcttctgtt gtctttcgct tccccaagcc agcccatgct ctcggcacat    2460
ggtatcggtg aaggacaacg cgagcaggga tcggactcag acgcgacggt ttgctccacg    2520
acttcctcta tggaatcact g                                              2541
```

<210> SEQ ID NO 80
<211> LENGTH: 1161
<212> TYPE: DNA
<213> ORGANISM: Artificial
<220> FEATURE:
<223> OTHER INFORMATION: Codon-optimized and/or mutated sequence

<400> SEQUENCE: 80

```
atgtccctgt ccccttttgga tcaaaatcgc attgagtcct tctggcaata ttgtttgcag     60
catcagtact tcaatctggc ttatcccgaa tctgcggatt tcgactacgc cccccttgcat    120 cgtttcctcc ggttctctat caacaactgc ggagattgga acgagtcctc aaattacctg    180
cttaactcgt ttgatttcga gcgggaggta atgcacttct tcgcggaatt gtttcatatt    240 cccctttgatg agtcttgggg ttatgttact aatggaggta ctgaaggcaa tatgtttggc    300
tgctaccttg ctcgcgagtt gttccctgat gcaaccttgt attactcaaa agatagccat    360
tactccgtcg ctaagattat caaattgttg cggatcaaat cgcgcgctgt ggacagcctc    420
cctagcggtg aaatcgatta tgacgatctt gtggcaaaga ttcaacagga tcaggaacgt    480
cacccaatcg ttttgttaa cgtgggtacg actatgaaag gcgctgtgga cgatattgga    540
gttattcagc acaaacttgc tgaagcaggt atccccccgc aagattacta cttgcatgcg    600
gatgcggcac tttccggcat gatcctcccg tttgtggatg caccccaacc ctattccttt    660
gctgatggaa ttgacagcat ctccgtatct ggacataaga tgattggaag cccgatgcct    720
tgtggcattg ttttggcaaa acggtccaat gtctctcgga ttagcgtaga gatcgattac    780
atctccgcaa aggaccagac gatctctgga tcccgtaatg gtcacacccc tatgatgctc    840
```

```
tgggctgcaa tcaaatcacg gccgcttgcg gaatggcgtc ggaaggttcg ccattgtttg      900
gatatggctc agtacgcgat tgatcgtctc caagctgcag gtattcaagc gtggcgctgc      960
aagaacagca ttacggttgt atttccttcg ccctcagagc ctgtgtgcga caagcatggc     1020
ttggcccgct ctggcggtac cgcgcaccct attaccactc cgcatcacca tgactcccaa     1080
cgcttggacc gtctcttgga cgacatcgtc caagacttgg gcgcaatgac ggctcctgct     1140
ggtgcaacta tgtctgccgc a                                                1161
```

<210> SEQ ID NO 81
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 81

```
atgttggaca atacgcgcct ccgcatcgcc atccaaaaaa gcggccgtct gtcagacgac       60
tcgcgtgaac tgctcgcccg gtgcggtatc aagattaacc ttcacaccca acgtctgatt      120
gcaatggcgg aaaacatgcc tattgacatt ttgcgtgtcc gggacgatga cattcctggc      180
ctggtaatgg acggcgtcgt tgatctggga attattggtg agaatgtgct tgaggaggag      240
ctcctgaacc ggcgcgcgca gggtgaggac cctcgctacc tgactctgcg ccgcctggat      300
tttggcggat gtcggctgtc gcttgcaacg cccgtggatg aagcctggga tggacctgct      360
gcgctggacg gcaagcgtat tgctacctca tatcctcatc ttttgaagcg ttatttggat      420
caaaaaggtg tatccttcaa gagctgcctt cttaacggtt cagtggaggt cgccccgcgc      480
gccggtcttg ctgatgctat ttgtgacctc gtttcgacgg gtgccaccct tgaggcgaac      540
ggtctgcgcg aagtggaagt aatttatcgc tcgaaagcgt gtcttatcca gcgggacgga      600
gagatggcgc agtccaaact tatcgataaa ctgcttactc gtattcaggg tgtgatccaa      660
gcccgggaaa gcaagtatat catgatgcac gccccgtcgg aacgcctgga agaagtcatt      720
gcgcttcttc cgggagctga acgtccaacc atcctgccgc tggcaggcga caacaacgt      780 gttgctatgc acatggtttc aagcgaaact ctgttctggg agacgatgga aaagcttaag      840
gctcttggcg cgtccagcat tttggtgttg ccgattgaaa aaatgatgga a               891
```

<210> SEQ ID NO 82
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 82

```
atgtccgagt tagacgcaaa gctaaataaa ctgggtgtcg acagaatcgc aatttctcca       60
tataagcaat ggacgagagg gtatatggag ccagggaata tcgggaacgg ctacgtcact      120
ggacttaaag tagacgccgg ggttagagac aaaagcgatg atgacgtcct agatggaata      180
gtatcctacg atagagctga aaccaagaac gcatacattg gcagataaa tatgacgact       240 gctagctctt ttacgggtgt acagggtagg gttattggat cgacatcttc gagatccccg      300
gaagtcgata aggccaaacc gttatttaca gaaacgcagt gggatgggtc agagctaccg      360
atatatgacg caaaaccatt gcaagatgcg ttagtggagt acttcgggac cgaacaagat      420
agaagacact accctgctcc cggttcattc atagtatgcg ccaataaagg cgtaacagcc      480
```

| | |
|---|---|
| gaaaggccga aaaacgatgc ggacatgaaa ccaggtcaag gttacggtgt gtggtctgct | 540 |
| atagcgatta gttttgcgaa agatcctacc aaagatagca gcatgttcgt cgaagacgct | 600 |
| ggtgtgtggg agacccctaa cgaggacgaa ttacttgagt atttggaagg cagaagaaaa | 660 |
| gcgatggcta agtcaattgc tgaatgcggg caggacgcac acgcgtcctt tgaaagcagc | 720 |
| tggataggct ttgcatatac aatgatggag ccaggtcaaa taggtaacgc gatcaccgta | 780 |
| gcaccttacg tgtcccttcc tatcgattcc atccctggag gtagcatttt gacgcctgac | 840 |
| aaggatatgg agatcatgga gaaccttaca atgcctgagt ggctagagaa gatggggtac | 900 |
| aaatccctat ccgcgaacaa cgcgctaaag tac | 933 |

<210> SEQ ID NO 83
<211> LENGTH: 1239
<212> TYPE: DNA
<213> ORGANISM: Artificial
<220> FEATURE:
<223> OTHER INFORMATION: Codon-optimized and/or mutated sequence

<400> SEQUENCE: 83

| | |
|---|---|
| atggaatcag acattaagaa cgagacctct ttccaagagc ttgatatgat cctgacacag | 60 |
| tacctggaaa cactatcaga aagaaaaaag tatcatatag gctaccccat aaacatgtgt | 120 |
| tacgagcatc atgcgaccct ggcacccttg cttcagtttc acctgaataa ctgcggtgat | 180 |
| ccgttcacac aacaccccac tgactttcac agcaaggact tgaggttgc ggtgcttgac | 240 |
| tggttcgccc aactgtggga gatagagaag gacgagtact ggggttatat aacttccgga | 300 |
| ggaactgaag ggatctgca tggttttgg ttaggtagaa gagagttgtt gccaaatggt | 360 |
| tacctatatg ccagcaaaga ttcccattac tccatattta agccgctag aatgtacaga | 420 |
| atggagttac aaactatcaa tacgctagtt aatggagaga ttgattacga agacttgcag | 480 |
| agtaaactgc ttgtcaacaa gaacaagccc gcgataatta atatcaatat tgggacaact | 540 |
| tttaaaggtg ctatagatga cttggatttc gttatacaga cattagaaaa ctgcggctat | 600 |
| tctaatgata actattacat tcactgcgac agggctctat gtggactaat tcttccatt | 660 |
| atcaaacacg cgaagaagat cacgttcaag aagccccattg ggagcatcag catttctggg | 720 |
| cacaagttct taggttgccc gatgagctgc ggcgtgcaaa taacacgtag gtcatatgta | 780 |
| agtacactga gcaaaatcga gtacattaac tccgcggacg caaccattag tggcagccgt | 840 |
| aacggattca cgccgatctt tctgtggtat tgtctatcta agaaaggaca tgcgagatta | 900 |
| caacaagatt ctattacctg tattgagaat gcgagatacc taaaggatag gctgctggaa | 960 |
| gccgggatta gcgtaatgct gaatgatttt agcatcacag tagtattcga acgtccctgt | 1020 |
| gatcataaat ttattagaag atggaacctg tgctgtctgc gtggcatggc tcacgtagtc | 1080 |
| atcatgccgg ggataactcg tgagacgatt gatagttttt tcaaggatct gatgcaggag | 1140 |
| cgtaattata atggtacca ggacgtgaaa gccctaccac cttgtttggc agatgactta | 1200 |
| gcattgaact gcatgtgtag caataagaaa atgcataac | 1239 |

<210> SEQ ID NO 84
<211> LENGTH: 1986
<212> TYPE: DNA
<213> ORGANISM: Artificial
<220> FEATURE:
<223> OTHER INFORMATION: Codon-optimized and/or mutated sequence

<400> SEQUENCE: 84

| | |
|---|---|
| atgatggagc cgtgtgaata cagggagtac agggagtatt acagagcgag gggtaaagag | 60 |

```
atggttgatt atatcagcca gtatttaagt acagtcaggg agagacaggt caccccctaat    120
gtacagcccg ggtatctacg tgcgcagttg ccagcatccg caccagaaga gcctgattct    180
tgggattcta tctttgggga tatagagaga gtcattatgc ctggggtcgt ccattggcaa    240
tctccgcaca tgcatgctta ctatcccgcg ctgactagtt ggccgtccct acttggagat    300
atgttagctg atgcgattaa ctgtcttggc ttcacctggg ccagctcacc cgcttgcact    360
gaactggaaa tgaatattat ggactggtta gcgaagatgt tagggcttcc ggaatatttt    420
cttcaccatc acccatcatc cagaggagga ggggtcttac aatccacagt ctctgagtcc    480
acgctgatag cacttttagc ggctcgtaaa aataaaatct tagccatgaa ggcttgcgaa    540
cccgatgcaa atgagagttc actaaacgca aggctggtag cgtataccttc agatcaagcg    600
cattcctcag ttgaaaaggc cgggcttatt agcttggtta agatcaggtt cctaccggtt    660
gatgataatt ttagtctaag gggggaagcg ctgcaaaagg ctatcgaaga agataagcag    720
cagggacttg tacctgtctt cgtgtgcgcg actcttggaa ctacgggtgt tgtgcattc     780
gatcgtctga gcgaactagg accaatctgc gcctccgagg ggttgtggct acacgtagat    840
gccgcctatg ctggcactgc tttcttatgc ccagagctga gagggtttct agagggtatc    900
gagtacgctg attcattcac ttttaatcca tccaagtgga tgatggtcca cttcgattgt    960
acaggcttct gggtaaagga caaatataag ttgcagcaaa cgttctctgt aaacccgatt   1020
tatcttaggc atgctaattc cggggcagcc accgacttca tgcactggca gatccccctt   1080
tctcgtaggt ttagaagcat aaagttatgg ttcgtaatca gatctttcgg tgtaaagaat   1140
ttgcaggcgc atgttaggca cggaactgaa atggccaaat atttcgaatc cttggttaga   1200
agcgacccca gtttcgagat ccccgcgaaa agacatctgg gtctagtagt tttcagactt   1260
aaaggtccta attgtttgac agagtcagtt ttgaaggaga tcgcaaaagc gggtcagtta   1320
tttttgatac cagcgacaat acaagacaaa ttgataatca ggtttacggt cacatcacag   1380
tttactacaa aggaggatat attacgtgat tggcacttaa tccaagaggc cgcaaatctg   1440
gtcctatctc agcactgcac ttctcagccc agccccgtg cgaagaatgt gatcccaccc    1500
ccgcctggta cacgtggatt aagcttagaa tctgttctg aaggaggtga tgatccggca    1560
caagcaagga aaataatcaa gcaaccaggg gctagcttgg cgcgtcgtga aggcggttcc   1620
gatttggaga caatgccgga ccccttcgac gattgtttca gtgaagaagc gccaaacacg   1680
acaaagcaca aattgtcaag ctttttattt agctatttat cagttcaaaa cagacgtaag   1740
acaacacgtt ccctgagctg taatagtgta ccaatgagcg cacaaaaatc attgccagct   1800
gacgcatctt tgaagaacgg tggaagtttc cgtgcaagaa ttttttctgg gtttcccgaa   1860
caaatgatga tgatgaagaa gggggcattc aagaagttaa taaagttcta tagtgtacct   1920
agtttcccgg agtgcagtag ccagtgcgcg cgtcaactac cctgttgtcc gttagaagct   1980
atggtt                                                              1986
```

<210> SEQ ID NO 85
<211> LENGTH: 2541
<212> TYPE: DNA
<213> ORGANISM: Artificial
<220> FEATURE:
<223> OTHER INFORMATION: Codon-optimized and/or mutated sequence

<400> SEQUENCE: 85

```
atggacttta aggagtatag gcagagaggt aaagaaatgg tagactatat agcagactac      60
```

-continued

```
ttggaaaata ttcgtgaaag acgtgtattc cccgatgtct caccaggcta tatgcgtcag      120
ttattaccag aaagcgcccc catagagggg gagccttggc ccaaaatctt cagcgatgta      180
gaacgtatcg ttatgcccgg gataacccat tggcaatccc cgcatatgca tgcgtatttt      240
ccggccctga actcaatgcc aagtctgttg ggggatatgc tagccgacgc catcaattgt      300
ctgggtttta cctgggcttc ttcaccagcc tgcacggagc tggagatcat cgtgatgaac      360
tggttgggaa aaatgattgg actgcctgac gcttttctac acttatcctc ccaatcccaa      420
ggtgggggcg tcttacagac aactgccagc gaggccacgc tggtgtgcct tctagctggt      480
cgtactagag caatacagag gttccacgaa agacatcctg gtaccagga cgctgaaata      540 aacgctagat tagttgccta ttgcagcgac caggcgcatt cttctgttga aaagcggca      600 ctaataggcc tagtgagaat gagatatatt gaggccgatg atgatctggc gatgagaggg      660
aagcttctgc gtgaagctat tgaagacgac atcaaacaag ggttggtccc tttctgggtg      720
tgtgctacac taggcacaac cgggagctgt tcatttgata atctggagga gatcggaata      780
gtttgcgcag agcatcacct atggttacac gtagatgctg cttatgcagg atcagctttt      840
atatgtcctg agtttcgtac atggctgagg gggattgaac gtgcggacag catcgctttt      900
aacccatcca agtggttgat ggttcacttt gatgctacgg cactgtgggt cagggatagt      960
acagccgtac acagaacatt caatgtcgag cccctttatc tgcaacacga gaactctggt     1020
gtagcagttg attttatgca ttggcagatc ccattatcaa ggcgttttag agccctgaaa     1080
gtatggttcg ttctgaggag ctatggtata aaagggttac aaagacatat aagggaggga     1140
gtgaggttgg cacagaaatt tgaggctttg gtcttggccg atcacaggtt cgaactaccc     1200
gcgaaaagac acctgggact ggttgttttc cgtatcagag gcgataatga aataacagag     1260
aaattgctga agagattgaa tcatcgtggc aacttacact gtataccctc atccctaaaa     1320
ggacaatacg tcataaggtt tactatcacc tccactcaca cgacactgga tgatatagta     1380
aaagactgga tggaaatacg tcaggtcgcc agtaccgtgt tagaagagat gaacataacg     1440
attagcaata gagtttatct taaagagaca aaagaaaaga acgaggcgtt tggttcttct     1500
ttattgctgt ctaacagccc tctatcccct aaggtagtaa acggctcctt tgctgcaatc     1560
ttcgacgcgg acgagttcct agcgaaaaca tacgcaggcg tcaggatcgc tcatcaagaa     1620
tctcctagta tgcgtaggag ggtcagagga atcttgatgt ctggaaagca attttcctta     1680
gattcacaca tggatgttgt tgtccaaacc acacttgacg ctgggaatgg tgcaacgaga     1740
acttcaacca ctaatagcta cggacatacg acgagcgcgg cgcaggccaa ttccgaaagg     1800
caagctagca tacaagaaga taacgaagag tccccggaag aaactgaact tctgagtcta     1860
tgcaggacat ccaacgtccc gagtccgaaa catgcgcatt cattgtctac accaagcagg     1920
tcctgttcat cttcatctca ctcccttatc cattcactta cccaatccag ccctcgtagt     1980
tcacccgtca atcagttcag gccgattact ctttgcgcgg tcccgtccca atctcaactt     2040
tccatgccgt tggctatgcc actaccaaat agaaacgtta cagtttctgt agattctctt     2100
ctaaaccctg taactacatg taatgtatat catggcaaaa gatttctgga gccactggaa     2160
aacctggccc agacgagcgc aagttttagc agctcaattt ttagacttcc aacaccgatc     2220
gcaacgccga ccagagagtc cccagaagat cctgattggc cggctaagac attcagtcaa     2280
ttgctgttgg agaggtactc cagccagtcc cagtcattag gtaacaactc tagcaccgaa     2340
tcctcatcat tgtccggagg ggctactccc acacctaccc ccatgtccag tttgatgaa      2400 ttggtcacac cgttattatt gtctttcgca tcccccttctc aaccgatgct atctgcacat     2460
```

```
gggataggcg aaggtcaaag ggagcagggc tctgatagtg atgcaactgt gtgtagtact    2520
acaagctcta tggaaagcct a                                              2541

<210> SEQ ID NO 86
<211> LENGTH: 1161
<212> TYPE: DNA
<213> ORGANISM: Artificial
<220> FEATURE:
<223> OTHER INFORMATION: Codon-optimized and/or mutated sequence

<400> SEQUENCE: 86
atgtctcttt ccccacttga ccagaacagg attgaatctt tctggcaata ttgcttgcag      60
caccaatact tcaacttggc ctaccccgag tcagctgact tcgactatgc cccttttgcac    120 cgttttttgc gtttctccat taataactgc ggcgactgga atgagtcctc aaattacttg     180
ttaaattcat tcgatttcga gagggaagtt atgcacttct tgccgaattg ttccacatt      240 ccgtttgacg agtcatgggg atacgtgacg aatggcggaa cggaagggaa tatgttcggg     300
tgctacctgg cgagggagct gtttcctgat gcaacccttt actatagtaa agactcccac    360
tacagtgtag ctaagattat aaagttgctg agaatcaaat ccagagcagt agactcacta    420
ccgagcggcg agatagatta cgacgacctt gtagccaaga ttcaacaaga ccaggagaga    480
catccaattg tattcgtaaa tgttggaacg actatgaaag gtgccgtaga tgacatagga    540
gttatccaac ataaacttgc ggaagctggt ataccgcgtc aagattacta cttgcacgcg    600
gatgcggctc tttcaggtat gatcttaccc ttcgtggacg caccacaacc gtactcattt    660
gcggatggga tagactcaat atctgtgagc ggtcataaaa tgataggaag ccctatgcca    720
tgtggtatag tattggcaaa gaggagcaac gtgagtcgta tatctgtaga aatcgattat    780
atatcagcga aagaccagac gatttctggg agtaggaacg gtcacacccc gatgatgttg    840
tgggctgcta ttaaatcaag gcccctagcg gaatggagaa gaaaggttag acattgctta    900
gacatggcac aatacgcaat cgacaggcta caggcggccg ggatacaagc ttggagatgt    960
aagaatagta ttaccgtagt tttccccagc ccctccgaac cggtctgcga caagcatggc   1020
ttagcccgtt ctgggggaac cgcacattta atcaccacgc cccaccacca cgatagtcaa   1080
agattggatc gtctgttaga tgacatagtg caagatttag gcgcgatgac tgcccctgct   1140
ggtgcgacaa tgtctgctgc c                                             1161

<210> SEQ ID NO 87
<211> LENGTH: 1002
<212> TYPE: DNA
<213> ORGANISM: Artificial
<220> FEATURE:
<223> OTHER INFORMATION: Codon-optimized and/or mutated sequence

<400> SEQUENCE: 87
atgcagaaat atgaatacga tccgaagtgg gtaattaata atgcaattag cagtgagcgt     60
gaattttgca ctggctacca aaatccaggt gcgtccggta atggatacgt caccacgatc    120
aaattgagca agggctagt cgatattacc ccctgggaaa agttcaagc gatgagtgaa     180 catgaggtaa taaattcga tagagggtgc agtaatatcg tgagctacga taggtgtgaa    240
tgtaatgatg cctacattgg tgccattaat atgttgacgg ccagctcctt ttcaggactt    300
caaggagtta tctggggtta cgatatagct gttgtcgaga acctgcgttc cagaaaactt    360
tacgaccaaa agtggcccag tggtgatcct aatagtgaat acagtactcc agtctactca    420
```

```
atcgagccgc tgttgaacgc aactgagaga ctgtttggac acgcggagcc aggaaaaaga    480
aggtttaatc caatcccagg ttctatggta gtatgtgcca acaaatctgc cactagtgat    540
ccttcctcag acgtcaaaga aggctgggcg ttcagtgtca ttagcttagc aatcttggag    600
aatagaaatt ctggaagtaa cctattcatc gaagattgcg acattatcga tataaacaac    660
ccggacggaa cgcgtaagac gaaagaggac gtgaaggcta tgctggacac tactctacgt    720
aaggtgactg agtgcacggt gctatgtggg ttggaccagc acattaagta caaagaaata    780
ttcattggct acaaagtcat caagtttaat gagaagcaag ttgggtgcgc actagcatgc    840
gcgccttatg ttccttggc gaggaacgct gttccccagg gtatgaagcc ttcaaagttg    900
acggatatga atatctctca gtgggagaat gcattaaatt tacaacccctt ggagaaaatt    960 gaaaaatcta agattggaat tctgggaatg ggcgttctgg at                      1002
```

<210> SEQ ID NO 88
<211> LENGTH: 1047
<212> TYPE: DNA
<213> ORGANISM: Artificial
<220> FEATURE:
<223> OTHER INFORMATION: Codon-optimized and/or mutated sequence

<400> SEQUENCE: 88

```
atgaccctgc acagtagata tagcaagtta aagggtgaaa ataaaatgca aaagtacgag    60
tatgatccca gtgggttat caataacgct atttctagtg aaagagaatt ctgcacggga    120
taccagaacc ctggggcaag cggcaacggt tatgtgacaa ctatcaaatt gtctaccggc    180
ttagttgata taacaccctg ggagaaagtt caagcaatgt ccgaacacga ggttatcaag    240
tttgataggg ggtgttcaaa catagtcagc tatgaccgtt gtgaatgcaa cgatgcttat    300
atcggtgcaa tcaacatgct aacggcgtct agcttctctg gctacaagg ggtcatatgg    360 gggtacgaca ttgcggtggt cgaaaatcta agatcaagaa agctgtatga ccagaaatgg    420
cccagtggcg atccaaattc cgaatacagc acgccagtgt actctattga gccacttctt    480
aatgccacag aaagactatt cggacacgca gaaccaggta aaggagatt taatccaatc    540 ccaggatcaa tggtagtgtg tgctaacaag tccgcaacgt cagatccatc atcagatgta    600
aaagaaggtt gggccttctc tgtgataagc ttggctattt tggagaacag aaatagcggt    660
tctaaccttt ttatcgagga ttgcgacatt atcgacatta acaatccgga tgggacgcgt    720
aagaccaagg aggacgtcaa agcgatgttg acactacat tgaggaaagt aacggaatgc    780
acagtcctgt gtggtttgga ccagcacata agtataaag agattttcat agggtataag    840
gtaataaagt tcaatgagaa acaagttggt tgtgcactag catgcgcccc ctatgtaacc    900
ttagccagaa atgcagtacc acaagggatg aagccctcca agctgacgga tatgaacatt    960
agccagtggg agaatgcact taacctacaa ccgttggaaa agatagagaa aagcaaaatc    1020
ggcatcttgg gaatgggcgt gcttgat                                       1047
```

<210> SEQ ID NO 89
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 89

```
atgctaaaga tagcagtacc caacaaaggt agcctaagcg agagagctat ggaaatcttg    60
gctgaggctg gctatgctgg gagaggagac tccaaatctc taaatgtgtt tgacgaggct    120
```

```
aataatgttg agtttttttt tcttagacca aggatatcg ccatatatgt cgcgggagga    180
cagctagacc taggcatcac cggcagggat ctagccaggg acagccaagc agatgtccac    240
gaggtcctgt ctttaggatt tggatcttct accttcaggt atgcagcccc tgccgatgaa    300
gagtggtcta tcgagaagct agatggcaaa cgtatcgcca caagttatcc caatttggtc    360
agggatgatc tagccgcgag aggtttatca gccgaggtcc tgagacttga tggggccgtc    420
gaggttagta tcaaactagg tgttgcggat gcgattgcag acgtggtatc caccggaagg    480
acgctacgtc aacaagggct tgccccattc ggtgaggtgc tgtgcacatc cgaggctgtt    540
atcgtgggaa gaaaagacga aaaggttaca cctgagcagc agatattact aagaaggata    600
cagggaattc tgcacgctca aaactttcta atgctggatt ataaggttga tagggataac    660
ctagacgccg ccacagccgt tactcctggt ttctccggtc ccgctgtcag tcctctagct    720
agggacaact gggtcgccgt cagggctatg gttccaagac gtagcgctaa cgcaataatg    780
gacaaattgg cgggccttgg ggccgaagca atactggcga gcgaaatcag gattgcacgt    840
att                                                                  843
```

<210> SEQ ID NO 90
<211> LENGTH: 891
<212> TYPE: DNA
<213> ORGANISM: Artificial
<220> FEATURE:
<223> OTHER INFORMATION: Codon-optimized and/or mutated sequence

<400> SEQUENCE: 90

```
atgttagata atactcgtct tagaatagcg atacagaaaa gtgggaggct ttccgatgac     60
tctcgtgaat tactagcgag gtgcgggatt aagataaacc ttcatacaca aggttgatt    120 gcaatggccg agaacatgcc gatagacatt ttaagagtca gggatgatga tatcccagga   180
ctagtgatgg atggggtggt tgatttagga attattggag agaatgtttt agaggaagaa   240
ctgttgaacc gtcgtgcgca aggtgaagat cctaggtacc ttacccttag gagacttgat   300
tttggcggtt gccgtttaag cctagcaact ccagtcgatg aggcatggga cgggcccgct   360
gccctggatg gtaaacgtat agccacatcc tacccacacc tactgaaaag atatctggac   420
cagaaggggg tttctttcaa aagttgtttg cttaacggct ccgtcgaagt cgcgcctcgt   480
gcgggattgg ccgatgcgat atgcgatctg gtctccacgg tgctaccct ggaggctaat    540 ggccttagag aagtggaagt aatatacagg agcaaagcgt gccttatcca gagagacggt   600
gaaatggccc agagcaaact tatagataag ctactaacga gaattcaagg tgttatccaa   660
gcaagagagt ccaagtatat aatgatgcac gcgccctctg agagattaga ggaggtcatc   720
gcattgttgc caggggcaga acgtcccacc atacttcctc tagcgggtga gcaacagagg   780
gtagccatgc acatggtgtc cagcgaaact ttgttctggg aaacgatgga aaagctaaag   840
gcccttggag cctcttcaat tctagttctg ccgatcgaaa agatgatgga g             891
```

<210> SEQ ID NO 91
<211> LENGTH: 738
<212> TYPE: DNA
<213> ORGANISM: Corynebacterium glutamicum

<400> SEQUENCE: 91

```
atgaccttca ctattcttcc tgcagtcgat gtagttaacg acaagcagt tcgcctagat      60 cagggcgagg ccggcactga aaatctttat ggcaccccctt tggaatctgc actgaagtgg   120
```

| | |
|---|---|
| caggagcagg gtgcaaagtg gttgcactt t gtggacctgg acgcagcgtt caaccgtggt | 180 |
| tccaatcatg agatgatggc ggaaattgtc ggcaagctcg atgttgatgt ggagctcact | 240 |
| ggcggtatcc gtgatgatga gtctctggag cgcgcgctgg caaccggtgc acgtcgtgta | 300 |
| aacattggta ccgctgctct ggagaagcca gagtggattg cttctgcgat tcaacgctat | 360 |
| ggcgagaaga ttgctgtcga tatcgctgtg cgtttggaag atggtgaatg cgcacccgt | 420 |
| ggaaacggtt gggtctccga tggtggcgat ctgtgggacg ttctcgagcg tttggattcc | 480 |
| caaggttgtg cacgtttcgt ggttaccgat gtgtccaagg acggcacctt gagtggtcca | 540 |
| aatgttgagc tgctgcgtga ggttgctgca gctacagacg cacctatcgt ggcatctggt | 600 |
| ggaatttctg ttttggaaga tgttttggaa ctagccaagt accaggatga gggcattgat | 660 |
| tccgtcatca ttggcaaggc actttatgag cacaagttca ccctcgaaga ggctttggct | 720 |
| gcagtagaaa agctcggt | 738 |

<210> SEQ ID NO 92
<211> LENGTH: 606
<212> TYPE: DNA
<213> ORGANISM: Corynebacterium glutamicum

<400> SEQUENCE: 92

| | |
|---|---|
| atgactgtcg caccaagaat tggtaccgca acccgcacca ccagcgaatc cgacatcacc | 60 |
| gtcgagatca acctggacgg caccggcaaa gtagatatcg ataccggcct gccatttttc | 120 |
| gaccacatgc tcactgcatt cggcgtgcac ggcagttttg atctgaaagt ccatgccaag | 180 |
| ggcgacatcg agatcgacgc acaccacacc gtggaagata ccgccatcgt gctcggccaa | 240 |
| gcactccttg acgctattgg cgacaagaaa ggcatccgcc gtttcgcatc ctgccagctg | 300 |
| cccatggatg aggcattagt ggagtccgtg gtggatatct ccggtcgccc atacttcgtg | 360 |
| atctccggcg aaccagacca catgatcacc tccgtgatcg gtggacacta cgcaaccgtg | 420 |
| atcaacgagc acttctttga aaccctcgcg ctcaactccc gaatcaccct ccacgtgatc | 480 |
| tgccactacg ccgcgacccc tcaccacatc accgaagcag agtacaaggc tgttgcccgt | 540 |
| gcgctgcgcg gtgccgtaga gatggatcct cgtcaaacag gaatcccatc caccaaggga | 600 |
| gcgctc | 606 |

<210> SEQ ID NO 93
<211> LENGTH: 1098
<212> TYPE: DNA
<213> ORGANISM: Corynebacterium glutamicum

<400> SEQUENCE: 93

| | |
|---|---|
| atgaccaaaa ttactttgag cgatttgcca ttgcgtgaag aactgcgcgg tgagcacgct | 60 |
| tacggcgcac cccagctcaa cgttgatatt cgcctcaaca ccaacgaaaa cccttaccca | 120 |
| ccgtcagagg cattggtcgc tgacttggtt gccaccgtgg ataagatcgc caccgagctg | 180 |
| aaccgctacc cagagcgcga tgctgtgaa ctgcgtgatg agttggctgc gtacatcacc | 240 |
| aagcaaaccg gcgtggctgt caccagggat aacctgtggg ctgccaatgg ttccaatgaa | 300 |
| attctgcagc agctgctgca ggcttttggt ggacctggac gcaccgcatt gggattccaa | 360 |
| cccagctatt ccatgcaccc aattttggct aaaggcaccc acactgaatt cattgcggtg | 420 |
| tcccgaggtg ctgatttccg catcgatatg gatgtggcgc tggaagaaat tcgtgcaaag | 480 |
| cagcctgaca ttgttttgt caccaccccg aacaacccga ccggtgatgt gacctcgctg | 540 |
| gacgatattg agcgcatcat caacgttgcc ccaggcatcg tgatcgtgga tgaagcttat | 600 |

```
gcggaattct ccccatcacc ttcagcaacc actcttctgg agaagtaccc aaccaagctg      660
gtggtgtccc gcaccatgag taaggctttt gatttcgcag gtggacgcct cggctacttc      720
gtggccaacc cagcgtttat cgacgccgtg atgctagtcc gccttccgta tcatctttca      780
gcgctaagcc aagcagccgc aatcgtagcg ctgcgtcact ccgctgacac gctgggaacc      840
gtcgaaaagc tctctgtaga gcgtgttcgc gtggcagcac gcttggagga actgggctac      900
gctgtggtgc caagtgagtc caactttgtg ttctttggag attctctcga tcagcacgct      960
gcatggcagg cattttggga taggggagtg ctcatccgcg atgtgggaat cgccgggcac     1020
ttgcgcacta ccattggtgt gcctgaggaa aatgatgcgt ttttggacgc agctgcagag     1080
atcatcaagc tgaacctg                                                  1098

<210> SEQ ID NO 94
<211> LENGTH: 1326
<212> TYPE: DNA
<213> ORGANISM: Corynebacterium glutamicum

<400> SEQUENCE: 94
atgttgaatg tcactgacct gcgaggtcaa acaccatcca agagcgacat ccgacgtgct       60
ttgccacgtg gtggcactga cgtgtggtct gtgcttccca tagtgcagcc tgttgtagaa      120
gatgtccaaa accgcggcgc tgaagctgct ttggattacg gcgagaagtt cgaccatatt      180
cgccccgcct cggtgcgggt gccagctgag gttattgctg cagcagaaaa caccttggat      240
ccgttggtgc gtgaatcgat tgaagagtcg attcgtcgcg tccgcaaggt tcacgctgag      300
caaaagccag ccgagcacac cactgaactt tcaccaggtg gcaccgtcac tgagcgtttc      360
atgccgattg atcgcgtggg actgtacgtt ccaggcggca atgcggtgta cccatcaagc      420
gtgattatga atactgtccc agctcaagag gctggtgtga actcccttgt ggttgcgtcg      480
cctcctcagg ctgagcacgg tggctggcct caccccacca ttttggcggc gtgttccatc      540
ttgggtgttg atgaggtgtg ggctgtcggc ggcggtcagg ccgtggcgtt gctggcttat      600
ggtgatgacg ctgcaggtct cgagcctgtg gatatgatca ctggacctgg caatatcttt      660
gtcaccgctg cgaagcgcct ggtcagggga gtggtaggta ctgattctga ggctggccct      720
acagaaatcg ctgtgcttgc tgatgcctct gccaacgccg tcaacgttgc ctacgatctg      780
atcagccaag cagaacacga tgtcatggct gcgtccgtgc tcatcactga ctccgagcag      840
cttgccaagg acgtaaacag ggaaatcgag gcgcgttact caatcacgcg caacgccgag      900
cgcgtcgcag aagctttgcg cggggcccag agtggcatcg tgcttgtcga cgacatttcc      960
gtgggtatcc aagtagccga tcaatacgca gcggaacacc tggaaatcca cactgagaac     1020
gcgcgcgccc tagcagagca gatcaccaac gcgggtgcga tcttcgtggg cgatttctca     1080
ccagtaccac tgggtgatta ctccgcagga tccaaccacg tgctgccaac ctctggatcc     1140
gctcgtttct ccgcaggtct atccacgcac atgttccttc gcccagtcaa cctcattgaa     1200
tacgatgagg ctgctctgaa ggacgtctcg caggttgtca tcaactttgc caacgccgaa     1260
gatcttccag cgcacggcga agcaatccgt gcacgctttg aaaacctccc caccaccgac     1320
gaggcc                                                                1326

<210> SEQ ID NO 95
<211> LENGTH: 261
<212> TYPE: DNA
<213> ORGANISM: Corynebacterium glutamicum
```

<400> SEQUENCE: 95

```
gtgaagacat ttgactcgct gtacgaagaa cttcttaacc gtgctcagac ccgccctgaa    60
gggtctggaa ccgtggccgc cttggataaa ggcatccatc atctaggtaa gaaggtcatc   120
gaagaagccg agaggtctg gattgcagcc gagtatgaga ccgatgaaga gctagccgga    180
gaaatctccc agctcattta ttggacccag gtcatcatgg ttgctcgcgg cctgaagcca   240
gaagatatct acaagaacct g                                             261
```

<210> SEQ ID NO 96
<211> LENGTH: 774
<212> TYPE: DNA
<213> ORGANISM: Corynebacterium glutamicum

<400> SEQUENCE: 96

```
atgggcgtgg caattcgagt tattccttgc ctggacgtgg acaacggccg ggttgttaaa    60
ggcgtgaact ttgaaaacct ccgcgatgct ggcgatcctg tggagttggc aaagcgctat   120
gacgaggaag gggcagatga gctgaccttc ttggatgtca ccgcctcgaa gcatggtcgc   180
ggcaccatgc tggatgttgt tcgacgcacc gctgatcagg tgttcatccc tctgactgtc   240
ggtggcggcg tgcgcagcga agaagatgtt gatcaattgc tgcgcgcggg cgccgacaag   300
gtttcggtga acacgtctgc gattgcccgt ccagaactgc tatcagagct gtccaagcgt   360
tttggtgctc agtgcatcgt gttgtctgtg atgccaggc gcgttcctga aggtggaact    420
cctcagccat ctggttttga agtcaccact cacggcggtt ccaagtccgc agaacttgat   480
gcaatcgagt gggcaaagcg cggcgaagag ctgggcgttg cgaaattct gctcaactcc    540
atggacggcg acggcaccaa aaacggcttt gacctagagc tgctggaaaa agttcgcgca   600
gccgtatcca ttcctgtaat cgcctccggc ggcgctggca aggcggagca tttcccacca   660
gctgttgcag ctggcgccaa cgcagtgctt gccgcgacca ttttccactt ccgcgaagta   720
accatcgccg aagtaaaggg agccattaaa gatgcaggat ttgaggtgcg gaaa          774
```

<210> SEQ ID NO 97
<211> LENGTH: 633
<212> TYPE: DNA
<213> ORGANISM: Corynebacterium glutamicum

<400> SEQUENCE: 97

```
atgaccaaaa ctgtcgccct tctcgactac ggatctggaa accttcgttc tgctcaacgc    60
gcattagagc gtgctggtgc agaagttacc gtgagctctg atccagaagt ttgcaccaac   120
gctgatggcc tcctagttcc tggggtgggc gcatttgatg cctgcatgaa gggtttgaaa   180
aacgtcttcg acatcgcat tatcggacag cgtcttgctg gtgggcgtcc agtgatgggt    240
atttgtgtgg gcatgcagat cctgtttgat gaaggcgatg agcatggcat taagtcagct   300
ggttgtggcg agtggcctgg caaggtgaa cgcctccagg cggagatcct gcctcacatg    360
gggtggaaca cacttgaaat gcctaccaac tcaccaatgt tgagggaat ttcacctgat    420
gagcgtttct acttcgtgca ctcctatggt gtgcgcaagt ggacgttgga aaccgacgat   480
ctgaccacgc ctccagaggt tgtgtgggcg aagcacgaaa atgatcgttt tgtggctgct   540
gtggaaaacg gcacgctgtg ggctactcaa ttccacccag aaaaatcagg tgacgtaggc   600
gcaaagctac tgcgaaactg gatcaactac atc                                633
```

<210> SEQ ID NO 98
<211> LENGTH: 354

```
<212> TYPE: DNA
<213> ORGANISM: Corynebacterium glutamicum

<400> SEQUENCE: 98
atgagtgaca atccacaaga gtatgagctg gattgggacg tcgaaaagcg attaaagctt      60
aacgacgccg gcctggtgcc ggcaatcgtc caggccgacg ggaccaacga ggtcctcatg     120
atggcctgga tggataccca cgcgctagcc tatactttgg cgacccgccg tggaacctat     180
ttttctaggt cccgcaacga gtactggatc aagggcctga cctctggaaa cgtccaagaa     240
gtcaccggac ttgccctcga ctgcgacggc gacactgtcc ttctgaccgt gaaacaaacc     300
ggcggtgcgt gccacactgg tgcccacaca tgtttcgaca tgacgttttt gctg           354

<210> SEQ ID NO 99
<211> LENGTH: 891
<212> TYPE: DNA
<213> ORGANISM: Saccharomyces cerevisiae

<400> SEQUENCE: 99
atggatttgg tgaaccatct aaccgataga ctactgtttg caatcccaaa gaaaggtcgt      60
ttatattcta aaagtgtttc tattttgaat ggtgctgata ttacatttca ccgctctcaa     120
agattagaca ttgcactaag cacaagctta cctgtagcgt tgatctttct gcccgctgca     180
gatattccaa cttttgttgg tgaaggtaaa tgtgatcttg gtataactgg tgttgaccaa     240
gttcgtgaat ctgacgtcga cgtagactta gcaatcgatt tgcaatttgg taactgtaaa     300
ttgcaggtac aagtccccgt aaatggcgag tataaaaagc cagaacagtt aattggcaaa     360
accattgtta ccagtttcgt gaaacttgct gaaaaatact ttgccgattt ggaaggtact     420
actgttgaaa aaatgaccac aaggataaag tttgtcagtg gttccgtgga ggcatcatgt     480
gctctgggaa ttggtgatgc tattgtagat cttgtagaga gtggtgagac aatgagggca     540
gcaggtttag ttgatattgc caccgtccta agcacaagtg cctacctaat agaatcaaag     600
aacccaaaga gcgataagag tttgattgct actatcaaat caagaattga aggtgtcatg     660
accgctcaaa ggttcgtttc atgtatttat aacgcacctg aagacaagct gcctgaactg     720
ttgaaggtga cgcctggccg tagagcacca accatttcca aaattgacga tgaaggatgg     780
gttgctgtta gttccatgat tgagagaaaa acgaagggtg ttgttttaga tgaattgaaa     840
agactcggcg catctgatat catggttttc gaaatttcta attgtcgtgt a              891

<210> SEQ ID NO 100
<211> LENGTH: 1656
<212> TYPE: DNA
<213> ORGANISM: Saccharomyces cerevisiae

<400> SEQUENCE: 100
atgccggtcg ttcacgtgat tgacgttgaa agtggtaacc tacagtcact aaccaatgca      60
attgagcatt taggttacga agtacaactg gtgaaatcac caaaggattt taacatatca     120
ggcacgtcaa gattgatttt gcctggtgtc ggaaattatg ccatttcgt cgacaattta     180 tttaatagag gattcgaaaa gccgataaga gaatacattg aatctggaaa accaataatg     240
ggaatttgcg tcgggctaca agcgctcttt gccggttccg tggaaagccc taagagtacg     300
ggtctgaact acattgattt taagttgtcc aggttcgatg attcagaaaa gccagtacca     360
gaaataggtt ggaattcttg cattccctcg gaaaacctat tctttggatt ggatccatac     420
aagaggtact atttcgtcca ttcttttgct gccattctga attcagaaaa gaaaaaaaac     480
```

```
ctagaaaatg acggttggaa aattgcaaaa gctaagtacg gttcagagga atttattgcg    540
gcagtcaaca agaataatat attcgctact cagttccatc ctgaaaaatc aggtaaagct    600
ggtttgaacg tcattgagaa ttttttgaag caacaaagtc ctccgattcc aaactatagt    660
gcggaagaga aggaactctt aatgaatgac tattcaaatt atggtctaac acgcagaatt    720
attgcttgtc ttgatgtacg tactaatgac caaggtgatt tggtggttac taaaggtgat    780
caatacgatg tacgtgaaaa aagtgatggt aaaggtgtta gaaaccttgg taagcctgtt    840
cagttggcac agaaatatta ccaacagggt gcggatgaag taacatttt gaatataact    900 tcttttagag attgtccttt gaaggatact ccgatgctag aggttctgaa acaagccgca    960
aagacagtct ttgttccatt gacagtcggt gggggatca aggatattgt cgatgttgat    1020
ggaaccaaaa tacctgcttt agaagttgca agtctatact tcagatctgg tgctgataaa    1080
gtatcgatcg gtacggatgc agtctatgca gccgaaaaat actacgagtt gggtaacaga    1140
ggagatggaa cgtcaccaat agagacaatc tcgaaagcat acggtgctca ggcagttgtt    1200
atttctgtcg atcctaagag agtatatgta aattcacaag cagatacgaa gaacaaagtc    1260
ttcgagacag aatatccggg ccccaatgga gagaaatact gctggtacca atgtacaatc    1320
aaaggtggaa gagaatctag agaccttggt gtgtgggaat aacaagggc atgtgaagct    1380 ctaggtgctg gggagatttt attgaactgc atagacaagg atggctctaa ttctggttat    1440
gatctggaat tgatagaaca tgttaaagat gcggtcaaga ttcccgtcat tgcatccagt    1500
ggcgccggtg tacccgaaca tttcgaagag gccttcctaa agacccgcgc agatgcttgc    1560
ttgggtgcag gtatgttcca cagaggtgaa ttcactgtta acgatgtaaa ggagtattta    1620
ctagagcacg gattaaaggt tagaatggat gaagag                             1656

<210> SEQ ID NO 101
<211> LENGTH: 1158
<212> TYPE: DNA
<213> ORGANISM: Saccharomyces cerevisiae

<400> SEQUENCE: 101 atggttttg atttgaaaag aattgttaga ccaaaaattt ataacttgga accttatcgc     60
tgtgcaagag atgatttcac cgagggtata ttgctagacg ccaatgaaaa tgcccatgga    120
cctactccag ttgaattgag caagaccaat ttacatcgtt acccggatcc tcaccaattg    180
gaattcaaga ccgcaatgac gaaatacagg acaaaaacaa gcagttatgc caatgaccca    240
gaggtaaaac ctttaactgc tgacaatctg tgcctaggtg tgggatctga tgagagtatt    300
gatgctatta ttagagcatg ctgtgttccc gggaaagaaa agattctggt tcttccacca    360
acatattcta tgtactctgt ttgtgcaaac attaatgata tagaagtcgt ccaatgtcct    420
ttaactgttt ccgacggttc ttttcaaatg ataccgaag ctgtattaac catttttgaaa    480 aacgactcgc taattaagtt gatgttcgtt acttcaccag gtaatccaac cggagccaaa    540
attaagacca gtttaatcga aaaggtctta cagaattggg acaatggggtt agtcgttgtt    600 gatgaagctt acgtagattt ttgtggtggc tctacagctc cactagtcac caagtatcct    660
aacttggtta ctttgcaaac tctatccaag tcattcggtt tagccgggat taggttgggt    720
atgacatatg caacagcaga gttggccaga attttaaatg caatgaaggc gccttataat    780
atttcctccc tagcctctga atatgcacta aaagctgttc aagacagtaa tctaaagaag    840
atggaagcca cttcgaaaat aatcaatgaa gagaaaatgc gcctcttaaa ggaattaact    900
gctttggatt acgttgatga ccaatatgtt ggtggattag atgctaattt tcttttaata    960
```

```
cggatcaacg ggggtgacaa tgtcttggca aagaagttat attaccaatt ggctactcaa   1020
tctggggttg tcgtcagatt tagaggtaac gaattaggct gttccggatg tttgagaatt   1080
accgttggaa cccatgagga gaacacacat ttgataaagt acttcaagga gacgttatat   1140
aagctggcca atgaataa                                                  1158

<210> SEQ ID NO 102
<211> LENGTH: 660
<212> TYPE: DNA
<213> ORGANISM: Saccharomyces cerevisiae

<400> SEQUENCE: 102
atgacagagc agaaagccct agtaaagcgt attacaaatg aaaccaagat tcagattgcg    60
atctctttaa agggtggtcc cctagcgata gagcactcga tcttcccaga aaaagaggca   120
gaagcagtag cagaacaggc cacacaatcg caagtgatta acgtccacac aggtataggg   180
tttctggacc atatgataca tgctctggcc aagcattccg gctggtcgct aatcgttgag   240
tgcattggtg acttacacat agacgaccat cacaccactg aagactgcgg gattgctctc   300
ggtcaagctt ttaaagaggc cctaggggcc gtgcgtggag taaaaaggtt tggatcagga   360
tttgcgcctt tggatgaggc actttccaga gcggtggtag atctttcgaa caggccgtac   420
gcagttgtcg aacttggttt gcaaagggag aaagtaggag atctctcttg cgagatgatc   480
ccgcattttc ttgaaagctt tgcagaggct agcagaatta ccctccacgt tgattgtctg   540
cgaggcaaga atgatcatca ccgtagtgag agtgcgttca aggctcttgc ggttgccata   600
agagaagcca cctcgcccaa tggtaccaac gatgttccct ccaccaaagg tgttcttatg   660

<210> SEQ ID NO 103
<211> LENGTH: 1005
<212> TYPE: DNA
<213> ORGANISM: Saccharomyces cerevisiae

<400> SEQUENCE: 103
atgcactcac accattcaca ctccggtgac tatagtgccc acggtacgga ccctttggat    60
tccgtggtcg atcaggtggt caacctcaac tttcacacgt actgtttgac agagcacata   120
ccaagaattg aggccaagtt tatataccc gaagagcagt cattgggcaa gaatcctgag   180
gaagtcataa gcaagctaga acatcgttc aagaatttca tgagtcatgc gcaagaaatc   240
aagactcgtt acgctgatag acccgatgtg cggactaaat tcattatagg aatggagatc   300
gaaagttgtg acatggctca tatcgaatat gcaaagcgac tcatgaagga gaataatgat   360
actttgaagt tttgtgtggg ttcggtccat cacgtcaacg ggatccctat tgatttcgac   420
caacaacaat ggtacaattc attgcattcc ttcaatgata atttgaaaga ttttctcctg   480
tcttacttcc aatcacagta cgaaatgctg atcaatatta aaccgttggt cgtgggtcac   540
ttcgaccttt acaaattatt tttgcccaat gacatgctag taaaccagaa atcgggcaac   600
tgcaacgaag aaaccggagt tcctgtagct tcactggacg tcatcagtga atggccagaa   660
atatacgatg cagttgtaag aaatttacaa tttatagact cctatggcgg cgcaattgaa   720
atcaatacgt ccgcattaag aaagggcctc gaggagccgt accccagcaa aaccttatgt   780
aatctggtca agaagcactg tggatccaga tttgttctaa gtgatgacgc acacggcgtg   840
gcgcaagtgg gtgtgtgcta tgacaaggta aagaaataca tagtagacgt gctacaatta   900
gagtacattt gctaccttga ggaaagccaa tcaccagaga atgtgttaac tgtaaagaga   960
```

-continued

| | |
|---|---|
| ttacccattt cgcaattcgt taatgatccc ttttgggcca atata | 1005 |

<210> SEQ ID NO 104
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 104

| | |
|---|---|
| atggcaaaaa ttgataaaat tctcaatcag gaaggcattg accgcattgc aatcaatcca | 60 |
| taccagaaat acagccgtgg atatatggaa ccgggcaacc ttggaggagg ctacgtgacc | 120 |
| ggtctcaagg tggatgcagg cacccgtgaa aagactgacg actctatgct ggatggcatt | 180 |
| gtgtcttatg atcgcgccga atgcaaaaat gcctacatcg ccagatcaa catgatgacc | 240 |
| gcatccagct ttacgggcgt gcaaggccac atccttggat atgatctgct gcgcaaccct | 300 |
| gccgttgaca ggcccagcc cctcttttat gaaacacaat gggatggtag caaactgcca | 360 |
| atctatgacg gcaagcctct tcaagattcc ttggtagaat ttttcggtac cgcggacaat | 420 |
| cgacgccatt atccagcccc gggatctttt atcgtatgtg ctaataaggg tgttaccgct | 480 |
| gaacgaccac ttgaggatcg accattgaat cctggagaag catacggtgt gtggtcagca | 540 |
| atcgctattt caattgcaaa ggacccggtc cataactcct ctatgtttat cgaggatgcg | 600 |
| ggtacctgga acacgccgaa cgaagatgac cttaacgagt tcctgtatca tcgccgcgaa | 660 |
| gccattgcac gcagcattgc gcaatgtggc caagacgcct caacttcatt tgcatcctcc | 720 |
| tggattggct tcgcacatgt gatgatgaag ccaggcgaga ttggcaacgc cattacggtc | 780 |
| ggcccgtact tcagcatgcc tgttgacgcc gttccaggtg gctctattct cactccggat | 840 |
| gttgatatga acattatgga agacctctcc ctccctgaat ggcttgaaaa gatgggctac | 900 |
| caatccattg tggaaaacca agacatccag tat | 933 |

<210> SEQ ID NO 105
<211> LENGTH: 1170
<212> TYPE: DNA
<213> ORGANISM: Artificial
<220> FEATURE:
<223> OTHER INFORMATION: Codon-optimized and/or mutated sequence

<400> SEQUENCE: 105

| | |
|---|---|
| atgtgccgcc atgcgtgcat cgccttggca atgggaatga ttatgggcct ttcatcagag | 60 |
| gacgccggaa agatcgaatc gttctggcgc tattgcgtgc agcaccaata cttcaatatc | 120 |
| ggttatcccg aggcagctga ttttgactac tccgccctta atcgttttct gaacttctct | 180 |
| attaacaact gcggagattg gtcacagcaa tccaactacc tcctgaactc gttcgacttc | 240 |
| gaacgtgaag tcatgcagtt cttcgctact ctgttctgca tcccattcga acagtcctgg | 300 |
| ggttatgtga caaacggcgg cactgagggc aacatgttcg gttgctactt ggctcgtgag | 360 |
| ctcttcccag aagccaccct gtactactcc aaggacaccc attacagcgt cgctaaaatc | 420 |
| atccgactct tgcgcgtgaa atcttgcatg gtggactccc tcccgaatgg tgaaatgaac | 480 |
| tacgatgact tgatcaatcg catccgtctg gatggagaac gccacccgat catctttgca | 540 |
| aacatcggca ctaccatgac cggcgctacg gataacatcg caacgatcca acgccgtctc | 600 |
| aaaaagatcg gtattactaa gggcgattac tacctgcacg ctgacgcagc actgtctggc | 660 |
| atgatcttgc ctttcattga taacccacaa ccgttcagct tcgcagatgg tgttgactct | 720 |
| atttccgtgt ccggacacaa gatgattgga tctccgatcc cctgcggtat cgtgcttgca | 780 |

```
cgccgtaaac acgtcgaaca cgtttctgtc gagattgatt acatttcagc ttgcgatcag    840
actatctccg gttcccgcaa cggttatact cctttgctgc tctggatggc cattaagtcc    900
cgctccttct ccgactggcg tcagcgtacc cagcactgcc tcgacatggc gcagtacgta    960
attgaacgct tccatgctaa gggtatccac gcttggcgca atcccaactc catcaccgtt   1020
gtcttcccga aaccagctga tcacatctgg aagaagcact gcctcgccac ctctggtaag   1080
atctcacaca tcatcacgat gccacatcac accggcaaag agactctgga tcgcgttatc   1140
aatgacatcg ctctcgaccg tgagccaaag                                    1170
```

<210> SEQ ID NO 106
<211> LENGTH: 1134
<212> TYPE: DNA
<213> ORGANISM: Artificial
<220> FEATURE:
<223> OTHER INFORMATION: Codon-optimized and/or mutated sequence

<400> SEQUENCE: 106

```
atgacgctga gcatcaacga ccaaaacaag ttggatgctt tctgggcata ctgtgttaaa     60
aaccaatatt ttaacatcgg ctaccctgaa agcgctgatt ttgactacac caaccttgag    120 cgcttttttgc gcttttcaat caacaactgt ggtgattggg gcgaatattg caattacctg    180
ttgaactcct tcgacttcga gaggaagtg atggaatatt cgctgacct cttcaagatc     240 ccattcgaga agtcctgggg atacgtcacc aacggcggaa cggaaggcaa catgttcggt    300
tgctatctgg gccgagaaat ttttcccgat ggtaccctgt actactctaa agatacacac    360
tattcagtgg cgaagatcgt taagcttctc cgaatcaagt ctcaggtagt agaagcccaa    420
ccaaacggcg aaattgatta cgatgatctt atgaagaaga ttgcagcaga caggaggcc    480 cacccaatta tctttgccaa tatcggtacc accgtacgcg gagctatcga cgatatcacc    540
gagatccaga aacgcatgaa ggccgccggc atcaagcgcg aggactacta cctgcatgca    600
gacgctgccc tctccggcat gatcctgcct tttgtggatg aacctcaggc cttcaccttt    660
gctgatggca ttgactccat tggcgtctcc ggtcataaga tgatcggcag cccgattccg    720
tgcggcatcg ttgtggcgaa aaaggaaaat gtggatcgca tctcagtgga aattgactat    780
atctcagcac atgacaaaac tatcactggc tcacgtaacg ccacacgcc actcatgctc    840 tgggaggcgg tgcgcgcgca ctctacggaa gattggaagc gtcgtatcgg tcgctctttg    900
gatatggcgc agtacgcagt agaccgtctg cagaaggccg gcatcaatgc ttggcgtaac    960
aaaaactcca ttaccgtcgt gtttccgtgc ccgagcgagc gtgtgtggaa ggaacactgc   1020
ctcgcaacct ctggtaatga tgcacatctg atcaccaccg cacaccattt ggacactgct   1080
cagattgatg ccctgatcga cgacgttatt gcagatgcca agctccacgc tgct        1134
```

<210> SEQ ID NO 107
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 107

```
atgcttaaga ttgcagtccc aaacaaaggt agcttgtccg agcgtgccat ggagatcttg     60
gccgaagcag gctatgccgg ccgtggcgat tcaaaatcgc ttaacgtctt cgacgaagcg    120
aataatgttg aattttttctt cctccgaccg aaagatatcc ctatttacgt ggcaggcggc    180
```

| | |
|---|---|
| caattggacc tgggcattac aggacgagac ttggcacgag attcccaggc ggacgtgcac | 240 |
| gaggtactga gcctgggatt cggctctagc acctttcgct atgcagctcc agccgacgag | 300 |
| gaatggagca tcgaaaagct cgatggtaag cgcatcgcaa cctcttaccc aaacctggtg | 360 |
| cgcgatgatc tcgcggcccg cggcctttcg gcagaagtgc ttcgccttga tggtgcagtt | 420 |
| gaagtcagca tcaagctggg agtcgccgat gccattgcag atgtcgtctc tacgggacgc | 480 |
| acattgcgcc aacagggact cgctcctttc ggagaggtgc tctgcacctc ggaagcggtg | 540 |
| atcgtaggcc gcaaggacga aaaggtcaca ccagagcagc agatcctcct ccgccgaatt | 600 |
| caaggcatcc tgcacgcaca gaactttctt atgctggatt acaacgttga ccgcgataat | 660 |
| ctggacgcag cgaccgcggt cacccccgga ctctccggtc ccaccgtgtc gccacttgct | 720 |
| cgtgataatt gggttgcggt gcgtgctatg gtccccccgcc gcagcgcgaa cgctattatg | 780 |
| gataaactgg cgggacttgg cgcggaagcc atccttgcat ccgaaatccg cattgcgcga | 840 |
| att | 843 |

<210> SEQ ID NO 108
<211> LENGTH: 945
<212> TYPE: DNA
<213> ORGANISM: Artificial
<220> FEATURE:
<223> OTHER INFORMATION: Codon-optimized and/or mutated sequence

<400> SEQUENCE: 108

| | |
|---|---|
| atgcctgaca tgaaattgtt cgcgggcaat gcgacacctg agctcgctca acgaatcgcc | 60 |
| aatcgactgt acaccagcct tggagatgcg gcggttggac gcttttcgga tggcgaggtt | 120 |
| tccgtacaga tcaacgaaaa cgtgcgcggc ggcgacatct tcatcattca gtccacgtgc | 180 |
| gctcccacca cgacaatctc gatggaactg gttgttatgg tcgatgccct cgccgcgca | 240 |
| tcggctggtc gcatcacagc agtgattcca tattttggct acgctcgcca ggatcgacgt | 300 |
| gtgcgatcgg cccgcgttcc catcaccgcc aaagtcgtgg cggatttcct ttcctctgtg | 360 |
| ggagttgacc gtgtgctcac tgtagacttg catgcggaac agattcaagg cttctttgat | 420 |
| gtgcctgttg acaacgtttt cggcagccct atcctgctcg aagatatgct ccaactgaac | 480 |
| ctcgataatc ctattgtcgt ttcaccagat attggtggtg tcgttcgtgc tcgagcaatc | 540 |
| gcgaagcttc tcaacgatac cgatatggca attatcgaca acgtcgccc acgcgcgaac | 600 |
| gtttcacaag ttatgcatat tattggtgat gttgccggcc gcgattgcgt gttggtggat | 660 |
| gatatgatcg acactggcgg cactttgtgc aaagcggcgg aagccctgaa ggaacgcggc | 720 |
| gccaaacgcg tatttgcata cgccacccac ccaatttttct ctggcaatgc cgcgaacaac | 780 |
| ctgcgcaact ccgtgatcga tgaagttgtg gtgtgtgata cgatcccctt gtctgacgaa | 840 |
| atcaaatccc tcccgaacgt cgcacactg actctctcag gcatgctggc cgaggccatt | 900 |
| cgacgaatct ctaacgagga gagcatctcc gcaatgtttg aacat | 945 |

<210> SEQ ID NO 109
<211> LENGTH: 1488
<212> TYPE: DNA
<213> ORGANISM: Artificial
<220> FEATURE:
<223> OTHER INFORMATION: Codon-optimized and/or mutated sequence

<400> SEQUENCE: 109

| | |
|---|---|
| atgtctatgt ccaatattgt cgtttttcgga ggagactcgc acccagaatt ggtgaccaag | 60 |
| atttgcgaaa atcttgacat tcaccccagc aaggttgagc tgggcaaatt ttctaacggt | 120 |

```
gaaactaaca tcgcactgcg tgaatcggtc cgagagaaag acgtctacat cattcagtcg      180
ggctgcggtc aagtgaacga tactttcatg caactgttga tcctcatctc cgcatgtaag      240
agcgcttccg catcccgtgt caccgcagtc atgccatacc tttgctattc gcgacaacca      300
gacatccctt acacagcgaa gggagcaccc attatttcca agccgaaaga aaactatacg      360
tttgaatcac atccaggaac ccccgtgtcc tcctccctta tgacccagcg acccggcgcg      420
gagtcgagcc ttaaaagctt ggattcagct atccgaagca ccatcaatct ggagaacccg      480
cagccaatcc gcactcccaa ttcttctgca accgcgaata caactttga tattaagaaa       540 accctgagct tctcacgtat cccaatgatc cccggcggaa aactgcagaa tacttcgaac      600
tctaccgatg cgggcgaact cttcaatgct caaaacgccg gatacaagct ttgggttgtc      660
caagcaggaa ccctgatcgc acacctgctg tctgccgctg gtgccgatca cgtcatcacc      720
atggatctgc atgacccaca attcccagga ttctttgata ttcctgtaga taacctgtat      780
tgcaaaccca tcgctcaaaa ctatattcag caccgcattc ccgattacca agatgctgtt      840
atcgtgtctc ccgacgctgg cggcgccaag cgcgctaccg ctatcgcgga tgcattggaa      900
ctctcctttg ctttgatcca aaggaacgc cgaagccagc tgcttaaggg acctccagat       960
gccactctga cttcaggcgg ctctctgcct gtttccccc gcccactcgt tacgaccctg      1020
gtctcctctc agaatacgac ttcctccggt gctacaggtg tggctgctct cgaaatgaag     1080
aaaactacct ccacaagctc cacctcatcg cagtccagca attcatctaa gtttgtccag     1140
accacaatgc ttgttggcga tgtccgcaat aaggtgtgca ttattgtcga tgacctggta     1200
gacactagct ataccattac ccgtgcagcc aaactcctca aggaccaggg ctcgacgaaa     1260
gtttacgccc tgattactca cggcgtattc agcggcgacg ctctggagcg cattggtcag     1320
agctccatcg ataagctgat catctctaac acagtccccc aggaccgtac cttgcaatac     1380
ctgggaaagg accgcgttga cgtaattgat gtgtcctgca tcatcggcga ggctatccgc     1440
cgtatccata acggagaatc gatctctatg ctgttcgagc atggttgg                  1488
```

<210> SEQ ID NO 110
<211> LENGTH: 1281
<212> TYPE: DNA
<213> ORGANISM: Artificial
<220> FEATURE:
<223> OTHER INFORMATION: Codon-optimized and/or mutated sequence

<400> SEQUENCE: 110

```
atgcgtaaat gcaaatctt cgtgggaaac tcacacccag aactgggaaa catggtatgc       60
caacgcttgg gtatcgagcc cgcaccttgt acccttaaaa agttcgccaa cggagagacc      120
tccgtccaaa tcggcgtgag cgtccgcgat gaagatgtct acgtgattca gtccggttcc      180
ccttcaatca cgatgacat tatggaattg ctgattctcg tttcagcgtg ccgaggcggt       240
tccgcccgta agatcaccgc tgtgatccca cagtttccat actcgaaaca gtgcaagatg     300
aaacgacacc gcggagcaat taccgcacgc atgctggcaa acttgcttgt catggcagga     360
gccgaccatg tggtatcgat ggatctgcat gcatcccaga tgcagggttt ctttaccaag     420
ccagttgaca accttacgg aggcccgtca cttgccaaat ggatccgaga gaacgtcgaa      480
gactacgagg acgcagtagt tgtctcaaag aaccccggcg gaaccaagcg tgttaccgca     540
cttgcagact ctctcaagat caacttcgcc atgatccaca ccgatcgccg ccgtagcaag     600 gaccttatt cgcagaataa ggacctccaa caactgaagt tgcgtaaaca gtccatgctc      660
```

| | |
|---|---|
| cgcaagaacc gtcccatcat tcgacagggc gatcatccaa acgaagaaga aaatatattt | 720 |
| ttgtcgaacg gcattcagac ggcccgtatc cgcaacggtc atgtgatcgg cgacgatgag | 780 |
| gccgacgatg acgaagatgc aattctcgaa agcgactcag agcttcactc catcgatggc | 840 |
| ctcgactcgc acggcctcgg aggcacttat gacgcagttg actccgaaga tgaagaagag | 900 |
| atcccggtgc tttaccgcga acagctcatt acattggtag gtaacgtgcg cggtcgcagc | 960 |
| gccatcatcc ttgatgatat gatcgatcgc cctggctctt ttatctccgc ggctgaacac | 1020 |
| ttggttcaga actgtggcgc aaagaaggtg tacgttgtgg ccacccacgg cattttacc | 1080 |
| ggtgattgtt tggaagagct cgagaagtcc gatgccatcg acactattgt ggttaccaac | 1140 |
| acctacccaa tttctggaga gcgcattgct ggtagcaaaa agctggttac catcgatgtt | 1200 |
| agccccatct tcgccgagtg cattcgtcgc gaccactatg gcgagtccat tagcgtgctt | 1260 |
| ttcgacagcc tggcggccct g | 1281 |

<210> SEQ ID NO 111
<211> LENGTH: 2040
<212> TYPE: DNA
<213> ORGANISM: Artificial
<220> FEATURE:
<223> OTHER INFORMATION: Codon-optimized and/or mutated sequence

<400> SEQUENCE: 111

| | |
|---|---|
| atgactcagt ttactgatat cgacaagctg cagtttcta ccatccgcat cctggcggtc | 60 |
| gacaccgtct caaaggcaaa ctccggccac cctggtgcgc tctgggtat ggctccagcg | 120 |
| gcccacgtcc tttggtcaca gatgcgaatg aatccaacga atcctgattg gatcaaccgc | 180 |
| gaccgcttcg ttctctccaa tggacacgca gttgctttgc tgtactcaat gcttcatctc | 240 |
| accggttacg atctgagcat tgaagatttg aagcaattcc gccagctggg ttcccgcacc | 300 |
| cccggtcacc ctgagttcga attgcccggc gttgaagtta cgaccggccc acttggacaa | 360 |
| ggtatttcca cgcagtcgg aatggctatg gcgcaggcga atctggcagc gacctacaac | 420 |
| aaaccgggtt ttacactctc cgacaattac acttacgttt tcctgggcga cggatgcctg | 480 |
| caagaaggca tctccagcga ggcgtcctcc ttggcgggcc acctcaaact gggtaacctg | 540 |
| attgcaatct atgacgataa caaaatcact attgacggcg ccacttccat ctctttcgac | 600 |
| gaggatgttg caaagcgcta cgaggcatac ggttgggaag tactgtacgt cgagaatgga | 660 |
| aacgaagatc tcgcaggcat cgcgaaagct atcgcccaag ccaagctgtc caaggataag | 720 |
| cccactctga ttaaaatgac gaccaccatt ggatacggct ccttgcacgc gggttcacac | 780 |
| tctgttcatg gtgctccttt gaaagccgat gatgttaagc aactcaaatc taagtttggc | 840 |
| ttcaatcctg ataagtcatt cgttgttcca caggaagtgt acgaccacta tcagaagacc | 900 |
| atcctcaaac ccggagttga agccaacaac aagtggaata gctcttcag cgaataccag | 960 |
| aagaagtttc ccgagctggg agcggaactt gcccgtcgtc tcagcggtca actgcctgcc | 1020 |
| aattgggaat ccaagctgcc cacgtacact gccaaggaca gcgccgttgc gacccgtaaa | 1080 |
| ctgtccgaaa ccgtcttgga ggacgtctac aaccaattgc ctgagctgat cggtggctcc | 1140 |
| gcggatctta caccgagcaa tttgacccgc tggaaggaag cgctcgattt tcagcctccc | 1200 |
| tcgtctggca gcggcaacta ctccggccgc tacatccgtt acggtatccg cgagcacgcc | 1260 |
| atgggcgcca tcatgaacgg aatcagcgca ttcggtgcca attacaagcc ttacggtggc | 1320 |
| acgttcctga atttcgtgag ctatgccgct ggtgcagttc gtttgtctgc actgtccggt | 1380 |
| caccccggtca tctgggtggc aactcacgac tctattggcg ttggagagga cggtccgacc | 1440 |

| | |
|---|---|
| catcaaccga tcgagactct ggcccacttc cgaagcctcc ccaacattca ggtctggcgc | 1500 |
| ccagccgacg gaaacgaggt ctctgcagcc tacaagaaca gccttgagtc caagcacacc | 1560 |
| cctagcatca tcgcgctctc tcgccagaat ctgccacagc tcgagggctc ctctatcgaa | 1620 |
| tccgcgtcca agggcggtta cgttttgcag gatgtgcaa atccggacat cattttggta | 1680 |
| gcaaccggct ccgaagtctc cctgtcagtg gaggccgcaa aaacactcgc ggcaaagaac | 1740 |
| atcaaggctc gagtggtctc gcttcccgat ttctttacct tcgataaaca gcccctggag | 1800 |
| taccgtttgt ctgtgttgcc agacaacgtg cccatcatgt cagtcgaggt actcgcaacc | 1860 |
| acgtgttggg gtaaatacgc gcaccagtcc ttcggcatcg atcgcttcgg agcgagcggc | 1920 |
| aaggcacccg aggtctttaa gttttttgga tttaccccag aaggagttgc agagcgtgcg | 1980 |
| caaaaaacca ttgcattcta taagggtgac aagctgatct cgccgctcaa gaaggcgttc | 2040 |

<210> SEQ ID NO 112
<211> LENGTH: 1809
<212> TYPE: DNA
<213> ORGANISM: Artificial
<220> FEATURE:
<223> OTHER INFORMATION: Codon-optimized and/or mutated sequence

<400> SEQUENCE: 112

| | |
|---|---|
| atgccgcgca acccgcttaa gaaggagtac tgggctgacg tggtcgatgg tttcaagcca | 60 |
| gccacctctc ctgcgttcga aaacgaaaag gaaagcacca ccttcgtgac agaactgact | 120 |
| tcaaagaccg actctgcgtt ccctctgtca tcaaaagata gccctggaat caaccaaacc | 180 |
| actaacgata tcaccagctc agaccgtttc cgccgaaacg aggataccga gcaggaggat | 240 |
| atcaataaca ccaacctctc gaaagatctg tcggttcgcc acctgttgac gttggcggtg | 300 |
| ggaggcgcta tcggcacagg tctctatgtg aataccggag ccgcgctttc taccggagga | 360 |
| ccagcttctt tggtcattga ctgggtcatc atttcaactt gtctgtttac tgtcatcaac | 420 |
| tccctgggtg agctgtcggc tgcgttccca gtggtgggag gatttaacgt ttactccatg | 480 |
| cgattcatcg agccctcatt tgcattcgcc gtgaatttga actacctggc gcagtggctg | 540 |
| gtgcttctgc cactggaact ggtggcagcg agcattacca tcaagtactg gaatgacaaa | 600 |
| atcaactctg atgcatgggt tgctatcttc tacgcaacca tcgcgctggc taacatgttg | 660 |
| gacgtgaagt catttggcga aaccgaattc gtgcttagca tgattaaaat tctgtcgatt | 720 |
| attggtttca ccatcctcgg catcgttctt tcatgcggag gtggccccca tggtggctac | 780 |
| attggcggca agtattggca tgaccccgga gctttcgtgg ccactcttc gggtacccag | 840 |
| ttcaagggcc tctgtagcgt ctttgtcacc gctgcattct cgtactctgg catcgaaatg | 900 |
| actgcggttt cggcagcaga aagcaaaaat cctcgcgaaa cgatcccaaa agcggcaaaa | 960 |
| cgcacattct ggttgattac cgcgagctac gttaccatct tgactctgat cggttgtctc | 1020 |
| gtaccaagca acgacccacg ccttcttaac ggtagctcat ccgttgacgc tgcatcctcc | 1080 |
| ccactggtaa tcgccattga aaacggcggc atcaagggct gcccagcct tatgaatgct | 1140 |
| attatcctga tcgcggtcgt ctcggttgca aactcggcgg tgtacgcttg cagccgatgc | 1200 |
| atggttgcca tggcgcacat cggaaacttg cccaaattcc tgaatcgtgt ggataaacgc | 1260 |
| ggtcgtccta tgaatgccat tctgcttacc cttttcttcg gtctgctgtc ctttgtggcg | 1320 |
| gctagcgaca acaagccga ggtgtttacc tggcttctg ccctgtccgg cctctccact | 1380 |
| atcttctgtt ggatggcaat caacttgtct catatccgct tccgtcaggc catgaaagtg | 1440 |

| | |
|---|---|
| caagagcgct ctctcgacga actgccgttc atctctcaga ccggcgtgaa aggctcctgg | 1500 |
| tacggattca tcgtgttgtt cctggtactt attgcatctt tttggacctc cctcttcccg | 1560 |
| ttgggaggca gcggcgcgtc ggcagagtcc ttcttcgaag gttacctttc cttccccatc | 1620 |
| cttatcgtct gctatgtggg ccacaaactt tacacccgta actggactct catggttaaa | 1680 |
| ttggaggata tggatttgga cactggccga aaacaagttg acttgactct ccgtcgcgag | 1740 |
| gaaatgcgta tcgagcgcga gaccctggca agcgctctt tgttacgcg atttctccac | 1800 |
| ttctggtgc | 1809 |

<210> SEQ ID NO 113
<211> LENGTH: 2397
<212> TYPE: DNA
<213> ORGANISM: Artificial
<220> FEATURE:
<223> OTHER INFORMATION: Codon-optimized and/or mutated sequence

<400> SEQUENCE: 113

| | |
|---|---|
| atggtgctcc caattctgcc tctgattgac gacttggcct cttggaactc taagaaggag | 60 |
| tacgtctctc ttgttggtca agttctcctg gacggatcca gcctgtccaa cgaggaaatc | 120 |
| ttgcaattct ctaaggaaga ggaggtgccg cttgtcgcgc tttccctgcc ttcgggtaag | 180 |
| ttctctgatg atgagatcat cgcgttcctc aacaacggag tatcctccct gttcatcgcc | 240 |
| tcccaggacg ctaagactgc tgagcatctt gtcgaacaac tgaacgttcc aaaggaacgt | 300 |
| gtggttgtag aagaaaacgg tgttttctcc aaccagttca tggtaaagca aaaattctcc | 360 |
| caagacaaaa ttgtttccat taagaagctg tccaagata tgttgaccaa agaagtactg | 420 |
| ggcgaagtcc gtactgaccg cccagacgga ctctatacca ctctcgtcgt tgatcagtac | 480 |
| gaacgctgtt tgggtctggt gtattcctcc aagaaatcca tcgcaaaagc tatcgatttg | 540 |
| ggacgcggtg tctactattc gcgatcccgc aacgagattt ggattaaggg cgagacatcc | 600 |
| ggtaatggcc agaaacttct gcagatttca accgattgcg atagcgacgc tctcaaattt | 660 |
| attgtggagc aggaaaacgt cggcttttgc cacttggaaa ccatgtcatg tttcggtgaa | 720 |
| tttaagcacg gattggtcgg tctcgaatca ctcctgaagc aacgtctcca ggacgctcca | 780 |
| gaggaaagct atacgacgac cctgtttaat gactccgctc tgctggacgc aaagatcaaa | 840 |
| gaggaagccg aggagttgac agaagctaag ggaaagaaag aactctcttg ggaagcagcg | 900 |
| gaccttttt acttcgccct cgccaagctc gtcgccaacg acgtctcgct caaagatgtc | 960 |
| gaaacaacc ttaacatgaa gcaccttaag gtgacccgtc gcaagggaga cgcaaaacca | 1020 |
| aaattcgtgg gccaaccgaa ggcagaggaa gaaaagctta ctggtcctat tcatctcgac | 1080 |
| gtggtgaagg cctccgacaa agttggtgtt cagaaggcac tgagccgccc aattcaaaaa | 1140 |
| acctccgaaa tcatgcacct cgttaaccca attatcgaaa atgttcgcga taaggaaat | 1200 |
| agcgcactgc ttgaatatac cgagaagttc gatggtgtga agttgtcaaa ccctgtactg | 1260 |
| aacgccccat tcccagagga atacttcgaa ggacttactg aggagatgaa ggaagcactc | 1320 |
| gacctctcca tcgaaaacgt gcgcaagttc cacgccgccc agctgccgac ggaaacactg | 1380 |
| gaagtggaga cccagccggg cgttctgtgt tcgcgtttcc cacgcccgat tgagaaggtt | 1440 |
| ggccttata tcccaggtgg cactgctatt ctgccctcaa ccgctttgat gttgggagtt | 1500 |
| ccggctcaag tggcgcagtg caaggagatc gtgttcgcct cccctccacg caagtccgat | 1560 |
| ggcaaggtct cccagaagt ggtgtacgtt gctgaaaagg ttggcgcgag caaaatcgtg | 1620 |
| ctcgcgggcg gtgcacaagc agttgcagca atggcttacg gcaccgaaac catccccaag | 1680 |

-continued

```
gttgataaga tccttggtcc aggtaatcaa ttcgtaaccg cggccaaaat gtacgttcag    1740
aacgataccc aggctctctg cagcatcgat atgcccgctg gtccgtcaga ggttctggtg    1800
atcgccgatg aagacgccga tgttgacttt gtggcctccg acctcctcag ccaggcggag    1860
cacggtattg atagccaagt aatcctcgtt ggtgttaacc tttcggagaa aaagattcaa    1920
gaaatccagg acgcggtgca caatcaagct ctgcagcttc cccgcgtgga tattgtgcgc    1980
aagtgcatcg cacactccac catcgttctg tgcgatggat atgaggaagc tttggagatg    2040
tcgaatcagt atgcaccaga acacctgatt ctccagattg caaacgctaa tgactacgtc    2100
aaactcgttg ataacgcagg ttctgtgttt gtaggtgcct acacccctga gtcctgcgga    2160
gattactcca gcggtacaaa ccacaccctg cccacctacg ttatgcgcg tcagtactct    2220 ggagcgaaca ctgccacctt tcaaaaattc atcacggctc aaaacatcac cccagaaggc    2280
ctggagaata tcggtcgagc tgtgatgtgc gttgcaaaga aagaaggcct cgatggtcac    2340
cgcaacgctg ttaaaatccg tatgtcaaag ctgggactga ttccgaagga cttccag      2397
```

<210> SEQ ID NO 114
<211> LENGTH: 1155
<212> TYPE: DNA
<213> ORGANISM: Artificial
<220> FEATURE:
<223> OTHER INFORMATION: Codon-optimized and/or mutated sequence

<400> SEQUENCE: 114

```
atggtgttcg acctcaaacg catcgttcgc cctaaaattt acaatctcga accatatcgc      60
tgtgctcgcg atgatttcac cgaaggcatc ctcctcgacg caaacgagaa cgcccacggt     120
cctacgcctg tagagttgtc taagaccaac ctgcatcgct acccggaccc acatcaactc     180
gagtttaaga ccgctatgac taagtaccgc aataagacca gcagctacgc gaacgacccc     240
gaggtgaagc cactcaccgc cgataaacctg tgcctgggtg tgggttctga tgaatccatt     300
gatgcgatca tccgagcttg ctgcgtgcca ggtaaggaaa gatccttgt acttccgccc      360 acgtactcca tgtattcagt ctgtgcaaat atcaacgata ttgaagtcgt acagtgtccc     420
cttacggtct ctgatggctc tttccagatg gacaccgagg cggtcttgac catcctgaag    480
aacgattccc ttatcaagtt gatgtttgtg acctcaccag gaaacccaac tggtgccaaa    540
atcaaaacct ccctcatcga aaaggtcctc caaaactggg acaacggcct ggtcgtcgtc    600
gatgaagcct acgtggactt ctgtggtggc tcgaccgcgc ccttgttac gaagtacccc    660 aacctcgtga cactccagac cttgagcaag tcctttggat tggccggtat ccgccttggt    720
atgacttatg caactgccga gctggctcgc atttgaacg ctatgaaagc accgtacaac    780
attagctcct tggcgtcaga gtacgcattg aaggcggtgc aggactccaa cttgaagaaa    840
atggaagcta cgagcaagat tatcaacgaa gaaaaaatgc gtcttttgaa ggagctgaca    900
gcgcttgact atgtggatga tcagtatgtc ggcggtctgg atgcaaactt tttgctcatt    960
cgcatcaacg gcggtgacaa tgtcctggca aagaagctgt actaccaact cgcaacccaa   1020
tcaggcgtgg tggttcgttt tcgcggcaac gagttgggct gttcaggatg ccttcgcatt   1080
accgttggta cacacgagga aaatacacac ttgatcaagt actttaaaga aacgttgtac   1140
aagttggcaa acgag                                                    1155
```

<210> SEQ ID NO 115
<211> LENGTH: 891
<212> TYPE: DNA

<213> ORGANISM: Artificial
<220> FEATURE:
<223> OTHER INFORMATION: Codon-optimized and/or mutated sequence

<400> SEQUENCE: 115

| | | | | |
|---|---|---|---|---|
| atggacctgg taaaccatct cactgatcgc cttcttttcg ccatcccaaa gaagggtcgc | | | | 60 |
| ctgtactcta atcggtatc catccttaac ggtgctgata tcacctttca ccgttcacag | | | | 120 |
| cgcctggata ttgcccttc tacttctctc cccgtggcct tggtgttctt gccagcggcc | | | | 180 |
| gacatcccaa cttttgttgg cgagggcaag tgtgatctgg gcattactgg cgttgaccag | | | | 240 |
| gttcgtgaaa gcaacgtcga tgttgatctg gctattgacc tgcaattcgg caactgcaag | | | | 300 |
| ctccaagtgc aggttcctgt taatggtgag tacaagaaac ccgaacagct cattggcaaa | | | | 360 |
| accattgtta cctcctttgt taaactggct gagaagtatt tcgcggattt ggagggtacc | | | | 420 |
| accgttgaaa aaatgacaac gcgcatcaag ttcgtgagcg gctcggttga ggcctcttgt | | | | 480 |
| gctcttggca ttggagatgc tattgtcgac ttggtcgaat ccggcgaaac gatgcgtgca | | | | 540 |
| gcaggtctgg ttgatatcgc gaccgtcctg tcaacctccg cctacctgat cgagtcgaaa | | | | 600 |
| aaccccaaga gcgacaaatc ccttatcgca acgattaaat cccgtatcga aggagttatg | | | | 660 |
| actgcacaac gcttcgtttc ttgtatttat aatgccccag aggacaaatt gcccgaactc | | | | 720 |
| ctgaaggtga ctccaggtcg tcgcgccccc accatttcca agattgacga tgagggttgg | | | | 780 |
| gttgccgttt cctctatgat cgagcgcaag accaagggcg tagtcctcga tgaactcaaa | | | | 840 |
| cgactgggcg catctgatat catggtattc gaaatctcta actgccgagt g | | | | 891 |

<210> SEQ ID NO 116
<211> LENGTH: 783
<212> TYPE: DNA
<213> ORGANISM: Artificial
<220> FEATURE:
<223> OTHER INFORMATION: Codon-optimized and/or mutated sequence

<400> SEQUENCE: 116

| | | | | |
|---|---|---|---|---|
| atgacgaaat tcatcggatg catcgacctt cacaatggcg aggttaagca gattgtcggc | | | | 60 |
| ggtacactga catccaagaa ggaagatgtc cctaagacta acttcgtttc ccaacatccg | | | | 120 |
| tcttcttact atgcgaagct ttacaaagat cgcgatgtac agggctgtca cgttatcaag | | | | 180 |
| cttggtccta acaatgatga tgctgcccgc gaagctcttc aggaatctcc ccagtttctt | | | | 240 |
| caagtcggtg gtggaattaa cgataccaac tgcttggaat ggctcaagtg gcttccaaa | | | | 300 |
| gtcattgtaa cctcctggct ctttaccaag gagggacatt ttcaattgaa gcgcctggaa | | | | 360 |
| cgtcttacgg agctttgtgg aaaggaccgc atcgttgtgg acctctcctg tcgtaaaact | | | | 420 |
| caggacggcc gctggattgt agccatgaac aagtggcaga cccttaccga tctcgagctt | | | | 480 |
| aacgccgata ctttccgcga actgcgcaaa tacactaacg aattcttgat tcacgcagca | | | | 540 |
| gatgtcgaag gattgtgtgg cggaatcgac gaactgctcg tgtccaagtt gttcgagtgg | | | | 600 |
| acaaaagact acgatgattt gaagattgtt tacgccggag cgccaagtc tgtggacgat | | | | 660 |
| cttaaacttg tggacgagct ctctcacggc aaagtggacc tcacgttcgg atcgtccctt | | | | 720 |
| gatattttcg gtggcaacct ggttaaattt gaggactgct gccgttggaa cgagaagcaa | | | | 780 |
| ggc | | | | 783 |

<210> SEQ ID NO 117
<211> LENGTH: 1656
<212> TYPE: DNA
<213> ORGANISM: Artificial
<220> FEATURE:
<223> OTHER INFORMATION: Codon-optimized and/or mutated sequence

<400> SEQUENCE: 117

```
atgcctgttg tgcacgtgat tgacgtggaa tctggcaatt tgcagtccct caccaatgca      60
atcgagcacc tcggttacga agtccagctt gtaaagtccc ccaaggattt taacatttcg     120
ggtacctccc gacttatctt gcccggcgtt ggtaattacg gacatttcgt cgacaatctt     180
tttaaccgag gttttgaaaa gccgattcgt gaatacatcg aatcgggcaa gcccattatg     240
ggcatttgtg tgggcctgca ggcccttttc gcgggttccg tcgaatcccc taagtccacc     300
ggccttaatt acattgattt caaactgtct cgcttcgacg attccgaaaa gcccgttccg     360
gaaatcggct ggaacagctg catccccagc gagaatctgt tcttcggact cgatccatac     420
aagcgatact actttgtaca ttctttcgct gcgattctga attccgaaaa gaaaagaac     480
ctggaaaacg acggttggaa gatcgcgaag gccaaatatg gctctgaaga attcattgcc     540
gccgtgaata agaacaacat tttttgcaacg cagttccatc cagaaaaatc tggtaaagcc    600
ggtcttaatg tgatcgagaa cttcttgaaa aacagtcac ccccaatccc caactactcc     660
gctgaggaaa aggaactttt gatgaacgac tatagcaact acggactcac ccgacgtatc    720
attgcatgcc ttgacgttcg caccaacgac cagggtgatt tggttgtcac caaaggtgac    780
caatatgatg ttcgcgagaa gtccgacggc aaaggcgtac gcaatctcgg taagcctgtt    840
caactggctc agaagtatta ccaacaaggc gccgacgagg taacgtttct gaatattact    900
tcatttcgcg actgccctct gaaggatacc cccatgctcg aagttttgaa gcaggccgca    960
aaaactgtgt tcgtaccgct gaccgtggga ggcggcatca aagacatcgt agatgtggat   1020
ggtaccaaga tcccagcact cgaggttgct tccctttact ttcgatctgg tgcagacaag   1080
gtttcaattg gcacggacgc tgtctacgct gccgagaagt attatgagtt gggtaaccgc   1140
ggcgacggca tcgccaat tgagacgatc agcaaagcct acggtgcaca ggcagttgtc    1200
atctctgtag acccaaaacg cgtgtatgtc aattctcagg ctgacactaa gaacaaggtc   1260
tttgagactg aatacccagg tcccaacggt gaaaaatatt gctggtacca gtgcacgatc   1320
aaaggaggcc gcgagtcccg tgatcttggc gtgtgggaat tgactcgcgc atgtgaggca   1380
ttgggtgccg gcgaaatcct tcttaactgt atcgacaagg acggctcgaa ctccggttac   1440
gatctcgaac tcatcgaaca cgtgaaggat gccgttaaga ttcccgtgat tgccagctcc   1500
ggcgcaggag tgcctgaaca cttcgaggaa gccttcctga aacccgcgc tgacgcatgc   1560
ttgggtgcgg gaatgtttca ccgtggcgaa ttcacagtca acgatgtaaa agaatatctt   1620
ctcgagcacg gccttaaggt tcgaatggac gaggaa                            1656
```

<210> SEQ ID NO 118
<211> LENGTH: 744
<212> TYPE: DNA
<213> ORGANISM: Artificial
<220> FEATURE:
<223> OTHER INFORMATION: Codon-optimized and/or mutated sequence

<400> SEQUENCE: 118

```
atggctcgta ccttcttcgt gggaggtaac ttcaagctca atggttctaa acagtcaatc      60
aaagagatcg tggaacgact caatactgcg tccatcccgg aaaacgtcga ggtcgtaatt     120
tgcccacccg ccacctatct tgattactcc gtctcccttg tgaagaaacc acaagttact     180
gttggcgcgc aaaacgccta tttgaaggct tccggtgcgt tcaccggaga gaattcagtg     240
```

```
gaccagatta aagatgtggg cgcaaaatgg gttatcctcg gacactcaga gcgccgctcg    300
tacttccacg aggacgacaa gttcatcgca gacaaaacta agtttgcact gggacagggc    360
gtaggcgtca tcctttgcat tggagaaacc ctggaggaaa aaaaggcagg caaaacactc    420
gacgttgtcg aacgccaact caacgccgtt ctggaagaag tgaaggattg gactaatgtg    480
gtggtggcat atgaaccagt ctgggccgtg ggtaccggcc tggcggcgac ccccgaagat    540
gcgcaggaca ttcacgcgag catccgtaaa tttctggcct ctaagctggg tgataaggcc    600
gcttccgagc tccgcattct ttacggtggt tcagccaacg gctcgaacgc tgtgaccttt    660
aaggacaagg ccgacgtcga tggattcttg gtcggcggtg catctcttaa accagagttc    720
gttgacatca tcaacagccg caac                                           744

<210> SEQ ID NO 119
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 119
atgctgaaga tcgcagtgcc aaacaagggt tcgctttccg aacgagctat ggagatcctg     60
gcggaagctg gttacgccgg ccgtggagat tccaagagcc tgaatgtgtt cgatgaggcc    120
aacaacgttg aattttctct tttgcgacca aaggacatcg cgatctatgt tgcaggtggt    180
caactggacc tgggtatcac cggtcgagat ctggcacgtg attcccaagc cgatgtgcac    240
gaagttctgt cgttgggctt cggctcttcc acgtttcgct atgccgctcc agctgatgaa    300
gaatggtcga tcgaaaaact cgatggaaag cgcatcgcga cctcatatcc aaaccttgtc    360
cgcgatgacc tggcagcacg cggattgtcg gccgaagtcc tccgtctgga tggcgcggta    420
gaagtcagca ttaagcttgg tgttgccgat gcaattgctg atgtggtgtc cacaggccgc    480
accctgcgcc aacagggcct cgcgcctttc ggagaagttc tgtgcacctc tgaagccgtg    540
atcgtgggcc gcaaagatga aaaggttact ccggaacaac agatccttt gcgacgcatc    600 caaggcattc tccacgcaca gaacttcctc atgttggatt acaacgtgga ccagagataac    660 ctggatgctg caaccgcggt caccccaggc ctttctggtc ccaccgtctc cccgctcgcc    720
cgcgacaact gggtggcggt tcgtgcaatg gtaccgcgcc gatccgccaa cgcgatcatg    780
gataaactgg ccggcctcgg cgcggaggca attttggctt ctgaaattcg tatcgcacgc    840
atc                                                                   843

<210> SEQ ID NO 120
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 120
atgcttaaga ttgcagtgcc gaataaaggc tccctgtcgg agcgagctat ggaaattctg      60
gcggaagcgg ttacgcgggg tcgcggtgat tctaagtccc tgaacgtctt cgatgaagcg    120
aacaacgttg aatttttttt tttgcgcccg aaggacattg caatctacgt agcgggaggt    180
cagctcgatc tgggtattac cggccgcgac ctggcacgtg attcacaggc tgatgtgcac    240
gaagtgctga gccttggctt cggctcctca acattccgct atgcggcacc agccgatgaa    300
gagtggtcga ttgaaaaact cgatggtaaa cgtatcgcaa cctcctatcc caacctggtc    360
```

```
cgtgatgatc ttgcggcgcg cggattgtcc gctgaagttc tccgactcga tggcgcggtc    420
gaggtatcca tcaagctggg cgtagcggat gcaatcgctg atgtcgtgag cactggccgt    480
accctccgcc agcaaggatt ggctccattc ggcgaggttc tctgtacttc ggaagctgtt    540
attgtgggcc gcaaggacga gaaagtgact ccagaacagc aaatcctcct gcgccgcatc    600
cagggtatcc tccatgccca aaacttttg atgcttgatt ataaggtgga ccgagataac     660
ctcgacgccg ccacggccgt gactccaggc ttttctggac ctgctgtttc gccgcttgca    720
cgtgataact gggttgcggt acgtgccatg gttcctcgtc gttctgccaa cgccattatg    780
gataagctcg caggcctcgg tgcggaagcg atcctcgctt ccgaaattcg cattgcgcgt    840
atc                                                                  843
```

<210> SEQ ID NO 121
<211> LENGTH: 948
<212> TYPE: DNA
<213> ORGANISM: Artificial
<220> FEATURE:
<223> OTHER INFORMATION: Codon-optimized and/or mutated sequence

<400> SEQUENCE: 121

```
atgtccgaat cgacaagaa acttaacacc ctcggagtgg accgaatctc ggtatcaccc      60
tataagaaat ggtcccgtgg ttacctggaa ccgggtaacg ttggcaacgg ttacgtctcc    120
ggtctcaaag tcgacgcagg cgtgatcgat aaaacagatg acatgattct cgacggtatc    180
gtgtcgtatg atcgcgcgga gaccaaaaac gcctacatcg ccagattaa tatgactacc      240 gcgtcctcat tttctggagt gggcggcacc gttctgggct atgatatcct tcgaaatccc    300
gaggtcgata agcgaaacc tctctttact gaaaaacagt gggatggttc cgagcttcct    360
atttatgacg cgaaaccact gcaggacacc ctggtggaat actttggcac caaagatgat    420
atgcgccatt accccgcacc gggcgcgttc gtttgctgcg caaataaagg agtgaccgcg    480
gaacgcccta aaaacgacgc cgatatgaaa ccggacaag gctacggagt gtggagcgct    540
atcgctatca gcttcgcgaa agatcccaca aagtactcgt ccatgtacgt ggaagatgcc    600
ggtgtctggg aaaccctaa tgaggatgag ttgatcgaat acctgaaggg ccgacgcaat    660
gccatggcaa agtctatcgc gcgtgcggt gagaacacag cagcagagaa cggcggagcc    720 gttttcaccct caagctggat cggattcgct catgcaatga tgaaaccagg ccaggtcgga    780
aacgcgatta ccgtggcccc gtatatcgcc atgccagtgg actcaattcc aggcggttca    840
attcttacgc cagatactga catggatatt atgcagaatt tgacgatgcc tgagtggctc    900
gataagatgg ataccagcc cctcacgaag ggaggaaaca tcaactat                   948
```

<210> SEQ ID NO 122
<211> LENGTH: 849
<212> TYPE: DNA
<213> ORGANISM: Artificial
<220> FEATURE:
<223> OTHER INFORMATION: Codon-optimized and/or mutated sequence

<400> SEQUENCE: 122

```
atggaaccag gcaacatcgg aaacggttat gtcaccggtt tgaaggtaga cgctggcgtt     60
cgcgacaaga ccgatgacga cgtgctggat ggaatcgtct catacgatcg tgctgaaact    120
aagaacgcat acatcggcca aatcaacatg accacggcaa gctccttcac gggcccgcag    180
ggccacgttg tgggatatga catcctgcga aatcctgagg tggacaaggt aaagccgctt    240
```

```
ttcgtggaaa agcaatggga tggctcggac ctgccaattt acgatgcaaa gccgcttcag    300
gacgccctgg tcgaatattt cggcatggag caggaacgcc gccactaccc agcaccgggc    360
tctttcatcg tttgcgccaa caaaggtgtc acggcggagc gccctaaagc tgacgagcca    420
cttaagccgg tcagggcta cggcgtgtgg tccgccatcg ctatctcttt cgctaaggac    480
ccgtcgaaaa actcatccat gttcattgaa gacgcgggcg tgtgggaaac ccctaacgag    540
gatgagctca tcgagtatct gaatggccgc gcaaggcaa tcgctaaatc tatcgctgag    600
tgcggtcagg acgctgatac cgctttcgaa tcttcctgga tcggctttgc ccatgttatg    660
atgaagcctg gtcagatcgg caatgcgatc accgttggac cgtacttttc gcttccggtg    720
gattccatcc ctaacggttc gattctgacc cctgataagg atatggagat catggagaac    780
ctttccctcc cggagtggct cgacaaaatg ggctatgagt cccttgtgaa gaagaataat    840
gtgacatac                                                            849
```

<210> SEQ ID NO 123
<211> LENGTH: 1212
<212> TYPE: DNA
<213> ORGANISM: Artificial
<220> FEATURE:
<223> OTHER INFORMATION: Codon-optimized and/or mutated sequence

<400> SEQUENCE: 123

```
atgaccctct cgccagcgga tcagcgcaag cttgaaggtt tttggcagca ctgcgttacc     60
caccagtact ttaatattgg ataccccgaa tctgccgact tcgactattc ccagctgcac    120
cgattccttc agttctccat caataactgc ggagattgga tgaatactc taactacttg    180 ttgaactctt tcgacttcga aaggacgtc atgacgtatt ttgcagaact cttcaatatc    240
gcactggagg actcctgggg ctacgtgaca aacggcggta ccgagggaaa catgttcggc    300
tgctacttgg ccgcgaact cttcccagat ggaaccctt actactcaaa ggacactcac    360
tactcggtgg ctaagattgt caagctcctc cgcatcaagt gtcgtgcagt gaatctctc    420 ccaaacggag agatcgacta tgatgatctg atggctaaga tcaccgctga tcaggagcgc    480
cacccgatca ttttcgcgaa tattggtaca acgatgcgcg cgctgtgga caatattgta    540 acgatccagc aacgccttca acaagctggc atcgcgcgcc acgattatta cctgcatgca    600
gatgctgccc tttccggcat gatcttgcct ttcgtggacc atcccagcc ttctcgttc    660 gctgacggca ttgactctat ctgtgtgtcc ggccacaaga tgatcggctc cccaattcca    720
tgcggcatcg tagttgcaaa acgcaataac gtcgctcgca ttagcgtcga agtcgactac    780
atccgtgcac acgacaagac aatttccgga tcgcgtaacg gccacactcc cctgatgatg    840
tgggcggcgc ttcgttctta ctcctgggca gaatggcgac atcgcattaa acactctctt    900
gatactgcgc agtacgcagt ggatcgattt caggcatcgg gtattgatgc gtggcgcaac    960
gaaaactcga tcaccgtcgt tttcccatgt ccatccgaac gtattgcgac caaatactgc   1020
ttggctactt ctggcaatag cgcccacctc atcacgaccc gcaccatca cgactgttcc   1080 atgatcgacg cgcttatcga tgaagtcgtc gccgaggcac agctgaatac tctgcgctcc   1140
aaacgtgcgt tcacggacca gactgtggtt gagcgtctgc cagcggcaag ctttaacttg   1200
cgcacccatt ac                                                       1212
```

<210> SEQ ID NO 124
<211> LENGTH: 1224
<212> TYPE: DNA
<213> ORGANISM: Artificial
<220> FEATURE:
<223> OTHER INFORMATION: Codon-optimized and/or mutated sequence

<400> SEQUENCE: 124

| | | | | | |
|---|---|---|---|---|---|
| atgactttgt | ctacggcaga | cactcatcgt | cttgatgact | tttggcagca | ctgtctcaag | 60 |
| caccagtttt | tcaacattgg | atatcctgaa | aacgccgatt | ttgactattc | cgcgctggag | 120 |
| cgtttcctgc | gattctccat | caataactgc | ggagactggt | cggagcactc | caactacgta | 180 |
| ttgaactcct | ttgatttcga | aaagaagtc | atggcttact | ttgcagactt | gtttgagatt | 240 |
| ccacgtgaag | actcatgggg | ctacgtgact | aacggcggaa | ccgaaggcaa | catgttcggt | 300 |
| tgttatctcg | ctcgcgaact | gttccctgat | ggtaccctct | actactcaaa | ggataccac | 360 |
| tactctgtag | ctaagatcgt | aaagcttctc | cgcatcaagt | gccgcgctgt | gaacgctctg | 420 |
| ccaaccggcg | aaatcgatta | cgacgacctg | ctcgccaaga | tcgcggccga | cggtgagcgc | 480 |
| catccaatta | tctttgcaaa | cattggcact | actatgcgcg | gcgcagttga | cgatatcgcc | 540 |
| gttattcaac | agcgcttgca | ggacgcaggc | attgcgcgcc | gcgattatta | cttgcacgct | 600 |
| gatgcggcac | tgtccggtat | gattctccca | ttcgtcgacg | caccacagcc | tttcactttc | 660 |
| gccgacggta | tcgattccat | ctgcgtctcc | ggccacaaga | tgatcggttc | cccgatccca | 720 |
| tgtggtatcg | ttgtggctaa | gcgtcgcaat | gtagcccgaa | tctccgtgga | ggtggactat | 780 |
| atctccgcct | ccgataaaac | tatctccggt | tcgcgcaacg | gccataccc | catgattatg | 840 |
| tgggcagcat | tgcgtagcca | ctcgtccgcg | cagtggcgac | gccgcgtcga | gcgttccctg | 900 |
| gcggccgcac | agtacgcggt | gaaccgcctg | caggccggcg | gtgtcaaggc | ttggcgtaac | 960 |
| cctaacagca | tcacggtggt | cttcccctgt | ccgtcggcag | atatcgctcg | aaagtacggc | 1020 |
| ttggctactt | ccggtgacac | cgctcatctc | attaccaccc | cacatcatcg | cgataatcgc | 1080 |
| gctattgacg | ctctgatcga | tgaagttatc | gcggatgcgc | gccccgaggt | ctggcgagca | 1140 |
| acattgcaac | gctcgtggca | gggttccgct | cagcgcttgc | cacgaaccgc | atcctggaac | 1200 |
| caggcggccg | gactgggccg | cttt | | | | 1224 |

<210> SEQ ID NO 125
<211> LENGTH: 1281
<212> TYPE: DNA
<213> ORGANISM: Artificial
<220> FEATURE:
<223> OTHER INFORMATION: Codon-optimized and/or mutated sequence

<400> SEQUENCE: 125

| | | | | | |
|---|---|---|---|---|---|
| atgacatttt | cgccagcaga | ccacaaacgc | cttgaggctt | tctggcagta | ttgtcttacc | 60 |
| caccagtatt | tcaacgtggg | ctatccggaa | tccgcagact | tcgactactc | actccttcac | 120 |
| cgcttcatgc | gtttttccat | caataactgc | ggcgattgga | acgaacccag | caactacttg | 180 |
| cttaacagct | tcgattttga | acgcgaagtt | atgcgatttt | ttgcggaact | ctttcacatc | 240 |
| cccttttgaag | actcgtgggg | ctacgtgacc | aacggaggaa | ccgagggaaa | tatgttcgga | 300 |
| tgttaccttg | cgcgcgaact | ttttccggac | gcaaccctct | actactccaa | agatacgcac | 360 |
| tactccgtcg | ctaagatcgt | ccgtctcctg | cgcatcaagg | cacaggtcgt | ggaatcacaa | 420 |
| gcaaacggag | agatggacta | tgatgatctt | gtggcccgta | ttgcagccga | cggcgaacgt | 480 |
| caccccatca | tcttcgccaa | tattggtacc | acgctgcgcg | gtgccaccga | taatattgcg | 540 |
| gtcatccaac | aacgtctggc | tcaagccggc | atccgtcgcg | aggattacta | cttgcacgcc | 600 |
| gatgccgcac | tgtcgggcat | gatcttgcca | tttgtggatg | ctccagaacc | atattcattt | 660 |

```
gcggatggca ttgactccat ctgtgtgtcg ggacacaaga tgattggctc tccaatgcct      720
tgcggcatcg tcgttgctcg tcgccacaat gtagaacgaa tctccgtgga aatcgactac      780
atctcagcac gagatcagac catttcaggt agccgcaacg gtcacactcc acttatgatg      840
tgggctgcct tgtgctcccg ctctcgcgag gactggcgcg cccgtatcca gcgttgtctc      900
gatttggcgc aacacgcggt ggatcgcctg cgtgcagctg gcatcgaggc atggcgcaac      960
ccaaactcca tcaccgtcgt ttttccatgc ccctctgcct cggtctggaa gcgccattgc     1020
ctcgcaacca gcggcgatac cgcacacttg atcactactg ctcatcatca ggattccacc     1080
cagatcgatg cactgttgga tgagttgatt gccgacttga aggcgcgcac ccgctaccct     1140
ttgcaggccc ccctggtcga aggtctgggt tcacgaacgc gcgtgtattc cactgcaggc     1200
cagccgcgcc cggagccact ccctgatcac gcacgccccg cgcgcgattc aggacttgca     1260
cgtctgaaag actccgaaat c                                               1281
```

<210> SEQ ID NO 126
<211> LENGTH: 1161
<212> TYPE: DNA
<213> ORGANISM: Artificial
<220> FEATURE:
<223> OTHER INFORMATION: Codon-optimized and/or mutated sequence

<400> SEQUENCE: 126

```
atgtcgctga gcccgcttga ccaaaaccgc attgaaagct ctggcagta ttgccttcag       60
catcagtatt tcaaccttgc ctatcctgaa tccgccgact ttgactatgc ccccttcac      120
cgtttcttgc gattctctat caataactgc ggtgattgga acgagtcctc caactacctc      180
ctcaattcgt tcgacttcga gcgcgaagtg atgcacttct tcgcggaatt gtttcacatt      240
ccatttgatg agagctgggg ttatgtcacc aacggcggaa ccgagggcaa catgttcggt      300
tgttacctgg cccgcgaatt gtttccagat gcaacattgt actattcgaa agattcacac      360
tactcggtcg ctaagatcat taagctgctg cgtattaagt ctcgtgccgt ggactccctc      420
ccatccggtg agatcgatta cgacgatctt gtcgcaaaaa tccaacagga tcaggaacgc      480
catcccattg tttttgttaa tgtaggtact accatgaagg gagcagtcga tgacatcggc      540
gtgatccagc ataaactcgc tgaagcggga attccccgtc aggactacta cctccacgcg      600
gacgcagcat tgtcgggtat gatcttgccc ttcgttgacg cgcctcagcc gtactcattc      660
gcagacggaa ttgattccat tagcgtgtcc ggccacaaga tgatcggctc tccaatgccc      720
tgcggcatcg tactggcaaa gcgctcgaat gtctctcgca tttctgttga gattgattat      780
atctcggcca aggatcaaac catctccggc tctcgtaacg gccacactcc aatgatgttg      840
tgggcggcaa tcaagtcccg tccgctcgcg gaatggcgcc gcaaggtccg ccactgtctc      900
gacatggcgc agtacgcgat tgatcgactc caggcggcag gtatccaggc atggcgctgc      960
aagaactcga ttactgtcgt tttcccatct ccttcagaac ccgtttgtga taaacacgga     1020
cttgctcgca gcggcggtac ggcgcacctc atcacgaccc acatcaccat gatagccaa     1080
cgccttgacc gccttctgga tgacatcgtt caggatctcg gtgcaatgac tgctccggct     1140
ggagctacaa tgtctgccgc g                                               1161
```

<210> SEQ ID NO 127
<211> LENGTH: 1134
<212> TYPE: DNA
<213> ORGANISM: Artificial
<220> FEATURE:
<223> OTHER INFORMATION: Codon-optimized and/or mutated sequence

<400> SEQUENCE: 127

```
atgaccttgt ccattgttga tcagaataag ctggacgctt tctggtctta ctgtgttaag      60
aaccaatact tcaacatcgg ttatccggaa agcgccgatt tgattatac catcctcgaa      120
cgtttcatgc gcttcagcat caacaactgc ggtgattggg gcgagtattg taactacctg     180
ctgaactcct tcgacttcga aaaagaagta atggaatatt tcgcccgtat ctttaagatt     240
cctttcgaag agtcgtgggg ctatgttacc aatggtggca ccgaaggcaa catgtttggc     300
tgttacttgg gccgtgaatt gttccctgaa ggaactcttt actattccaa ggacacgcac     360
tatagcgttg cgaaaattgt gaagttgctt cgcattaaat cctccctcgt agaatcgcaa     420
ccaaatggag aaatggatta cgacgatttg atccgcaaaa ttcaacgcga taatgaagaa     480
catcccatca tcttcgctaa cattggcacc accgttcgtg gagctatcga caacattgca     540
gaaattcaac aacgcattgg acagttggga atcaaacgag acgactacta tttgcacgcc     600
gatgctgccc tgagcggaat gattttgcca tttgtcaacg acccacaacc atttaatttt     660
gcagacggca tcgacagcat tggtgtgtca ggacacaaga tgatcggttc ccctattcca     720
tgtggcatcg tcgttgctaa acgtaagaac gtggatcgaa tctccgtcga gatcgattac     780
atttccgcgc atgataaaac catctccggc tctcgcaatg gtcatacacc actgatgatg     840
tgggaagcta tccgctcgca ctcttggagc gattggcagc gccgcatcga gcactcgctc     900
aacatggccc aatacgccgt ggatcgcctc caagctgctg gtatcgacgc atggcgtaac     960
aagaatagca tcaccgtcgt gtttccatgt ccgtccgaag cagtgtggaa gaagcactgc    1020
ttggctacga gcggcgatat cgctcatctt atcacaactg cacatcacct cgacagctct    1080
aagattgatg agttgattga cgacgttatt gctgatttga accagcaagc cgca          1134
```

<210> SEQ ID NO 128
<211> LENGTH: 1161
<212> TYPE: DNA
<213> ORGANISM: Artificial
<220> FEATURE:
<223> OTHER INFORMATION: Codon-optimized and/or mutated sequence

<400> SEQUENCE: 128

```
atgagcctgt cctccttgga tcaaaaccgc attgaatctt tctggcaata ttgtctccag      60
caccagtatt ttaaccttgc ctatcccgaa tccgccgact tcgattacac cccgttgcat     120
cgcttttgc gattctcaat caacaattgt ggtgattgga acgaaagctc caactacctc     180
cttaactctt tcgatttcga gcgcgaagtc atgcacttct tcgcggaact cttccacatc     240
cccttcgacg agtcctgggg ctacgtgacg aacggtggca cggagggaaa catgtttggc     300
tgctaccttg cccgagagtt gttccccgat gctaccctct attacagcaa ggatagccac     360
tactctgtgg caaaaatcat caaactcctg cgcattaaga gccgcgcggt ggactctctt     420
ccctccggtg agatcgatta tgacgatctt gtcgccaaga tccagcaaga ccaagagcgt     480
catccaatcg tttcgtcaa tgtgggcacg acaatgaagg gtgctgtgga cgacattggt     540
atcattcagg ataaactggc acaggcgggc attccgcgtc gcgattacta cctgcatgct     600
gacgcggcac tcagcggtat gatcctccca tttgtagacg cacctcaacc ttattctttt     660
gcagatggca tcgactccat ctccgtcagc ggtcacaaga tgatcggctc ccccatgcca     720
tgtggcattg tcttggcaaa acgttccaat gtatcgcgca tctccgtgga gatcgattac     780
atctctgccc gcgatcagac aatctctggc tcccgtaacg gacacacccc gatgatgctg    840
```

| | |
|---|---|
| tgggcagcaa tcaaatctcg ccccttggca gaatggcgcc gtaaagtacg ccactgtctg | 900 |
| gatatggctc agtacgccat cgaccgcttc cgcgccgcag gcattcaggc ttggcgctgt | 960 |
| caaaattcaa tcaccgtcgt cttcccatcg ccctccgagc ccgtctgcga taagcacggt | 1020 |
| ctcgcgcgct ccggcggtgc cgcccacttg atcacaactc cacatcacca tgattcccag | 1080 |
| cgcctcgacc gtctcatcga cgatatcatt caggatctgg gtgcagtaac ggctcctgcc | 1140 |
| ggtgccgcta tgtccgcagc a | 1161 |

<210> SEQ ID NO 129
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 129

| | |
|---|---|
| atgtctgaat tggatgccaa actgaacaaa ttgggagtcg atcgcattgc gatttcccca | 60 |
| tacaaacagt ggactcgagg atatatggaa ccaggcaaca ttggtaacgg ttacgtcacc | 120 |
| ggcttgaagg ttgatgcagg cgttcgcgat aagagcgatg atgatgtgct cgacggtatc | 180 |
| gtgagctacg atcgtgcaga aaccaagaac gcctatatcg acagattaa tatgactacc | 240 |
| gcgtcatcat tcactggtgt tcagggtcgc gtgatcggtt acgatattct gcgatccccg | 300 |
| gaagttgaca aggcaaagcc cttgttcaca gaaacccagt gggacggttc cgaactgccc | 360 |
| atctacgacg ccaaaccttt gcaagacgct cttgtcgagt attttggcac gaacaggat | 420 |
| cgtcgacact accctgctcc gggttctttc attgtctgcg ctaataaagg tgtgaccgct | 480 |
| gagcgtccca aaacgatgc ggatatgaaa ccaggtcaag gctatggtgt ctggtcggcc | 540 |
| attgcgattt cgtttgccaa ggacccaacg aaggactcgt ccatgttcgt tgaagatgca | 600 |
| ggtgtttggg aaaccccaa cgaggatgag ctgctcgagt accttgaagg ccgtcgaaaa | 660 |
| gctatggcga atctatcgc ggaatgcgga caggatgctc acgcctcatt cgaatcttcg | 720 |
| tggatcggtt ttgcgtacac aatgatggaa ccaggtcaga tcggaaatgc tattacagtt | 780 |
| gcgcccctacg tgtccttgcc tattgattca attcctggtg gttctatcct cactccggat | 840 |
| aaggatatgg agattatgga gaatctcacc atgcctgaat ggcttgagaa gatgggctac | 900 |
| aaatccttga cgctaacaa tgctctcaaa tat | 933 |

<210> SEQ ID NO 130
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 130

| | |
|---|---|
| atgtccgagc ttgacactaa attgcacaag ttgggcgttg atcgcattgc aatttctcct | 60 |
| tataagcaat ggtcccgagg atacatggag cccggcaata ttggtaacgg ttacgtaacc | 120 |
| ggtttgaagg tggacgccgg cgtgcgcgac aagaccgacg atgaagttct cgacggaatt | 180 |
| gtgtcatacg atcgagcaga aacgaaaaac gcatacattg ccagatcaa catgacgacc | 240 |
| gcctcgtcct tcaccggccc acaaggacac tgcattggct acgatcttct ccgcaaccct | 300 |
| gaggtggaca ccgccgaacc tctcttcact gttaagcaat gggatggcag cgaattgccg | 360 |
| atttacgacg ccaaaccgct gcaggattct cttgtggagt attcggcac caacaacaac | 420 |
| cgccgccact acccagcgcc tggctcgttc attgtttgcg caaacaaggg tgtaactgcc | 480 |

| | |
|---|---|
| gaacgcccaa tgaatgattc cgatatgaaa ccgggccagg gctacggagt gtggagcgca | 540 |
| attgcgcttt cctttgcgaa ggatccggca aaagactcct caatgtttat cgaagatgcg | 600 |
| ggcgtgtggg aaactccgaa tgaggacgag cttatcgagt atcttaaggg acgtcgtaag | 660 |
| gcgattgcaa aatccattgc agaatgcggt caagatgcca acacatcctt caaaggctct | 720 |
| tggatcggct ttgcccacgc catgatggaa ccgggccaga tcggaaacgc aattacagtt | 780 |
| gctccttata tttctatgcc ggtcgatagc attccaggcg gctcaatcct gactccggat | 840 |
| accgatatgg acattatgga aaatctcacc atgccagaat ggttggataa aatggagtac | 900 |
| aaatccctga ctgctaacgg tgcaatcaag tac | 933 |

<210> SEQ ID NO 131
<211> LENGTH: 954
<212> TYPE: DNA
<213> ORGANISM: Artificial
<220> FEATURE:
<223> OTHER INFORMATION: Codon-optimized and/or mutated sequence

<400> SEQUENCE: 131

| | |
|---|---|
| atgtccacta actcgatcaa actgctggct ggaaactcgc acccaggcct tgccgaactg | 60 |
| atctcgcagc gacttggcgt gccgctcagc aaagtcggcg tgtaccagta ctctaacaag | 120 |
| gagacctcag tcacaattgg cgaatccatt cgcgacgagg acgttacat tatccaaacc | 180 |
| ggttacggtg agcatgaaat caacgatttt cttatggagc tcctgatcct gattcacgct | 240 |
| tgcaagacag ccagcgtgcg ccgtatcacc gcggtcatcc ctaactttcc gtacgcacgc | 300 |
| caagataaga aagataagtc ccgtgcgccg atcaccgcca aattgatcgc caacctcctg | 360 |
| gagacggccg gctgcgatca cgtgatcacc atggacttgc atgcatcgca gattcagggt | 420 |
| ttcttccaca tcccggttga caaccttttac ggcgaaccgt cagtgctgaa ctacatccgc | 480 |
| acgaagaccg atttaataa cgcaattttg gtatcgcccg acgcaggcgg cgcgaaacgt | 540 |
| gttgcgtctt tggcagacaa gctggatatg aactttgctt tgatccacaa ggagcgccag | 600 |
| aaggcaaacg aggtctcccg catgctgctc gtcggtgatg tcgcgggcaa aagctgcctt | 660 |
| cttatcgacg atatggcaga cacatgtggt actctggtga aggcttgtga caccctgatg | 720 |
| gaccatggcg ccaaggaagt tattgcaatc gtgacccacg gcattttctc gggttcagct | 780 |
| cgcgagaaac tcattaattc gcgcctgtcc cgcattgtct gcacgaatac cgtaccggtg | 840 |
| gatctcgatc tcgacatcgt ggatcaggtc gatatctcac caacgattgc tgaagcaatt | 900 |
| cgccgtctcc acaacggcga atccgtttcg tacctcttca cgcatgcgcc agtc | 954 |

<210> SEQ ID NO 132
<211> LENGTH: 960
<212> TYPE: DNA
<213> ORGANISM: Artificial
<220> FEATURE:
<223> OTHER INFORMATION: Codon-optimized and/or mutated sequence

<400> SEQUENCE: 132

| | |
|---|---|
| atgcctacaa attcgatcaa gttgttggcg cccgatgttc accgcggtct tgcggagctg | 60 |
| gttgctaaac gcttgggact gcaacttact tcctcaaagc tgaagcgaga ccctaccggc | 120 |
| gaggtgtcct tcagcatcgg cgaatcagta cgcgaccagg atatcttcat catcactcaa | 180 |
| attggctccg gcgtggtgaa cgatcgtgtc ctggaactgc tgatcatgat caacgcctcg | 240 |
| aaaaccgcgt ccgcccgacg catcaccgcg atcatcccca attttccgta tgcgcgccag | 300 |

| | |
|---|---|
| gaccgcaagg ataagtcccg tgctccaatt accgctaaac ttatggcaga catgctgacc | 360 |
| accgcaggct gtgaccatgt tatcactatg gatctccacg cgtctcagat ccagggtttt | 420 |
| ttcgacgtgc cagtggataa tctgtacgcg gaaccatccg tcgtgcgcta tatcaaggaa | 480 |
| aacgtgaatt atatggattc cattatcatc agccccgatg cgggaggcgc caagcgcgcg | 540 |
| gcaaccctcg cggatcgcct ggatttgaat ttcgcactca tccacaagga gcgcgcgcgc | 600 |
| gctaatgaag tctcccgcat ggtgctcgtt ggcgatgtta ctgataagat ctgcattatc | 660 |
| gtagatgaca tggctgacac ttgtggaact ttggccaagg cagccgagat tctgctggaa | 720 |
| aaccgcgcga gtctgttat cgcgattgtc acccacggcg tcctttcggg tcgcgcaatt | 780 |
| gaaaatatca ataactccaa actcgatcgc gttgtgtgca ccaacacagt tccatttgaa | 840 |
| gaaaagatca aaaaatgccc caagctggct gtcatcgata ttagctctgt actggcagag | 900 |
| tccatccgcc gccttcacaa cggtgaatca atctcctatc tcttcaagaa ctatccgttg | 960 |

<210> SEQ ID NO 133
<211> LENGTH: 1005
<212> TYPE: DNA
<213> ORGANISM: Artificial
<220> FEATURE:
<223> OTHER INFORMATION: Codon-optimized and/or mutated sequence

<400> SEQUENCE: 133

| | |
|---|---|
| atgtccgaac cagcccaaaa aaagcaaaag gttgctaaca attccctgga gcaactgaag | 60 |
| gcctctggta ctgttgtagt ggctgatact ggtgatttcg gttccatcgc caagtttcag | 120 |
| cctcaggatt ccactacaaa cccctccttg atccttgccg ccgctaagca accaacctac | 180 |
| gccaagctca tcgacgtcgc agttgaatac ggcaagaaac acggtaagac tacggaggag | 240 |
| caagtcgaga cgcggtcga ccgcctgttg gtggagttcg gcaaggagat ccttaaaatc | 300 |
| gttcccggcc gcgtctccac cgaagtcgat gcccgattgt cctttgatac ccaagccacg | 360 |
| atcgaaaagg cccgtcacat cattaagctc tttgagcagg aaggcgtttc caaagaacga | 420 |
| gtcctcatta agattgcgtc aacctgggaa ggcatccaag cagccaaaga gcttgaggag | 480 |
| aaggacggta ttcattgtaa tctgacgctg ctctttttctt tcgttcaggc tgtagcttgt | 540 |
| gcagaggcgc aggttactct catctcccca ttcgtaggtc gaatcctgga ttggtacaaa | 600 |
| tcttcaaccg gcaaggatta caagggcgag gctgaccctg cgtcatctc cgtcaaaaag | 660 |
| atctataact actacaagaa gtatggctat aagaccatcg tcatgggcgc ctcttccgt | 720 |
| tccaccgatg aaattaaaaa ccttgctggc gttgactatc tgacgatttc ccccgcactc | 780 |
| ctggacaaac tgatgaattc aaccgaaccc tttccccgtg tcttggatcc tgtctcggcg | 840 |
| aaaaaggaag ccggcgataa aatttcatac atctctgacg agtctaagtt ccgttttgat | 900 |
| ctgaatgaag acgctatggc aaccgaaaaa ctgtcagaag gcatccgtaa gttctccgcc | 960 |
| gacatcgtta cccttttga cctcattgaa aagaaagtga cagcc | 1005 |

<210> SEQ ID NO 134
<211> LENGTH: 1011
<212> TYPE: DNA
<213> ORGANISM: Artificial
<220> FEATURE:
<223> OTHER INFORMATION: Codon-optimized and/or mutated sequence

<400> SEQUENCE: 134

| | |
|---|---|
| atgtctgaaa atgcagcaaa caacatcatg gaaactaaga tttgcaccga tgccatcgtg | 60 |
| tccgagcttc aaaagaaaaa ggtacatttg ttctactgcc tggaatgcga agaactcgct | 120 |

```
cgaaatatcg cagccgagtc cgatcatatc acccttcaaa gcattaactg gcgctccttc      180
gcagacggtt tccctaacct cttcatcaat aacgcacacg atatccgcgg ccagcacgtc      240
gcgttccttg caagcttcag ctccccagcc gttatctttg aacaaattag cgtgatttat      300
ttgcttcccc gcctcttcgt tgcctcattt actcttgtac ttccgttttt cccaacaggc      360
tccttcgaac gcatggaaga agagggagat gtcgcgaccg ctttcaccat ggctcgaatc      420
gtgagcaaca tcccgatctc ccgcggcgga cctactagcg ttgtgattta tgatatccac      480
gctctccaag aacgctttta ttttgccgac caggtcctgc ctttgttcga gactggcatc      540
cctcttttga cgaaacgtct gcaacaattg cccgaaaccg aaaaggtcat cgtggcattc      600
ccggatgatg gtgcctggaa gcgctttcac aaactcctgg atcattaccc caccgttgtc      660
tgtaccaaag tccgcgaggg tgacaagcgt attgtacgac ttaaagaggg caacccagct      720
ggctgccacg ttgtgatcgt ggatgacttg gtgcagtccg gtggaaccct tatcgaatgt      780
cagaaagtcc tcgcggcgca cggcgctgtt aaggtttccg catacgttac tcacggagtt      840
ttcccaaagt cttcctggga acgcttcact cataagaaaa atggcctgga agaggcattc      900
gcttattttt ggattacaga ctcgtgcccg cagactgtta aggctattgg taataaggct      960
ccattcgagg tcctcagcct ggctggctca attgctgatg ctctccaaat c             1011
```

<210> SEQ ID NO 135
<211> LENGTH: 1251
<212> TYPE: DNA
<213> ORGANISM: Artificial
<220> FEATURE:
<223> OTHER INFORMATION: Codon-optimized and/or mutated sequence

<400> SEQUENCE: 135

```
atggcccttc ttcccttctt cgacctcacc aacttcgagt ccgatgcttc cgaggaactg       60
ggttggctta aatacgtcgg ccagtacag acacgtgtgt ttccacagca ttttaaggac      120
aatttggaaa aagtgcgcaa aatctccgag actattgatg tcatcgtaga taccaccgct      180
gagttgggcc cggaagcatg tgtgaatctg ctcaatgctg gtgcattggc aatcttggtg      240
aacgaggaga tgcttaatga gttggcagac atctcaccta accgcttgt gttgaagacc       300 gataccaccg atatcggaaa aatcgaaaag ctgtcccagg ttgccggttc gatccagtgg      360
attggaagcg cagagaacta cccaccagat tttttcgaac gtgcatcgaa gatcatccat      420
aaggccgtca tgcctgaagg cggcggacgt actctgtacc tggaattccc agagcaacca      480
tcaatggagg tcctgaaaag cttttcggtg cacagcgttg ttcctgtgct ttcgtcctct      540
ttcctcaccg taaagcccgc agaagaacct aagaaactct ccctggcaga tctcatcctc      600
atctccgcga ataccgaccg cgaggatggc ctttttctcaa cactggtggt caacgagctg      660
ggaatcgcac tcggcctcgt gtattcctcc aaagagtcgg tcgcagaatc cttgaagacg      720
ggtactggag tgtaccaatc ccgtaagcga ggactctggt acaagggcgc agctccggc      780 gcagtccaac acctcattca cattgacgtt gattgcgacg aggattgcct cgcttcgtg      840 gtttatcaaa ccggaaaagg cttctgccac ctggacactc tgcattgctt tggtcaggcc      900
agcggcttgt gtcagctcga aaaacgctc atcgatcgta aaaacaatgc gcctgagggc      960
agctacacgg cccgcctgtt ctccgatccc aagcttcttc gagcgaagat tatggaggaa     1020
gccgaggagc tgtgtgatgc caccacgaag gaaaacgtga tctgggaaat ggcggatttg     1080
atgtattttg ccattactcg ttgtgtcggc tccggtgtct cactcaacga cattagccgt     1140
```

| | |
|---|---|
| catctggacc tgaagcaccg caaagtgaca cgccgtaaag gtgatgcgaa agtagcatgg | 1200 |
| caagagaaat tgaaggataa gggtggcgtg gcaaatacat cctatactgc g | 1251 |

<210> SEQ ID NO 136
<211> LENGTH: 1005
<212> TYPE: DNA
<213> ORGANISM: Artificial
<220> FEATURE:
<223> OTHER INFORMATION: Codon-optimized and/or mutated sequence

<400> SEQUENCE: 136

| | |
|---|---|
| atgcactccc accactcgca ctcgggagat tactccgctc atggcaccga tccctcgat | 60 |
| tccgttgtcg atcaagtcgt gaacttgaat ttccacactt actgcttgac agagcatatc | 120 |
| ccccgtattg aagccaaatt catttacccg gaggaacagt cgttgggtaa gaacccagag | 180 |
| gaagttatta ctaagctcga cgtccttc aagaatttca tgtcccacgc tcaggagatc | 240 |
| aagacccgtt atgccgaccg cccagacgtg cgcaccaaat tcattatcgg tatggagatc | 300 |
| gaaagctgtg acatggctca catcgagtat gccaaacgct tgatgaagga aaacaatgac | 360 |
| atcctcaagt tctgcgttgg atccgtacac cacgtgaatg gcatccccat tgattttgat | 420 |
| cagcagcagt ggtacaactc cctccattcc tttaacgata acctgaagca cttcttgttg | 480 |
| tcttactttc aatctcagta tgagatgctc attaacatta gcctctggt ggtcggtcat | 540 |
| ttcgacctgt acaaactctt cctgccgaat gacatgttgg ttaatcaaaa atctggtaac | 600 |
| tgtaacgaag aaaccggtgt acccgtcgca tcccttgatg ttatttcaga atggcctgag | 660 |
| atctacgatg cagtggttcg taaccttcag tttatcgatt catacggcgg cgctatcgaa | 720 |
| attaacacct ccgcgttgcg caagcgtctg gaggaaccat accctctaa aaccctgtgc | 780 |
| aacttggtca aaaagcattg cggttcccgc tttgtgctga cgacgatgc acacggagtg | 840 |
| gcacaggtcg gtgtgtgcta tgacaaagtt aagaagtaca ttgtggacgt gctccaactc | 900 |
| gaatacatct gttatctgga agaatcacaa tctccagaaa atctgctcac tgtcaagcga | 960 |
| ttgccaatct cccaatttgt taatgaccca ttttgggcga acatc | 1005 |

<210> SEQ ID NO 137
<211> LENGTH: 1542
<212> TYPE: DNA
<213> ORGANISM: Artificial
<220> FEATURE:
<223> OTHER INFORMATION: Codon-optimized and/or mutated sequence

<400> SEQUENCE: 137

| | |
|---|---|
| atgtctacca caccactcc ttcctcctgg accaatcctt tgcgtgatcc acaggataag | 60 |
| cgtctcccgc gcattgctgg tccttccggt atggttatct cggtgtaac tggtgatctg | 120 |
| gctcgtaaga agctgttgcc agcgatctat gacctggcca tcgcggcct gctcccccca | 180 |
| ggcttcagcc tggtcggtta cggccgccgc gagtggagca aggaggactt cgagaaatat | 240 |
| gtgcgcgatg cagcgtcagc cggtgcacgt accgaatttc gtgagaacgt ttgggaacgc | 300 |
| ctcgcggaag gtatggaatt cgttcgtggt aatttcgacg atgacgccgc ttttgataat | 360 |
| ctcgccgcga ccctcaaacg cattgacaaa acgcgcggta ctgcaggtaa ttgggcatac | 420 |
| tatctcagca ttcccccga tagctttgcg gcagtatgcc accagctgga acgctccggt | 480 |
| atggccgaat ccaccgagga ggcttggcgt cgcgtcatca tcgagaagcc attcggtcac | 540 |
| aacctggaat ccgcgcacga acttaaccag ttggtgaatg ccgtgtttcc agaatctagc | 600 |
| gtgttccgca tcgatcacta ccttggaaag gaaaccgtgc aaaacatcct tgctctgcgc | 660 |

```
ttcgctaacc agttgtttga gccgctgtgg aactcaaatt acgttgacca cgtgcagatc      720
actatgacgg aggatatcgg cttgggcggt cgcgccggct actacgacgg tattggagca      780
gcgcgtgacg tgattcaaaa ccatctcatc cagctgctcg cactggttgc aatggaagaa      840
ccgatttcat tcgtcccagc tcaactgcag gctgaaaaga tcaaagtcct gtctgcgaca      900
aagccttgct accctctcga caagacctcg gcacgcggac aatatgcagc cggctggcag      960
ggctccgaac tggttaaggg actccgcgaa gaggatggct taacccaga gtccacaacc     1020 gagactttcg ctgcatgcac acttgagatc acatcacgcc gttgggctgg cgtaccgttc     1080
tacctgcgta cgggcaagcg cctgggccgc gcgtaaccg agatcgcagt tgtgttcaag      1140
gatgctcccc accagccatt cgatggtgat atgaccgttt ctctgggtca aaacgctatt     1200
gtgattcgcg tacagcctga tgaaggcgtt ttgatccgtt tcggttcaaa agtgcctggc     1260
tccgcaatgg aggtacgcga tgtcaatatg gattttagct actctgagtc atttaccgag     1320
gaatcgccag aagcatacga acgcctgatc ctggatgcac tccttgatga gtcttcgctc     1380
ttccctacca acgaagaggt agaactttcc tggaaaattc tggacccaat tctggaagca     1440
tgggatgcag atggcgaacc tgaggactat ccggcaggca cgtggggccc taagtccgcg     1500
gacgaaatgt tgagccgcaa cggccacaca tggcgtcgtc ca                       1542
```

<210> SEQ ID NO 138
<211> LENGTH: 933
<212> TYPE: DNA
<213> ORGANISM: Artificial
<220> FEATURE:
<223> OTHER INFORMATION: Codon-optimized and/or mutated sequence

<400> SEQUENCE: 138

```
atgtctgagc tggatgctaa gctgaacaag ctcggagtgg accgaattgc tatctcgccc       60
tacaagcagt ggactcgagg atacatggag cccggcaaca tcggaaatgg atacgtcacg      120
ggacttaagg tcgatgcagg tgtgcgagac aagtccgacg acgacgtcct ggacggaatt      180
gtttcctacg atagagcaga gactaagaac gcttacattg acaaatcaa catgaccaca       240 gctagctctt tcactggcgt tcaaggccga gtgatcggat acgacattct tcgatctccc      300
gaggtcgata aggccaagcc tctgtttacc gagacccagt gggatggttc cgagcttcct      360
atctacgacg ctaagcctct tcaggatgct ctggttgagt actttggtac tgagcaggat      420
cgtcgtcact acccagctcc cggttccttc atcgtttgtg ctaacaaagg cgtcaccgcc      480
gaacgaccaa agaacgacgc cgatatgaag cccggtcaag gatacggcgt ttggtccgcc      540
atcgctatta gcttcgctaa ggaccctacc aaggactcct ctatgttcgt tgaggacgct      600
ggtgtgtggg agacccctaa cgaggacgag ctgcttgagt acctcgaggg tagacgaaag      660
gccatggcta agtccattgc agaatgtggt caggatgccc acgcctcgtt cgaatcctcc      720
tggattggtt tcgcatacac aatgatggag ccaggccaga ttggtaacgc tattaccgtt      780
gccccctacg tgtctctgcc cattgattcc atccctggtg gctctatcct tactcctgac      840
aaggatatgg agatcatgga gaacctcacc atgccagagt ggctcgaaaa aatgggctac      900
aagtctctct ctgctaacaa cgcccttaag tac                                   933
```

<210> SEQ ID NO 139
<211> LENGTH: 1161
<212> TYPE: DNA
<213> ORGANISM: Artificial
<220> FEATURE:

<223> OTHER INFORMATION: Codon-optimized and/or mutated sequence

<400> SEQUENCE: 139

| | |
|---|---|
| atgtcgctct ccccgctcga ccaaaaccgc atcgaaagct tctggcagta ttgtctccaa | 60 |
| caccagtatt ttaatttggc atatccggaa agcgctgatt ttgattacgc acccttgcat | 120 |
| cgctttctgc gcttttccat caacaattgc ggcgattgga acgaaagctc gaactacctg | 180 |
| ttgaactctt tcgactttga gcgcgaagtg atgcacttct tcgcagaact gttccacatt | 240 |
| ccgttcgacg agtcgtgggg ttacgtgacg aacggcggta cagaaggaaa catgttcggt | 300 |
| tgctatctgg ctcgcgaact cttccctgat gcgaccctct actactccaa agattcccac | 360 |
| tattccgttg ccaagatcat caaactcttg cgcattaagt cccgcgcagt ggattccctc | 420 |
| ccttccggag aaatcgacta cgacgatctc gtggcgaaga tccaacagga ccaggaacga | 480 |
| caccctatcg tctttgtcaa tgtaggcact acgatgaaag gtgcggtgga tgacatcggt | 540 |
| gtgatccagc ataagcttgc agaagcaggt atcccacgtc aagactacta cctgcacgca | 600 |
| gacgcagccc tctcaggtat gatcctccct tttgtgacg caccgcagcc gtattcattt | 660 |
| gctgatggca ttgatagcat ctccgtctca ggacataaga tgattggctc tccgatgcct | 720 |
| tgcggcattg tactggcgaa gcgctccaac gtgtctcgaa tctccgttga gatcgactac | 780 |
| atttccgcaa aggatcagac tatttctggc tctcgaaatg gtcacacgcc catgatgctc | 840 |
| tgggcagcta tcaaatcccg tcccctggct gaatggcgcc gtaaagtccg ccattgcctg | 900 |
| gatatggccc aatatgccat cgaccgcttg caagctgcag gcatccaagc atggcgctgt | 960 |
| aagaacagca ttacggtagt cttcccttcc ccctccgaac cagtgtgcga taaacacggt | 1020 |
| ctcgctcgct ccggaggcac cgctcacctc atcaccactc cacaccacca cgattcccag | 1080 |
| cgcctcgatc gcctgctgga cgacatcgta caggaccttg agcgatgac ggcaccagcg | 1140 |
| ggtgctacta tgtctgccgc g | 1161 |

<210> SEQ ID NO 140
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 140

| | |
|---|---|
| atgctgaaga ttgccgtgcc gaataagggc tctcttagcg aacgtgcgat ggagattctc | 60 |
| gccgaagctg gctatgccgg ccgcggcgac tcgaaatcgc tgaacgtgtt tgacgaagca | 120 |
| aataacgttg aatttttctt ccttcgaccg aaagacattg caatctatgt ggctggcggc | 180 |
| cagcttgatc tgggaatcac gggacgcgac ttggcacgcg actcacaggc agatgttcac | 240 |
| gaagtcttga gcttgggttt cggctcgtcg actttccgct acgcggcacc agctgatgag | 300 |
| gaatggtcca ttgaaaaact cgatggtaaa cgcattgcta ccagctaccc taatctcgtt | 360 |
| cgcgatgatc tcgcagcacg tggactcagc gccgaggtgt tgcgcttgga cggagccgtg | 420 |
| gaagtctcca tcaagctcgg cgtggctgac gcgatcgctg atgtggtgtc aaccggccgc | 480 |
| acactccgtc aacagggcct ggctcctttc ggtgaggtgc tttgtacctc gaagcggtg | 540 |
| attgtcggtc gtaaggatga aaggtgaca cccgagcagc agatcttgtt gcgacgaatt | 600 |
| cagggtatct tgcatgcgca gaacttcctt atgctggatt acaaggttga tcgagacaat | 660 |
| ctcgatgcag ctactgcagt taccctggc ttctccggcc ctgccgtatc accccttgcg | 720 |
| cgtgataatt gggtcgcagt gcgcgcaatg gttcctcgtc gctccgcgaa cgctatcatg | 780 |

```
gataaactgg ctggactggg tgccgaagct atccttgcta gcgaaatccg catcgcgcga    840
atc                                                                 843
```

<210> SEQ ID NO 141
<211> LENGTH: 843
<212> TYPE: DNA
<213> ORGANISM: Artificial
<220> FEATURE:
<223> OTHER INFORMATION: Codon-optimized and/or mutated sequence

<400> SEQUENCE: 141

```
atgctaaaga tagcagtacc caacaaaggt agcctaagcg agagagctat ggaaatcttg     60
gctgaggctg gctatgctgg gagaggagac tccaaatctc taaatgtgtt tgacgaggct    120
aataatgttg agtttttttt tcttagacca aaggatatcg ccatatatgt cgcgggagga    180
cagctagacc taggcatcac cggcagggat ctagccaggg acagccaagc agatgtccac    240
gaggtcctgt ctttaggatt tggatcttct accttcaggt atgcagcccc tgccgatgaa    300
gagtggtcta tcgagaagct agatggcaaa cgtatcgcca caagttatcc caatttggtc    360
agggatgatc tagccgcgag aggtttatca gccgaggtcc tgagacttga tggggccgtc    420
gaggttagta tcaaactagg tgttgcggat gcgattgcag acgtggtatc caccggaagg    480
acgctacgtc aacaagggct tgccccattc ggtgaggtgc tgtgcacatc cgaggctgtt    540
atcgtgggaa gaaaagacga aaaggttaca cctgagcagc agatattact aagaaggata    600
cagggaattc tgcacgctca aaactttcta atgctggatt ataaggttga tgggataac    660 ctagacgccg ccacagccgt tactcctggt ttctccggtc ccgctgtcag tcctctagct    720
agggacaact gggtcgccgt cagggctatg gttccaagac gtagcgctaa cgcaataatg    780
gacaaattgg cgggccttgg ggccgaagca atactggcga gcgaaatcag gattgcacgt    840
att                                                                 843
```

<210> SEQ ID NO 142
<211> LENGTH: 55
<212> TYPE: PRT
<213> ORGANISM: Artificial
<220> FEATURE:
<223> OTHER INFORMATION: Solubility tag

<400> SEQUENCE: 142

```
Met Gln Tyr Lys Leu Ala Leu Asn Gly Lys Thr Leu Lys Gly Glu Thr
1               5                  10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr
    50                  55
```

<210> SEQ ID NO 143
<211> LENGTH: 317
<212> TYPE: PRT
<213> ORGANISM: Artificial
<220> FEATURE:
<223> OTHER INFORMATION: Mutated

<400> SEQUENCE: 143

```
Met Ser Asn Glu Tyr Gly Asp Lys Asn Leu Lys Ile Phe Ser Leu Asn
1               5                  10                  15
```

-continued

```
Ser Asn Pro Glu Leu Ala Lys Glu Ile Ala Asp Asn Val Gly Val Gln
            20                  25                  30

Leu Gly Lys Cys Ser Val Thr Arg Phe Ser Asp Gly Glu Val Gln Ile
            35                  40                  45

Asn Ile Glu Glu Ser Ile Arg Gly Cys Asp Cys Tyr Ile Ile Gln Ser
 50                  55                  60

Thr Ser Ala Pro Val Asn Glu His Ile Met Glu Leu Leu Ile Met Val
 65                  70                  75                  80

Asp Ala Leu Lys Arg Ala Ser Ala Lys Thr Ile Asn Ile Val Ile Pro
            85                  90                  95

Tyr Tyr Gly Tyr Ala Arg Gln Asp Arg Lys Ala Arg Ser Arg Glu Pro
            100                 105                 110

Ile Thr Ala Lys Leu Phe Ala Asn Leu Leu Glu Thr Ala Gly Ala Thr
            115                 120                 125

Arg Val Ile Ala Leu Asp Ile His Ala Pro Gln Ile Gln Gly Phe Phe
            130                 135                 140

Asp Ile Pro Ile Asp His Leu Met Gly Val Pro Ile Leu Gly His Tyr
145                 150                 155                 160

Phe Glu Gly Lys Asp Leu Lys Asp Ile Val Ile Val Ser Pro Asp His
            165                 170                 175

Gly Gly Val Thr Arg Ala Arg Lys Leu Ala Asp Arg Leu Lys Ala Pro
            180                 185                 190

Ile Ala Ile Ile Asp Lys Arg Arg Pro Arg Pro Asn Glu Val Glu Val
            195                 200                 205

Met Asn Ile Val Gly Asn Val Glu Gly Lys Thr Ala Ile Leu Ile Asp
            210                 215                 220

Asp Ile Ile Asp Thr Ala Gly Thr Ile Thr Leu Ala Ala Asn Ala Leu
225                 230                 235                 240

Val Glu Asn Gly Ala Ala Glu Val Tyr Ala Cys Cys Thr His Pro Val
            245                 250                 255

Leu Ser Gly Pro Ala Val Glu Arg Ile Asn Asn Ser Lys Ile Lys Glu
            260                 265                 270

Leu Val Val Thr Asn Ser Ile Lys Leu Pro Glu Glu Lys Lys Ile Glu
            275                 280                 285

Arg Phe Lys Gln Leu Ser Val Gly Pro Leu Leu Ala Glu Ala Ile Ile
            290                 295                 300

Arg Val His Glu Lys Gln Ser Val Ser Tyr Leu Phe Ser
305                 310                 315
```

ENGINEERED BIOSYNTHETIC PATHWAYS FOR PRODUCTION OF HISTAMINE BY FERMENTATION

CROSS-REFERENCE TO RELATED APPLICATIONS

This application claims the benefit of U.S. provisional application No. 62/660,875, filed Apr. 20, 2018, which is hereby incorporated by reference in its entirety.

STATEMENT AS TO RIGHTS TO INVENTIONS MADE UNDER FEDERALLY SPONSORED RESEARCH AND DEVELOPMENT

This invention was made with Government support under Agreement No. HR0011-15-9-0014, awarded by DARPA. The Government has certain rights in the invention.

INCORPORATION BY REFERENCE OF THE SEQUENCE LISTING

This application includes a sequence listing which has been submitted electronically in ASCII format and is hereby incorporated by reference in its entirety. This ASCII copy, created on Apr. 17, 2019, is named ZMGNP011WO_Seq_List_ST25.txt and is 312,107 bytes in size.

FIELD OF THE DISCLOSURE

The present disclosure relates generally to the area of engineering microbes for production of histamine by fermentation.

BACKGROUND

Biogenic amines are organic bases endowed with biological activity, which are frequently found in fermented foods and beverages. Histamine is known to exist in nature in fermented foods such as yogurt (13-36 mg/kg) [1], miso (24 mg/kg) [2], and red wine (24 mg/L) [3]. Some bacteria that live in the human gut also make histamine, and it functions to regulate the immune system by an anti-inflammatory effect [4]. Production of histamine in fermented foods relies on a source of proteins that contain histidine and microbes that histidine decarboxylase. Histamine is the decarboxylation product of histidine that is catalyzed specifically by the enzyme histidine decarboxylase (EC 4.1.1.22). Production of histamine in an industrial fermentation from simple, non-protein, carbon and nitrogen sources requires assembly of a pathway with improved biosynthesis of the amino acid precursor histidine and a highly active histidine decarboxylase.

SUMMARY

The disclosure provides engineered microbial cells, cultures of the microbial cells, and methods for the production of histamine, including the following:

Embodiment 1: An engineered microbial cell that expresses a non-native histidine decarboxylase, wherein the engineered microbial cell produces histamine.

Embodiment 2: The engineered microbial cell of embodiment 1, wherein the engineered microbial cell includes increased activity of one or more upstream histamine pathway enzyme(s), said increased activity being increased relative to a control cell.

Embodiment 3: The engineered microbial cell of embodiment 2, wherein the one or more upstream histamine pathway enzyme(s) are selected from the group consisting of an ATP phosphoribosyltransferase, a phosphoribosyl-ATP pyrophosphatase, a phosphoribosyl-AMP cyclohydrolase, a 5'ProFAR isomerase, an imidazole-glycerol phosphate synthase, an imidazole-glycerol phosphate dehydratase, a histidinol-phosphate aminotransferase, a histidinol-phosphate phosphatase, histidinol dehydrogenase, and a ribose phosphate pyrophosphokinase.

Embodiment 4: The engineered microbial cell of any one of embodiments 1-3, wherein the engineered microbial cell includes reduced activity of one or more enzyme(s) that consume one or more histamine pathway precursors, said reduced activity being reduced relative to a control cell.

Embodiment 5: The engineered microbial cell of embodiment 4, wherein the one or more enzyme(s) that consume one or more histamine pathway precursors are selected from the group consisting of an enolase, a pyruvate dehydrogenase, a pentose phosphate pathway sugar isomerase, a transaldolase, a transketolase, a ribulose-5-phosphate epimerase, and a ribulose-5-phosphate isomerase.

Embodiment 6: The engineered microbial cell of embodiment 4 or embodiment 5, wherein the reduced activity is achieved by replacing a native promoter of a gene for said one or more enzymes with a less active promoter.

Embodiment 7: The engineered microbial cell of any one of embodiments 1-6, wherein the engineered microbial cell additionally expresses a feedback-deregulated glucose-6-phosphate dehydrogenase or a feedback-deregulated ATP phosphoribosyltransferase.

Embodiment 8: An engineered microbial cell, wherein the engineered microbial cell includes means for expressing a non-native histidine decarboxylase, wherein the engineered microbial cell produces histamine.

Embodiment 9: The engineered microbial cell of embodiment 8, wherein the engineered microbial cell includes means for increasing the activity of one or more upstream histamine pathway enzyme(s), said increased activity being increased relative to a control cell.

Embodiment 10: The engineered microbial cell of embodiment 9, wherein the one or more upstream histamine pathway enzyme(s) are selected from the group consisting of an ATP phosphoribosyltransferase, a phosphoribosyl-ATP pyrophosphatase, a phosphoribosyl-AMP cyclohydrolase, a 5'ProFAR isomerase, an imidazole-glycerol phosphate synthase, an imidazole-glycerol phosphate dehydratase, a histidinol-phosphate aminotransferase, a histidinol-phosphate phosphatase, a histidinol dehydrogenase, and a ribose phosphate pyrophosphokinase.

Embodiment 11: The engineered microbial cell of any one of embodiments 8-10, wherein the engineered microbial cell includes means for reducing the activity of one or more enzyme(s) that consume one or more histamine pathway precursors, said reduced activity being reduced relative to a control cell.

Embodiment 12: The engineered microbial cell of embodiment 11, wherein the one or more enzyme(s) that consume one or more histamine pathway precursors are selected from the group consisting of an enolase, a pyruvate dehydrogenase, pentose phosphate pathway sugar isomerase, a transketolase, a transaldolase, a ribulose-5-phosphate epimerase, and a ribulose-5-phosphate isomerase.

Embodiment 13: The engineered microbial cell of embodiment 11 or embodiment 12, wherein the reduced activity is achieved by means for replacing a native promoter of a gene for said one or more enzymes with a less active promoter.

Embodiment 14: The engineered microbial cell of any one of embodiments 8-13, wherein the engineered microbial cell additionally includes means for expressing glucose-6-phosphate dehydrogenase or a feedback-deregulated ATP phosphoribosyltransferase.

Embodiment 15: The engineered microbial cell of any one of embodiments 1-14, wherein the engineered microbial cell includes a fungal cell.

Embodiment 16: The engineered microbial cell of embodiment 15, wherein the engineered microbial cell includes a yeast cell.

Embodiment 17: The engineered microbial cell of embodiment 16, wherein the yeast cell is a cell of the genus *Saccharomyces* or *Yarrowia*.

Embodiment 18: The engineered microbial cell of embodiment 17, wherein the yeast cell is a cell of the genus *Saccharomyces* and of the species cerevisiae.

Embodiment 19: The engineered microbial cell of embodiment 17, wherein the yeast cell is a cell of the genus *Yarrowia* and of the species *lipolytica*.

Embodiment 20: The engineered microbial cell of any one of embodiments 1-19, wherein the non-native histidine decarboxylase includes a histidine decarboxylase having at least 70% amino acid sequence identity with a histidine decarboxylase from *Chromobacterium* sp. LK1 or from *Acinetobacter baumannii* strain AB0057.

Embodiment 21: The engineered microbial cell of any one of embodiments 1 and 16-20, wherein the engineered microbial cell includes increased activity of one or more upstream histamine pathway enzyme(s), said increased activity being increased relative to a control cell, wherein the one or more upstream histamine pathway enzyme(s) comprise an ATP phosphoribosyltransferase.

Embodiment 22: The engineered microbial cell of embodiment 21 wherein the increased activity of the ATP phosphoribosyltransferase is achieved by heterologously expressing it.

Embodiment 23: The engineered microbial cell of embodiment 22, wherein the heterologous ATP phosphoribosyltransferase has at least 70% amino acid sequence identity with an ATP phosphoribosyltransferase from *S. cerevisiae*.

Embodiment 24: The engineered microbial cell of any one of embodiments 16-23, wherein the engineered microbial cell includes a feedback-deregulated variant of a *Corynebacterium glutamicum* ATP phosphoribosyltransferase.

Embodiment 25: The engineered microbial cell of any one of embodiments 1-14, wherein the engineered microbial cell is a bacterial cell.

Embodiment 26: The engineered microbial cell of embodiment 25, wherein the bacterial cell is a cell of the genus *Corynebacteria* or *Bacillus*.

Embodiment 27: The engineered microbial cell of embodiment 26, wherein the bacterial cell is a cell of the genus *Corynebacteria* and of the species *glutamicum*.

Embodiment 28: The engineered microbial cell of embodiment 26, wherein the bacterial cell is a cell of the genus *Bacillus* and of the species *subtilis*.

Embodiment 29: The engineered microbial cell of any one of embodiments 25-28, wherein the non-native histidine decarboxylase includes a histidine decarboxylase having at least 70% amino acid sequence identity with a histidine decarboxylase from *Acinetobacter baumannii* or from *Lactobacillus* sp. (strain 30a).

Embodiment 30: The engineered microbial cell of any one of embodiments 1 and 25-29, wherein the engineered microbial cell includes increased activity of one or more upstream histamine pathway enzyme(s), said increased activity being increased relative to a control cell, wherein the one or more upstream histamine pathway enzyme(s) comprise an ATP phosphoribosyltransferase and an imidazole-glycerol phosphate dehydratase.

Embodiment 31: The engineered microbial cell of embodiment 30, wherein the increased activity of the ATP phosphoribosyltransferase or the imidazole-glycerol phosphate dehydratase is achieved by heterologously expressing it.

Embodiment 32: The engineered microbial cell of embodiment 31, wherein the heterologous ATP phosphoribosyltransferase has at least 70% amino acid sequence identity with an ATP phosphoribosyltransferase from *Saccharomyces cerevisiae* S288c or from *Salmonella typhimurium* LT2, or the heterologous imidazole-glycerol phosphate dehydratase has at least 70% amino acid sequence identity with an imidazole-glycerol phosphate dehydratase from *Corynebacterium glutamicum*.

Embodiment 33: The engineered microbial cell of any one of embodiments 25-32, wherein the engineered microbial cell includes a feedback-deregulated variant of a *Salmonella typhimurium* ATP phosphoribosyltransferase.

Embodiment 34: The engineered microbial cell of any one of embodiments 1-33, wherein, when cultured, the engineered microbial cell produces histamine at a level of at least 20 mg/L of culture medium.

Embodiment 35: The engineered microbial cell of embodiment 34, wherein, when cultured, the engineered microbial cell produces histamine at a level of at least 300 mg/L of culture medium.

Embodiment 36: A culture of engineered microbial cells according to any one of embodiments 1-35.

Embodiment 37: The culture of embodiment 36, wherein the engineered microbial cells are present in a concentration such that the culture has an optical density at 600 nm of 10-500.

Embodiment 38: The culture of any one of embodiments 36-37, wherein the culture includes histamine.

Embodiment 39: The culture of any one of embodiments 36-38, wherein the culture includes histamine at a level at least 20 mg/L of culture medium.

Embodiment 40: A method of culturing engineered microbial cells according to any one of embodiments 1-35, the method including culturing the cells under conditions suitable for producing histamine.

Embodiment 41: The method of embodiment 40, wherein the method includes fed-batch culture, with an initial glucose level in the range of 1-100 g/L, followed controlled sugar feeding.

Embodiment 42: The method of any one of embodiments 40-41, wherein the fermentation substrate includes glucose and a nitrogen source selected from the group consisting of urea, an ammonium salt, ammonia, and any combination thereof.

Embodiment 43: The method of any one of embodiments 40-42, wherein the culture is pH-controlled during culturing.

Embodiment 44: The method of any one of embodiments 40-43, wherein the culture is aerated during culturing.

Embodiment 45: The method of any one of embodiments 40-44, wherein the engineered microbial cells produce histamine at a level at least 20 mg/L of culture medium.

Embodiment 46: The method of any one of embodiments 40-45, wherein the method additionally includes recovering histamine from the culture.

Embodiment 47: A method for preparing histamine using microbial cells engineered to produce histamine, the method including: (a) expressing a non-native histidine decarboxylase in microbial cells; (b) cultivating the microbial cells in a suitable culture medium under conditions that permit the microbial cells to produce histamine, wherein the histamine is released into the culture medium; and isolating histamine from the culture medium.

DETAILED DESCRIPTION

Figure 1:
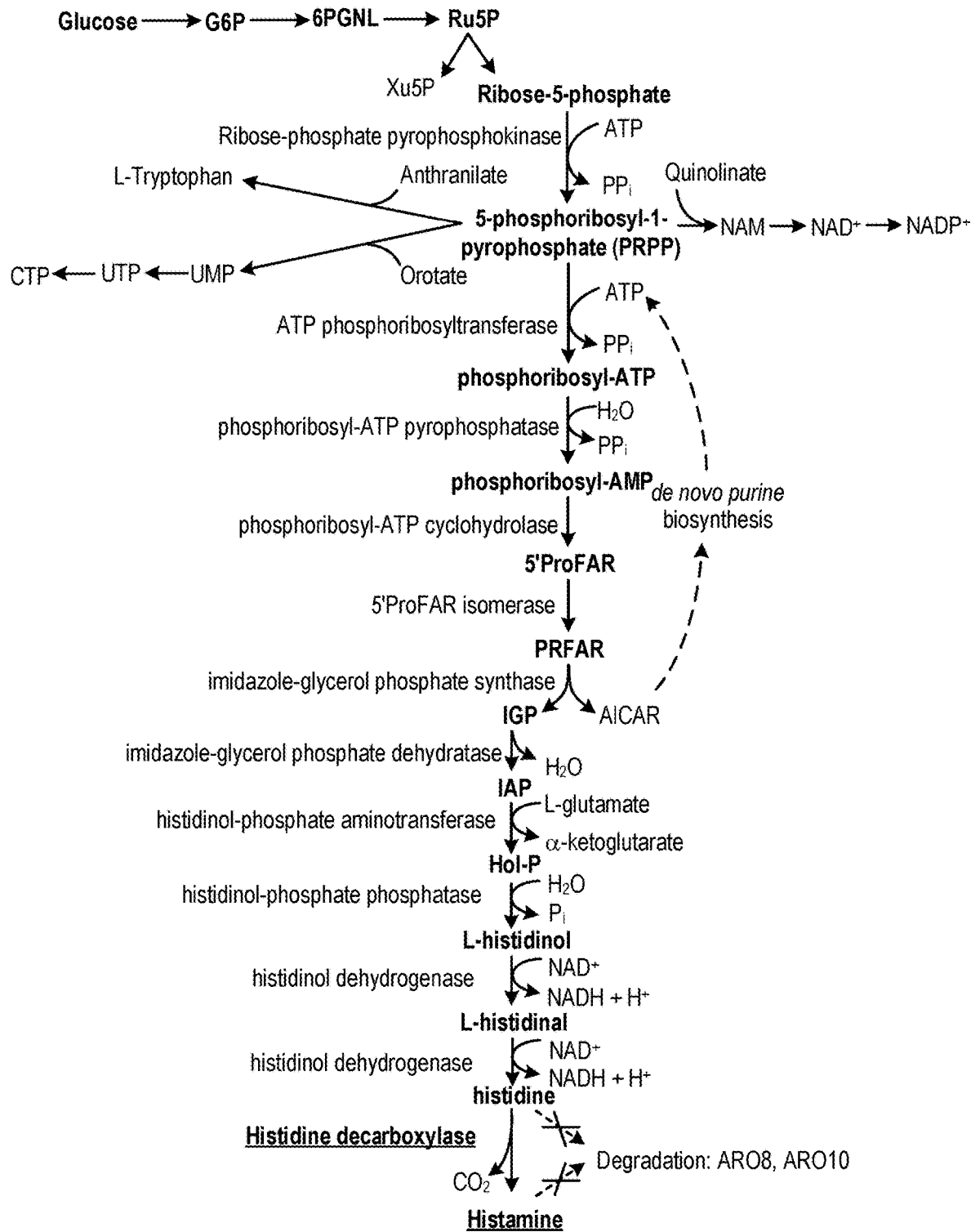
FIG. 1: Biosynthetic pathway for histamine.

This disclosure describes a method for the production of the small molecule histamine via fermentation by a microbial host from simple carbon and nitrogen sources, such as glucose and urea, respectively. This objective can be achieved by introducing a non-native metabolic pathway into a suitable microbial host for industrial fermentation of large-scale chemical products. Illustrative hosts include *Saccharomyces cerevisiae, Yarrowia lypolytica, Corynebacteria glutamicum*, and *Bacillus subtilis*. The engineered metabolic pathway links the central metabolism of the host to a non-native pathway to enable the production of histamine. The simplest embodiment of this approach is the expression of an enzyme, a non-native histidine decarboxylase enzyme, in a microbial host strain that can produce histidine. Further engineering of the metabolic pathway by modification of the microbial host central metabolism through overexpression and mutation of a key upstream pathway enzyme, ATP phosphoribosyltransferase, enabled titers of 505 mg/L histamine to be achieved.

The following disclosure describes how to engineer a microbe with the necessary characteristics to produce industrially feasible titers of histamine from simple carbon and nitrogen sources. Active histidine decarboxylases have been identified, and it has been found that feedback-deregulated ATP phosphoribosyltransferase and/or constitutive expression of native ATP phosphoribosyltransferase improve the titers of histidine by fermentation.

Definitions

Terms used in the claims and specification are defined as set forth below unless otherwise specified.

The term "fermentation" is used herein to refer to a process whereby a microbial cell converts one or more substrate(s) into a desired product (such as histamine) by means of one or more biological conversion steps, without the need for any chemical conversion step.

The term "engineered" is used herein, with reference to a cell, to indicate that the cell contains at least one targeted genetic alteration introduced by man that distinguishes the engineered cell from the naturally occurring cell.

The term "native" is used herein to refer to a cellular component, such as a polynucleotide or polypeptide, that is naturally present in a particular cell. A native polynucleotide or polypeptide is endogenous to the cell.

When used with reference to a polynucleotide or polypeptide, the term "non-native" refers to a polynucleotide or polypeptide that is not naturally present in a particular cell.

When used with reference to the context in which a gene is expressed, the term "non-native" refers to a gene expressed in any context other than the genomic and cellular context in which it is naturally expressed. A gene expressed in a non-native manner may have the same nucleotide sequence as the corresponding gene in a host cell, but may be expressed from a vector or from an integration point in the genome that differs from the locus of the native gene.

The term "heterologous" is used herein to describe a polynucleotide or polypeptide introduced into a host cell. This term encompasses a polynucleotide or polypeptide, respectively, derived from a different organism, species, or strain than that of the host cell. In this case, the heterologous polynucleotide or polypeptide has a sequence that is different from any sequence(s) found in the same host cell. However, the term also encompasses a polynucleotide or polypeptide that has a sequence that is the same as a sequence found in the host cell, wherein the polynucleotide or polypeptide is present in a different context than the native sequence (e.g., a heterologous polynucleotide can be linked to a different promotor and inserted into a different genomic location than that of the native sequence). "Heterologous expression" thus encompasses expression of a sequence that is non-native to the host cell, as well as expression of a sequence that is native to the host cell in a non-native context.

As used with reference to polynucleotides or polypeptides, the term "wild-type" refers to any polynucleotide having a nucleotide sequence, or polypeptide having an amino acid, sequence present in a polynucleotide or polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized. The term "wild-type" is also used to denote naturally occurring cells.

A "control cell" is a cell that is otherwise identical to an engineered cell being tested, including being of the same genus and species as the engineered cell, but lacks the specific genetic modification(s) being tested in the engineered cell.

Enzymes are identified herein by the reactions they catalyze and, unless otherwise indicated, refer to any polypeptide capable of catalyzing the identified reaction. Unless otherwise indicated, enzymes may be derived from any organism and may have a native or mutated amino acid sequence. As is well known, enzymes may have multiple functions and/or multiple names, sometimes depending on the source organism from which they derive. The enzyme names used herein encompass orthologs, including enzymes that may have one or more additional functions or a different name.

The term "feedback-deregulated" is used herein with reference to an enzyme that is normally negatively regulated by a downstream product of the enzymatic pathway (i.e., feedback-inhibition) in a particular cell. In this context, a "feedback-deregulated" enzyme is a form of the enzyme that is less sensitive to feedback-inhibition than the native enzyme native to the cell. A feedback-deregulated enzyme may be produced by introducing one or more mutations into a native enzyme. Alternatively, a feedback-deregulated enzyme may simply be a heterologous, native enzyme that, when introduced into a particular microbial cell, is not as sensitive to feedback-inhibition as the native, native enzyme. In some embodiments, the feedback-deregulated enzyme shows no feedback-inhibition in the microbial cell.

The term "histamine" refers to 2-(1I-Imidazol-4-yl) ethanamine (CAS #51-45-6).

The term "sequence identity," in the context of two or more amino acid or nucleotide sequences, refers to two or more sequences that are the same or have a specified percentage of amino acid residues or nucleotides that are the same, when compared and aligned for maximum correspondence, as measured using a sequence comparison algorithm or by visual inspection.

For sequence comparison to determine percent nucleotide or amino acid sequence identity, typically one sequence acts as a "reference sequence," to which a "test" sequence is compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence relative to the reference sequence, based on the designated program parameters. Alignment of sequences for comparison can be conducted using BLAST set to default parameters.

The term "titer," as used herein, refers to the mass of a product (e.g., histamine) produced by a culture of microbial cells divided by the culture volume.

As used herein with respect to recovering histamine from a cell culture, "recovering" refers to separating the histamine from at least one other component of the cell culture medium.

Engineering Microbes for Histamine Production
  Histamine Biosynthesis Pathway
  Histamine is typically derived from the amino acid histidine. The histamine biosynthesis pathway is shown in FIG. 1. The first enzyme of the amino acid biosynthesis pathway, ATP phosphoribosyltransferase, is subject to feedback inhibition by histidine. Histamine production is enabled by the addition of a single non-native enzymatic step in *Saccharomyces cerevisiae*, *Yarrowia lypolytica*, *Corynebacteria glutamicum*, and *Bacillus subtilis* hosts, which is catalyzed by histidine decarboxylase (EC 4.1.1.22).

Engineering for Microbial Histamine Production
  Any histidine decarboxylase that is active in the microbial cell being engineered may be introduced into the cell, typically by introducing and expressing the gene(s) encoding the enzyme(s)s using standard genetic engineering techniques. Suitable histidine decarboxylase may be derived from any source, including plant, archaeal, fungal, gram-positive bacterial, and gram-negative bacterial sources. Exemplary sources include, but are not limited to: *Aeromonas salmonicida* subsp. *pectinolytica* 34mel, *Acinetobacter baumannii* (strain AB0057), *Chromobacterium haemolyticum, Chromobacterium* sp. LK1, *Citrobacter pasteurii, Drosophila melanogaster, Lactobacillus aviarius* DSM 20655, *Lactobacillus fructivorans, Lactobacillus reuteri, Lactobacillus* sp. (strain 30a), *Methanosarcina barkeri* (strain Fusaro/DSM804), *Methanosarcina barkeri* str. Wiesmoor, *Morganella psychrotolerans, Mus musculus, Oenococcus oeni* (*Leuconostoc oenos*), *Pseudomonas putida* (*Arthrobacter siderocapsulatus*), *Pseudomonas rhizosphaerae, Pseudomonas* sp. bs2935, *Solanum lycopersicum, Oryza sativa, Penicillium marneffei, Streptomyces hygroscopicus, Pseudomonas putida, Arabidopsis thaliana* (Mouse-ear cress), *Glycine soja* (Wild soybean), *Solanum lycopersicum* (Tomato) (*Lycopersicon esculentum*), *Clostridium perfringens, Lactobacillus buchneri, Drosophila melanogaster* (Fruit fly), *Morganella morganii* (*Proteus morgani*), *E. coli, Bos taurus* (Bovine), *Raoutella planticol* (*Klebsiella planticola*), *Acinetobacter baumannii, Acinetobacter haemolyticus, Photobacterium damselae, Tetragenococcus muriaticus, Moritella* sp JT01, *Streptococcus thermophilus, Enterobacter aerogenes, Citrobacter youngae, Raoultella omithinolytica*, and *Raoultella planticola*.

One or more copies of histidine decarboxylase gene can be introduced into a selected microbial host cell. If more than one copy of a gene is introduced, the copies can have the same or different nucleotide sequences. In some embodiments, one or both of the heterologous gene(s) is/are expressed from a strong, constitutive promoter. In some embodiments, the heterologous histidine decarboxylase gene(s) is/are expressed from an inducible promoter. The heterologous gene(s) can optionally be codon-optimized to enhance expression in the selected microbial host cell. Illustrative codon-optimization tables for hosts used in the Examples are as follows: *Bacillus subtilis* Kazusa codon table: www.kazusa.or.jp/codon/cgi-bin/showcodin.cgi?species=1423&aa=1&style=N; *Yarrowia lipolytica* Kazusa codon table: www.kazusa.or.jp/codon/cgi-bin/showcodoon/cgi?species=4952&aa=1&style=N; *Corynebacteria glutamicum* Kazusa codon table: www.kazusa.or.jp/codon/cgi-bin/showcodoon/cgi?species=340322&aa=1&style=N; *Saccharomyces cerevisiae* Kazusa codon table: www.kazusa.or.jp/codon/cgi-bin/ showcodoon/cgi?species=4932&aa=1&style=N. Also used, was a modified, combined codon usage scheme for *S. cereviae* and *C. glutamicum*, which is reproduced below.

Modified Codon Usage Table for Sc and Cg

| Amino Acid | Codon | Fraction |
|---|---|---|
| A | GCG | 0.22 |
| A | GCA | 0.29 |
| A | GCT | 0.24 |
| A | GCC | 0.25 |
| C | TGT | 0.36 |
| C | TGC | 0.64 |
| D | GAT | 0.56 |
| D | GAC | 0.44 |
| E | GAG | 0.44 |
| E | GM | 0.56 |
| F | TTT | 0.37 |
| F | TTC | 0.63 |
| G | GGG | 0.08 |
| G | GGA | 0.19 |
| G | GGT | 0.3 |
| G | GGC | 0.43 |
| H | CAT | 0.32 |
| H | CAC | 0.68 |
| I | ATA | 0.03 |
| I | ATT | 0.38 |
| I | ATC | 0.59 |
| K | MG | 0.6 |
| K | AAA | 0.4 |
| L | TTG | 0.29 |
| L | TTA | 0.05 |
| L | CTG | 0.29 |
| L | CTA | 0.06 |
| L | CTT | 0.17 |
| L | CTC | 0.14 |
| M | ATG | 1 |
| N | MT | 0.33 |
| N | MC | 0.67 |
| P | CCG | 0.22 |
| P | CCA | 0.35 |
| P | CCT | 0.23 |
| P | CCC | 0.2 |
| Q | CAG | 0.61 |
| Q | CM | 0.39 |
| R | AGG | 0.11 |
| R | AGA | 0.12 |
| R | CGG | 0.09 |
| R | CGA | 0.17 |
| R | CGT | 0.34 |
| R | CGC | 0.18 |
| S | AGT | 0.08 |
| S | AGC | 0.16 |
| S | TCG | 0.12 |
| S | TCA | 0.13 |
| S | TCT | 0.17 |
| S | TCC | 0.34 |
| T | ACG | 0.14 |
| T | ACA | 0.12 |
| T | ACT | 0.2 |
| T | ACC | 0.53 |
| V | GTG | 0.36 |
| V | GTA | 0.1 |
| V | GTT | 0.26 |
| V | GTC | 0.28 |
| W | TGG | 1 |
| Y | TAT | 0.34 |
| Y | TAC | 0.66 |

Increasing the Activity of Upstream Enzymes

One approach to increasing histamine production in a microbial cell that is capable of such production is to increase the activity of one or more upstream enzymes in the histamine biosynthesis pathway. Upstream pathway enzymes include all enzymes involved in the conversions from a feedstock all the way to into the last native metabolite (histidine, in the illustrative microbial cells described in the Examples below). Such enzymes include an ATP phosphoribosyltransferase, a phosphoribosyl-ATP pyrophosphatase, a phosphoribosyl-AMP cyclohydrolase, a 5'ProFAR isomerase, an imidazole-glycerol phosphate synthase, an imidazole-glycerol phosphate dehydratase, a histidinol-phosphate aminotransferase, a histidinol-phosphate phosphatase, histidinol dehydrogenase, and a ribose phosphate pyrophosphokinase. Suitable upstream pathway genes encoding these enzymes may be derived from any source, including, for example, those discussed above as sources for a histidine decarboxylase gene.

In some embodiments, the activity of one or more upstream pathway enzymes is increased by modulating the expression or activity of the native enzyme(s). For example, native regulators of the expression or activity of such enzymes can be exploited to increase the activity of suitable enzymes.

Figure 12:
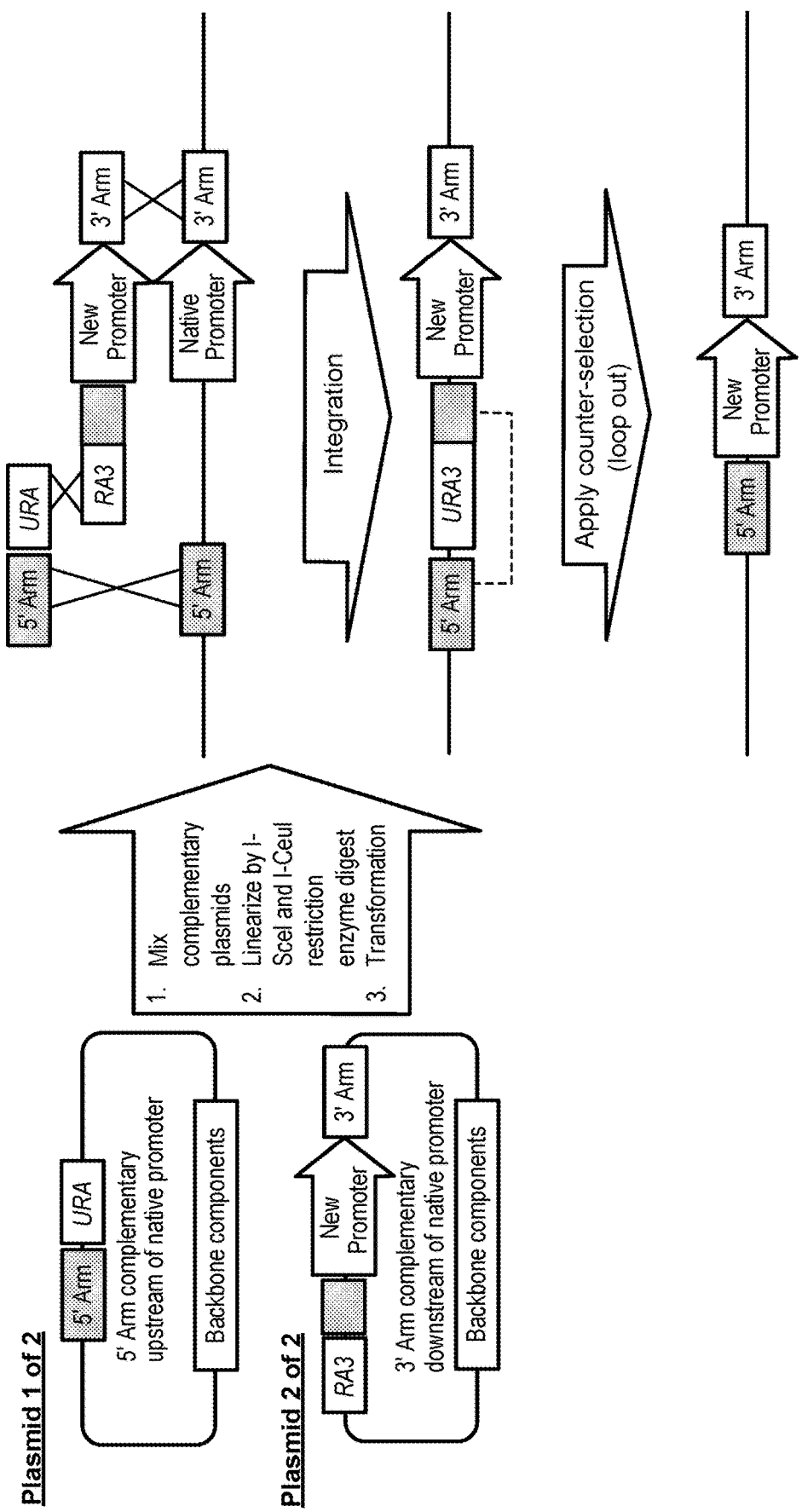
FIG. 12: Promoter replacement in *Saccharomyces cerevisiae* and *Yarrowia lipolytica*.

Alternatively, or in addition, one or more promoters can be substituted for native promoters using, for example, a technique such as that illustrated in FIG. 12. In certain embodiments, the replacement promoter is stronger than the native promoter and/or is a constitutive promoter.

In some embodiments, the activity of one or more upstream pathway enzymes is supplemented by introducing one or more of the corresponding genes into the histidine decarboxylase-expressing microbial host cell. An introduced upstream pathway gene may be from an organism other than that of the host cell or may simply be an additional copy of a native gene. In some embodiments, one or more such genes are introduced into a microbial host cell capable of histamine production and expressed from a strong constitutive promoter and/or can optionally be codon-optimized to enhance expression in the selected microbial host cell.

Example 1 describes the successful engineering of *C. glutamicum* to express a heterologous histamine decarboxylase from *Acinetobacter baumannii* (SEQ ID NO:1) and to constitutively express a heterologous *C. glutamicum* imidazoleglycerol-phosphate dehydratase (SEQ ID NO:2). This strain resulted from two rounds of genetic engineering and produced histamine at a titer of 24 mg/L of culture medium. This titer was increased to 68 mg/L in a *C. glutamicum* strain engineered to express a histamine decarboxylase from *Acinetobacter baumannii* (strain AB0057) (SEQ ID NO:1) and an ATP phosphoribosyltransferase from *S. cerevisiae* S288c (SEQ ID NO:3).

Example 2 describes the successful engineering of *Y. lypolytica* to express a histidine decarboxylase from *Acinetobacter baumannii* (strain AB0057) (SEQ ID NO:1) and an ATP phosphoribosyltransferase from *S. cerevisiae* S288c (SEQ ID NO:3) to give a histamine titer of 505 mg/L. Example 2 also describes the engineering *B. subtilis* to express a histamine decarboxylase from *Lactobacillus* sp. (strain 30a) (SEQ ID NO:4) and an ATP phosphoribosyltransferase from *Salmonella typhimurium* LT2 (SEQ ID NO:5) to give a histamine titer of 18 mg/L. Also in Example 2, *S. cerevisiae* was engineered to express a histamine decarboxylase from *Chromobacterium* sp. LK1 (SEQ ID NO:6) and an ATP phosphoribosyltransferase *S. cerevisiae* S288c (SEQ ID NO:3) to give a histamine titer of 111 mg/L.

In various embodiments, the engineering of a histamine-producing microbial cell to increase the activity of one or more upstream pathway enzymes increases the histamine titer by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold. In various embodiments, the increase in histamine titer is in the range of 10 percent to 100-fold, 2-fold to 50-fold, 5-fold to 40-fold, 10-fold to 30-fold, or any range bounded by any of the values listed above. (Ranges herein include their endpoints.) These increases are determined relative to the histamine titer observed in a histamine-producing microbial cell that lacks any increase in activity of upstream pathway enzymes. This reference cell may have one or more other genetic alterations aimed at increasing histamine production, e.g., the cell may express a feedback-deregulated enzyme.

In various embodiments, the histamine titers achieved by increasing the activity of one or more upstream pathway genes are at least 1, 10, 20, 30, 40, 50, 75, 100, 200, 300, 400, 500, 600, 700, 800, or 900 mg/L or at least 1, 1.5, 2, 2.5, 3, 3.5, 4, 4.5, 5, or 10 gm/L. In various embodiments, the titer is in the range of 10 mg/L to 10 gm/L, 20 mg/L to 5 gm/L, 50 mg/L to 4 gm/L, 100 mg/L to 3 gm/L, 500 mg/L to 2 gm/L or any range bounded by any of the values listed above.

Introduction of Feedback-Deregulated Enzymes

Since histidine biosynthesis is subject to feedback inhibition, another approach to increasing histamine production in a microbial cell engineered to produce histamine is to introduce feedback-deregulated forms of one or more enzymes that are normally subject to feedback regulation. Examples of such enzymes include glucose-6-phosphate dehydrogenase and ATP phosphoribosyltransferase. A feedback-deregulated form can be a heterologous, native enzyme that is less sensitive to feedback inhibition than the native enzyme in the particular microbial host cell. Alternatively, a feedback-deregulated form can be a variant of a native or heterologous enzyme that has one or more mutations or truncations rendering it less sensitive to feedback inhibition than the corresponding native enzyme. Examples of the latter include a variant ATP phosphoribosyltransferase (from *C. glutamicum*) containing the amino acid substitutions N215K, L231F, and T235A (SEQ ID NO:7) and a variant ATP phosphoribosyltransferase (from *Salmonella typhimurium*) containing the deletion of amino acids Q207 and E208 (SEQ ID NO:5).

In various embodiments, the engineering of a histamine-producing microbial cell to express a feedback-deregulated enzymes increases the histamine titer by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold. In various embodiments, the increase in histamine titer is in the range of 10 percent to 100-fold, 2-fold to 50-fold, 5-fold to 40-fold, 10-fold to 30-fold, or any range bounded by any of the values listed above. These increases are determined relative to the histamine titer observed in a histamine-producing microbial cell that does not express a feedback-deregulated enzyme. This reference cell may (but need not) have other genetic alterations aimed at increasing histamine production, i.e., the cell may have increased activity of an upstream pathway enzyme resulting from some means other than feedback-insensitivity.

In various embodiments, the histamine titers achieved by using a feedback-deregulated enzyme to increase flux though the histamine biosynthetic pathway are at least 100, 200, 300, 400, 500, 600, 700, 800, or 900 µg/L, or at least 1, 10, 50, 75, 100, 200, 300, 400, 500, 600, 700, 800, or 900 mg/L or at least 1, 1.5, 2, 2.5, 3, 3.5, 4, 4.5, 5, 10, 20, 50 g/L. In various embodiments, the titer is in the range of 50 µg/L to 50 g/L, 75 µg/L to 20 g/L, 100 µg/L to 10 g/L, 200 µg/L to 5 g/L, 500 µg/L to 4 g/L, 1 mg/L to 3 g/L, 500 mg/L to 2 g/L or any range bounded by any of the values listed above.

The approaches of supplementing the activity of one or more native enzymes and/or introducing one or more feedback-deregulated enzymes can be combined in histamine decarboxylase-expressing microbial cells to achieve even higher histamine production levels. For example, a histamine titer of 385 mg/L was achieved in *S. cerevisiae* in two rounds of engineering from the introduction of three genes: a histidine decarboxylase gene (from *Chromobacterium* sp. LK1) (SEQ ID NO:6), an ATP phosphoribosyltransferase (from *C. glutamicum*) containing the amino acid substitutions N215K, L231F, and T235A (SEQ ID NO:7), and a constitutively expressed ATP phosphoribosyltransferase from *S. cerevisiae* S288c (SEQ ID NO:3). (Example 1.)

Reduction of Precursor Consumption

Figure 13:
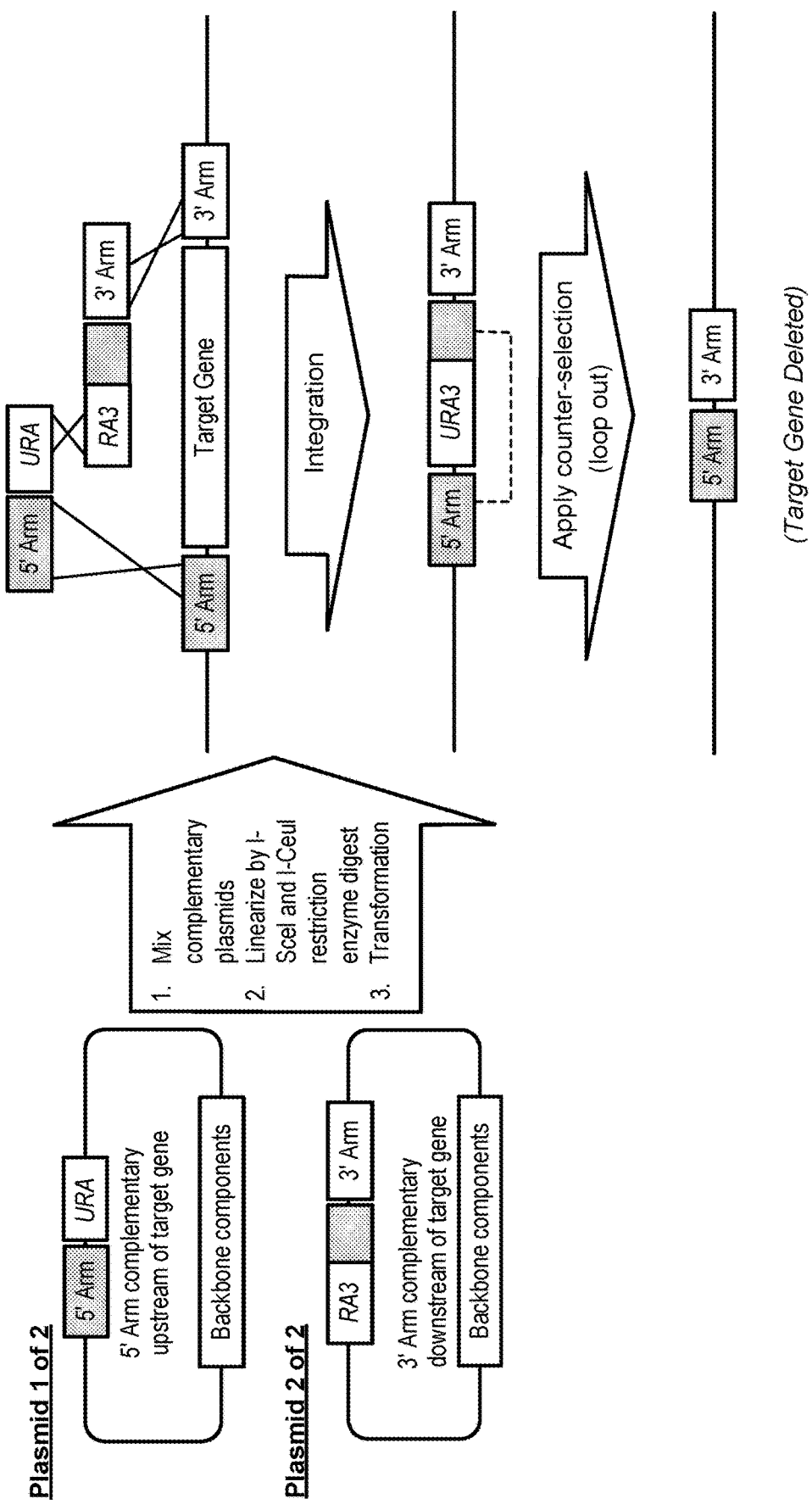
FIG. 13: Targeted gene deletion in *Saccharomyces cerevisiae* and *Yarrowia lipolytica*.

Another approach to increasing histamine production in a microbial cell that is capable of such production is to decrease the activity of one or more enzymes that consume one or more histamine pathway precursors. In some embodiments, the activity of one or more such enzymes is reduced by modulating the expression or activity of the native enzyme(s). Illustrative enzymes of this type include an enolase, a pyruvate dehydrogenase, a pentose phosphate pathway sugar isomerase, a transaldolase, a transketolase, a ribulose-5-phosphate epimerase, and a aribulose-5-phosphate isomerase. The activity of such enzymes can be decreased, for example, by substituting the native promoter of the corresponding gene(s) with a less active or inactive promoter or by deleting the corresponding gene(s). See FIGS. 12 and 13 for examples of schemes for promoter replacement and targeted gene deletion, respectively, in *S. cervisiae* and *Y. lipolytica*.

In various embodiments, the engineering of a histamine-producing microbial cell to reduce precursor consumption by one or more side pathways increases the histamine titer by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold. In various embodiments, the increase in histamine titer is in the range of 10 percent to 100-fold, 2-fold to 50-fold, 5-fold to 40-fold, 10-fold to 30-fold, or any range bounded by any of the values listed above. These increases are determined relative to the histamine titer observed in a histamine-producing microbial cell that does not include genetic alterations to reduce precursor consumption. This reference cell may (but need not) have other genetic alterations aimed at increasing histamine production, i.e., the cell may have increased activity of an upstream pathway enzyme.

In various embodiments, the histamine titers achieved by reducing precursor consumption by one or more side pathways are at least 100, 200, 300, 400, 500, 600, 700, 800, or 900 µg/L, or at least 1, 10, 50, 75, 100, 200, 300, 400, 500, 600, 700, 800, or 900 mg/L or at least 1, 1.5, 2, 2.5, 3, 3.5, 4, 4.5, 5, 10, 20, 50 g/L. In various embodiments, the titer is in the range of 50 µg/L to 50 g/L, 75 µg/L to 20 g/L, 100 µg/L to 10 g/L, 200 µg/L to 5 g/L, 500 µg/L to 4 g/L, 1 mg/L to 3 g/L, 500 mg/L to 2 g/L or any range bounded by any of the values listed above.

The approaches of increasing the activity of one or more native enzymes and/or introducing one or more feedback-deregulated enzymes and/or reducing precursor consumption by one or more side pathways can be combined to achieve even higher histamine production levels.

Microbial Host Cells

Any microbe that can be used to express introduced genes can be engineered for fermentative production of histamine as described above. In certain embodiments, the microbe is one that is naturally incapable of fermentative production of histamine. In some embodiments, the microbe is one that is readily cultured, such as, for example, a microbe known to be useful as a host cell in fermentative production of compounds of interest. Bacteria cells, including gram positive or gram negative bacteria can be engineered as described above. Examples include, in addition to *C. glutamicum* cells, *Bacillus subtilus, B. lichenformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes, P. citrea, Lactobacilis* spp. (such as *L. lactis, L. plantarum), L. grayi, E. coli, E. faecium, E. gallinarum, E. casseliflavus,* and/or *E. faecalis* cells.

There are numerous types of anaerobic cells that can be used as microbial host cells in the methods described herein. In some embodiments, the microbial cells are obligate anaerobic cells. Obligate anaerobes typically do not grow well, if at all, in conditions where oxygen is present. It is to be understood that a small amount of oxygen may be present, that is, there is some level of tolerance level that obligate anaerobes have for a low level of oxygen. Obligate anaerobes engineered as described above can be grown under substantially oxygen-free conditions, wherein the amount of oxygen present is not harmful to the growth, maintenance, and/or fermentation of the anaerobes.

Alternatively, the microbial host cells used in the methods described herein can be facultative anaerobic cells. Facultative anaerobes can generate cellular ATP by aerobic respiration (e.g., utilization of the TCA cycle) if oxygen is present. However, facultative anaerobes can also grow in the absence of oxygen. Facultative anaerobes engineered as described above can be grown under substantially oxygen-free conditions, wherein the amount of oxygen present is not harmful to the growth, maintenance, and/or fermentation of the anaerobes, or can be alternatively grown in the presence of greater amounts of oxygen.

In some embodiments, the microbial host cells used in the methods described herein are filamentous fungal cells. (See, e.g., Berka & Barnett, Biotechnology Advances, (1989), 7(2):127-154). Examples include *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp. (such as *A. oryzae, A. niger, A. sojae, A. japonicus, A. nidulans,* or *A. awamori*), *Fusarium* sp. (such as *F. roseum, F. graminum F. cerealis, F. oxysporuim,* or *F. venenatum*), *Neurospora* sp. (such as *N. crassa* or *Hypocrea* sp.), *Mucor* sp. (such as *M. miehei*), *Rhizopus* sp., and *Emericella* sp. cells. In particular embodiments, the fungal cell engineered as described above is *A. nidulans, A. awamori, A. oryzae, A. aculeatus, A. niger, A. japonicus, T. reesei, T. viride, F. oxysporum,* or *F. solani*. Illustrative plasmids or plasmid components for use with such hosts include those described in U.S. Patent Pub. No. 2011/0045563.

Yeasts can also be used as the microbial host cell in the methods described herein. Examples include: *Saccharomyces* sp., *Schizosaccharomyces* sp., *Pichia* sp., *Hansenula polymorpha, Pichia stipites, Kluyveromyces marxianus, Kluyveromyces* spp., *Yarrowia lipolytica* and *Candida* sp. In some embodiments, the *Saccharomyces* sp. is *S. cerevisiae* (See, e.g., Romanos et al., Yeast, (1992), 8(6):423-488). Illustrative plasmids or plasmid components for use with such hosts include those described in U.S. Pat. No. 7,659,097 and U.S. Patent Pub. No. 2011/0045563.

In some embodiments, the host cell can be an algal cell derived, e.g., from a green algae, red algae, a glaucophyte, a chlorarachniophyte, a euglenid, a chromista, or a dinoflagellate. (See, e.g., Saunders & Warmbrodt, "Gene Expression in Algae and Fungi, Including Yeast," (1993), National Agricultural Library, Beltsville, Md.). Illustrative plasmids or plasmid components for use in algal cells include those described in U.S. Patent Pub. No. 2011/0045563.

In other embodiments, the host cell is a cyanobacterium, such as cyanobacterium classified into any of the following groups based on morphology: Chlorococcales, Pleurocapsales, Oscillatoriales, Nostocales, Synechosystic or Stigonematales (See, e.g., Lindberg et al., Metab. Eng., (2010) 12(1):70-79). Illustrative plasmids or plasmid components for use in cyanobacterial cells include those described in U.S. Patent Pub. Nos. 2010/0297749 and 2009/0282545 and in Intl. Pat. Pub. No. WO 2011/034863.

Genetic Engineering Methods

Microbial cells can be engineered for fermentative histamine production using conventional techniques of molecular biology (including recombinant techniques), microbiology, cell biology, and biochemistry, which are within the skill of the art. Such techniques are explained fully in the literature, see e.g., "Molecular Cloning: A Laboratory Manual," fourth edition (Sambrook et al., 2012); "Oligonucleotide Synthesis" (M. J. Gait, ed., 1984); "Culture of Animal Cells: A Manual of Basic Technique and Specialized Applications" (R. I. Freshney, ed., 6th Edition, 2010); "Methods in Enzymology" (Academic Press, Inc.); "Current Protocols in Molecular Biology" (F. M. Ausubel et al., eds., 1987, and periodic updates); "PCR: The Polymerase Chain Reaction," (Mullis et al., eds., 1994); Singleton et al., Dictionary of Microbiology and Molecular Biology 2nd ed., J. Wiley & Sons (New York, N.Y. 1994).

Vectors are polynucleotide vehicles used to introduce genetic material into a cell. Vectors useful in the methods described herein can be linear or circular. Vectors can integrate into a target genome of a host cell or replicate independently in a host cell. For many applications, integrating vectors that produced stable transformants are preferred. Vectors can include, for example, an origin of replication, a multiple cloning site (MCS), and/or a selectable marker. An expression vector typically includes an expression cassette containing regulatory elements that facilitate expression of a polynucleotide sequence (often a coding sequence) in a particular host cell. Vectors include, but are not limited to, integrating vectors, prokaryotic plasmids, episomes, viral vectors, cosmids, and artificial chromosomes.

Illustrative regulatory elements that may be used in expression cassettes include promoters, enhancers, internal ribosomal entry sites (IRES), and other expression control elements (e.g., transcription termination signals, such as polyadenylation signals and poly-U sequences). Such regulatory elements are described, for example, in Goeddel, Gene Expression Technology: Methods In Enzymology 185, Academic Press, San Diego, Calif. (1990).

In some embodiments, vectors may be used to introduce systems that can carry out genome editing, such as CRISPR systems. See U.S. Patent Pub. No. 2014/0068797, published 6 Mar. 2014; see also Jinek M., et al., "A programmable dual-RNA-guided DNA endonuclease in adaptive bacterial immunity," Science 337:816-21, 2012). In Type II CRISPR-Cas9 systems, Cas9 is a site-directed endonuclease, namely an enzyme that is, or can be, directed to cleave a polynucleotide at a particular target sequence using two distinct endonuclease domains (HNH and RuvC/RNase H-like domains). Cas9 can be engineered to cleave DNA at any desired site because Cas9 is directed to its cleavage site by RNA. Cas9 is therefore also described as an "RNA-guided nuclease." More specifically, Cas9 becomes associated with one or more RNA molecules, which guide Cas9 to a specific polynucleotide target based on hybridization of at least a portion of the RNA molecule(s) to a specific sequence in the target polynucleotide. Ran, F. A., et al., ("In vivo genome editing using *Staphylococcus aureus* Cas9," Nature 520 (7546):186-91, 2015 Apr. 9], including all extended data) present the crRNA/tracrRNA sequences and secondary structures of eight Type II CRISPR-Cas9 systems. Cas9-like synthetic proteins are also known in the art (see U.S. Published Patent Application No. 2014-0315985, published 23 Oct. 2014).

Example 1 describes illustrative integration approaches for introducing polynucleotides and other genetic alterations into the genomes of *C. glutamicum* and *S. cerevisiae* cells.

Vectors or other polynucleotides can be introduced into microbial cells by any of a variety of standard methods, such as transformation, conjugation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. Transformants can be selected by any method known in the art. Suitable methods for selecting transformants are described in U.S. Patent Pub. Nos. 2009/0203102, 2010/0048964, and 2010/0003716, and International Publication Nos. WO 2009/076676, WO 2010/003007, and WO 2009/132220.

Engineered Microbial Cells

The above-described methods can be used to produce engineered microbial cells that produce, and in certain embodiments, overproduce, histamine. Engineered microbial cells can have at least 1, 2, 3, 4, 5, 6, 7, 8, 9, 10, 20, 30, 40, 50, 60, 70, 80, 90, 100 or more genetic alterations, such as 30-100 alterations, as compared to a native microbial cell, such as any of the microbial host cells described herein. Engineered microbial cells described in the Example below have one, two, or three genetic alterations, but those of skill in the art can, following the guidance set forth herein, design microbial cells with additional alterations. In some embodiments, the engineered microbial cells have not more than 15, 14, 13, 12, 11, 10, 9, 8, 7, 6, 5, or 4 genetic alterations, as compared to a native microbial cell. In various embodiments, microbial cells engineered for histamine production can have a number of genetic alterations falling within the any of the following illustrative ranges: 1-10, 1-9, 1-8, 2-7, 2-6, 2-5, 2-4, 2-3, 3-7, 3-6, 3-5, 3-4, etc.

In some embodiments, an engineered microbial cell expresses at least one heterologous histamine decarboxylase, such as in the case of a microbial host cell that does not naturally produce histamine. In various embodiments, the microbial cell can include and express, for example: (1) a single heterologous histamine decarboxylase gene, (2) two or more heterologous histamine decarboxylase genes, which can be the same or different (in other words, multiple copies of the same heterologous histamine decarboxylase genes can be introduced or multiple, different heterologous histamine decarboxylase genes can be introduced), (3) a single heterologous histamine decarboxylase gene that is not native to the cell and one or more additional copies of an native histamine decarboxylase gene, or (4) two or more non-native histamine decarboxylase genes, which can be the same or different, and one or more additional copies of an native histamine decarboxylase gene.

This engineered host cell can include at least one additional genetic alteration that increases flux through the pathway leading to the production of histidine (the immediate precursor of histamine). These "upstream" enzymes in the pathway include: an ATP phosphoribosyltransferase, a phosphoribosyl-ATP pyrophosphatase, a phosphoribosyl-AMP cyclohydrolase, a 5'ProFAR isomerase, an imidazole-glycerol phosphate synthase, an imidazole-glycerol phosphate dehydratase, a histidinol-phosphate aminotransferase, a histidinol-phosphate phosphatase, histidinol dehydrogenase, and a ribose phosphate pyrophosphokinase, including any isoforms, paralogs, or orthologs having these enzymatic activities (which as those of skill in the art readily appreciate may be known by different names). The at least one additional alteration can increase the activity of the upstream pathway enzyme(s) by any available means, e.g., by: (1) modulating the expression or activity of the native enzyme(s), (2) expressing one or more additional copies of the genes for the native enzymes, and/or (3) expressing one or more copies of the genes for one or more non-native enzymes.

In some embodiments, increased flux through the pathway can be achieved by expressing one or more genes encoding a feedback-deregulated enzyme, as discussed above. For example, the engineered host cell can include and express one or more feedback-deregulated ATP phosphoribosyltransferase genes.

The engineered microbial cells can contain introduced genes that have a native nucleotide sequence or that differ from native. For example, the native nucleotide sequence can be codon-optimized for expression in a particular host cell. The amino acid sequences encoded by any of these introduced genes can be native or can differ from native. In various embodiments, the amino acid sequences have at least 60 percent, 70 percent, 75 percent, 80 percent, 85 percent, 90 percent, 95 percent or 100 percent amino acid sequence identity with a native amino acid sequence.

In some embodiments, increased availability of precursors to histamine can be achieved by reducing the expression or activity of enzymes that consume one or more histamine pathway precursors, such as an enolase, a pyruvate dehydrogenase, a pentose phosphate pathway sugar isomerase, a transaldolase, a transketolase, a ribulose-5-phosphate epimerase, and a aribulose-5-phosphate isomerase. For example, the engineered host cell can include one or more promoter swaps to down-regulate expression of any of these enzymes and/or can have their genes deleted to eliminate their expression entirely.

The approach described herein has been carried out in bacterial cells, namely *C. glutamicum* and *B. subtilis* (prokaryotes) and in fungal cells, namely the yeasts *S. cerevisiae* and *Y. lipolytica* (eukaryotes). (See Examples 1 and 2.)

Illustrative Engineered Yeast Cells

In certain embodiments, the engineered yeast (e.g., *S. cerevisiae*) cell expresses a heterologous histamine decarboxylase having at least 70 percent, 75 percent, 80 percent, 85 percent, 90 percent, 95 percent or 100 percent amino acid sequence identity to a histamine decarboxylase from *Chromobacterium* sp. LK1 (e.g., SEQ ID NO:6). In particular embodiments, the *Chromobacterium* sp. LK1 histamine decarboxylase can include SEQ ID NO:6. The engineered yeast (e.g., *S. cerevisiae*) cell can also express a heterologous ATP phosphoribosyltransferase having at least 70 percent, 75 percent, 80 percent, 85 percent, 90 percent, 95 percent or 100 percent amino acid sequence identity with an ATP phosphoribosyltransferase from *S. cerevisiae* (SEQ ID NO:3). In particular embodiments, the *S. cerevisiae* ATP phosphoribosyltransferase includes SEQ ID NO:3.

In certain embodiments, the engineered yeast (e.g., *Y. lipolytica*) cell expresses a heterologous histamine decarboxylase having at least 70 percent, 75 percent, 80 percent, 85 percent, 90 percent, 95 percent or 100 percent amino acid sequence identity to a histamine decarboxylase from *Acinetobacter baumannii* strain AB0057 (e.g., SEQ ID NO:1). In particular embodiments, the *Acinetobacter baumannii* strain AB0057 histamine decarboxylase can include SEQ ID NO:1. The engineered yeast (e.g., *Y. lipolytica*) cell can also express a heterologous ATP phosphoribosyltransferase having at least 70 percent, 75 percent, 80 percent, 85 percent, 90 percent, 95 percent or 100 percent amino acid sequence identity with an ATP phosphoribosyltransferase from *S. cerevisiae* S288c (SEQ ID NO:3). In particular embodiments, the *S. cerevisiae* S288c ATP phosphoribosyltransferase includes SEQ ID NO:3.

These may be the only genetic alterations of the engineered yeast cell, or the yeast cell can include one or more additional genetic alterations, as discussed more generally above.

For example, in particular embodiments, the engineered yeast *S. cerevisiae* cell described above additionally expresses a feedback deregulated variant of a *C. glutamicum* ATP phosphoribosyltransferase, which typically has at least 70 percent, 75 percent, 80 percent, 85 percent, 90 percent, or 95 percent amino acid sequence identity to a variant of a *C. glutamicum* ATP phosphoribosyltransferase containing the amino acid substitutions N215K, L231F, and T235A (SEQ ID NO:7) In particular embodiments, the *C. glutamicum* ATP phosphoribosyltransferase variant can include SEQ ID NO:7.

Illustrative Engineered Bacterial Cells

In certain embodiments, the engineered bacterial (e.g., *C. glutamicum*) cell expresses a heterologous histamine decarboxylase having at least 70 percent, 75 percent, 80 percent, 85 percent, 90 percent, 95 percent or 100 percent amino acid sequence identity to a histamine decarboxylase from *Acinetobacter baumannii* (e.g., SEQ ID NO:1). In particular embodiments, the *Acinetobacter baumannii* histamine decarboxylase can include SEQ ID NO:1. The engineered bacterial (e.g., *C. glutamicum*) cell can also express a heterologous ATP phosphoribosyltransferase having at least 70 percent, 75 percent, 80 percent, 85 percent, 90 percent, 95 percent or 100 percent amino acid sequence identity with an ATP phosphoribosyltransferase from *Saccharomyces cerevisiae* S288c (SEQ ID NO:3). In particular embodiments, the *S. cerevisiae* S288c ATP phosphoribosyltransferase includes SEQ ID NO:3. In some embodiments, the engineered bacterial (e.g., *C. glutamicum*) cell expresses, instead of the ATP phosphoribosyltransferase, an imidazole-glycerol phosphate dehydratase having at least 70 percent, 75 percent, 80 percent, 85 percent, 90 percent, 95 percent or 100 percent amino acid sequence identity to an imidazole-glycerol phosphate dehydratase from *C. glutamicum* (SEQ ID NO:2). In particular embodiments, the *C. glutamicum* imidazole-glycerol phosphate dehydratase includes SEQ ID NO:2.

In certain embodiments, the engineered bacterial (e.g., *B. subtilis*) cell expresses a heterologous histamine decarboxylase having at least 70 percent, 75 percent, 80 percent, 85 percent, 90 percent, 95 percent or 100 percent amino acid sequence identity to a histamine decarboxylase from *Lactobacillus* sp. (strain 30a) (e.g., SEQ ID NO:4). In particular embodiments, the *Lactobacillus* sp. (strain 30a) histamine decarboxylase can include SEQ ID NO:4. The engineered bacterial (e.g., *B. subtilis*) cell can also express a heterologous ATP phosphoribosyltransferase having at least 70 percent, 75 percent, 80 percent, 85 percent, 90 percent, 95 percent or 100 percent amino acid sequence identity with an ATP phosphoribosyltransferase from *Salmonella typhimurium* LT2 (SEQ ID NO:5). In particular embodiments, the *Salmonella typhimurium* LT2 ATP phosphoribosyltransferase includes SEQ ID NO:5.

Culturing of Engineered Microbial Cells

Any of the microbial cells described herein can be cultured, e.g., for maintenance, growth, and/or histamine production.

In some embodiments, the cultures are grown to an optical density at 600 nm of 10-500, such as an optical density of 50-150.

In various embodiments, the cultures include produced histamine at titers of at least 10, 25, 50, 75, 100, 200, 300, 400, 500, 600, 700, 800, or 900 µg/L, or at least 1, 10, 50, 75, 100, 200, 300, 400, 500, 600, 700, 800, or 900 mg/L or at least 1, 1.5, 2, 2.5, 3, 3.5, 4, 4.5, 5, 10, 20, 50 g/L. In various embodiments, the titer is in the range of 10 µg/L to 10 g/L, 25 µg/L to 20 g/L, 100 µg/L to 10 g/L, 200 µg/L to 5 g/L, 500 µg/L to 4 g/L, 1 mg/L to 3 g/L, 500 mg/L to 2 g/L or any range bounded by any of the values listed above.

Culture Media

Microbial cells can be cultured in any suitable medium including, but not limited to, a minimal medium, i.e., one containing the minimum nutrients possible for cell growth. Minimal medium typically contains: (1) a carbon source for microbial growth; (2) salts, which may depend on the particular microbial cell and growing conditions; and (3) water. Suitable media can also include any combination of the following: a nitrogen source for growth and product formation, a sulfur source for growth, a phosphate source for growth, metal salts for growth, vitamins for growth, and other cofactors for growth.

Any suitable carbon source can be used to cultivate the host cells. The term "carbon source" refers to one or more carbon-containing compounds capable of being metabolized by a microbial cell. In various embodiments, the carbon source is a carbohydrate (such as a monosaccharide, a disaccharide, an oligosaccharide, or a polysaccharide), or an invert sugar (e.g., enzymatically treated sucrose syrup). Illustrative monosaccharides include glucose (dextrose), fructose (levulose), and galactose; illustrative oligosaccharides include dextran or glucan, and illustrative polysaccharides include starch and cellulose. Suitable sugars include C6 sugars (e.g., fructose, mannose, galactose, or glucose) and C5 sugars (e.g., xylose or arabinose). Other, less expensive carbon sources include sugar cane juice, beet juice, sorghum juice, and the like, any of which may, but need not be, fully or partially deionized.

The salts in a culture medium generally provide essential elements, such as magnesium, nitrogen, phosphorus, and sulfur to allow the cells to synthesize proteins and nucleic acids.

Minimal medium can be supplemented with one or more selective agents, such as antibiotics.

To produce histamine, the culture medium can include, and/or is supplemented during culture with, glucose and/or a nitrogen source such as urea, an ammonium salt, ammonia, or any combination thereof.

Culture Conditions

Materials and methods suitable for the maintenance and growth of microbial cells are well known in the art. See, for example, U.S. Pub. Nos. 2009/0203102, 2010/0003716, and 2010/0048964, and International Pub. Nos. WO 2004/033646, WO 2009/076676, WO 2009/132220, and WO 2010/003007, Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass.

In general, cells are grown and maintained at an appropriate temperature, gas mixture, and pH (such as about 20° C. to about 37° C., about 6% to about 84% $CO_2$, and a pH between about 5 to about 9). In some aspects, cells are grown at 35° C. In certain embodiments, such as where thermophilic bacteria are used as the host cells, higher temperatures (e.g., 50° C.-75° C.) may be used. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the particular cell.

Standard culture conditions and modes of fermentation, such as batch, fed-batch, or continuous fermentation that can be used are described in U.S. Publ. Nos. 2009/0203102, 2010/0003716, and 2010/0048964, and International Pub. Nos. WO 2009/076676, WO 2009/132220, and WO 2010/003007. Batch and Fed-Batch fermentations are common and well known in the art, and examples can be found in Brock, Biotechnology: A Textbook of Industrial Microbiology, Second Edition (1989) Sinauer Associates, Inc.

In some embodiments, the cells are cultured under limited sugar (e.g., glucose) conditions. In various embodiments, the amount of sugar that is added is less than or about 105% (such as about 100%, 90%, 80%, 70%, 60%, 50%, 40%, 30%, 20%, or 10%) of the amount of sugar that can be consumed by the cells. In particular embodiments, the amount of sugar that is added to the culture medium is approximately the same as the amount of sugar that is consumed by the cells during a specific period of time. In some embodiments, the rate of cell growth is controlled by limiting the amount of added sugar such that the cells grow at the rate that can be supported by the amount of sugar in the cell medium. In some embodiments, sugar does not accumulate during the time the cells are cultured. In various embodiments, the cells are cultured under limited sugar conditions for times greater than or about 1, 2, 3, 5, 10, 15, 20, 25, 30, 35, 40, 50, 60, or 70 hours or even up to about 5-10 days. In various embodiments, the cells are cultured under limited sugar conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited sugar conditions can allow more favorable regulation of the cells.

In some aspects, the cells are grown in batch culture. The cells can also be grown in fed-batch culture or in continuous culture. Additionally, the cells can be cultured in minimal medium, including, but not limited to, any of the minimal media described above. The minimal medium can be further supplemented with 1.0% (w/v) glucose (or any other six-carbon sugar) or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. In some cultures, significantly higher levels of sugar (e.g., glucose) are used, e.g., at least 10% (w/v), 20% (w/v), 30% (w/v), 40% (w/v), 50% (w/v), 60% (w/v), 70% (w/v), or up to the solubility limit for the sugar in the medium. In some embodiments, the sugar levels falls within a range of any two of the above values, e.g.: 0.1-10% (w/v), 1.0-20% (w/v), 10-70% (w/v), 20-60% (w/v), or 30-50% (w/v). Furthermore, different sugar levels can be used for different phases of culturing. For fed-batch culture (e.g., of S. cerevisiae or C. glutamicum), the sugar level can be about 100-200 g/L (10-20% (w/v)) in the batch phase and then up to about 500-700 g/L (50-70% in the feed).

Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), or 0.02% (w/v) yeast extract. In some cultures, significantly higher levels of yeast extract can be used, e.g., at least 1.5% (w/v), 2.0% (w/v), 2.5% (w/v), or 3% (w/v). In some cultures (e.g., of S. cerevisiae or C. glutamicum), the yeast extract level falls within a range of any two of the above values, e.g.: 0.5-3.0% (w/v), 1.0-2.5% (w/v), or 1.5-2.0% (w/v).

Illustrative materials and methods suitable for the maintenance and growth of the engineered microbial cells described herein can be found below in Example 1.

Histamine Production and Recovery

Any of the methods described herein may further include a step of recovering histamine. In some embodiments, the produced histamine contained in a so-called harvest stream is recovered/harvested from the production vessel. The harvest stream may include, for instance, cell-free or cell-containing aqueous solution coming from the production vessel, which contains histamine as a result of the conversion of production substrate by the resting cells in the production vessel. Cells still present in the harvest stream may be separated from the histamine by any operations known in the art, such as for instance filtration, centrifugation, decantation, membrane crossflow ultrafiltration or microfiltration, tangential flow ultrafiltration or microfiltration or dead end filtration. After this cell separation operation, the harvest stream is essentially free of cells.

Further steps of separation and/or purification of the produced histamine from other components contained in the harvest stream, i.e., so-called downstream processing steps may optionally be carried out. These steps may include any means known to a skilled person, such as, for instance, concentration, extraction, crystallization, precipitation, adsorption, ion exchange, and/or chromatography. Any of these procedures can be used alone or in combination to purify histamine. Further purification steps can include one or more of, e.g., concentration, crystallization, precipitation, washing and drying, treatment with activated carbon, ion exchange, nanofiltration, and/or re-crystallization. The design of a suitable purification protocol may depend on the cells, the culture medium, the size of the culture, the production vessel, etc. and is within the level of skill in the art.

The following examples are given for the purpose of illustrating various embodiments of the disclosure and are not meant to limit the present disclosure in any fashion. Changes therein and other uses which are encompassed within the spirit of the disclosure, as defined by the scope of the claims, will be identifiable to those skilled in the art.

Example 1—Construction and Selection of Strains of *Corynebacteria glutamicum* and *Saccharomyces cerevisiae* Engineered to Produce Histamine Plasmid/DNA Design All strains tested for this work were transformed with plasmid DNA designed using proprietary software. Plasmid designs were specific to each of the host organisms engineered in this work. The plasmid DNA was physically constructed by a standard DNA assembly method. This plasmid DNA was then used to integrate metabolic pathway inserts by one of two host-specific methods, each described below.

*C. glutamicum* Pathway Integration

Figure 14:
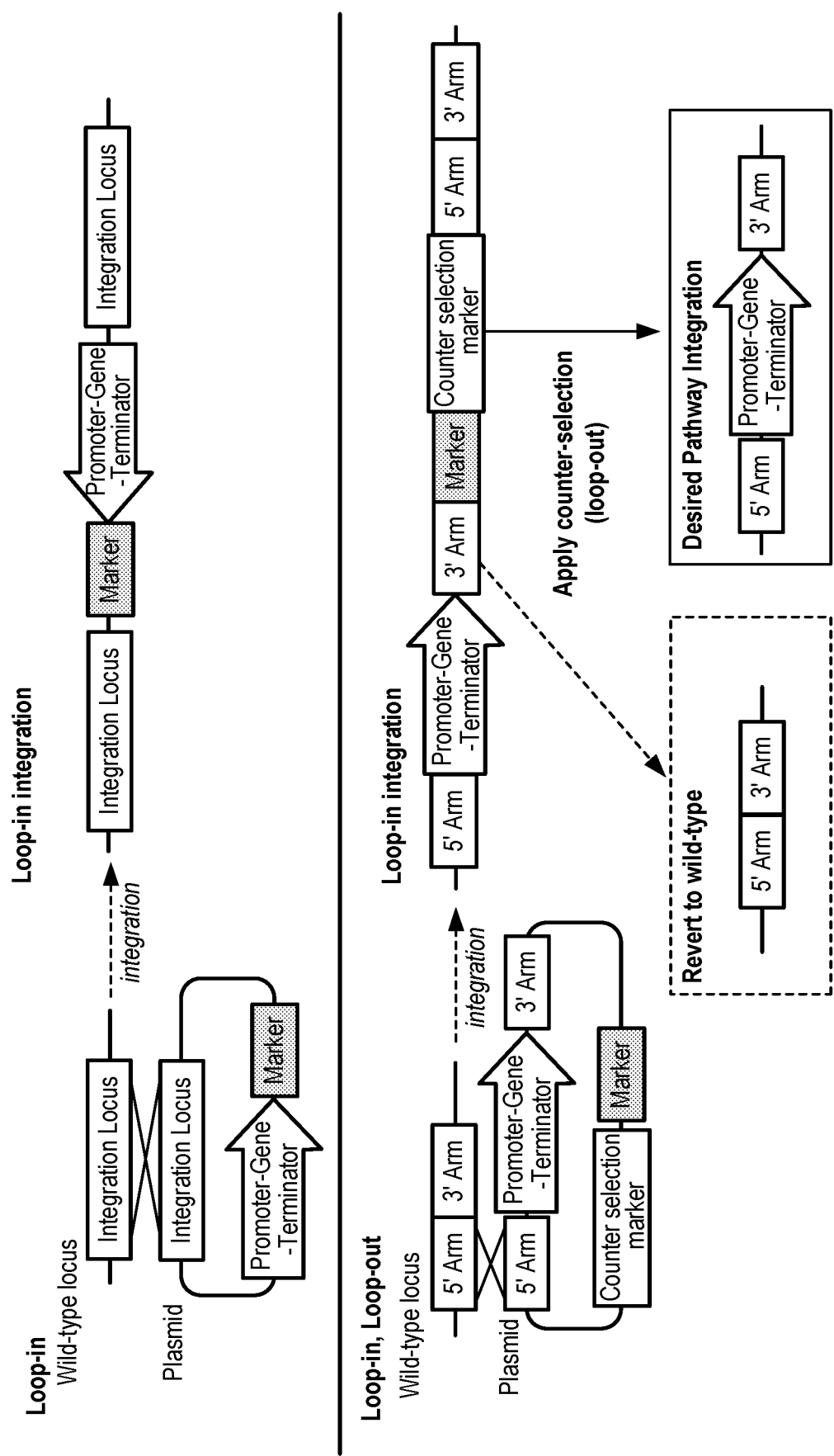
FIG. 14: Integration of Promoter-Gene-Terminator into *Corynebacteria glutamicum* and *Bacillus subtilis*.

A "loop-in, single-crossover" genomic integration strategy has been developed to engineer *C. glutamicum* strains. FIG. 14 illustrates genomic integration of loop-in only and loop-in/loop-out constructs and verification of correct integration via colony PCR. Loop-in only constructs (shown under the heading "Loop-in") contained a single 2-kb homology arm (denoted as "integration locus"), a positive selection marker (denoted as "Marker")), and gene(s) of interest (denoted as "promoter-gene-terminator"). A single crossover event integrated the plasmid into the *C. glutamicum* chromosome. Integration events are stably maintained in the genome by growth in the presence of antibiotic (25p g/ml kanamycin). Correct genomic integration in colonies derived from loop-in integration were confirmed by colony PCR with UF/IR and DR/IF PCR primers.

Loop-in, loop-out constructs (shown under the heading "Loop-in, loop-out) contained two 2-kb homology arms (5' and 3' arms), gene(s) of interest (arrows), a positive selection marker (denoted "Marker"), and a counter-selection marker. Similar to "loop-in" only constructs, a single crossover event integrated the plasmid into the chromosome of *C. glutamicum*. Note: only one of two possible integrations is shown here. Correct genomic integration was confirmed by colony PCR and counter-selection was applied so that the plasmid backbone and counter-selection marker could be excised. This results in one of two possibilities: reversion to wild-type (lower left box) or the desired pathway integration (lower right box). Again, correct genomic loop-out is confirmed by colony PCR. (Abbreviations: Primers: UF=upstream forward, DR=downstream reverse, IR=internal reverse, IF=internal forward.)

*S. cerevisiae* Pathway Integration

Figure 11:
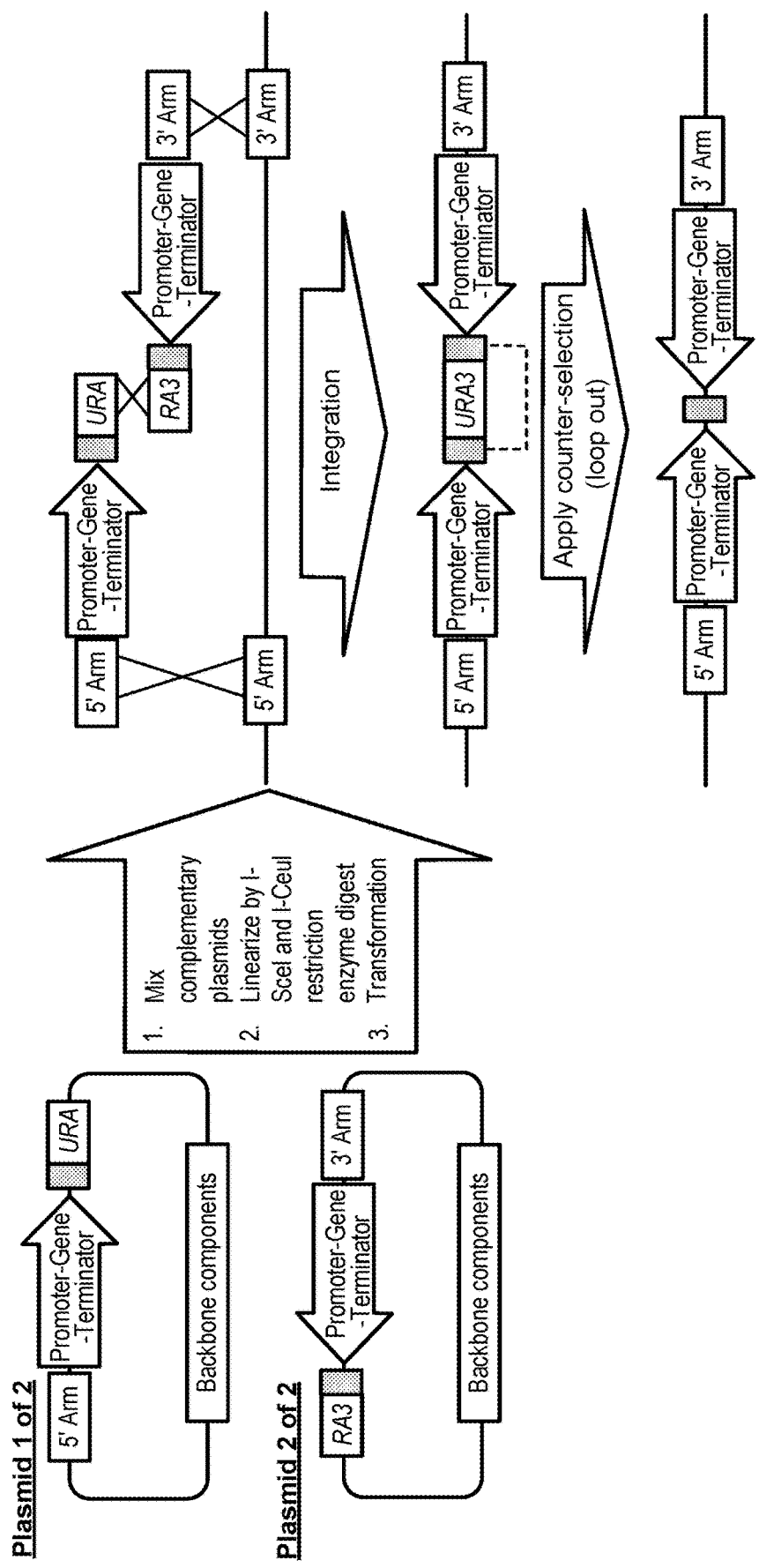
FIG. 11: Integration of Promoter-Gene-Terminator into *Saccharomyces cerevisiae* and *Yarrowia lipolytica*.

A "split-marker, double-crossover" genomic integration strategy has been developed to engineer *S. cerevisiae* strains. FIG. 11 illustrates genomic integration of complementary, split-marker plasmids and verification of correct genomic integration via colony PCR in *S. cerevisiae*. Two plasmids with complementary 5' and 3' homology arms and overlapping halves of a URA3 selectable marker (direct repeats shown by the hashed bars) were digested with meganucleases and transformed as linear fragments. A triple-crossover event integrated the desired heterologous genes into the targeted locus and re-constituted the full URA3 gene. Colonies derived from this integration event were assayed using two 3-primer reactions to confirm both the 5' and 3' junctions (UF/IF/wt-R and DR/IF/wt-F). For strains in which further engineering is desired, the strains can be plated on 5-FOA plates to select for the removal of URA3, leaving behind a small single copy of the original direct repeat. This genomic integration strategy can be used for gene knockout, gene knock-in, and promoter titration in the same workflow.

Cell Culture

The workflow established for *S. cerevisiae* involved a hit-picking step that consolidated successfully built strains using an automated workflow that randomized strains across the plate. For each strain that was successfully built, up to four replicates were tested from distinct colonies to test colony-to-colony variation and other process variation. If fewer than four colonies were obtained, the existing colonies were replicated so that at least four wells were tested from each desired genotype.

The colonies were consolidated into 96-well plates with selective medium (SD-ura for *S. cerevisiae*) and cultivated for two days until saturation and then frozen with 16.6% glycerol at −80° C. for storage. The frozen glycerol stocks were then used to inoculate a seed stage in minimal media with a low level of amino acids to help with growth and recovery from freezing. The seed plates were grown at 30° C. for 1-2 days. The seed plates were then used to inoculate a main cultivation plate with minimal medium and grown for 48-88 hours. Plates were removed at the desired time points and tested for cell density (OD600), viability and glucose, supernatant samples stored for LC-MS analysis for product of interest.

Cell Density

Cell density was measured using a spectrophotometric assay detecting absorbance of each well at 600 nm. Robotics were used to transfer fixed amounts of culture from each cultivation plate into an assay plate, followed by mixing with 175 mM sodium phosphate (pH 7.0) to generate a 10-fold dilution. The assay plates were measured using a Tecan M1000 spectrophotometer and assay data uploaded to a LIMS database. A non-inoculated control was used to subtract background absorbance. Cell growth was monitored by inoculating multiple plates at each stage, and then sacrificing an entire plate at each time point.

To minimize settling of cells while handling large number of plates (which could result in a non-representative sample during measurement) each plate was shaken for 10-15 seconds before each read. Wide variations in cell density within a plate may also lead to absorbance measurements outside of the linear range of detection, resulting in underestimate of higher OD cultures. In general, the tested strains so far have not varied significantly enough for this be a concern.

Liquid-Solid Separation

To harvest extracellular samples for analysis by LC-MS, liquid and solid phases were separated via centrifugation. Cultivation plates were centrifuged at 2000 rpm for 4 minutes, and the supernatant was transferred to destination plates using robotics. 75 μL of supernatant was transferred to each plate, with one stored at 4° C., and the second stored at 80° C. for long-term storage.

First-Round Genetic Engineering Results in *Corynebacteria glutamicum* and *Saccharomyces cerevisiae*

A library approach was taken to screen heterologous pathway enzymes to establish the histamine pathway. For histidine decarboxylase, 18 heterologous sequences were tested from Bacteria, Archaea, Viridiplantae, Vertebrata, Metazoa, and Arthropoda sources listed in Table 1. The histidine decarboxylases were codon-optimized and expressed in both *Saccharomyces cerevisiae* and *Corynebacteria glutamicum* hosts.

Histidine biosynthesis is subject to feedback inhibition, therefore a feedback deregulated ATP phosphoribosyltransferase was tested with the histidine decarboxylases to improve production of histidine, the substrate for histidine decarboxylase. The ATP phosphoribosyltransferases tested were from *Salmonella typhimurium* and *Corynebacteria glutamicum*, harboring known deletions and point mutations that render them resistant to feedback inhibition.

Figure 2:
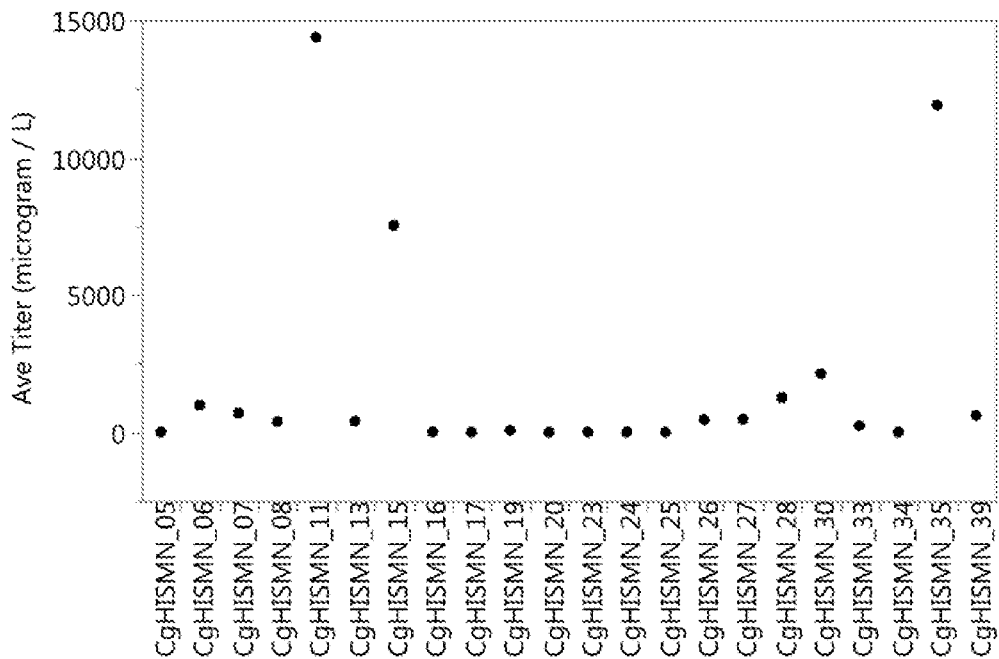
FIG. 2: Histamine titers measured in the extracellular broth following fermentation by the first-round engineered host *Corynebacteria glutamicum*. (See also Example 1, Table 1.)
Figure 3:
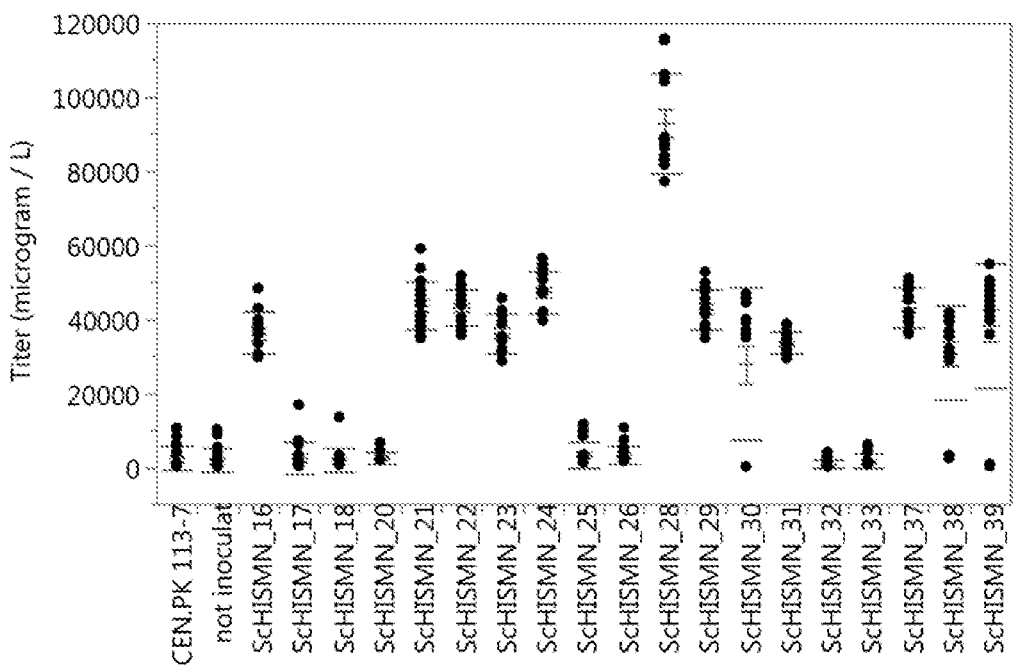
FIG. 3: Histamine titers measured in the extracellular broth following fermentation by the first-round engineered host *Saccharomyces cerevisiae*. (See also Example 1, Table 1.)

First-round genetic engineering results are shown in Table 1 and FIGS. 2 (*C. glutamicum*) and 3 (*S. cerevisiae*).

TABLE 1

First-round genetic engineering results in *Corynebacteria glutamicum* and *Saccharomyces cerevisiae*

| Strain name | Titer (µg/L) | E1 Uniprot ID | Enzyme 1— activity name | Enzyme 1— source organism | E1 Codon Optimization Abbrev. | E2 Uniprot ID | Enzyme 2— activity name | E2 Modifications | Enzyme 2— source organism | E2 Codon Optimization Abbrev. |
|---|---|---|---|---|---|---|---|---|---|---|
| *Corynebacterium glutamicum* | | | | | | | | | | |
| CgHISM N_06 | 985.0 | E3QMN8 | histidine decarboxylase | *Methanosarcina barkeri* str. Wiesmoor | Cg | | | | | |
| CgHISM N_07 | 695.7 | Q467R8 | histidine decarboxylase | *Methanosarcina barkeri* (strain Fusaro / DSM 804) | Cg | | | | | |
| CgHISM N_08 | 385.0 | P00862 | histidine decarboxylase | *Lactobacillus* sp. (strain 30a) | Cg | | | | | |
| CgHISM N_11 | 14370.2 | B71459 | histidine decarboxylase | *Acinetobacter baumannii* (strain AB0057) | Cg | | | | | |
| CgHISM N_13 | 401.1 | E3QMN8 | histidine decarboxylase | *Methanosarcina barkeri* str. Wiesmoor | Cg | | | | | |
| CgHISM N_15 | 7529.8 | P00862 | histidine decarboxylase | *Lactobacillus* sp. (strain 30a) | Cg | P00499 | ATP phosphoribosyl-transferase | Deletion of Q207-E208 | *Salmonella typhimurium* | Cg |
| CgHISM N_16 | 4.0 | P00862 | histidine decarboxylase | *Lactobacillus* sp. (strain 30a) | Cg | P00499 | ATP phosphoribosyl-transferase | Deletion of Q207-E208 | *Salmonella typhimurium* | Cg |
| CgHISM N_17 | 3.9 | P23738 | histidine decarboxylase | *Methanosarcina barkeri* (strain Fusaro / DSM 804) | Cg | P00499 | ATP phosphoribosyl-transferase | Deletion of Q207-E208 | *Salmonella typhimurium* | Cg |
| CgHISM N_19 | 75.0 | Q05733 | histidine decarboxylase | *Drosophila melanogaster* | Cg | P00499 | ATP phosphoribosyl-transferase | Deletion of Q207-E208 | *Salmonella typhimurium* | Cg |
| CgHISM N_24 | 3.8 | J6KM89 | histidine decarboxylase | *Chromobacterium* sp. LK1 | Cg | P00499 | ATP phosphoribosyl-transferase | Deletion of Q207-E208 | *Salmonella typhimurium* | Cg |
| CgHISM N_25 | 1.7 | E3QMN8 | histidine decarboxylase | *Methanosarcina barkeri* str. Wiesmoor | Cg | P00499 | ATP phosphoribosyl-transferase | Deletion of Q207-E208 | *Salmonella typhimurium* | Cg |
| CgHISM N_26 | 458.5 | E3QMN8 | histidine decarboxylase | *Methanosarcina barkeri* str. Wiesmoor | Cg | P00499 | ATP phosphoribosyl-transferase | Deletion of Q207-E208 | *Salmonella typhimurium* | Cg |
| CgHISM N_27 | 462.1 | Q467R8 | histidine decarboxylase | *Methanosarcina barkeri* (strain Fusaro / DSM 804) | Cg | P00499 | ATP phosphoribosyl-transferase | Deletion of Q207-E208 | *Salmonella typhimurium* | Cg |
| CgHISM N_28 | 1258.2 | Q467R8 | histidine decarboxylase | *Methanosarcina barkeri* (strain Fusaro / DSM 804) | Cg | P00499 | ATP phosphoribosyl-transferase | Deletion of Q207-E208 | *Salmonella typhimurium* | Cg |
| CgHISM N_30 | 2126.4 | P00862 | histidine decarboxylase | *Lactobacillus* sp. (strain 30a) | Cg | P00499 | ATP phosphoribosyl-transferase | Deletion of Q207-E208 | *Salmonella typhimurium* | Cg |
| CgHISM N_33 | 234.7 | Q05733 | histidine decarboxylase | *Drosophila melanogaster* | Cg | P00499 | ATP phosphoribosyl-transferase | Deletion of Q207-E208 | *Salmonella typhimurium* | Cg |
| CgHISM N_35 | 11905.3 | B71459 | histidine decarboxylase | *Acinetobacter baumannii* (strain AB0057) | Cg | P00499 | ATP phosphoribosyl-transferase | Deletion of Q207-E208 | *Salmonella typhimurium* | Cg |
| CgHISM N_39 | 615.0 | E3QMN8 | histidine decarboxylase | *Methanosarcina barkeri* str. Wiesmoor | Cg | P00499 | ATP phosphoribosyl-transferase | Deletion of Q207-E208 | *Salmonella typhimurium* | Cg |
| *Saccharomyces cerevisiae* | | | | | | | | | | |
| ScHISM N_16 | 36145.0 | P00862 | histidine decarboxylase | *Lactobacillus* sp. (strain 30a) | Sc | Q9Z472 | ATP phosphoribosyl-transferase | N215K, L231F, T235A | *Corynebacterium glutamicum* | Sc |
| ScHISM N_17 | 2369.9 | P54772 | histidine decarboxylase | *Solanum lycopersicum* | Sc | P00499 | ATP phosphoribosyl-transferase | Deletion of Q207-E208 | *Salmonella typhimurium* | Sc |
| ScHISM N_18 | 1747.7 | P23738 | histidine decarboxylase | *Mus musculus* | Sc | P00499 | ATP phosphoribosyl-transferase | Deletion of Q207-E208 | *Salmonella typhimurium* | Cg |

TABLE 1-continued

First-round genetic engineering results in *Corynebacteria glutamicum* and *Saccharomyces cerevisiae*

| Strain name | Titer (μg/L) | E1 Uniprot ID | Enzyme 1— activity name | Enzyme 1— source organism | E1 Codon Optimization Abbrev. | E2 Uniprot ID | Enzyme 2 activity name | E2 Modifications | Enzyme 2— source organism | E2 Codon Optimization Abbrev. |
|---|---|---|---|---|---|---|---|---|---|---|
| ScHISM N_20 | 2432.4 | Q05733 | histidine decarboxylase | *Drosophila melanogaster* | Sc | P00499 | ATP phosphoribosyl-transferase | Deletion of Q207-E208 | *Salmonella typhimurium* | Sc |
| ScHISM N_21 | 43606.9 | J6KM89 | histidine decarboxylase | *Chromobacterium sp.* LK1 | Sc | P00499 | ATP phosphoribosyl-transferase | Deletion of Q207-E208 | *Salmonella typhimurium* | Cg |
| ScHISM N_22 | 43021.9 | E3QMN8 | histidine decarboxylase | *Methanosarcina barkeri* str. Wiesmoor | Sc | Q9Z472 | ATP phosphoribosyl-transferase | N215K, L231F, T235A | *Corynebacterium glutamicum* | Sc |
| ScHISM N_23 | 36145.8 | Q467R8 | histidine decarboxylase | *Methanosarcina barkeri* (strain Fusaro / DSM 804) | Sc | P00499 | ATP phosphoribosyl-transferase | Deletion of Q207-E208 | *Salmonella typhimurium* | Sc |
| ScHISM N_24 | 47208.0 | P00862 | histidine decarboxylase | *Lactobacillus sp.* (strain 30a) | Cg | P00499 | ATP phosphoribosyl-transferase | Deletion of Q207-E208 | *Salmonella typhimurium* | Cg |
| ScHISM N_25 | 3130.1 | P23738 | histidine decarboxylase | *Mus musculus* | Cg | Q9Z472 | ATP phosphoribosyl-transferase | N215K, L231F, T235A | *Corynebacterium glutamicum* | Sc |
| ScHISM N_26 | 3262.5 | Q05733 | histidine decarboxylase | *Drosophila melanogaster* | Cg | P00499 | ATP phosphoribosyl-transferase | Deletion of Q207-E208 | *Salmonella typhimurium* | Sc |
| ScHISM N_28 | 90811.0 | J6KM89 | histidine decarboxylase | *Chromobacterium sp.* LK1 | Cg | Q9Z472 | ATP phosphoribosyl-transferase | N215K, L231F, T235A | *Corynebacterium glutamicum* | Sc |
| ScHISM N_29 | 42708.8 | E3QMN8 | histidine decarboxylase | *Methanosarcina barkeri* str. Wiesmoor | Cg | P00499 | ATP phosphoribosyl-transferase | Deletion of Q207-E208 | *Salmonella typhimurium* | Sc |
| ScHISM N_30 | 27660.1 | Q467R8 | histidine decarboxylase | *Methanosarcina barkeri* (strain Fusaro / DSM 804) | Cg | P00499 | ATP phosphoribosyl-transferase | Deletion of Q207-E208 | *Salmonella typhimurium* | Cg |
| ScHISM N_31 | 33356.6 | P00862 | histidine decarboxylase | *Lactobacillus sp.* (strain 30a) | Cg | Q9Z472 | ATP phosphoribosyl-transferase | N215K, L231F, T235A | *Corynebacterium glutamicum* | Sc |
| ScHISM N_32 | 711.5 | P54772 | histidine decarboxylase | *Solanum lycopersicum* | Sc | P00499 | ATP phosphoribosyl-transferase | Deletion of Q207-E208 | *Salmonella typhimurium* | Sc |
| ScHISM N_33 | 1523.1 | P23738 | histidine decarboxylase | *Mus musculus* | Sc | P00499 | ATP phosphoribosyl-transferase | Deletion of Q207-E208 | *Salmonella typhimurium* | Cg |
| ScHISM N_37 | 43170.7 | E3QMN8 | histidine decarboxylase | *Methanosarcina barkeri* str. Wiesmoor | Sc | Q9Z472 | ATP phosphoribosyl-transferase | N215K, L231F, T235A | *Corynebacterium glutamicum* | Sc |
| ScHISM N_38 | 30675.5 | Q467R8 | histidine decarboxylase | *Methanosarcina barkeri* (strain Fusaro / DSM 804) | Sc | P00499 | ATP phosphoribosyl-transferase | Deletion of Q207-E208 | *Salmonella typhimurium* | Sc |
| ScHISM N_39 | 38293.2 | P00862 | histidine decarboxylase | *Lactobacillus sp.* (strain 30a) | Cg | P00499 | ATP phosphoribosyl-transferase | Deletion of Q207-E208 | *Salmonella typhimurium* | Cg |

Note:
"Cg" refers to codon optimization for *Corynebacterium glutamicum*; "Sc" refers to codon optimization for *Saccharomyces cerevisiae*.

Second-Round Genetic Engineering Results in *Corynebacteria glutamicum* and *Saccharomyces cerevisiae*

A library approach was taken to improve histamine production by separately expressing each upstream pathway enzyme with a constitutive promoter to screen for the rate-limiting step. The histidine pathway enzymes screened are listed in Table 2. In addition, the enzymes in Table 2, the strains contained the best enzymes from first round: the *Corynebacteria glutamicum* host contains histidine decarboxylase (UniProt ID B7I459) (SEQ ID NO: 1) and ATP phosphoribosyltransferase (UniProt ID P00499) (SEQ ID NO: 5) containing the deletion Q207-E208, and the *Saccharomyces cerevisiae* host contains histidine decarboxylase (UniProt ID J6KM89)(SEQ ID NO: 6) and ATP phosphoribosyltransferase (UniProt ID Q9Z472) (SEQ ID NO: 7) containing the amino acid substitutions N215K, L231F and T235A.

Figure 4:
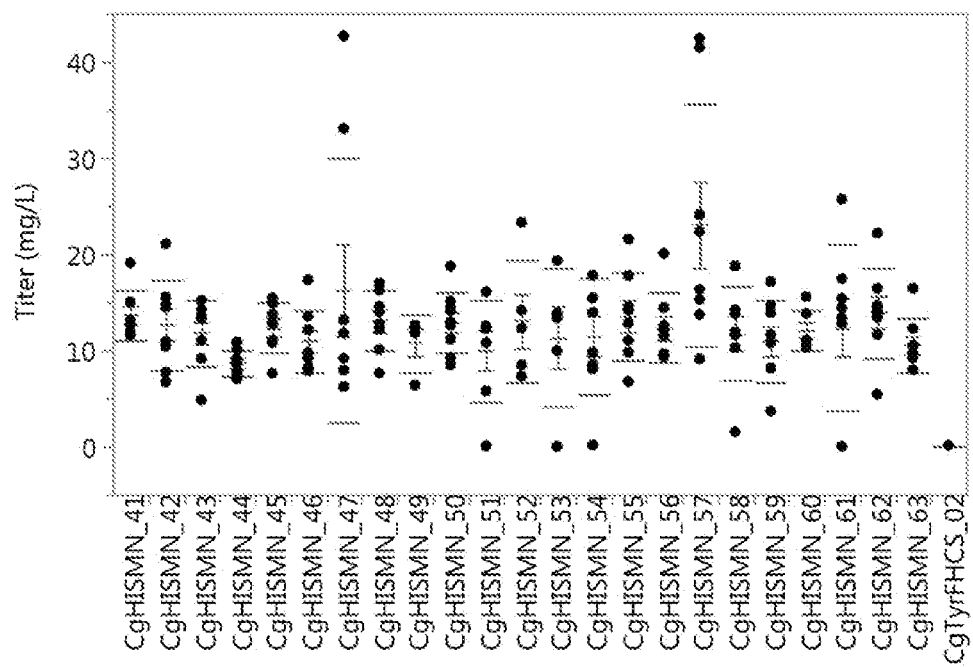
FIG. 4: Histamine titers measured in the extracellular broth following fermentation by the second-round engineered host *Corynebacteria glutamicum*. (See also Example 1, Table 2.)
Figure 5:
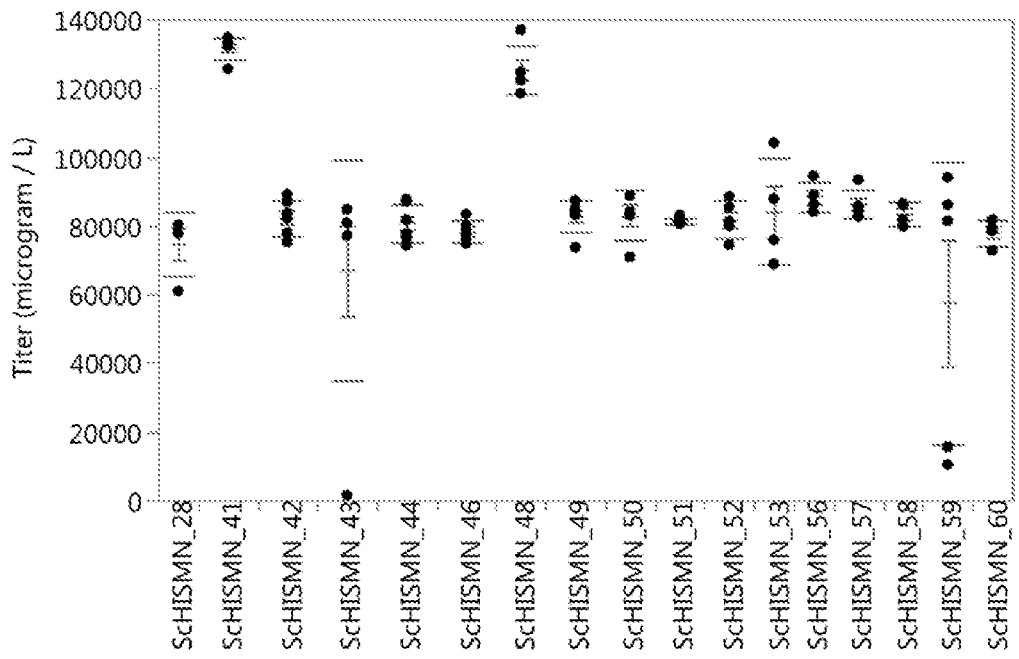
FIG. 5: Histamine titers measured in the extracellular broth following fermentation by the second-round engineered host *Saccharomyces cerevisiae*. (See also Example 1, Table 2.)

Second-round genetic engineering results are shown in Table 2 and FIGS. 4 (*C. glutamicum*) and 5 (*S. cerevisiae*).

In *C. glutamicum*, a titer of 24 mg/L was achieved after two rounds of engineering from the integration of two genes: a histidine decarboxylase gene from *Acinetobacter baumannii*, and constitutive expression of an imidazoleglycerol-phosphate dehydratase from *C. glutamicum*.

In *S. cerevisiae*, a titer of 385 mg/L was achieved in two rounds of engineering from the integration of three genes: a histidine decarboxylase gene from *Chromobacterium* sp. LK1 (SEQ ID NO: 6), an ATP phosphoribosyltransferase from *C. glutamicum* containing the amino acid substitutions N215K, L231F, and T235A (SEQ ID NO: 7), and a constitutively expressed ATP phosphoribosyltransferase from *S. cerevisiae* (SEQ ID NO: 3).

TABLE 2

Second-round genetic engineering results in genetic engineering results in Corynebacteria glutamicum and Saccharomyces cerevisiae

| Strain name | Titer (μg/L) | E1 Uniprot ID | Enzyme 1-activity name | Enzyme 1-source organism | E1 Codon Optimization Abbrev. |
|---|---|---|---|---|---|
| Corynebacteria glutamicum | | | | | |
| CgHISMN_41 | 13702.1 | O68602 | 1-(5-phosphoribosyl)5[(5-phosphoribosylamino) methylideneamino] imidazole-4-carboxamide isomerase | Corynebacterium glutamicum | Native |
| CgHISMN_42 | 12671.2 | Q9KJU3 | Imidazoleglycerol-phosphate dehydratase | Corynebacterium glutamicum | Native |
| CgHISMN_43 | 11800.4 | Q9KJU4 | Histidinol-phosphate aminotransferase | Corynebacterium glutamicum | Native |
| CgHISMN_44 | 8667.2 | Q8NNT5 | Histidinol dehydrogenase | Corynebacterium glutamicum | Native |
| CgHISMN_45 | 12375.3 | Q9Z471 | Phosphoribosyl-ATP pyrophosphatase | Corynebacterium glutamicum | Native |
| CgHISMN_46 | 10963.6 | O31139 | Imidazole glycerol phosphate synthase subunit | Corynebacterium glutamicum | Native |
| CgHISMN_47 | 16246.0 | O69043 | Imidazole glycerol phosphate synthase subunit | Corynebacterium glutamicum | Native |
| CgHISMN_48 | 13038.8 | Q9Z472 | ATP phosphoribosyltransferase | Corynebacterium glutamicum | Native |
| CgHISMN_49 | 10749.0 | Q8NNT9 | phosphoribosyl-AMP cyclohydrolase | Corynebacterium glutamicum | Native |
| CgHISMN_50 | 12960.8 | O68602 | 1-(5-phosphoribosyl)5[(5-phosphoribosylamino) methylideneamino] imidazole-4-carboxamide isomerase | Corynebacterium glutamicum | Native |
| CgHISMN_51 | 9958.4 | Q9KJU3 | Imidazoleglycerol-phosphate dehydratase | Corynebacterium glutamicum | Native |
| CgHISMN_52 | 18963.0 | Q9KJU4 | Histidinol-phosphate aminotransferase | Corynebacterium glutamicum | Native |
| CgHISMN_53 | 20328.9 | Q8NNT5 | Histidinol dehydrogenase | Corynebacterium glutamicum | Native |
| CgHISMN_54 | 20051.4 | O31139 | Imidazole glycerol phosphate synthase subunit | Corynebacterium glutamicum | Native |
| CgHISMN_55 | 15070.9 | O69043 | Imidazole glycerol phosphate synthase subunit | Corynebacterium glutamicum | Native |
| CgHISMN_56 | 12799.1 | O68602 | 1-(5-phosphoribosyl)5[(5-phosphoribosylamino) methylideneamino] imidazole-4-carboxamide isomerase | Corynebacterium glutamicum | Native |
| CgHISMN_57 | 24773.6 | Q9KJU3 | Imidazoleglycerol-phosphate dehydratase | Corynebacterium glutamicum | Native |
| CgHISMN_58 | 15268.6 | Q9KJU4 | Histidinol-phosphate aminotransferase | Corynebacterium glutamicum | Native |
| CgHISMN_59 | 12555.0 | Q8NNT5 | Histidinol dehydrogenase | Corynebacterium glutamicum | Native |
| CgHISMN_60 | 17725.6 | Q9Z471 | Phosphoribosyl-ATP pyrophosphatase | Corynebacterium glutamicum | Native |
| CgHISMN_61 | 18777.4 | O69043 | Imidazole glycerol phosphate synthase subunit | Corynebacterium glutamicum | Native |
| CgHISMN_62 | 19782.8 | Q9Z472 | ATP phosphoribosyltransferase | Corynebacterium glutamicum | Native |
| CgHISMN_63 | 15092.7 | Q8NNT9 | phosphoribosyl-AMP cyclohydrolase | Corynebacterium glutamicum | Native |
| Saccharomyces cerevisiae | | | | | |
| ScHISMN_41 | 385518.2 | P00498 | ATP phosphoribosyltransferase | Saccharomyces cerevisiae | Native |
| ScHISMN_42 | 70003.1 | P00815 | histidinol dehydrogenase, phosphoribosyl-AMP cyclohydrolase, phosphoribosyl-ATP diphosphatase | Saccharomyces cerevisiae | Native |
| ScHISMN_43 | 75039.5 | P33734 | Imidazole glycerol phosphate synthase subunit HisF | Saccharomyces cerevisiae | Native |
| ScHISMN_44 | 71402.5 | P07172 | histidinol-phosphate transaminase | Saccharomyces cerevisiae | Native |

TABLE 2-continued

Second-round genetic engineering results in genetic engineering results in
Corynebacteria glutamicum and Saccharomyces cerevisiae

| Strain name | Titer (μg/L) | E1 Uniprot ID | Enzyme 1-activity name | Enzyme 1-source organism | E1 Codon Optimization Abbrev. |
|---|---|---|---|---|---|
| ScHISMN_46 | 64866.5 | P06633 | Imidazoleglycerol-phosphate dehydratase | Saccharomyces cerevisiae | Native |
| ScHISMN_48 | 113026.6 | P00498 | ATP phosphoribosyltransferase | Saccharomyces cerevisiae | Native |
| ScHISMN_49 | 79488.5 | P00815 | histidinol dehydrogenase, phosphoribosyl-AMP cyclohydrolase, phosphoribosyl-ATP diphosphatase | Saccharomyces cerevisiae | Native |
| ScHISMN_50 | 92719.6 | P33734 | Imidazole glycerol phosphate synthase subunit HisF | Saccharomyces cerevisiae | Native |
| ScHISMN_51 | 88847.1 | P07172 | histidinol-phosphate transaminase | Saccharomyces cerevisiae | Native |
| ScHISMN_52 | 70650.9 | P38635 | histidinol-phosphatase | Saccharomyces cerevisiae | Native |
| ScHISMN_53 | 74127.8 | P06633 | Imidazoleglycerol-phosphate dehydratase | Saccharomyces cerevisiae | Native |
| ScHISMN_56 | 73080.2 | P00815 | histidinol dehydrogenase, phosphoribosyl-AMP cyclohydrolase, phosphoribosyl-ATP diphosphatase | Saccharomyces cerevisiae | Native |
| ScHISMN_57 | 78656.1 | P33734 | Imidazole glycerol phosphate synthase subunit HisF | Saccharomyces cerevisiae | Native |
| ScHISMN_58 | 69769.0 | P07172 | histidinol-phosphate transaminase | Saccharomyces cerevisiae | Native |
| ScHISMN_59 | 59139.1 | P38635 | histidinol-phosphatase | Saccharomyces cerevisiae | Native |
| ScHISMN_60 | 65506.7 | P06633 | Imidazoleglycerol-phosphate dehydratase | Saccharomyces cerevisiae | Native |

Third-Round Genetic Engineering Results in *Saccharomyces cerevisiae*

Histamine production was further pursued in *S. cerevisiae*, and we designed plasmids to integrate additional copies of upstream pathway genes expressed by a strong constitutive promoter to avoid native regulation of a gene (Table 3). An expanded search was undertaken to test additional histidine decarboxylases that have similar sequences to the enzymes initially identified as active (Table 3).

In parallel we pursued modulating native gene expression to further improve histamine production. Our engineering approach was to take a best *S. cerevisiae* strain from the second round and test either a strong or weak constitutive promoter in place of the native promoter. Gene targets for promoter changes were selected to redirect flux supply precursors to histidine. Strain designs being tested include designs for increasing pentose phosphate pathway flux by expressing a non-native feedback deregulated glucose-6-phosphate dehydrogenase (zwf) and decreasing the "lower" pentose phosphate pathway flux thru the sugar isomerase enzymes.

Promoter replacements for lower expression of genes that are thought to be essential (i.e., cannot be deleted), but were expected to increase the upper glycolysis metabolite pool available for histamine production, targeted: 1) enolase (Eno2), to reduce flux through lower glycolysis, 2) pyruvate dehydrogenase (PDH, Lpd1) for lower flux through the C3/C2 node, and 3) pentose phosphate pathway sugar isomerases, which use the histamine metabolite precursor ribose-5-phosphate (Tal1). An illustrative list of promoter-swap ("proswap") and deletion ("knockout") targets in *S. cerevisiae* includes:

| Annotation_name | Type | Promoter_name | Gene_name |
|---|---|---|---|
| YDR380W | knockout | | Aro10 |
| YDL047W | knockout | | Sit4 |
| YML035C | knockout | | Amd1 |
| YMR020W | knockout | | Fms1 |
| YNL229C | knockout | | Ure2 |
| YJL052W | proswap | pRnr1 | Tdh1 |
| YJR009C | proswap | pRnr1 | Tdh2 |
| YGR192C | proswap | pRnr1 | Tdh3 |
| YFL018C | proswap | pRnr1 | Lpd1 |
| YHR174W | proswap | pRnr1 | Eno2 |
| YNR001C | proswap | pRnr1 | Cit1 |
| YCR012W | proswap | pRnr1 | Pgk1 |
| YLR354C | proswap | pRnr1 | Tal1 |
| YBR117C | proswap | pRnr1 | Tkl2 |
| YPR074C | proswap | pRnr1 | Tkl1 |
| YML035C | proswap | pRev1 | Amd1 |
| YHR216W | proswap | pRev1 | Imd2 |
| YOR155C | proswap | pRev1 | Isn1 |
| YNL229C | proswap | pRev1 | Ure2 |
| YER086W | proswap | pRnr1 | Ilv1 |
| YDR380W | proswap | pRnr1 | Aro10 |
| YEL009C | proswap | pRev1 | Gcn4 |

Promoters were selected based on expression data from Lee et al [7].

Figure 10:
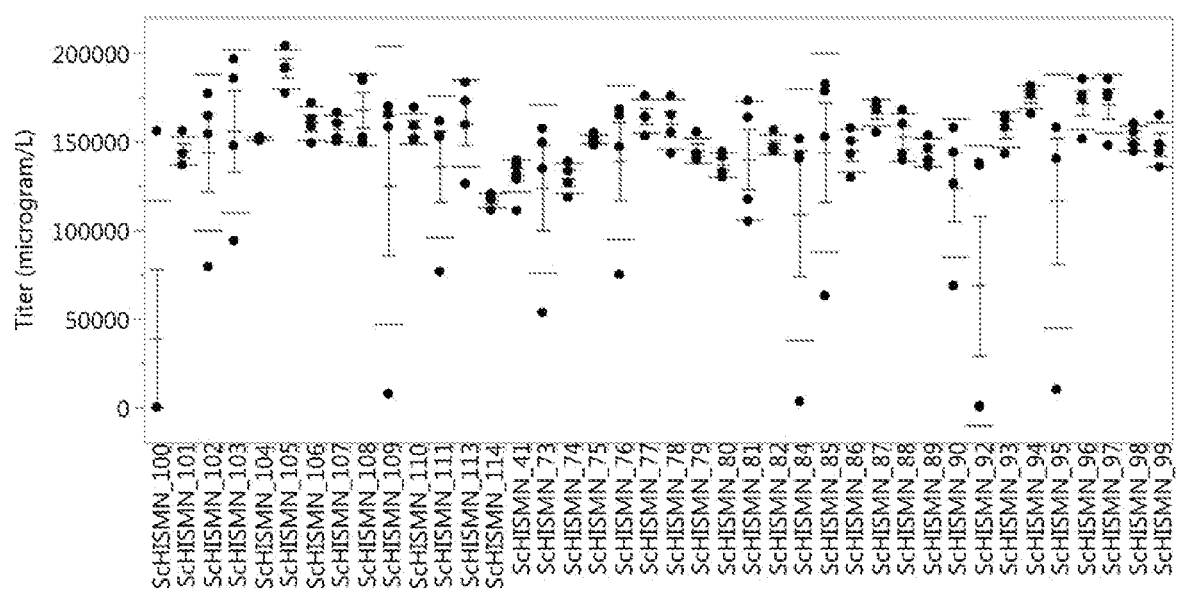
FIG. 10: Histamine titers measured in the extracellular broth following fermentation by the third-round engineered host *Saccharomyces cerevisiae*. (Improvement round.)

Additional genetic engineering results for *S. cerevisiae* are shown in Table 3 and FIG. 10. The parent strain for the strain designs shown in Table 3 (also the reference strain, ScHISMN_41) contained a histidine decarboxylase (UniProt ID J6KM89) and an ATP phosphoribosyltransferase (UniProt ID Q9Z472) harboring the amino acid substitutions N215K, L231F and T235A, and the ATP phosphoribosyltransferase from *S. cerevisiae*. The reference strain had a histamine titer of 131 mg/L.

Improved titer was observed in strains that expressed each of the following enzymes from a strong constitutive promoter:

1. Transketolase (EC 2.2.1.1) (SEQ ID NO: 27), which catalyzes the interconversion of sugars in the pentose phosphate pathway and produces ribose-5-phosphate, which is a precursor to PPRP, the initial metabolite in the histidine biosynthesis pathway.
2. Ribose-phosphate pyrophosphokinase (EC 2.7.6.1) (SEQ ID NO: 28) (highest titer: 191 mg/L relative to control in experiment 131 mg/L).
3. ATP phosphoribosyltransferase (EC 2.4.2.17) (SEQ ID NO: 3).
4. Trifunctional histidinol dehydrogenase (EC 1.1.1.23)/phosphoribosyl-AMP cyclohydrolase (EC 3.5.4.19)/phosphoribosyl-ATP diphosphatase (EC 3.6.1.31) (SEQ ID NO: 29).
5. Histidinol-phosphate aminotransferase (EC 2.6.1.9) (SEQ ID NO: 14).
6. 5'ProFAR isomerase (EC 5.3.1.16) (SEQ ID NO: 31).
7. Imidazole glycerol phosphate synthase (EC 4.3.1.B2) (SEQ ID NO: 21).
8. Triose-phosphate isomerase (EC 5.3.1.1), harboring the amino acid substitutions harboring the amino acid substitutions I170V (SEQ ID NO: 32) or I170T [8].
9. Glucose-6-phosphate 1-dehydrogenase (EC 1.1.1.49), harboring the amino acid substitution A243T (SEQ ID NO: 26).
10. Various histidine decarboxylases (EC 4.1.1.22):
   a. UniProt ID A0A089YPE5 (SEQ ID NO: 33)
   b. UniProt ID A0A126S6G9 (SEQ ID NO: 34)
   c. UniProt ID A0A0A1R6V3 (SEQ ID NO: 35)
   d. UniProt ID A0A1W0CM88 (SEQ ID NO: 36)
   e. UniProt ID P00862 (SEQ ID NO: 4)
   f. UniProt ID A0A0K6GJ74 (SEQ ID NO: 37)
   g. UniProt ID T0QL99 (SEQ ID NO: 38)
   h. UniProt ID A0A1B8HLR1 (SEQ ID NO: 39)

TABLE 3

Third-round genetic engineering results in *Saccharomyces cerevisiae*
Built and tested strain designs:

| Strain name | Titer (µg/L) | E1 Uniprot ID | Enzyme 1—activity name | E1 Modifications | Enzyme 1—source organism | E2 Uniprot ID | Enzyme 2—activity name | Enzyme 2—source organism | E3 Uniprot ID | Enzyme 3—activity name | E3 Modifications | Enzyme 3—source organism |
|---|---|---|---|---|---|---|---|---|---|---|---|---|
| ScHISMN_100 | 39059 | A0A0C1PR48 | Histidine decarboxylase | | *Lactobacillus fructivorans* | | | | | | | |
| ScHISMN_101 | 144871 | T0QL99 | Histidine decarboxylase | | *Aeromonas salmonicida* subsp. *pectinolytica* 34mel | | | | | | | |
| ScHISMN_102 | 143763 | A0A1B8HLR1 | Histidine decarboxylase | | *Morganella psychrotolerans* | | | | | | | |
| ScHISMN_103 | 155931 | Q9Z472 | ATP phosphoribosyltransferase | | *Corynebacterium glutamicum* (strain ATCC 13032 / DSM 20300 / JCM 1318 / LMG 3730 / NCIMB 10025) | P00815 | trifunctional histidinol dehydrogenase/phosphoribosyl-AMP cyclohydrolase/phosphoribosyl-ATP diphosphatase | *Saccharomyces cerevisiae* S288c | P0A717 | Ribose-phosphate pyrophosphokinase | | *Escherichia coli* (strain K12) |
| ScHISMN_104 | 151846 | P0A717 | Ribose-phosphate pyrophosphokinase | | *Escherichia coli* (strain K12) | | | | | | | |
| ScHISMN_105 | 191110 | Q12265 | Ribose-phosphate pyrophosphokinase | | *Saccharomyces cerevisiae* (strain ATCC 204508 / S288c) (Baker's yeast) | P38620 | Ribose-phosphate pyrophosphokinase | *Saccharomyces cerevisiae* S288c | Q680A5 | Ribose-phosphate pyrophosphokinase | | *Arabidopsis thaliana* (Mouse-ear cress) |
| ScHISMN_106 | 160586 | P32895 | Ribose-phosphate pyrophosphokinase | | *Saccharomyces cerevisiae* (strain ATCC 204508 / S288c) (Baker's yeast) | P38689 | Ribose-phosphate pyrophosphokinase | *Saccharomyces cerevisiae* S288c | | | | |

TABLE 3-continued

Third-round genetic engineering results in *Saccharomyces cerevisiae*
Built and tested strain designs:

| Strain name | Titer (μg/L) | E1 Uniprot ID | Enzyme 1—activity name | E1 Modifications | Enzyme 1—source organism | E2 Uniprot ID | Enzyme 2—activity name | Enzyme 2—source organism | E3 Uniprot ID | Enzyme 3—activity name | E3 Modifications | Enzyme 3—source organism |
|---|---|---|---|---|---|---|---|---|---|---|---|---|
| ScHISMN_107 | 157191 | P23254 | Transketolase | | *Saccharomyces cerevisiae* (strain ATCC 204508 / S288c) (Baker's yeast) | P32895 | Ribose-phosphate pyrophos-phokinase | *Saccharomyces cerevisiae* S288c | P38689 | Ribose-phosphate pyro-phos-pho-kinase | | *Saccharomyces cerevisiae* S288c |
| ScHISMN_108 | 168183 | P23254 | Transketolase | | *Saccharomyces cerevisiae* (strain ATCC 204508 / S288c) (Baker's yeast) | Q12265 | Ribose-phosphate pyrophos-phokinase | *Saccharomyces cerevisiae* S288c | P38620 | Ribose-phosphate pyro-phos-pho-kinase | | *Saccharomyces cerevisiae* S288c |
| ScHISMN_109 | 125249 | P23254 | Transketolase | | *Saccharomyces cerevisiae* (strain ATCC 204508 / S288c) (Baker's yeast) | Q12265 | Ribose-phosphate pyrophos-phokinase | *Saccharomyces cerevisiae* S288c | Q680A5 | Ribose-phosphate pyro-phos-pho-kinase | | *Arabidopsis thaliana* (Mouse-ear cress) |
| ScHISMN_110 | 157653 | P23254 | Transketolase | | *Saccharomyces cerevisiae* (strain ATCC 204508 / S288c) (Baker's yeast) | P0A717 | Ribose-phosphate pyrophos-phokinase | *Escherichia coli* (strain K12) | | | | |
| ScHISMN_111 | 136093 | P23254 | Transketolase | | *Saccharomyces cerevisiae* (strain ATCC 204508 / S288c) (Baker's yeast) | P15019 | Transaldolase | *Saccharomyces cerevisiae* S288c | P0A717 | Ribose-phosphate pyro-phos-pho-kinase | | *Escherichia coli* (strain K12) |
| ScHISMN_112 | | P06775 | Histidine permease | | *Saccharomyces cerevisiae* (strain ATCC 204508 / S288c) (Baker's yeast) | | | | | | | |
| ScHISMN_113 | 160417 | P00815 | trifunctional histidinol dehydrogenase/phosphoribosyl-AMP cyclohydrolase/phosphoribosyl-ATP diphosphatase | | *Saccharomyces cerevisiae* (strain ATCC 204508 / S288c) (Baker's yeast) | P40545 | 5'ProFAR isomerase | *Saccharomyces cerevisiae* S288c | O59667 | Bifunctional phosphoribosyl-AMP cyclohydrolase and phosphoribosyl-ATP pyrophosphatase | | *Schizosaccharomyces pombe* ATCC 24843 |

TABLE 3-continued

Third-round genetic engineering results in *Saccharomyces cerevisiae*
Built and tested strain designs:

| Strain name | Titer (μg/L) | E1 Uniprot ID | Enzyme 1— activity name | E1 Modifications | Enzyme 1— source organism | E2 Uniprot ID | Enzyme 2— activity name | Enzyme 2— source organism | E3 Uniprot ID | Enzyme 3— activity name | E3 Modifications | Enzyme 3— source organism |
|---|---|---|---|---|---|---|---|---|---|---|---|---|
| ScHISMN_114 | 116907 | P06633 | Imidazole-glycerol-phosphate dehydratase | | *Saccharomyces cerevisiae* (strain ATCC 204508 / S288c) (Baker's yeast) | P07172 | Histidinol-phosphate aminotransferase | *Saccharomyces cerevisiae* S288c | P38635 | Histidinol-phosphatase | | *Saccharomyces cerevisiae* S288c |
| ScHISMN_41 | 131308 | | | | | | | | | | | |
| ScHISMN_73 | 123614 | P00815 | trifunctional histidinol dehydrogenase/ phosphoribosyl-AMP cyclohydrolase/ phosphoribosyl-ATP diphosphatase | | *Saccharomyces cerevisiae* (strain ATCC 204508 / S288c) (Baker's yeast) | | | | | | | |
| ScHISMN_74 | 129393 | P06633 | Imidazole-glycerol-phosphate dehydratase | | *Saccharomyces cerevisiae* (strain ATCC 204508 / S288c) (Baker's yeast) | | | | | | | |
| ScHISMN_75 | 151455 | P07172 | Histidinol-phosphate aminotransferase | | *Saccharomyces cerevisiae* (strain ATCC 204508 / S288c) (Baker's yeast) | | | | | | | |
| ScHISMN_76 | 138833 | P00498 | ATP phosphoribosyltransferase | | *Saccharomyces cerevisiae* (strain ATCC 204508 / S288c) (Baker's yeast) | | | | | | | |
| ScHISMN_77 | 164217 | P40545 | 5'ProFAR isomerase | | *Saccharomyces cerevisiae* (strain ATCC 204508 / S288c) (Baker's yeast) | | | | | | | |
| ScHISMN_78 | 159871 | P33734 | Imidazole glycerol phosphate synthase | | *Saccharomyces cerevisiae* (strain ATCC 204508 / S288c) (Baker's yeast) | | | | | | | |

TABLE 3-continued

Third-round genetic engineering results in *Saccharomyces cerevisiae*
Built and tested strain designs:

| Strain name | Titer (µg/L) | E1 Uniprot ID | Enzyme 1— activity name | E1 Modifications | Enzyme 1— source organism | E2 Uniprot ID | Enzyme 2— activity name | Enzyme 2— source organism | E3 Uniprot ID | Enzyme 3— activity name | E3 Modifications | Enzyme 3— source organism |
|---|---|---|---|---|---|---|---|---|---|---|---|---|
| ScHIS MN_79 | 145179 | P00942 | Triosephosphate isomerase | I170V | *Saccharomyces cerevisiae* (strain ATCC 204508 / S288c) (Baker's yeast) | | | | | | | |
| ScHIS MN_80 | 137192 | P00942 | Triosephosphate isomerase | I170T | *Saccharomyces cerevisiae* (strain ATCC 204508 / S288c) (Baker's yeast) | | | | | | | |
| ScHIS MN_81 | 139699 | Q9Z472 | ATP phosphoribosyltransferase | | *Corynebacterium glutamicum* (strain ATCC 13032 / DSM 20300 / JCM 1318 / LMG 3730 / NCIMB 10025) | | | | | | | |
| ScHIS MN_82 | 148665 | Q9Z472 | ATP phosphoribosyltransferase | N215K, L231F, T235A | *Corynebacterium glutamicum* (strain ATCC 13032 / DSM 20300 / JCM 1318 / LMG 3730 / NCIMB 10025) | | | | | | | |
| ScHIS MN_84 | 109350 | Q9Z472 | ATP phosphoribosyltransferase | N215K, L231F, T235A | *Corynebacterium glutamicum* (strain ATCC 13032 / DSM 20300 / JCM 1318 / LMG 3730 / NCIMB 10025) | P00815 | tri-functional histidinol dehydrogenase/ phosphoribosyl-AMP cyclohydrolase/ phosphoribosyl-ATP diphosphatase | *Saccharomyces cerevisiae* S288c | | | | |
| ScHIS MN_85 | 144154 | Q9Z472 | ATP phosphoribosyltransferase | | *Corynebacterium glutamicum* (strain ATCC 13032 / DSM 20300 / JCM 1318 / LMG | P00815 | tri-functional histidinol dehydrogenase/ phosphoribosyl-AMP cyclohydrolase/ | *Saccharomyces cerevisiae* S288c | P00942 | Triosephosphate isomerase | I170V | *Saccharomyces cerevisiae* S288c |

TABLE 3-continued

Third-round genetic engineering results in Saccharomyces cerevisiae
Built and tested strain designs:

| Strain name | Titer (μg/L) | E1 Uniprot ID | Enzyme 1—activity name | E1 Modifications | Enzyme 1—source organism | E2 Uniprot ID | Enzyme 2—activity name | Enzyme 2—source organism | E3 Uniprot ID | Enzyme 3—activity name | E3 Modifications | Enzyme 3—source organism |
|---|---|---|---|---|---|---|---|---|---|---|---|---|
| ScHISMN_86 | 145171 | Q9Z472 | ATP phosphoribosyltransferase | N215K, L231F, T235A | Corynebacterium glutamicum (strain ATCC 13032 / DSM 20300 / JCM 1318 / LMG 3730 / NCIMB 10025) | P00815 | tri-functional histidinol dehydrogenase/ phosphoribosyl-AMP cyclohydrolase/ phosphoribosyl-ATP diphosphatase | Saccharomyces cerevisiae S288c | P00942 | Triose-phosphate isomerase | I170V | Saccharomyces cerevisiae S288c |
| ScHISMN_87 | 166497 | Q9Z472 | ATP phosphoribosyltransferase | | Corynebacterium glutamicum (strain ATCC 13032 / DSM 20300 / JCM 1318 / LMG 3730 / NCIMB 10025) | P00815 | tri-functional histidinol dehydrogenase/ phosphoribosyl-AMP cyclohydrolase/ phosphoribosyl-ATP diphosphatase | Saccharomyces cerevisiae S288c | A4QEF2 | Glucose-6-phosphate 1-dehydrogenase | A243T | Corynebacterium glutamicum (strain R) |
| ScHISMN_88 | 152555 | Q9Z472 | ATP phosphoribosyltransferase | N215K, L231F, T235A | Corynebacterium glutamicum (strain ATCC 13032 / DSM 20300 / JCM 1318 / LMG 3730 / NCIMB 10025) | P00815 | tri-functional histidinol dehydrogenase/ phosphoribosyl-AMP cyclohydrolase/ phosphoribosyl-ATP diphosphatase | Saccharomyces cerevisiae S288c | A4QEF2 | Glucose-6-phosphate 1-dehydrogenase | A243T | Corynebacterium glutamicum (strain R) |
| ScHISMN_89 | 143866 | O66000 | Histidine decarboxylase | | Oenococcus oeni (Leuconostoc oenos) | | | | | | | |
| ScHISMN_90 | 124157 | A0A0R1Y874 | Histidine decarboxylase | | Lactobacillus aviarius subsp. aviarius DSM 20655 | | | | | | | |

TABLE 3-continued

Third-round genetic engineering results in *Saccharomyces cerevisiae*
Built and tested strain designs:

| Strain name | Titer (μg/L) | E1 Uniprot ID | Enzyme 1— activity name | E1 Modifications | Enzyme 1— source organism | E2 Uniprot ID | Enzyme 2— activity name | Enzyme 2— source organism | E3 Uniprot ID | Enzyme 3— activity name | E3 Modifications | Enzyme 3— source organism |
|---|---|---|---|---|---|---|---|---|---|---|---|---|
| ScHISMN_92 | 68849 | A0A1H1TEB8 | Histidine decarboxylase | S9R | *Pseudomonas* sp. bs2935 | | | | | | | |
| ScHISMN_93 | 157127 | A0A089YPE5 | Histidine decarboxylase | | *Pseudomonas rhizosphaerae* | | | | | | | |
| ScHISMN_94 | 175497 | A0A126S6G9 | Histidine decarboxylase | | *Pseudomonas putida* (*Arthrobacter siderocapsulatus*) | | | | | | | |
| ScHISMN_95 | 116642 | A0A0J6KM89 | Histidine decarboxylase | | *Chromobacterium* sp. LK1 | | | | | | | |
| ScHISMN_96 | 171681 | A0A0A1R6V3 | Histidine decarboxylase | | *Citrobacter pasteurii* | | | | | | | |
| ScHISMN_97 | 171393 | A0A1W0CM88 | Histidine decarboxylase | | *Chromobacterium haemolyticum* | | | | | | | |
| ScHISMN_98 | 152065 | P00862 | Histidine decarboxylase | | *Lactobacillus* sp. (strain 30a) | | | | | | | |
| ScHISMN_99 | 148362 | A0A0K6GJ74 | Histidine decarboxylase | | *Lactobacillus reuteri* | | | | | | | |

Note:
E1, E2, and E3 genes were codon-optimized according to modified codon usage for Cg and Sc Example 2—Host Evaluation for Histamine Production Histamine production was also tested in two additional hosts, *Bacillus subtilus* and *Yarrowia lipolytica*, which were engineered to express the enzymes from the best-performing *Corynebacterium glutamicum* and *Saccharomyces cerevisiae* strains.

Host evaluation designs were selected to express 1-3 enzymes and, each design was tested with four different codon optimizations based on the host organisms *C. glutamicum*, *S. cerevisiae*, *B. subtilis*, and *Y. lipolytica*. The codon optimizations tested were based on the Kazusa codon usage tables tabulated for each host for gene codon optimization (www.kazusa.or.jp/codon/).

Figure 6:
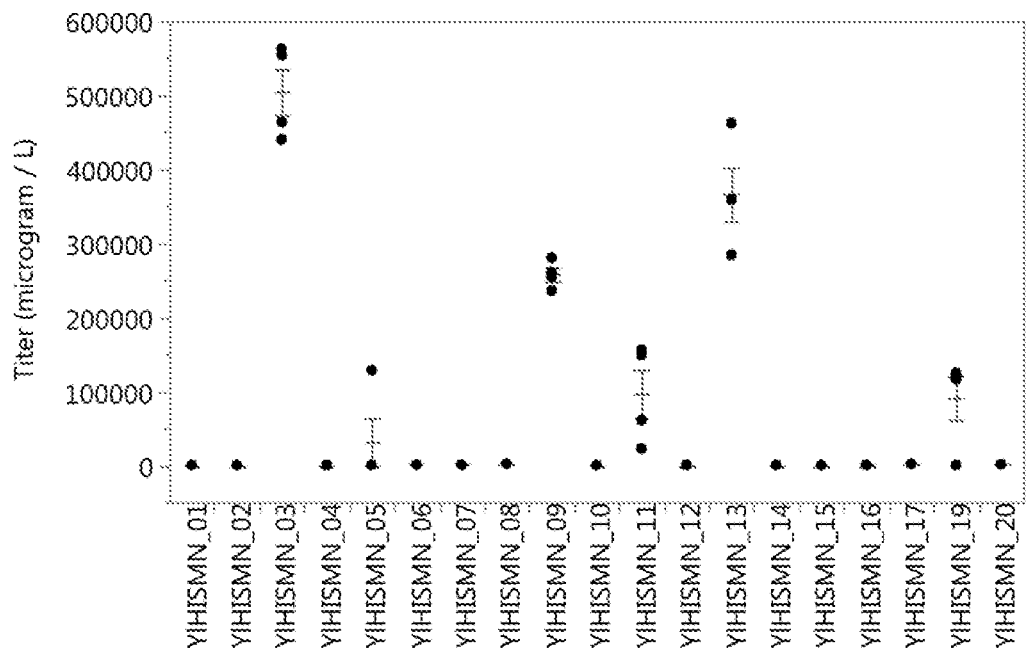
FIG. 6: Histamine titers measured in the extracellular broth following fermentation by the first-round engineered host *Yarrowia lipolytica*. (See also Example 2, Table 4.)
Figure 7:
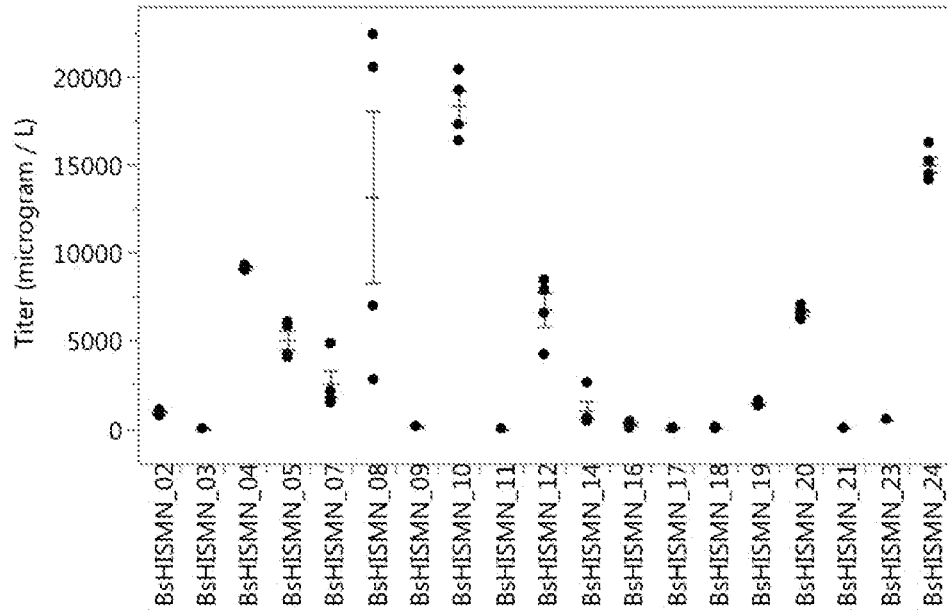
FIG. 7: Histamine titers measured in the extracellular broth following fermentation by the first-round engineered host *Bacillus subtilis*.
Figure 8:
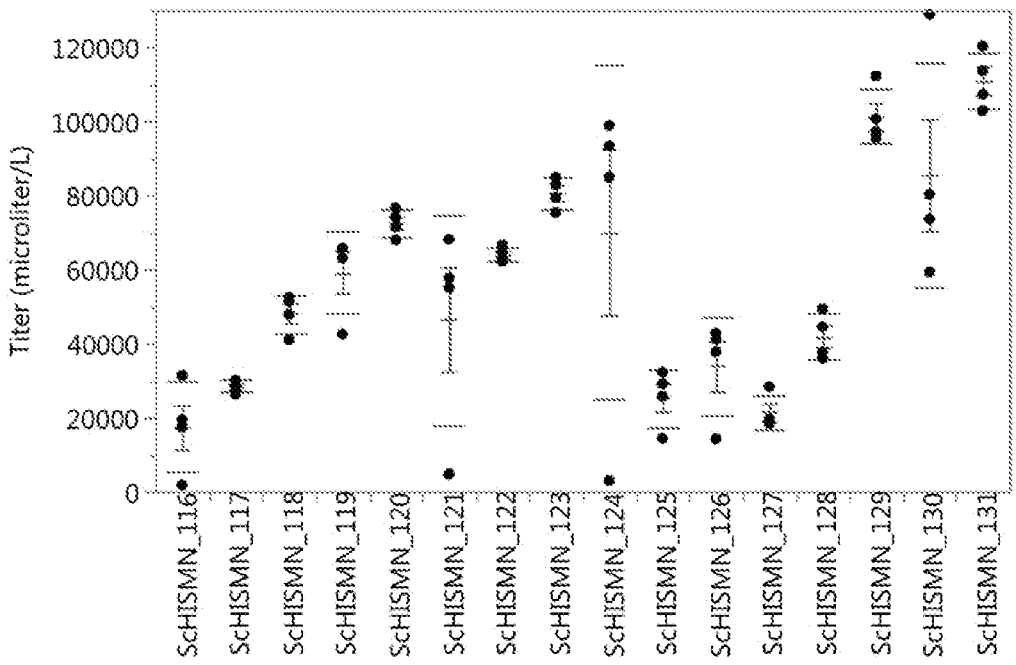
FIG. 8: Histamine acid titers measured in the extracellular broth following fermentation of *Saccharomyces cerevisiae* expressing the host evaluation designs.
Figure 9:
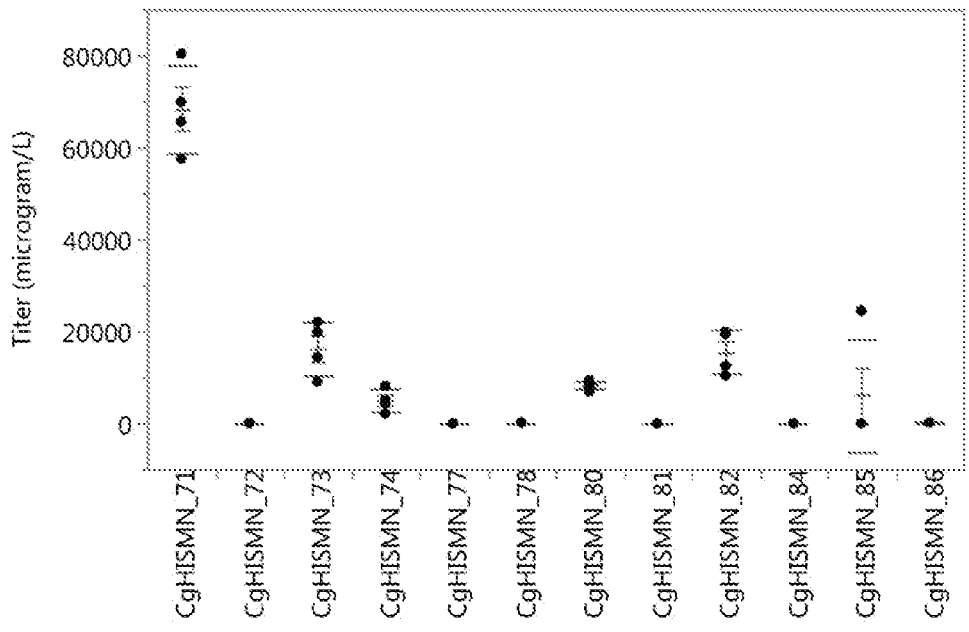
FIG. 9: Histamine acid titers measured in the extracellular broth following fermentation of *Corynebacteria glutamicum* expressing the host evaluation designs.

Histamine production was demonstrated in *Y. lipolytica* (FIG. 6) and *B. subtilis* (FIG. 7) and further improved in *C. glutamicum* (FIG. 9) and *S. cerevisiae* (FIG. 8).

In *Y. lipolytica* (FIG. 6, Table 4, below) the best performing strain produced 505 mg/L histamine and expressed the histidine decarboxylase from *Acinetobacter baumannii* strain AB0057 (UniProt ID B7I459), where the DNA sequence was codon-optimized for *Y. lipolytica*, and the ATP phosphoribosyltransferase from *S. cerevisiae* S288c (UniProt ID P00498), where the DNA sequence was codon optimized for *Y. lipolytica*. The same two genes were also tested where the DNA sequence was codon-optimized for *B. subtilis* and *S. cerevisiae* and the resulting strains produced no histamine titer.

The second best-performing strain in *Y. lipolytica* also expressed the histidine decarboxylase from *Acinetobacter baumannii* strain AB0057 (UniProt ID B7I459), where the DNA sequence was codon-optimized for *Y. lipolytica*, and the ATP phosphoribosyltransferase from *Salmonella typhimurium* LT2 (UniProt ID P00499), where the DNA was codon optimized for *Y. lipolytica*. Versions of these two genes were also tested where the DNA sequence was codon optimized for *B. subtilis* (which produced 0 titer), codon-optimized for *S. cerevisiae* (which produced 33 micrograms histamine) and codon-optimized using a combined codon table for *S. cerevisiae* and *C. glutamicum* (produced 97 mg/L histamine).

The third best-performing strain in *Y. lipolytica* produced 258 mg/L histamine and expressed the histidine decarboxylase from *Chromobacterium* sp. LK1 (UniProt ID A0A0J6KM89), where the DNA sequence was codon optimized for *Y. lipolytica*, and the ATP phosphoribosyltransferase from *C. glutamicum* ATCC 13032 (UniProt ID Q9Z472) harboring the amino acid substitutions N215K, L231F, T235A (SEQ ID NO: 7), where the DNA sequence was codon-optimized for *Y. lipolytica* (SEQ ID NO: 64). Versions of these two genes were also tested where the DNA sequences were codon-optimized for *S. cerevisiae* (SEQ ID NO: 65, 66) or *B. subtilis* (SEQ ID NO: 67, 68), and these *Y. lipolytica* strains produced 1.8 mg/L and 0.3 mg/L, respectively. Accordingly, codon-optimization of genes affects expression in *Y. lipolytica*.

In *B. subtilis* (FIG. 7, Table 5, below) the best performing strain produced 18 mg/L histamine and expressed the histamine decarboxylase from *Lactobacillus* sp. (strain 30a) (UniProt ID P00862)(SEQ ID NO: 4) with the ATP phosphoribosyltransferase from *Salmonella typhimurium* LT2 (UniProt ID P00499)(SEQ ID NO: 5) where the DNA sequence was codon optimized for *Bacillus subtilis* (SEQ ID NO: 69, 59). The same two genes were also tested where the DNA sequence was codon-optimized for *S. cerevisiae* (SEQ ID NO: 70, 60) or modified codon usage table for *C.* glutamicum and *S. cerevisiae* (SEQ ID NO: 71, 62), and these strains produced 6.7 mg/L or 0 mg/L histamine, respectively.

The host evaluation designs were also tested in *S. cerevisiae* and *C. glutamicum*. In *S. cerevisiae* (FIG. 8, Table 6, below) the best-performing strain produced 111 mg/L histamine and expressed the histamine decarboxylase from *Chromobacterium* sp. LK1 (UniProt ID A0A0J6KM89) (SEQ ID NO: 51) and the ATP phosphoribosyltransferase from *Saccharomyces cerevisiae* S288c (UniProt ID P00498) (SEQ ID NO: 3), where the DNA sequences were codon-optimized for *Y. lipolytica* (SEQ ID NO: 63, 53). The same two genes were also tested where the DNA sequences were codon optimized for *S. cerevisiae* (SEQ ID NO: 65, 57) and *B. subtilis* (SEQ ID NO: 67, 55) produced 86 mg/L and 101 mg/L, respectively.

In *C. glutamicum* (FIG. 9, Table 7), the best-performing strain produced 68 mg/L histamine and expressed the histamine decarboxylase from *Acinetobacter baumannii* (strain AB0057) (UniProt ID B7I459) (SEQ ID NO: 1) with the ATP phosphoribosyltransferase from *Saccharomyces cerevisiae* S288c (UniProt ID P00498) (SEQ ID NO: 3) where the DNA sequences were codon-optimized using a modified codon usage table for *C. glutamicum* and *S. cerevisiae* (SEQ ID NO: 72, 73). The same two genes were also tested where the DNA sequence was codon-optimized for *Y. lipolytica* (SEQ ID NO: 52, 53) or *S. cerevisiae* (SEQ ID NO: 56, 57), and these strains produced 16 mg/L and 18 microgram/L histamine, respectively.

The second best-performing strain in *C. glutamicum* produced 15 mg/L histamine and also expressed a histidine decarboxylase from *Acinetobacter baumannii* strain AB0057 (UniProt ID B7I459) (SEQ ID NO: 1), where the DNA sequence was codon optimized for *Y. lipolytica* (SEQ ID NO: 52), and an ATP phosphoribosyltransferase from *Salmonella typhimurium* LT2 (UniProt ID P00499) (SEQ ID NO: 5), where the DNA was codon optimized for *Y. lipolytica* (SEQ ID NO: 58). These same two genes were also tested, where the DNA sequences were codon-optimized for *B. subtilis* (SEQ ID NO: 54, 59) (which produced 8 mg/L histamine) or codon-optimized for *S. cerevisiae* (SEQ ID NO: 56, 60)(which produced 9.3 mg/L histamine).

Since the best performing strain is in the host *Y. lipolytica*, further strain improvements can be pursued in this host organism. Designs that can further enhance histamine production in *Y. lipolytica* include:

1. Transketolase (EC 2.2.1.1) (SEQ ID NO: 27), which catalyzes the interconversion of sugars in the pentose phosphate pathway and produces ribose-5-phosphate, which is a precursor to PPRP, the initial metabolite in the histidine biosynthesis pathway.
2. Ribose-phosphate pyrophosphokinase (EC 2.7.6.1) (SEQ ID NO: 28).
3. ATP phosphoribosyltransferase (EC 2.4.2.17) (SEQ ID NO: 5).
4. Trifunctional histidinol dehydrogenase (EC 1.1.1.23)/phosphoribosyl-AMP cyclohydrolase (EC 3.5.4.19)/phosphoribosyl-ATP diphosphatase (EC 3.6.1.31) (SEQ ID NO: 20).
5. Histidinol-phosphate aminotransferase (EC 2.6.1.9) (SEQ ID NO: 14).
6. 5'ProFAR isomerase (EC 5.3.1.16) (SEQ ID NO: 31).
7. Imidazole glycerol phosphate synthase (EC 4.3.1.B2) (SEQ ID NO: 21).
8. Triose-phosphate isomerase (EC 5.3.1.1) harboring the amino acid substitution I170V (SEQ ID NO: 32).
9. Glucose-6-phosphate 1-dehydrogenase (EC 1.1.1.49) harboring the amino acid substitution A243T (SEQ ID NO: 26).
10. Various histidine decarboxylases:
    a. UniProt ID A0A089YPE5 (SEQ ID NO: 33)
    b. UniProt ID A0A126S6G9 (SEQ ID NO: 34)
    c. UniProt ID A0A0A1R6V3 (SEQ ID NO: 35)
    d. UniProt ID A0A1W0CM88 (SEQ ID NO: 36)
    e. UniProt ID P00862 (SEQ ID NO: 4)
    f. UniProt ID A0A0K6GJ74 (SEQ ID NO: 37)
    g. UniProt ID T0QL99 (SEQ ID NO: 38)
    h. UniProt ID A0A1B8HLR1 (SEQ ID NO: 39)

Example 3—Improvement of Histamine Production in *Yarrowia lipolytica* Engineered to Produce Histamine Three improvement rounds of genetic engineering were carried out in *Yarrowia lipolytica*.

First-Improvement Round Genetic Engineering in *Yarrowia lipolytica*

Strategy: Improve flux into histidine and then histamine by overexpression of two enzymes.

| Enzyme Name | UniProt ID | Organism | Description | Codon optmization | Mutation |
|---|---|---|---|---|---|
| Histidine decarboxylase (HDC) | B7I459 | Acinetobacter baumannii | Last decarboxylation step of histamine biosynthesis | Yarrowia lypolytica | None |
| ATP phosphoribosyltransferase (ATP-PRase) | P00498 | Saccharomyces cerevisiae | Upstream step of histidine biosynthesis. Utilization of ATP to covert PRPP to PR-ATP | Yarrowia lypolytica | None |

Summary: ATP phosphoribosyltransferase catalyzes the first committed step of histidine biosynthesis pathway. This enzyme would be allosterically feedback-inhibited by histidine and competitively inhibited by AMP and ADP. The results did not indicate activity and/or inhibition of P00498.

Second-Improvement Round Genetic Engineering in *Yarrowia lipolytica*

Strategy: Overexpression of one enzyme. The final step of histamine biosynthesis was enhanced by utilizing the best first-round histidine decarboxylase which was modified to include a solubility tag to improve protein folding.

| Enzyme Name | UniProt ID | Organism | Description | Codon optmization | Mutation |
|---|---|---|---|---|---|
| Histidine decarboxylase (HDC) | B71459 | Acinetobacter baumannii | Last decarboxylation step of histamine biosynthesis | Yarrowia lypolytica | None |

Summary: The histidine decarboxylase used for the second round of genetic engineering was the same as for the first round, although the codon optimization was different. Furthermore, an N-terminal solubility tag (MQYKLAL-NGKTLKGETTTEAVDAATAEKVFKQY-ANDNGVDGEWTYDDATKTFT VT, SEQ ID NO:142) was included in the second-round enzyme.

Third-Improvement Round Genetic Engineering in *Yarrowia lipolytica*

Strategy: Overexpression of two enzymes in pathways upstream of histidine biosynthesis to improve flux into phosphoribosyl pyrophosphate (PRPP).

| Enzyme Name | UniProt ID | Organism | Description | Codon optmization | Mutation |
|---|---|---|---|---|---|
| Ribose-phosphate pyrophosphokinase (RPPK) | E7EAU9 | Bacillus amyloliquefaciens | ATP dependent step for synthesis of PRPP | Yarrowia lypolytica | L135I |
| Glocose-6-phosphate 1-dehydrogenase (G6PDH) | A4QEF2 | Corynebacterium glutamicum | Upstream pathway to push carbon flux into ribose-5-phosphate | Yarrowia lypolytica | A243T |

Summary: Ribose-phosphate pyrophosphokinase is competitively inhibited ADP. The L135I mutation at the ATP binding site on the enzyme relieves ADP inhibition. This strain expressed histamine at a titer of 1.68 g/L of culture medium.

TABLE 4

First-round results for histamine production in Yarrowia lipolytica

| Strain name | Titer (μg/L) | E1 Uniprot ID | Enzyme 1 activity name | Enzyme 1 source organism | E1 Codon Optimization Abbrev. | E2 Uniprot ID | Enzyme 2 activity name | E2 Modifications | Enzyme 2 source organism | E2 Codon Optimization Abbrev. |
|---|---|---|---|---|---|---|---|---|---|---|
| Yarrowia lipolytica YIHISMN_01 | 0 | B71459 | Histidine decarboxylase | Acinetobacter baumannii (strain AB0057) | Bacillus subtilis | P00498 | ATP phosphoribosyl-transferase | | Saccharomyces cerevisiae S288c | Bacillus subtilis |
| YIHISMN_02 | 0 | B71459 | Histidine decarboxylase | Acinetobacter baumannii (strain AB0057) | Saccharomyces cerevisiae | P00498 | ATP phosphoribosyl-transferase | | Saccharomyces cerevisiae S288c | Saccharomyces cerevisiae |
| YIHISMN_03 | 505019 | B71459 | Histidine decarboxylase | Acinetobacter baumannii (strain AB0057) | Yarrowia lipolytica | P00498 | ATP phosphoribosyl-transferase | | Saccharomyces cerevisiae S288c | Yarrowia lipolytica |

TABLE 4-continued

First-round results for histamine production in Yarrowia lipolytica

| Strain name | Titer (μg/L) | E1 Uniprot ID | Enzyme 1 activity name | Enzyme 1 source organism | E1 Codon Optimization Abbrev. | E2 Uniprot ID | Enzyme 2 activity name | E2 Modifications | Enzyme 2 source organism | E2 Codon Optimization Abbrev. |
|---|---|---|---|---|---|---|---|---|---|---|
| YIHISMN_04 | 0 | P00862 | Histidine decarboxylase | Lactobacillus sp. (strain 30a) | Bacillus subtilis | P00499 | ATP phosphoribosyl-transferase | | Salmonella typhimurium (strain LT2/ SGSC1412/ ATCC 700720) | Bacillus subtilis |
| YIHISMN_05 | 32011 | P00862 | Histidine decarboxylase | Lactobacillus sp. (strain 30a) | Saccharomyces cerevisiae | P00499 | ATP phosphoribosyl-transferase | | Salmonella typhimurium (strain LT2/ SGSC1412/ ATCC 700720) | Saccharomyces cerevisiae |
| YIHISMN_06 | 833 | P00862 | Histidine decarboxylase | Lactobacillus sp. (strain 30a) | Yarrowia lipolytica | P00499 | ATP phosphoribosyl-transferase | | Salmonella typhimurium (strain LT2/ SGSC1412/ ATCC 700720) | Yarrowia lipolytica |
| YIHISMN_07 | 299 | A0A0J6KM89 | Histidine decarboxylase | Chromobacterium sp. LK1 | Bacillus subtilis | Q9Z472 | ATP phosphoribosyl-transferase | N215K, L231F, T235A | Corynebacterium glutamicum ATCC 13032 | Bacillus subtilis |
| YIHISMN_08 | 1778 | A0A0J6KM89 | Histidine decarboxylase | Chromobacterium sp. LK1 | Saccharomyces cerevisiae | Q9Z472 | ATP phosphoribosyl-transferase | N215K, L231F, T235A | Corynebacterium glutamicum ATCC 13032 | Saccharomyces cerevisiae |
| YIHISMN_09 | 257949 | A0A0J6KM89 | Histidine decarboxylase | Chromobacterium sp. LK1 | Yarrowia lipolytica | Q9Z472 | ATP phosphoribosyl-transferase | N215K, L231F, T235A | Corynebacterium glutamicum ATCC 13032 | Yarrowia lipolytica |
| YIHISMN_10 | 0 | B71459 | Histidine decarboxylase | Acinetobacter baumannii (strain AB0057) | Bacillus subtilis | P00499 | ATP phosphoribosyl-transferase | | Salmonella typhimurium LT2 | Bacillus subtilis |
| YIHISMN_11 | 96836 | B71459 | Histidine decarboxylase | Acinetobacter baumannii (strain AB0057) | modified codon usage for Cg and Sc | P00499 | ATP phosphoribosyl-transferase | | Salmonella typhimurium LT2 | modified codon usage for Cg and Sc |
| YIHISMN_12 | 33 | B71459 | Histidine decarboxylase | Acinetobacter baumannii (strain AB0057) | Saccharomyces cerevisiae | P00499 | ATP phosphoribosyl-transferase | | Salmonella typhimurium LT2 | Saccharomyces cerevisiae |
| YIHISMN_13 | 366139 | B71459 | Histidine decarboxylase | Acinetobacter baumannii (strain AB0057) | Yarrowia lipolytica | P00499 | ATP phosphoribosyl-transferase | | Salmonella typhimurium LT2 | Yarrowia lipolytica |
| YIHISMN_14 | 23 | P00862 | Histidine decarboxylase | Lactobacillus sp. (strain 30a) | Bacillus subtilis | Q9Z472 | ATP phosphoribosyl-transferase | N215K, L231F, T235A | Corynebacterium glutamicum ATCC 13032 | Bacillus subtilis |
| YIHISMN_15 | 26 | P00862 | Histidine decarboxylase | Lactobacillus sp. (strain 30a) | modified codon usage for Cg and Sc | Q9Z472 | ATP phosphoribosyl transferase | N215K, L231F, T235A | Corynebacterium glutamicum ATCC 13032 | modified codon usage for Cg and Sc |
| YIHISMN_16 | 56 | P00862 | Histidine decarboxylase | Lactobacillus sp. (strain 30a) | Saccharomyces cerevisiae | Q9Z472 | ATP phosphoribosyl-transferase | N215K, L231F, T235A | Corynebacterium glutamicum ATCC 13032 | Saccharomyces cerevisiae |
| YIHISMN_17 | 1406 | P00862 | Histidine decarboxylase | Lactobacillus sp. (strain 30a) | Yarrowia lipolytica | Q9Z472 | ATP phosphoribosyl-transferase | N215K, L231F, T235A | Corynebacterium glutamicum ATCC 13032 | Yarrowia lipolytica |
| YIHISMN_18 | | A0A0J6KM89 | Histidine decarboxylase | Chromobacterium sp. LK1 | Bacillus subtilis | P00498 | ATP phosphoribosyl-transferase | | Saccharomyces cerevisiae S288c | Bacillus subtilis |
| YIHISMN_19 | 90046 | A0A0J6KM89 | Histidine decarboxylase | Chromobacterium sp. LK1 | modified codon usage for Cg and Sc | P00498 | ATP phosphoribosyl-transferase | | Saccharomyces cerevisiae S288c | modified codon usage for Cg and Sc |
| YIHISMN_20 | 1639 | A0A0J6KM89 | Histidine decarboxylase | Chromobacterium sp. LK1 | Saccharomyces cerevisiae | P00498 | ATP phosphoribosyl-transferase | | Saccharomyces cerevisiae S288c | Saccharomyces cerevisiae |

TABLE 5

First-round results for production of histamine in Bacillus subtilis

| Strain name | Titer (μg/L) | E1 Uniprot ID | Enzyme 1 activity name | Enzyme 1 source organism | E1 Codon Optimization Abbrev. | E2 Uniprot ID | Enzyme 2 activity name | E2 Modifications | Enzyme 2 source organism | E2 Codon Optimization Abbrev. |
|---|---|---|---|---|---|---|---|---|---|---|
| BsHISMN_01 |  | B71459 | Histidine decarboxylase | Acinetobacter baumannii (strain AB0057) | Yarrowia lipolytica | P00498 | ATP phosphoribosyl-transferase |  | Saccharomyces cerevisiae S288c | Yarrowia lipolytica |
| BsHISMN_02 | 919.7 | P00862 | Histidine decarboxylase | Lactobacillus sp. (strain 30a) | Yarrowia lipolytica | P00499 | ATP phosphoribosyl-transferase |  | Salmonella typhimurium LT2 | Yarrowia lipolytica |
| BsHISMN_03 | 2.4 | A0A0J6KM89 | Histidine decarboxylase | Chromobacterium sp. LK1 | modified codon usage for Cg and Sc | Q9Z472 | ATP phosphoribosyl-transferase | N215K, L231F, T235A | Corynebacterium glutamicum ATCC 13032 | modified codon usage for Cg and Sc |
| BsHISMN_04 | 9156.1 | P00862 | Histidine decarboxylase | Lactobacillus sp. (strain 30a) | Bacillus subtilis | Q9Z472 | ATP phosphoribosyl-transferase | N215K, L231F, T235A | Corynebacterium glutamicum ATCC 13032 | Bacillus subtilis |
| BsHISMN_05 | 5057.2 | P00862 | Histidine decarboxylase | Lactobacillus sp. (strain 30a) | modified codon usage for Cg and Sc | Q9Z472 | ATP phosphoribosyl-transferase | N215K, L231F, T235A | Corynebacterium glutamicum ATCC 13032 | modified codon usage for Cg and Sc |
| BsHISMN_06 |  | P00862 | Histidine decarboxylase | Lactobacillus sp. (strain 30a) | Yarrowia lipolytica | Q9Z472 | ATP phosphoribosyl-transferase | N215K, L231F, T235A | Corynebacterium glutamicum ATCC 13032 | Yarrowia lipolytica |
| BsHISMN_07 | 2532.4 | B71459 | Histidine decarboxylase | Acinetobacter baumannii (strain AB0057) | Bacillus subtilis | P00498 | ATP phosphoribosyl-transferase |  | Saccharomyces cerevisiae S288c | Bacillus subtilis |
| BsHISMN_08 | 13183.4 | B71459 | Histidine decarboxylase | Acinetobacter baumannii (strain AB0057) | modified codon usage for Cg and Sc | P00498 | ATP phosphoribosyl-transferase |  | Saccharomyces cerevisiae S288c | modified codon usage for Cg and Sc |
| BsHISMN_09 | 114.3 | B71459 | Histidine decarboxylase | Acinetobacter baumannii (strain AB0057) | Saccharomyces cerevisiae | P00498 | ATP phosphoribosyl-transferase |  | Saccharomyces cerevisiae S288c | Saccharomyces cerevisiae |
| BsHISMN_10 | 18336.5 | P00862 | Histidine decarboxylase | Lactobacillus sp. (strain 30a) | Bacillus subtilis | P00499 | ATP phosphoribosyl-transferase |  | Salmonella typhimurium LT2 | Bacillus subtilis |
| BsHISMN_11 | 0 | P00862 | Histidine decarboxylase | Lactobacillus sp. (strain 30a) | modified codon usage for Cg and Sc | P00499 | ATP phosphoribosyl-transferase |  | Salmonella typhimurium LT2 | modified codon usage for Cg and Sc |
| BsHISMN_12 | 6778.2 | P00862 | Histidine decarboxylase | Lactobacillus sp. (strain 30a) | Saccharomyces cerevisiae | P00499 | ATP phosphoribosyl-transferase |  | Salmonella typhimurium LT2 | Saccharomyces cerevisiae |
| BsHISMN_13 |  | A0A0J6KM89 | Histidine decarboxylase | Chromobacterium sp. LK1 | Bacillus subtilis | Q9Z472 | ATP phosphoribosyl-transferase | N215K, L231F, T235A | Corynebacterium glutamicum ATCC 13032 | Bacillus subtilis |
| BsHISMN_14 | 1071.1 | A0A0J6KM89 | Histidine decarboxylase | Chromobacterium sp. LK1 | Saccharomyces cerevisiae | Q9Z472 | ATP phosphoribosyl-transferase | N215K, L231F, T235A | Corynebacterium glutamicum ATCC 13032 | Saccharomyces cerevisiae |
| BsHISMN_15 |  | A0A0J6KM89 | Histidine decarboxylase | Chromobacterium sp. LK1 | Yarrowia lipolytica | Q9Z472 | ATP phosphoribosyl-transferase | N215K, L231F, T235A | Corynebacterium glutamicum ATCC 13032 | Yarrowia lipolytica |
| BsHISMN_16 | 233.4 | B71459 | Histidine decarboxylase | Acinetobacter baumannii (strain AB0057) | Bacillus subtilis | P00499 | ATP phosphoribosyl-transferase |  | Salmonella typhimurium LT2 | Bacillus subtilis |
| BsHISMN_17 | 16.2 | B71459 | Histidine decarboxylase | Acinetobacter baumannii (strain AB0057) | modified codon usage for Cg and Sc | P00499 | ATP phosphoribosyl-transferase |  | Salmonella typhimurium LT2 | modified codon usage for Cg and Sc |
| BsHISMN_18 | 61 | B71459 | Histidine decarboxylase | Acinetobacter baumannii (strain AB0057) | Saccharomyces cerevisiae | P00499 | ATP phosphoribosyl-transferase |  | Salmonella typhimurium LT2 | Saccharomyces cerevisiae |
| BsHISMN_19 | 1413.5 | B71459 | Histidine decarboxylase | Acinetobacter baumannii (strain AB0057) | Yarrowia lipolytica | P00499 | ATP phosphoribosyl-transferase |  | Salmonella typhimurium LT2 | Yarrowia lipolytica |
| BsHISMN_20 | 6630.6 | P00862 | Histidine decarboxylase | Lactobacillus sp. (strain 30a) | Saccharomyces cerevisiae | Q9Z472 | ATP phosphoribosyl-transferase | N215K, L231F, T235A | Corynebacterium glutamicum ATCC 13032 | Saccharomyces cerevisiae |
| BsHISMN_21 | 43.8 | A0A0J6KM89 | Histidine decarboxylase | Chromobacterium sp. LK1 | Bacillus subtilis | P00498 | ATP phosphoribosyl-transferase |  | Saccharomyces cerevisiae S288c | Bacillus subtilis |

TABLE 5-continued

First-round results for production of histamine in Bacillus subtilis

| Strain name | Titer (µg/L) | E1 Uniprot ID | Enzyme 1 activity name | Enzyme 1 source organism | E1 Codon Optimization Abbrev. | E2 Uniprot ID | Enzyme 2 activity name | E2 Modifi-cations | Enzyme 2 source organism | E2 Codon Optimization Abbrev. |
|---|---|---|---|---|---|---|---|---|---|---|
| BsHISMN_22 |  | A0A0J6 KM89 | Histidine decarboxylase | Chromo-bacterium sp. LK1 | modified codon usage for Cg and Sc | P00498 | ATP phosphoribosyl-transferase |  | Saccharomyces cerevisiae S288c | modified codon usage for Cg and Sc |
| BsHISMN_23 | 529 | A0A0J6 KM89 | Histidine decarboxylase | Chromo-bacterium sp. LK1 | Saccharo-myces cerevisiae | P00498 | ATP phosphoribosyl-transferase |  | Saccharomyces cerevisiae S288c | Saccharo-myces cerevisiae |
| BsHISMN_24 | 15026.1 | A0A0J6 KM89 | Histidine decarboxylase | Chromo-bacterium sp. LK1 | Yarrowia lipolytica | P00498 | ATP phosphoribosyl-transferase |  | Saccharomyces cerevisiae S288c | Yarrowia lipolytica |
| BsHISMN_25 |  | A0A0J6 KM89 | Histidine decarboxylase | Chromo-bacterium sp. LK1 | modified codon usage for Cg and Sc | Q9Z472 | ATP phosphoribosyl-transferase |  | Corynebacterium glutamicum ATCC 13032 | modified codon usage for Cg and Sc |

TABLE 6

Host evaluation designs for production of histamine tested in Saccharomyces cerevisiae

| Strain name | Titer (µg/L) | E1 Uniprot ID | Enzyme 1 activity name | Enzyme 1 source organism | E1 Codon Optimization Abbrev. | E2 Uniprot ID | Enzyme 2 activity name | E2 Modifi-cations | Enzyme 2 source organism | E2 Codon Optimization Abbrev. |
|---|---|---|---|---|---|---|---|---|---|---|
| Saccharomyces cerevisiae |  |  |  |  |  |  |  |  |  |  |
| ScHISMN_116 | 17466 | P00862 | Histidine decarboxylase | Lactobacillus sp. (strain 30a) | Bacillus subtilis | P00499 | ATP phosphoribosyl-transferase |  | Salmonella typhimurium LT2 | Bacillus subtilis |
| ScHISMN_117 | 28646 | P00862 | Histidine decarboxylase | Lactobacillus sp. (strain 30a) | Saccharo-myces cerevisiae | P00499 | ATP phosphoribosyl-transferase |  | Salmonella typhimurium LT2 | Saccharo-myces cerevisiae |
| ScHISMN_118 | 48150 | P00862 | Histidine decarboxylase | Lactobacillus sp. (strain 30a) | Yarrowia lipolytica | P00499 | ATP phosphoribosyl-transferase |  | Salmonella typhimurium LT2 | Yarrowia lipolytica |
| ScHISMN_119 | 59265 | A0A0J6 KM89 | Histidine decarboxylase | Chromo-bacterium sp. LK1 | Bacillus subtilis | Q9Z472 | ATP phosphoribosyl-transferase | N215K, L231F, T235A | Corynebacterium glutamicum ATCC 13032 | Bacillus subtilis |
| ScHISMN_120 | 72566 | A0A0J6 KM89 | Histidine decarboxylase | Chromo-bacterium sp. LK1 | modified codon usage for Cg and Sc | Q9Z472 | ATP phosphoribosyl-transferase | N215K, L231F, T235A | Corynebacterium glutamicum ATCC 13032 | modified codon usage for Cg and Sc |
| ScHISMN_121 | 46418 | A0A0J6 KM89 | Histidine decarboxylase | Chromo-bacterium sp. LK1 | Saccharo-myces cerevisiae | Q9Z472 | ATP phosphoribosyl-transferase | N215K, L231F, T235A | Corynebacterium glutamicum ATCC 13032 | Saccharo-myces cerevisiae |
| ScHISMN_122 | 64087 | A0A0J6 KM89 | Histidine decarboxylase | Chromo-bacterium sp. LK1 | Yarrowia lipolytica | Q9Z472 | ATP phosphoribosyl-transferase | N215K, L231F, T235A | Corynebacterium glutamicum ATCC 13032 | Yarrowia lipolytica |
| ScHISMN_123 | 80704 | B71459 | Histidine decarboxylase | Acinetobacter baumannii (strain AB0057) | Bacillus subtilis | P00499 | ATP phosphoribosyl-transferase |  | Salmonella typhimurium LT2 | Bacillus subtilis |
| ScHISMN_124 | 70043 | B71459 | Histidine decarboxylase | Acinetobacter baumannii (strain AB0057) | Yarrowia lipolytica | P00499 | ATP phosphoribosyl-transferase |  | Salmonella typhimurium LT2 | Yarrowia lipolytica |
| ScHISMN_125 | 25331 | P00862 | Histidine decarboxylase | Lactobacillus sp. (strain 30a) | Bacillus subtilis | Q9Z472 | ATP phosphoribosyl-transferase | N215K, L231F, T235A | Corynebacterium glutamicum ATCC 13032 | Bacillus subtilis |
| ScHISMN_126 | 33970 | P00862 | Histidine decarboxylase | Lactobacillus sp. (strain 30a) | modified codon usage for Cg and Sc | Q9Z472 | ATP phosphoribosyl-transferase | N215K, L231F, T235A | Corynebacterium glutamicum ATCC 13032 | modified codon usage for Cg and Sc |
| ScHISMN_127 | 21402 | P00862 | Histidine decarboxylase | Lactobacillus sp. (strain 30a) | Saccharo-myces cerevisiae | Q9Z472 | ATP phosphoribosyl-transferase | N215K, L231F, T235A | Corynebacterium glutamicum ATCC 13032 | Saccharo-myces cerevisiae |
| ScHISMN_128 | 41854 | P00862 | Histidine decarboxylase | Lactobacillus sp. (strain 30a) | Yarrowia lipolytica | Q9Z472 | ATP phosphoribosyl-transferase | N215K, L231F, T235A | Corynebacterium glutamicum ATCC 13032 | Yarrowia lipolytica |
| ScHISMN_129 | 101496 | A0A0J6 KM89 | Histidine decarboxylase | Chromo-bacterium sp. LK1 | Bacillus subtilis | P00498 | ATP phosphoribosyl-transferase |  | Saccharomyces cerevisiae S288c | Bacillus subtilis |

TABLE 6-continued

Host evaluation designs for production of histamine tested in Saccharomyces cerevisiae

| Strain name | Titer (µg/L) | E1 Uniprot ID | Enzyme 1 activity name | Enzyme 1 source organism | E1 Codon Optimization Abbrev. | E2 Uniprot ID | Enzyme 2 activity name | E2 Modifications | Enzyme 2 source organism | E2 Codon Optimization Abbrev. |
|---|---|---|---|---|---|---|---|---|---|---|
| ScHISMN_130 | 85546 | A0A0J6KM89 | Histidine decarboxylase | Chromobacterium sp. LK1 | Saccharomyces cerevisiae | P00498 | ATP phosphoribosyl-transferase | | Saccharomyces cerevisiae S288c | Saccharomyces cerevisiae |
| ScHISMN_131 | 111109 | A0A0J6KM89 | Histidine decarboxylase | Chromobacterium sp. LK1 | Yarrowia lipolytica | P00498 | ATP phosphoribosyl-transferase | | Saccharomyces cerevisiae S288c | Yarrowia lipolytica |

TABLE 7

Host evaluation designs for production of histamine tested in Corynebacterium glutamicum

| Strain name | Titer (µg/L) | E1 Uniprot ID | Enzyme 1 activity name | Enzyme 1 source organism | E1 Codon Optimization Abbrev. | E2 Uniprot ID | Enzyme 2 activity name | E2 Modifications | Enzyme 2 source organism | E2 Codon Optimization Abbrev. |
|---|---|---|---|---|---|---|---|---|---|---|
| CgHISMN_70 | | B71459 | Histidine decarboxylase | Acinetobacter baumannii (strain AB0057) | Bacillus subtilis | P00498 | ATP phosphoribosyl-transferase | | Saccharomyces cerevisiae S288c | Bacillus subtilis |
| CgHISMN_71 | 68395.9 | B71459 | Histidine decarboxylase | Acinetobacter baumannii (strain AB0057) | modified codon usage for Cg and Sc | P00498 | ATP phosphoribosyl-transferase | | Saccharomyces cerevisiae S288c | modified codon usage for Cg and Sc |
| CgHISMN_72 | 18 | B71459 | Histidine decarboxylase | Acinetobacter baumannii (strain AB0057) | Saccharomyces cerevisiae | P00498 | ATP phosphoribosyl-transferase | | Saccharomyces cerevisiae S288c | Saccharomyces cerevisiae |
| CgHISMN_73 | 16325.5 | B71459 | Histidine decarboxylase | Acinetobacter baumannii (strain AB0057) | Yarrowia lipolytica | P00498 | ATP phosphoribosyl-transferase | | Saccharomyces cerevisiae S288c | Yarrowia lipolytica |
| CgHISMN_74 | 4883.6 | P00862 | Histidine decarboxylase | Lactobacillus sp. (strain 30a) | Bacillus subtilis | P00499 | ATP phosphoribosyl-transferase | | Salmonella typhimurium LT2 | Bacillus subtilis |
| CgHISMN_75 | | P00862 | Histidine decarboxylase | Lactobacillus sp. (strain 30a) | Saccharomyces cerevisiae | P00499 | ATP phosphoribosyl-transferase | | Salmonella typhimurium LT2 | Saccharomyces cerevisiae |
| CgHISMN_76 | | P00862 | Histidine decarboxylase | Lactobacillus sp. (strain 30a) | Yarrowia lipolytica | P00499 | ATP phosphoribosyl-transferase | | Salmonella typhimurium LT2 | Yarrowia lipolytica |
| CgHISMN_77 | 5.4 | A0A0J6KM89 | Histidine decarboxylase | Chromobacterium sp. LK1 | Bacillus subtilis | Q9Z472 | ATP phosphoribosyl-transferase | N215K, L231F, T235A | Corynebacterium glutamicum ATCC 13032 | Bacillus subtilis |
| CgHISMN_78 | 88.6 | A0A0J6KM89 | Histidine decarboxylase | Chromobacterium sp. LK1 | Saccharomyces cerevisiae | Q9Z472 | ATP phosphoribosyl-transferase | N215K, L231F, T235A | Corynebacterium glutamicum ATCC 13032 | Saccharomyces cerevisiae |
| CgHISMN_79 | | A0A0J6KM89 | Histidine decarboxylase | Chromobacterium sp. LK1 | Yarrowia lipolytica | Q9Z472 | ATP phosphoribosyl-transferase | N215K, L231F, T235A | Corynebacterium glutamicum ATCC 13032 | Yarrowia lipolytica |
| CgHISMN_80 | 8368.2 | B71459 | Histidine decarboxylase | Acinetobacter baumannii (strain AB0057) | Bacillus subtilis | P00499 | ATP phosphoribosyl- | | Salmonella typhimurium LT2 | Bacillus subtilis |
| CgHISMN_81 | 9.3 | B71459 | Histidine decarboxylase | Acinetobacter baumannii (strain AB0057) | Saccharomyces cerevisiae | P00499 | ATP phosphoribosyl-transferase | | Salmonella typhimurium LT2 | Saccharomyces cerevisiae |
| CgHISMN_82 | 15529.4 | B71459 | Histidine decarboxylase | Acinetobacter baumannii (strain AB0057) | Yarrowia lipolytica | P00499 | ATP phosphoribosyl-transferase | | Salmonella typhimurium LT2 | Yarrowia lipolytica |
| CgHISMN_83 | | P00862 | Histidine decarboxylase | Lactobacillus sp. (strain 30a) | Bacillus subtilis | Q9Z472 | ATP phosphoribosyl-transferase | N215K, L231F, T235A | Corynebacterium glutamicum ATCC 13032 | Bacillus subtilis |
| CgHISMN_84 | 2.6 | P00862 | Histidine decarboxylase | Lactobacillus sp. (strain 30a) | Saccharomyces cerevisiae | Q9Z472 | ATP phosphoribosyl-transferase | N215K, L231F, T235A | Corynebacterium glutamicum ATCC 13032 | Saccharomyces cerevisiae |
| CgHISMN_85 | 6134 | P00862 | Histidine decarboxylase | Lactobacillus sp. (strain 30a) | Yarrowia lipolytica | Q9Z472 | ATP phosphoribosyl-transferase | N215K, L231F, T235A | Corynebacterium glutamicum ATCC 13032 | Yarrowia lipolytica |

TABLE 7-continued

Host evaluation designs for production of histamine tested in Corynebacterium glutamicum

| Strain name | Titer (µg/L) | E1 Uniprot ID | Enzyme 1 activity name | Enzyme 1 source organism | E1 Codon Optimization Abbrev. | E2 Uniprot ID | Enzyme 2 activity name | E2 Modifications | Enzyme 2 source organism | E2 Codon Optimization Abbrev. |
|---|---|---|---|---|---|---|---|---|---|---|
| CgHISMN_86 | 197 | A0A0J6KM89 | Histidine decarboxylase | Chromobacterium sp. LK1 | Bacillus subtilis | P00498 | ATP phosphoribosyltransferase | | Saccharomyces cerevisiae S288c | Bacillus subtilis |

TABLE 8

SEQ ID NO Cross-Reference Table

| SEQ ID NO | Sequence Type with Modifications | Uniprot ID | Activity name | Source organism | Codon Optimization Abbrev. |
|---|---|---|---|---|---|
| 1 | AA seq for enzyme B71459 | B71459 | histidine decarboxylase | Acinetobacter baumannii (strain AB0057) | |
| 2 | AA seq for enzyme Q9KJU3 | Q9KJU3 | Imidazoleglycerol-phosphate dehydratase | Corynebacterium glutamicum | |
| 3 | AA seq for enzyme P00498 | P00498 | ATP phosphoribosyltransferase | Saccharomyces cerevisiae | |
| 4 | AA seq for enzyme P00862 | P00862 | histidine decarboxylase | Lactobacillus sp. (strain 30a) | |
| 5 | AA seq for enzyme P00499 with deletion of Q207-E208 | P00499 | ATP phosphoribosyltransferase | Salmonella typhimurium (strain LT2/SGSC1412/ATCC 700720) | |
| 6 | AA seq for enzyme J6KM89 | J6KM89 | histidine decarboxylase | Chromobacterium sp. LK1 | |
| 7 | AA seq for enzyme Q9Z472 with substitution N215K, L231F, T235A | Q9Z472 | ATP phosphoribosyltransferase | Corynebacterium glutamicum (strain ATCC 13032/DSM 20300/JCM 1318/LMG 3730/NCIMB 10025) | |
| 8 | AA seq for enzyme E3QMN8 | E3QMN8 | histidine decarboxylase | Methanosarcina barkeri str. Wiesmoor | |
| 9 | AA seq for enzyme Q467R8 | Q467R8 | histidine decarboxylase | Methanosarcina barkeri (strain Fusaro/DSM 804) | |
| 10 | AA seq for enzyme Q05733 | Q05733 | histidine decarboxylase | Drosophila melanogaster | |
| 11 | AA seq for enzyme P54772 | P54772 | histidine decarboxylase | Solanum lycopersicum | |
| 12 | AA seq for enzyme P23738 | P23738 | histidine decarboxylase | Mus musculus | |
| 13 | AA seq for enzyme O68602 | O68602 | 1-(5-phosphoribosyl)5[(5-phosphoribosylamino)methylideneamino] imidazole-4-carboxamide isomerase | Corynebacterium glutamicum | |
| 14 | AA seq for enzyme Q9KJU4 | Q9KJU4 | Histidinol-phosphate aminotransferase | Corynebacterium glutamicum | |
| 15 | AA seq for enzyme Q8NNT5 | Q8NNT5 | Histidinol dehydrogenase | Corynebacterium glutamicum | |
| 16 | AA seq for enzyme Q9Z471 | Q9Z471 | Phosphoribosyl-ATP pyrophosphatase | Corynebacterium glutamicum | |
| 17 | AA seq for enzyme O31139 | O31139 | Imidazole glycerol phosphate synthase subunit | Corynebacterium glutamicum | |
| 18 | AA seq for enzyme O69043 | O69043 | Imidazole glycerol phosphate synthase subunit | Corynebacterium glutamicum | |
| 19 | AA seq for enzyme Q8NNT9 | Q8NNT9 | phosphoribosyl-AMP cyclohydrolase | Corynebacterium glutamicum | |
| 22 | AA seq for enzyme Q9Z472 | Q9Z472 | ATP phosphoribosyltransferase | Corynebacterium glutamicum (strain ATCC 13032/DSM 20300/JCM 1318/LMG 3730/NCIMB 10025) | |
| 20 | AA seq for enzyme P00815 | P00815 | histidinol dehydrogenase, phosphoribosyl-AMP cyclohydrolase, phosphoribosyl-ATP diphosphatase | Saccharomyces cerevisiae | |
| 21 | AA seq for enzyme P33734 | P33734 | Imidazole glycerol phosphate synthase subunit HisF | Saccharomyces cerevisiae | |
| 23 | AA seq for enzyme P07172 | P07172 | histidinol-phosphate transaminase | Saccharomyces cerevisiae | |
| 24 | AA seq for enzyme P06633 | P06633 | Imidazoleglycerol-phosphate dehydratase | Saccharomyces cerevisiae | |

TABLE 8-continued

SEQ ID NO Cross-Reference Table

| SEQ ID NO | Sequence Type with Modifications | Uniprot ID | Activity name | Source organism | Codon Optimization Abbrev. |
|---|---|---|---|---|---|
| 25 | AA seq for enzyme P38635 | P38635 | histidinol-phosphatase | Saccharomyces cerevisiae | |
| 26 | AA seq for enzyme A4QEF2 with substitution A243T | A4QEF2 | Glucose-6-phosphate 1-dehydrogenase (G6PD) (EC 1.1.1.49) | Corynebacterium glutamicum (strain R) | |
| 27 | AA seq for enzyme P23254 | P23254 | Transketolase | Saccharomyces cerevisiae (strain ATCC 204508/S288c) (Baker's yeast) | |
| 28 | AA seq for enzyme Q12265 | Q12265 | Ribose-phosphate pyrophosphokinase 5 (EC 2.7.6.1) (Phosphoribosyl pyrophosphate synthase 5) | Saccharomyces cerevisiae (strain ATCC 204508/S288c) (Baker's yeast) | |
| 30 | DNA seq1 for enzyme Q9Z472 | Q9Z472 | ATP phosphoribosyltransferase | Corynebacterium glutamicum | native |
| 29 | DNA seq1 for enzyme P00815 | P00815 | histidinol dehydrogenase, phosphoribosyl-AMP cyclohydrolase, phosphoribosyl-ATP diphosphatase | Saccharomyces cerevisiae | native |
| 31 | AA seq for enzyme P40545 | P40545 | 1-(5-phosphoribosyl)-5-[(5-phosphoribosylamino) methylideneamino] imidazole-4-carboxamide isomerase (EC 5.3.1.16) (5-proFAR isomerase) (Phosphoribosylformimino-5-aminoimidazole carboxamide ribotide isomerase) | Saccharomyces cerevisiae (strain ATCC 204508/S288c) (Baker's yeast) | |
| 32 | AA seq for enzyme P00942 with substitution I170V | P00942 | Triosephosphate isomerase (TIM) (EC 5.3.1.1) (Triose-phosphate isomerase) | Saccharomyces cerevisiae (strain ATCC 204508/S288c) (Baker's yeast) | |
| 33 | AA seq for enzyme A0A089YPE5 | A0A089YPE5 | Histidine decarboxylase (HDC) (EC 4.1.1.22) | Pseudomonas rhizosphaerae | |
| 34 | AA seq for enzyme A0A12656G9 | A0A12656G9 | Histidine decarboxylase (HDC) (EC 4.1.1.22) | Pseudomonas putida (Arthrobacter siderocapsulatus) | |
| 35 | AA seq for enzyme A0A0A1R6V3 | A0A0A1R6V3 | Histidine decarboxylase (HDC) (EC 4.1.1.22) | Citrobacter pasteurii | |
| 36 | AA seq for enzyme A0A1W0CM88 | A0A1W0CM88 | Histidine decarboxylase (HDC) (EC 4.1.1.22) | Chromobacterium haemolyticum | |
| 37 | AA seq for enzyme A0A0K6GJ74 | A0A0K6GJ74 | Histidine decarboxylase proenzyme | Lactobacillus reuteri | |
| 38 | AA seq for enzyme T0QL99 | T0QL99 | Histidine decarboxylase (EC 4.1.1.22) (Fragment) | Aeromonas salmonicida subsp. pectinolytica 34mel | |
| 39 | AA seq for enzyme A0A1B8HLR1 | A0A1B8HLR1 | Histidine decarboxylase (HDC) (EC 4.1.1.22) | Morganella psychrotolerans | |
| 40 | AA seq for enzyme A0A0C1PR48 | A0A0C1PR48 | Histidine decarboxylase proenzyme | Lactobacillus fructivorans | |
| 41 | AA seq for enzyme P0A717 | P0A717 | Ribose-phosphate pyrophosphokinase (RPPK) (EC 2.7.6.1) (5-phospho-D-ribosyl alpha-1-diphosphate) (Phosphoribosyl diphosphate synthase) (Phosphoribosyl pyrophosphate synthase) (P-Rib-PP synthase) (PRPP synthase) (PRPPase) | Escherichia coli (strain K12) | |
| 42 | AA seq for enzyme Q680A5 | Q680A5 | Ribose-phosphate pyrophosphokinase 4 (EC 2.7.6.1) (Phosphoribosyl pyrophosphate synthase 4) | Arabidopsis thaliana (Mouse-ear cress) | |
| 43 | AA seq for enzyme P38620 | P38620 | Ribose-phosphate pyrophosphokinase 2 (EC 2.7.6.1) (Phosphoribosyl pyrophosphate synthase 2) | Saccharomyces cerevisiae (strain ATCC 204508/S288c) (Baker's yeast) | |
| 44 | AA seq for enzyme P32895 | P32895 | Ribose-phosphate pyrophosphokinase 1 (EC 2.7.6.1) (Phosphoribosyl pyrophosphate synthase 1) | Saccharomyces cerevisiae (strain ATCC 204508/S288c) (Baker's yeast) | |

TABLE 8-continued

SEQ ID NO Cross-Reference Table

| SEQ ID NO | Sequence Type with Modifications | Uniprot ID | Activity name | Source organism | Codon Optimization Abbrev. |
|---|---|---|---|---|---|
| 45 | AA seq for enzyme P38689 | P38689 | Ribose-phosphate pyrophosphokinase 3 (EC 2.7.6.1) (Phosphoribosyl pyrophosphate synthase 3) | Saccharomyces cerevisiae (strain ATCC 204508/S288c) (Baker's yeast) | |
| 46 | AA seq for enzyme P15019 | P15019 | Transaldolase (EC 2.2.1.2) | Saccharomyces cerevisiae (strain ATCC 204508/S288c) (Baker's yeast) | |
| 47 | AA seq for enzyme P06775 | P06775 | Histidine permease | Saccharomyces cerevisiae (strain ATCC 204508/S288c) (Baker's yeast) | |
| 48 | AA seq for enzyme O59667 | O59667 | Histidine biosynthesis bifunctional protein his7 [Includes: Phosphoribosyl-AMP cyclohydrolase (EC 3.5.4.19); Phosphoribosyl-ATP pyrophosphatase (EC 3.6.1.31)] | Schizosaccharomyces pombe (strain 972/ATCC 24843) (Fission yeast) | |
| 49 | AA seq for enzyme O66000 | O66000 | Histidine decarboxylase proenzyme | Oenococcus oeni (Leuconostoc oenos) | |
| 50 | AA seq for enzyme A0A0R1Y874 | A0A0R1Y874 | Pyruvoyl family histidine decarboxylase | Lactobacillus aviarius subsp. aviarius DSM 20655 | |
| 51 | AA seq for enzyme A0A0J6KM89 | A0A0J6KM89 | Histidine decarboxylase (HDC) (EC 4.1.1.22) | Chromobacterium sp. LK1 | |
| 52 | DNA seq1 for enzyme B71459 | B71459 | Histidine decarboxylase | Acinetobacter baumannii (strain AB0057) | Yarrowia lipolytica |
| 53 | DNA seq1 for enzyme P00498 | P00498 | ATP phosphoribosyltransferase | Saccharomyces cerevisiae (strain ATCC 204508/S288c) (Baker's yeast) | Yarrowia lipolytica |
| 54 | DNA seq2 for enzyme B71459 | B71459 | Histidine decarboxylase | Acinetobacter baumannii (strain AB0057) | Bacillus subtillus |
| 55 | DNA seq2 for enzyme P00498 | P00498 | ATP phosphoribosyltransferase | Saccharomyces cerevisiae (strain ATCC 204508/S288c) (Baker's yeast) | Bacillus subtillus |
| 56 | DNA seq3 for enzyme B71459 | B71459 | Histidine decarboxylase | Acinetobacter baumannii (strain AB0057) | Saccharomyces cerevisiae |
| 57 | DNA seq3 for enzyme P00498 | P00498 | ATP phosphoribosyltransferase | Saccharomyces cerevisiae (strain ATCC 204508/S288c) (Baker's yeast) | Saccharomyces cerevisiae |
| 58 | DNA seq1 for enzyme P00499 with deletion of Q207-E208 | P00499 | ATP phosphoribosyltransferase | Salmonella typhimurium (strain LT2/SGSC1412/ATCC 700720) | Yarrowia lipolytica |
| 59 | DNA seq2 for enzyme P00499 with deletion of Q207-E208 | P00499 | ATP phosphoribosyltransferase | Salmonella typhimurium (strain LT2/SGSC1412/ATCC 700720) | Bacillus subtillus |
| 60 | DNA seq3 for enzyme P00499 with deletion of Q207-E208 | P00499 | ATP phosphoribosyltransferase | Salmonella typhimurium (strain LT2/SGSC1412/ATCC 700720) | Saccharomyces cerevisiae |
| 61 | DNA seq4 for enzyme B71459 | B71459 | Histidine decarboxylase (HDC) (EC 4.1.1.22) | Acinetobacter baumannii (strain AB0057) | modified codon usage for Corynebacterium glutamicum and Saccharomyces cerevisiae |
| 62 | DNA seq4 for enzyme P00499 with deletion of Q207-E208 | P00499 | ATP phosphoribosyltransferase | Salmonella typhimurium (strain LT2/SGSC1412/ATCC 700720) | modified codon usage for Corynebacterium glutamicum and Saccharomyces cerevisiae |
| 63 | DNA seq1 for enzyme A0A0J6KM89 | A0A0J6KM89 | Histidine decarboxylase | Chromobacterium sp. LK1 | Yarrowia lipolytica |
| 64 | DNA seq1 for enzyme Q9Z472 with substitution N215K, L231F, T235A | Q9Z472 | ATP phosphoribosyltransferase | Corynebacterium glutamicum (strain ATCC 13032/DSM 20300/JCM 1318/LMG 3730/NCIMB 10025) | Yarrowia lipolytica |
| 65 | DNA seq2 for enzyme A0A0J6KM89 | A0A0J6KM89 | Histidine decarboxylase | Chromobacterium sp. LK1 | Saccharomyces cerevisiae |
| 66 | DNA seq2 for enzyme Q9Z472 with substitution N215K, L231F, T235A | Q9Z472 | ATP phosphoribosyltransferase | Corynebacterium glutamicum (strain ATCC 13032/DSM 20300/JCM 1318/LMG 3730/NCIMB 10025) | Saccharomyces cerevisiae |
| 67 | DNA seq3 for enzyme A0A0J6KM89 | A0A0J6KM89 | Histidine decarboxylase | Chromobacterium sp. LK1 | Bacillus subtillus |

TABLE 8-continued

SEQ ID NO Cross-Reference Table

| SEQ ID NO | Sequence Type with Modifications | Uniprot ID | Activity name | Source organism | Codon Optimization Abbrev. |
|---|---|---|---|---|---|
| 68 | DNA seq3 for enzyme Q9Z472 with substitution N215K, L231F, T235A | Q9Z472 | ATP phosphoribosyltransferase | Corynebacterium glutamicum (strain ATCC 13032/ DSM 20300/JCM 1318/ LMG 3730/NCIMB 10025) | Bacillus subtillus |
| 69 | DNA seq1 for enzyme P00862 | P00862 | Histidine decarboxylase proenzyme | Lactobacillus sp. (strain 30a) | Bacillus subtillus |
| 70 | DNA seq2 for enzyme P00862 | P00862 | Histidine decarboxylase proenzyme | Lactobacillus sp. (strain 30a) | Saccharomyces cerevisiae |
| 71 | DNA seq3 for enzyme P00862 | P00862 | Histidine decarboxylase proenzyme | Lactobacillus sp. (strain 30a) | modified codon usage for Corynebacterium glutamicum and Saccharomyces cerevisiae |
| 72 | DNA seq5 for enzyme B71459 | B71459 | Histidine decarboxylase | Acinetobacter baumannii (strain AB0057) | modified codon usage for Corynebacterium glutamicum and Saccharomyces cerevisiae |
| 73 | DNA seq4 for enzyme P00498 | P00498 | ATP phosphoribosyltransferase | Saccharomyces cerevisiae (strain ATCC 204508/S288c) (Baker's yeast) | modified codon usage for Corynebacterium glutamicum and Saccharomyces cerevisiae |
| 74 | AA seq for enzyme A0A1H1TEB8 | A0A1H1 TEB8 | Histidine decarboxylase (HDC) (EC 4.1.1.22) | Pseudomonas sp. bs2935 | modified codon usage for Corynebacterium glutamicum and Saccharomyces cerevisiae |
| 75 | DNA seq1 for enzyme E3QMN8 | E3QMN8 | histidine decarboxylase | Methanosarcina barkeri str. Wiesmoor | Corynebacterium glutamicum |
| 76 | DNA seq1 for enzyme Q467R8 | Q467R8 | histidine decarboxylase | Methanosarcina barkeri (strain Fusaro/DSM 804) | Corynebacterium glutamicum |
| 77 | DNA seq4 for enzyme P00862 | P00862 | histidine decarboxylase | Lactobacillus sp. (strain 30a) | Corynebacterium glutamicum |
| 78 | DNA seq6 for enzyme B71459 | B71459 | histidine decarboxylase | Acinetobacter baumannii (strain AB0057) | Corynebacterium glutamicum |
| 79 | DNA seq1 for enzyme Q05733 | Q05733 | histidine decarboxylase | Drosophila melanogaster | Corynebacterium glutamicum |
| 80 | DNA seq1 for enzyme J6KM89 | J6KM89 | histidine decarboxylase | Chromobacterium sp. LK1 | Corynebacterium glutamicum |
| 81 | DNA seq5 for enzyme P00499 with deletion of Q207-E208 | P00499 | ATP phosphoribosyltransferase | Salmonella typhimurium (strain LT2/SGSC1412/ ATCC 700720) | Corynebacterium glutamicum |
| 82 | DNA seq5 for enzyme P00862 | P00862 | histidine decarboxylase | Lactobacillus sp. (strain 30a) | Saccharomyces cerevisiae |
| 83 | DNA seq for enzyme P54772 | P54772 | histidine decarboxylase | Solanum lycopersicum | Saccharomyces cerevisiae |
| 84 | DNA seq for enzyme P23738 | P23738 | histidine decarboxylase | Mus musculus | Saccharomyces cerevisiae |
| 85 | DNA seq2 for enzyme Q05733 | Q05733 | histidine decarboxylase | Drosophila melanogaster | Saccharomyces cerevisiae |
| 86 | DNA seq2 for enzyme J6KM89 | J6KM89 | histidine decarboxylase | Chromobacterium sp. LK1 | Saccharomyces cerevisiae |
| 87 | DNA seq2 for enzyme E3QMN8 | E3QMN8 | histidine decarboxylase | Methanosarcina barkeri str. Wiesmoor | Saccharomyces cerevisiae |
| 88 | DNA seq2 for enzyme Q467R8 | Q467R8 | histidine decarboxylase | Methanosarcina barkeri (strain Fusaro/DSM 804) | Saccharomyces cerevisiae |
| 89 | DNA seq4 for enzyme Q9Z472 with substitution N215K, L231F, T235A | Q9Z472 | ATP phosphoribosyltransferase | Corynebacterium glutamicum (strain ATCC 13032/ DSM 20300/JCM 1318/ LMG 3730/NCIMB 10025) | Saccharomyces cerevisiae |
| 90 | DNA seq6 for enzyme P00499 with deletion of Q207-E208 | P00499 | ATP phosphoribosyltransferase | Salmonella typhimurium (strain LT2/SGSC1412/ ATCC 700720) | Saccharomyces cerevisiae |
| 91 | DNA seq for enzyme O68602 | O68602 | 1-(5-phosphoribosyl)5[(5-phosphoribosylamino) methylideneamino]imidazole-4-carboxamide isomerase | Corynebacterium glutamicum | native |
| 92 | DNA seq for enzyme Q9KJU3 | Q9KJU3 | Imidazoleglycerol-phosphate dehydratase | Corynebacterium glutamicum | native |
| 93 | DNA seq for enzyme Q9KJU4 | Q9KJU4 | Histidinol-phosphate aminotransferase | Corynebacterium glutamicum | native |
| 94 | DNA seq for enzyme Q8NNT5 | Q8NNT5 | Histidinol dehydrogenase | Corynebacterium glutamicum | native |
| 95 | DNA seq for enzyme Q9Z471 | Q9Z471 | Phosphoribosyl-ATP pyrophosphatase | Corynebacterium glutamicum | native |
| 96 | DNA seq for enzyme O31139 | O31139 | Imidazole glycerol phosphate synthase subunit | Corynebacterium glutamicum | native |
| 97 | DNA seq for enzyme O69043 | O69043 | Imidazole glycerol phosphate synthase subunit | Corynebacterium glutamicum | native |
| 98 | DNA seq for enzyme Q8NNT9 | Q8NNT9 | phosphoribosyl-AMP cyclohydrolase | Corynebacterium glutamicum | native |

TABLE 8-continued

SEQ ID NO Cross-Reference Table

| SEQ ID NO | Sequence Type with Modifications | Uniprot ID | Activity name | Source organism | Codon Optimization Abbrev. |
|---|---|---|---|---|---|
| 99 | DNA seq5 for enzyme P00498 | P00498 | ATP phosphoribosyltransferase | Saccharomyces cerevisiae | native |
| 100 | DNA seq1 for enzyme P33734 | P33734 | Imidazole glycerol phosphate synthase subunit HisF | Saccharomyces cerevisiae | native |
| 101 | DNA seq1 for enzyme P07172 | P07172 | histidinol-phosphate transaminase | Saccharomyces cerevisiae | native |
| 102 | DNA seq for enzyme P06633 | P06633 | Imidazoleglycerol-phosphate dehydratase | Saccharomyces cerevisiae | native |
| 103 | DNA seq1 for enzyme P38635 | P38635 | histidinol-phosphatase | Saccharomyces cerevisiae | native |
| 104 | DNA seq for enzyme A0A0C1PR48 | A0A0C1 PR48 | Histidine decarboxylase proenzyme | Lactobacillus fructivorans | modified codon usage for Corynebacterium glutamicum and Saccharomyces cerevisiae |
| 105 | DNA seq for enzyme T0QL99 | T0QL99 | Histidine decarboxylase (EC 4.1.1.22) (Fragment) | Aeromonas salmonicida subsp. pectinolytica 34mel | modified codon usage for Corynebacterium glutamicum and Saccharomyces cerevisiae |
| 106 | DNA seq for enzyme A0A1B8HLR1 | A0A1B8 HLR1 | Histidine decarboxylase (HDC) (EC 4.1.1.22) | Morganella psychrotolerans | modified codon usage for Corynebacterium glutamicum and Saccharomyces cerevisiae |
| 107 | DNA seq2 for enzyme Q9Z472 | Q9Z472 | ATP phosphoribosyltransferase (ATP-PRT) (ATP-PRTase) | Corynebacterium glutamicum (strain ATCC 13032/ DSM 20300/JCM 1318/ LMG 3730/NCIMB 10025) | modified codon usage for Corynebacterium glutamicum and Saccharomyces cerevisiae |
| 108 | DNA seq for enzyme P0A717 | P0A717 | Ribose-phosphate pyrophosphokinase (RPPK) (EC 2.7.6.1) (5-phospho-D-ribosyl alpha-1-diphosphate) (Phosphoribosyl diphosphate synthase) (Phosphoribosyl pyrophosphate synthase) (P-Rib-PP synthase) (PRPP synthase) (PRPPase) | Escherichia coli (strain K12) | modified codon usage for Corynebacterium glutamicum and Saccharomyces cerevisiae |
| 109 | DNA seq for enzyme Q12265 | Q12265 | Ribose-phosphate pyrophosphokinase 5 (EC 2.7.6.1) (Phosphoribosyl pyrophosphate synthase 5) | Saccharomyces cerevisiae (strain ATCC 204508/S288c) (Baker's yeast) | modified codon usage for Corynebacterium glutamicum and Saccharomyces cerevisiae |
| 110 | DNA seq for enzyme P32895 | P32895 | Ribose-phosphate pyrophosphokinase 1 (EC 2.7.6.1) (Phosphoribosyl pyrophosphate synthase 1) | Saccharomyces cerevisiae (strain ATCC 204508/S288c) (Baker's yeast) | modified codon usage for Corynebacterium glutamicum and Saccharomyces cerevisiae |
| 111 | DNA seq for enzyme P23254 | P23254 | Transketolase | Saccharomyces cerevisiae (strain ATCC 204508/S288c) (Baker's yeast) | modified codon usage for Corynebacterium glutamicum and Saccharomyces cerevisiae |
| 112 | DNA seq for enzyme P06775 | P06775 | Histidine permease | Saccharomyces cerevisiae (strain ATCC 204508/S288c) (Baker's yeast) | modified codon usage for Corynebacterium glutamicum and Saccharomyces cerevisiae |
| 113 | DNA seq2 for enzyme P00815 | P00815 | trifunctional histidinol dehydrogenase/ phosphoribosyl-AMP cyclohydrolase/ phosphoribosyl-ATP diphosphatase | Saccharomyces cerevisiae (strain ATCC 204508/S288c) (Baker's yeast) | modified codon usage for Corynebacterium glutamicum and Saccharomyces cerevisiae |
| 114 | DNA seq2 fo enzyme P07172 | P07172 | Histidinol-phosphate aminotransferase | Saccharomyces cerevisiae (strain ATCC 204508/S288c) (Baker's yeast) | modified codon usage for Corynebacterium glutamicum and Saccharomyces cerevisiae |
| 115 | DNA seq6 for enzyme P00498 | P00498 | ATP phosphoribosyltransferase (ATP-PRT) (ATP-PRTase) | Saccharomyces cerevisiae (strain ATCC 204508/S288c) (Baker's yeast) | modified codon usage for Corynebacterium glutamicum and Saccharomyces cerevisiae |
| 116 | DNA seq for enzyme P40545 | P40545 | 1-(5-phosphoribosyl)-5-[(5-phosphoribosylamino) methylideneamino] imidazole-4-carboxamide isomerase (EC 5.3.1.16) (5-proFAR isomerase) (Phosphoribosylformimino-5-aminoimidazole carboxamide ribotide isomerase) | Saccharomyces cerevisiae (strain ATCC 204508/S288c) (Baker's yeast) | modified codon usage for Corynebacterium glutamicum and Saccharomyces cerevisiae |
| 117 | DNA seq2 for enzyme P33734 | P33734 | Imidazole glycerol phosphate synthase hisHF | Saccharomyces cerevisiae (strain ATCC 204508/S288c) (Baker's yeast) | modified codon usage for Corynebacterium glutamicum and Saccharomyces cerevisiae |

TABLE 8-continued

SEQ ID NO Cross-Reference Table

| SEQ ID NO | Sequence Type with Modifications | Uniprot ID | Activity name | Source organism | Codon Optimization Abbrev. |
|---|---|---|---|---|---|
| 118 | DNA seq for enzyme P00942 with substitution I170V | P00942 | Triosephosphate isomerase (TIM) (EC 5.3.1.1) (Triose-phosphate isomerase) | Saccharomyces cerevisiae (strain ATCC 204508/S288c) (Baker's yeast) | modified codon usage for Corynebacterium glutamicum and Saccharomyces cerevisiae |
| 119 | DNA seq3 for enzyme Q9Z472 | Q9Z472 | ATP phosphoribosyltransferase (ATP-PRT) (ATP-PRTase) (EC 2.4.2.17) | Corynebacterium glutamicum (strain ATCC 13032/ DSM 20300/JCM 1318/ LMG 3730/NCIMB 10025) | modified codon usage for Corynebacterium glutamicum and Saccharomyces cerevisiae |
| 120 | DNA seq5 for enzyme Q9Z472 with substitution N215K, L231F, T235A | Q9Z472 | ATP phosphoribosyltransferase (ATP-PRT) (ATP-PRTase) (EC 2.4.2.17) | LMG 3730/NCIMB 10025) (strain ATCC 13032/ DSM 20300/JCM 1318/ LMG 3730/NCIMB 10025) | modified codon usage for Corynebacterium glutamicum and Saccharomyces cerevisiae |
| 121 | DNA seq for enzyme O66000 | O66000 | Histidine decarboxylase proenzyme | Oenococcus oeni (Leuconostoc oenos) | modified codon usage for Corynebacterium glutamicum and Saccharomyces cerevisiae |
| 122 | DNA seq for enzyme A0A0R1Y874 | A0A0R1 Y874 | Pyruvoyl family histidine decarboxylase | Lactobacillus aviarius subsp. aviarius DSM 20655 | modified codon usage for Corynebacterium glutamicum and Saccharomyces cerevisiae |
| 123 | DNA seq for enzyme A0A1H1TEB8 with substitution S9R | A0A1H1 TEB8 | Histidine decarboxylase (HDC) (EC 4.1.1.22) | Pseudomonas sp. bs2935 | modified codon usage for Corynebacterium glutamicum and Saccharomyces cerevisiae |
| 124 | DNA seq for enzyme A0A089YPE5 | A0A089 YPE5 | Histidine decarboxylase (HDC) (EC 4.1.1.22) | Pseudomonas rhizosphaerae | modified codon usage for Corynebacterium glutamicum and Saccharomyces cerevisiae |
| 125 | DNA seq for enzyme A0A12656G9 | A0A126 56G9 | Histidine decarboxylase (HDC) (EC 4.1.1.22) | Pseudomonas putida (Arthrobacter siderocapsulatus) | modified codon usage for Corynebacterium glutamicum and Saccharomyces cerevisiae |
| 126 | DNA seq4 for enzyme A0A0J6KM89 | A0A0J6K M89 | Histidine decarboxylase (HDC) (EC 4.1.1.22) | Chromobacterium sp. LK1 | modified codon usage for Corynebacterium glutamicum and Saccharomyces cerevisiae |
| 127 | DNA seq for enzyme A0A0A1R6V3 | A0A0A1 R6V3 | Histidine decarboxylase (HDC) (EC 4.1.1.22) | Citrobacter pasteurii | modified codon usage for Corynebacterium glutamicum and Saccharomyces cerevisiae |
| 128 | DNA seq for enzyme A0A1W0CM88 | A0A1W0 CM88 | Histidine decarboxylase (HDC) (EC 4.1.1.22) | Chromobacterium haemolyticum | modified codon usage for Corynebacterium glutamicum and Saccharomyces cerevisiae |
| 129 | DNA seq6 for enzyme P00862 | P00862 | Histidine decarboxylase proenzyme (EC 4.1.1.22) (Pi chain) [Cleaved into: Histidine decarboxylase beta chain; Histidine decarboxylase alpha chain] | Lactobacillus sp. (strain 30a) | modified codon usage for Corynebacterium glutamicum and Saccharomyces cerevisiae |
| 130 | DNA seq for enzyme A0A0K6GJ74 | A0A0K6 GJ74 | Histidine decarboxylase proenzyme | Lactobacillus reuteri | modified codon usage for Corynebacterium glutamicum and Saccharomyces cerevisiae |
| 131 | DNA seq for enzyme P38620 | P38620 | Ribose-phosphate pyrophosphokinase 2 (EC 2.7.6.1) (Phosphoribosyl pyrophosphate synthase 2) | Saccharomyces cerevisiae (strain ATCC 204508/S288c) (Baker's yeast) | modified codon usage for Corynebacterium glutamicum and Saccharomyces cerevisiae |
| 132 | DNA seq for enzyme P38689 | P38689 | Ribose-phosphate pyrophosphokinase 3 (EC 2.7.6.1) (Phosphoribosyl pyrophosphate synthase 3) | Saccharomyces cerevisiae (strain ATCC 204508/S288c) (Baker's yeast) | modified codon usage for Corynebacterium glutamicum and Saccharomyces cerevisiae |
| 133 | DNA seq for enzyme P15019 | P15019 | Transaldolase (EC 2.2.1.2) | Saccharomyces cerevisiae (strain ATCC 204508/S288c) (Baker's yeast) | modified codon usage for Corynebacterium glutamicum and Saccharomyces cerevisiae |
| 134 | DNA seq for enzyme Q680A5 | Q680A5 | Ribose-phosphate pyrophosphokinase 4 (EC 2.7.6.1) (Phosphoribosyl pyrophosphate synthase 4) | Arabidopsis thaliana (Mouse-ear cress) | modified codon usage for Corynebacterium glutamicum and Saccharomyces cerevisiae |
| 135 | DNA seq for enzyme O59667 | O59667 | Histidine biosynthesis bifunctional protein his7 [Includes: Phosphoribosyl-AMP cyclohydrolase (EC 3.5.4.19); Phosphoribosyl-ATP pyrophosphatase (EC 3.6.1.31)] | Schizosaccharomyces pombe (strain 972/ATCC 24843) (Fission yeast) | modified codon usage for Corynebacterium glutamicum and Saccharomyces cerevisiae |
| 136 | DNA seq2 for enzyme P38635 | P38635 | Histidinol-phosphatase (HolPase) (EC 3.1.3.15) | Saccharomyces cerevisiae (strain ATCC 204508/S288c) (Baker's yeast) | modified codon usage for Corynebacterium glutamicum and Saccharomyces cerevisiae |
| 137 | DNA seq for enzyme A4QEF2 with substitution A243T | A4QEF2 | Glucose-6-phosphate 1-dehydrogenase (G6PD) (EC 1.1.1.49) | Corynebacterium glutamicum (strain R) | modified codon usage for Corynebacterium glutamicum and Saccharomyces cerevisiae |

TABLE 8-continued

SEQ ID NO Cross-Reference Table

| SEQ ID NO | Sequence Type with Modifications | Uniprot ID | Activity name | Source organism | Codon Optimization Abbrev. |
|---|---|---|---|---|---|
| 138 | DNA seq7 for enzyme P00862 | P00862 | Histidine decarboxylase proenzyme | Lactobacillus sp. (strain 30a) | Yarrowia lipolytica |
| 139 | DNA seq5 for enzyme A0A0J6KM89 | A0A0J6KM89 | Histidine decarboxylase | Chromobacterium sp. LK1 | modified codon usage for Corynebacterium glutamicum and Saccharomyces cerevisiae |
| 140 | DNA seq6 for enzyme Q9Z472 with substitution N215K, L231F, T235A | Q9Z472 | ATP phosphoribosyl transferase | Corynebacterium glutamicum ATCC 13032 | modified codon usage for Corynebacterium glutamicum and Saccharomyces cerevisiae |
| 141 | DNA seq4 for enzyme Q9Z472 | Q9Z472 | ATP phosphoribosyltransferase | Corynebacterium glutamicum (strain ATCC 13032/ DSM 20300/JCM 1318/ LMG 3730/NCIMB 10025) | Saccharomyces cerevisiae |
| 142 | AA seq for N-terminal solubility tag | | | | |
| 143 | AA seq for enzyme E7EAU9 | E7EAU9 | Ribose-phosphate pyrophosphokinase (RPPK) | Bacillus amyloliquefaciens | Yarrowia lypolytica |

REFERENCES

1. Gezginc, Y., et al., Biogenic amines formation in *Streptococcus thermophilus* isolated from home-made natural yogurt. Food Chem, 2013. 138(1): p. 655-62.
2. Byun, B. Y. and J. H. Mah, Occurrence of biogenic amines in Miso, Japanese traditional fermented soybean paste. J Food Sci, 2012. 77(12): p. T216-23.
3. Landete, J. M., et al., Molecular methods for the detection of biogenic amine-producing bacteria on foods. Int J Food Microbiol, 2007. 117(3): p. 258-69.
4. Ferstl, R., et al., Histamine receptor 2 is a key influence in immune responses to intestinal histamine-secreting microbes. J Allergy Clin Immunol, 2014. 134(3): p. 744-746 e3.
5. Tabanelli, G., et al., Effect of chemico-physical parameters on the histidine decarboxylase (HdcA) enzymatic activity in *Streptococcus thermophilus* PRI60. J Food Sci, 2012. 77(4): p. M231-7.
6. Wauters, G., et al., *Histidine decarboxylase in Enterobacteriaceae revisited*. J Clin Microbiol, 2004. 42(12): p. 5923-4.
7. Lee, M. E., et al., A Highly Characterized Yeast Toolkit for Modular, Multipart Assembly. ACS Synth Biol, 2015. 4(9): p. 975-86.
8. Roland, B. P., et al., Triosephosphate isomerase I170V alters catalytic site, enhances stability and induces pathology in a *Drosophila* model of TPI deficiency. Biochim Biophys Acta, 2015. 1852(1): p. 61-9.

What is claimed is:

1. An engineered fungal cell that expresses:
  a non-native histidine decarboxylase having at least 70% amino acid sequence identity with a histidine decarboxylase from *Chromobacterium* sp. LK1 having SEQ ID NO:6 or from *Acinetobacter baumannii* strain AB0057 having SEQ ID NO:1; and
  at least one ATP phosphoribosyltransferase, wherein the ATP phosphoribosyltransferase comprises:
    an ATP phosphoribosyltransferase having at least 70% amino acid sequence identity with an ATP phosphoribosyltransferase from *S. cerevisiae* S288c having SEQ ID NO:3; and/or
    a feedback-deregulated ATP phosphoribosyltransferase comprising a feedback-deregulated variant of a *Corynebacterium glutamicum* ATP phosphoribosyltransferase having at least 70% amino acid sequence identity with SEQ ID NO:7;
  wherein the engineered fungal cell produces histamine at a level at least 75 mg/L of culture medium.

2. The engineered fungal cell of claim 1, wherein the engineered fungal cell comprises increased activity of one or more upstream histamine pathway enzyme(s) in addition to said ATP phosphoribosyltransferase(s), said increased activity being increased relative to a control cell.

3. The engineered fungal cell of claim 2, wherein the one or more upstream histamine pathway enzyme(s) are selected from the group consisting of a phosphoribosyl-ATP pyrophosphatase, a phosphoribosyl-AMP cyclohydrolase, a 5'ProFAR isomerase, an imidazole-glycerol phosphate synthase, an imidazole-glycerol phosphate dehydratase, a histidinol-phosphate aminotransferase, a histidinol-phosphate phosphatase, histidinol dehydrogenase, and a ribose phosphate pyrophosphokinase.

4. The engineered fungal cell of claim 1, wherein the engineered fungal cell comprises reduced activity of one or more enzyme(s) that consume one or more histamine pathway precursors, said reduced activity being reduced relative to a control cell.

5. The engineered fungal cell of claim 1, wherein the engineered fungal cell expresses a feedback-deregulated glucose-6-phosphate dehydrogenase or said feedback-deregulated ATP phosphoribosyltransferase.

6. A culture of engineered fungal cells according to claim 1.

7. The culture of claim 6, wherein the culture comprises histamine at a level at least 300 mg/L of culture medium.

8. A method of culturing engineered fungal cells according to claim 1, the method comprising culturing the cells under conditions suitable for producing histamine.

9. A method for preparing histamine using the engineered fungal cells of claim 1, the method comprising:
  (a) cultivating the fungal cells in a suitable culture medium under conditions that permit the fungal cells to produce histamine, wherein the histamine is released into the culture medium; and
  (b) isolating histamine from the culture medium.

10. The engineered fungal cell of claim 1, wherein the fungal cell is a cell of the genus *Saccharomyces* and of the species cerevisiae.

11. The engineered fungal cell of claim 10, wherein the fungal cell expresses:
  said non-native histidine decarboxylase having at least 70% amino acid sequence identity with a histidine decarboxylase from *Chromobacterium* sp. LK1 having SEQ ID NO:6 or from *Acinetobacter baumannii* strain AB0057 having SEQ ID NO:1;
  said ATP phosphoribosyltransferase having at least 70% amino acid sequence identity with an ATP phosphoribosyltransferase from *S. cerevisiae* S288c having SEQ ID NO:3; and
  said feedback-deregulated ATP phosphoribosyltransferase comprising a feedback-deregulated variant of a *Corynebacterium glutamicum* ATP phosphoribosyltransferase having at least 70% amino acid sequence identity with SEQ ID NO:7.

12. The engineered fungal cell of claim 11, wherein the fungal cell expresses:
  said non-native histidine decarboxylase, which has 100% amino acid sequence identity with a histidine decarboxylase from *Chromobacterium* sp. LK1 having SEQ ID NO:6;
  said ATP phosphoribosyltransferase, which has 100% amino acid sequence identity with an ATP phosphoribosyltransferase from *S. cerevisiae* S288c having SEQ ID NO:3; and
  said feedback-deregulated ATP phosphoribosyltransferase comprising a feedback-deregulated variant of a *Corynebacterium glutamicum* ATP phosphoribosyltransferase, which has 100% amino acid sequence identity with SEQ ID NO:7.

13. The engineered fungal cell of claim 1, wherein the fungal cell is a cell of the genus *Yarrowia* and of the species *lipolytica*.

14. The engineered fungal cell of claim 13, wherein the fungal cell expresses:
  said non-native histidine decarboxylase having at least 70% amino acid sequence identity with a histidine decarboxylase from *Chromobacterium* sp. LK1 having SEQ ID NO:6 or from *Acinetobacter baumannii* strain AB0057 having SEQ ID NO:1; and
  said ATP phosphoribosyltransferase having at least 70% amino acid sequence identity with an ATP phosphoribosyltransferase from *S. cerevisiae* S288c having SEQ ID NO:3.

15. The engineered fungal cell of claim 14, wherein the fungal cell expresses:
  said non-native histidine decarboxylase, which has 100% amino acid sequence identity with a histidine decarboxylase from *Chromobacterium* sp. LK1 having SEQ ID NO:6 or from *Acinetobacter baumannii* strain AB0057 having SEQ ID NO:1; and
  said ATP phosphoribosyltransferase, which has 100% amino acid sequence identity with an ATP phosphoribosyltransferase from *S. cerevisiae* S288c having SEQ ID NO:3.

* * * * *